US012682984B2

(12) United States Patent
Ulz et al.

(10) Patent No.: US 12,682,984 B2
(45) Date of Patent: Jul. 14, 2026

(54) TRANSCRIPTION FACTOR PROFILING

(71) Applicant: Freenome Holdings, Inc., South San Francisco, CA (US)

(72) Inventors: Peter Ulz, Graz (AT); Michael R. Speicher, Hart Bei Graz (AT); Ellen Heitzer, Graz (AT)

(73) Assignee: Freenome Holdings, Inc., Brisbane, CA (US)

( * ) Notice: Subject to any disclaimer, the term of this patent is extended or adjusted under 35 U.S.C. 154(b) by 0 days.

(21) Appl. No.: 17/159,725

(22) Filed: Jan. 27, 2021

(65) Prior Publication Data

US 2021/0272653 A1      Sep. 2, 2021

Related U.S. Application Data

(63) Continuation of application No. PCT/US2019/055119, filed on Oct. 8, 2019.

(60) Provisional application No. 62/849,097, filed on May 16, 2019, provisional application No. 62/752,270, filed on Oct. 29, 2018, provisional application No. 62/742,854, filed on Oct. 8, 2018.

(51) Int. Cl.
| | |
|---|---|
| *G16B 30/10* | (2019.01) |
| *G06N 20/00* | (2019.01) |
| *G16B 15/30* | (2019.01) |
| *G16B 40/20* | (2019.01) |

(52) U.S. Cl.
CPC ............ *G16B 30/10* (2019.02); *G06N 20/00* (2019.01); *G16B 15/30* (2019.02); *G16B 40/20* (2019.02)

(58) Field of Classification Search
None
See application file for complete search history.

(56) References Cited

U.S. PATENT DOCUMENTS

| | | |
|---|---|---|
| 7,270,960 B2 | 9/2007 | Hellstrom et al. |
| 7,727,720 B2 | 6/2010 | Dhallan |
| 7,754,429 B2 | 7/2010 | Rigatti et al. |
| 8,168,385 B2 | 5/2012 | Brenner |
| 8,318,433 B2 | 11/2012 | Brenner |
| 9,035,035 B2 | 5/2015 | Cherkasov et al. |
| 9,040,239 B1 | 5/2015 | Zheng et al. |
| 9,080,210 B2 | 7/2015 | Van Eijk et al. |
| 9,447,452 B2 | 9/2016 | Rao et al. |
| 10,337,053 B2 | 7/2019 | Rao et al. |
| 10,443,091 B2 | 10/2019 | Rao et al. |
| 10,533,213 B2 | 1/2020 | Rao et al. |
| 10,731,204 B2 | 8/2020 | Rao et al. |
| 10,767,216 B2 | 9/2020 | Rao et al. |
| 10,774,373 B2 | 9/2020 | Rao et al. |
| 10,978,175 B2 | 4/2021 | Van Eijk et al. |
| 11,072,818 B2 | 7/2021 | Rao et al. |
| 11,208,683 B2 | 12/2021 | Rao et al. |
| 11,514,289 B1 | 11/2022 | Otte et al. |
| 11,681,953 B2 | 6/2023 | Drake et al. |
| 11,781,959 B2 | 10/2023 | Delubac |
| 2010/0131286 A1 | 5/2010 | Houlgatte et al. |
| 2010/0151471 A1 | 6/2010 | Faham et al. |
| 2013/0116930 A1 | 5/2013 | Karczewski et al. |
| 2013/0309666 A1 | 11/2013 | Deciu et al. |
| 2014/0365243 A1 | 12/2014 | Varadan et al. |
| 2015/0368708 A1 | 12/2015 | Talasaz |
| 2016/0153054 A1 | 6/2016 | Feng et al. |
| 2017/0277844 A1 | 9/2017 | Apte et al. |
| 2017/0357763 A1 | 12/2017 | Apte et al. |
| 2018/0102187 A1 | 4/2018 | Apte et al. |
| 2020/0232894 A1 | 7/2020 | Delubac |
| 2021/0010076 A1 | 1/2021 | Delubac et al. |
| 2021/0057046 A1 | 2/2021 | Liu et al. |
| 2021/0174958 A1 | 6/2021 | Drake et al. |
| 2021/0210205 A1 | 7/2021 | Drake et al. |
| 2021/0230684 A1 | 7/2021 | Ariazi et al. |

FOREIGN PATENT DOCUMENTS

| | | |
|---|---|---|
| CN | 103403182 A | 11/2013 |
| CN | 107636171 A | 1/2018 |
| KR | 20170044660 A | 4/2017 |
| TW | 201833329 A | 9/2018 |
| WO | WO-2015070086 A1 | 5/2015 |
| WO | WO-2016015058 A2 | 1/2016 |
| WO | WO-2016094853 A1 | 6/2016 |
| WO | WO-2016119190 A1 | 8/2016 |
| WO | WO-2017083366 A1 | 5/2017 |
| WO | WO-2018009723 A1 | 1/2018 |
| WO | WO-2019060716 A1 | 3/2019 |
| WO | WO-2019100024 A1 | 5/2019 |
| WO | WO-2019147663 A1 | 8/2019 |
| WO | WO-2019191649 A1 | 10/2019 |

(Continued)

OTHER PUBLICATIONS

Mlack et al., Recent discoveries concerning the involvement of transcription factors from the Grainyhead-like family in cancer, Experimental Biology and Medicine 2015; 240: 1396-1401. DOI: 10.1177/1535370215588924.*
Odom, Identification of Transcription Factor-DNA Interactions in vivo, Subcell Biochem. 2011 ; 52: 175-191. doi:10.1007/978-90-481-9069-0_8. Author manuscript; available in PMC Jun. 11, 2014.*
Wang et al. The function of homeobox genes and lncRNAs in cancer (Review) Oncology Letters 12: 1635-1641, 2016.*
Ananthakrishnan et al. Epidemiology and risk factors for IBD. Nat Rev Gastroenterol Hepatol 12(4):205-17 (2015).
Belic et al. Genomic alterations in plasma DNA from patients with metastasized prostate cancer receiving abiraterone or enzalutamide. Int J Cancer 143(5):1236-1248 (2018).
Bramsen et al. Molecular-Subtype-Specific Biomarkers Improve Prediction of Prognosis in Colorectal Cancer. Cell Reports 19:1268-1280 (2017).

(Continued)

*Primary Examiner* — Joseph Woitach

(74) *Attorney, Agent, or Firm* — WILSON SONSINI GOODRICH & ROSATI

(57) ABSTRACT

Methods and systems disclosed herein can improve analysis capabilities of genomic materials. The methods provided herein may examine transcription factor binding site accessibility to diagnose a disease or monitor progression of a disease in a subject.

34 Claims, 90 Drawing Sheets

(56)                References Cited

FOREIGN PATENT DOCUMENTS

| WO | WO-2019200410 A1 | 10/2019 |
| WO | WO-2020076772 A1 | 4/2020 |
| WO | WO-2020243609 A1 | 12/2020 |
| WO | WO-2021202351 A1 | 10/2021 |
| WO | WO-2021222220 A2 | 11/2021 |
| WO | WO-2022076237 A1 | 4/2022 |
| WO | WO-2022140116 A1 | 6/2022 |
| WO | WO-2022204358 A1 | 9/2022 |
| WO | WO-2022261192 A1 | 12/2022 |
| WO | WO-2023003851 A1 | 1/2023 |
| WO | WO-2023147472 A1 | 8/2023 |
| WO | WO-2023183468 A2 | 9/2023 |

OTHER PUBLICATIONS

Bullman. How the Microbiome Impacts Cancer, Immunity, and Response to Therapy. Presentation slides San Francisco Jan. 25, 2020 (10 pgs).

Cleary et al. Detection of low-abundance bacterial strains in metagenomic datasets by eigengenome partitioning. Nat Biotechnol 33(10):1053-60 (2015).

Dadkhah et al. Gut microbiome identifies risk for colorectal polyps. BMJ Open Gastro 6:e000297 (2019).

De Palma et al. The Molecular Hallmarks of the Serrated Pathway in Colorectal Cancer. Cancer 11:1017 (2019).

Ding et al. DectICO: an alignment-free supervised metagenomic classification method based on feature extraction and dynamic selection. BMC Medical Genomics 16:323 (2015).

Ditzler et al. Multi-Layer and Recursive Neural Networks for Metagenomic Classification. IEEE Transactions on Nanobioscience 14(6):608-616 (2015).

Essaghir et al. A Minimal Connected Network of Transcription Factors Regulated in Human Tumors and Its Application to the Quest for Universal Cancer Biomarkers. PLoS One 7(6):e39666 (2012).

Fournie, et al. Plasma DNA as a marker of cancerous cell death. Investigations in patients suffering from lung cancer and in nude mice bearing human tumours. Cancer Lett. May 8, 1995;91(2):221-7.

Giacona, et al. Cell-free DNA in human blood plasma: length measurements in patients with pancreatic cancer and healthy controls. Pancreas. Jul. 1998;17(1):89-97.

Gopalakrishnan et al. Gut microbiome modulates response to anti-PD-1 immunotherapy in melanoma patients. Science 359(6371):97-103 (2018).

Havel et al. The evolving landscape of biomarkers for checkpoint inhibitor immunotherapy. Nat Rev Cancer 19(3):133-150 (2019).

Heitzer et al. Tumor-associated copy number changes in the circulation of patients with prostate cancer identified through whole-genome sequencing. Genome Med. 5(4):30 (2013).

Huang et al. Analysis of microbial sequences in plasma cell-free DNA for early-onset breast cancer patients and healthy females. BMC Medical Genomics 11(Suppl 1):16 (2018).

Kowarsky et al. Numerous uncharacterized and highly divergent microbes which colonize humans are revealed by circulating cell-free DNA. PNAS USA 114(36):9623-9628 (2017).

Lambert et al. The Human Transcription Factors. Cell 172:650-665 (Feb. 8, 2018).

Li et al. Systematic Target Function Annotation of Human Transcription Factors. BMC Biology 16(4):1-18 (2018).

Mandel et al. Nuclear Acids In Human Blood Plasma. C R Acad. Sci. Paris, 142:241-243 (1948) (French).

PCT/US2019/055119 International Search Report and Written Opinion dated Dec. 30, 2019.

Piening et al. Integrative Personal Omics Profiles during Periods of Weight Gain and Loss. Cell Systems 6:1-14 (2018).

Pomerantz et al. The androgen receptor cistrome is extensively reprogrammed in human prostate tumorigenesis. Nat Genet 47(11):1346-1351 (2015).

Spira et al. Precancer Atlas to Drive Precision Prevention Trials. Cancer Res. 77(7):1510-1541 (2017).

Sun et al. Transcription Factor Profiling Reveals Molecular Choreography and Key Regulators of Human Retrotransposon Expression. PNAS USA 115(24):E5526-E5535 (2018).

Tong et al. Diagnostic developments involving cell-free (circulating) nucleic acids. Clinica Chimica Acta. 363:187-96 (2006).

Ulz et al. Inference of transcription factor binding from cellfree DNA enables tumor subtype prediction and early detection. Nat Commun 10(1):4666 (2019).

Ulz et al. Inference of Tumor Cell-Specific Transcription Factor Binding from Cell-Free DNA. BioRxiv BioRxiv 2018:456681 (2018).

Ulz et al. Inferring expressed genes by whole-genome sequencing of plasma DNA. Nat Genet 48(10):1273-8 (2016).

Ulz et al. Whole-genome plasma sequencing reveals focal amplifications as a driving force in metastatic prostate cancer. Nat Commun 7:12008 (2016).

Wang et al. Evaluation of antibody level against Fusobacterium nucleatum in the serological diagnosis of colorectal cancer. Scientific reports 6:33440 (2016).

Yevshin et al. GTRD: a database on gene transcription regulation—2019 update. Nucleic Acids Res. 47(D1):D100-D105 (2019).

Zhang et al. Identification of low abundance microbiome in clinical samples using whole genome sequencing. Genome Biology 16:265 (2015).

Snyder, M.W. et al. Cell-free DNA comprises an in vivo nucleosome footprint that informs its tissues-of-origin. Cell 2016; 164:57-68.

Friedland et al.: Development and Clinical Validation of a blood test for early detection of colorectal adenomas and cancer. Abstract 32305, Poster ASCO GI Meeting [1-1] (2021).

Golub et al. Molecular classification of cancer: Class discovery and class prediction by gene expression monitoring, Science, American Association for the Advancement of Science, 286:5439 (Oct. 15, 1999).

Kourou et al.: Machine learning applications in cancer prognosis and prediction. Comput Struct Biotechnol J.13:8-17 (2014).

Liu et al.: An individualized predictor of health and disease using paired reference and target samples. BMC Bioinformatics 17:47 [1-15] (2016).

Manghnani et al.: METCC: METric learning for Confounder Control Making distance matter in high dimensional biological analysis. arXiv:1812.03188v1 [cs.LG] [1-10] (2018).

Singh, et al. "Gene expression correlates of clinical prostate cancer behavior." Cancer Cell. vol. 1, pp. 203-209 (2002).

Wan et al.: Machine learning enables detection of early-stage colorectal cancer by whole-genome sequencing of plasma cell-free DNA. bioRxiv prePrint URL:https://doi.org/10.1101/478065 [1-22] (2018).

KR Serial No. 20217010231 Office Action dated May 12, 2025, and an English translation.

SG Serial No. 11202100960R Written Opinion dated Jun. 24, 2025.

Snyder, et al. Cell-Free DNA Comprises an In Vivo Nucleosome Footprint that Informs Its Tissues-Of-Origin. Cell 164(1-2):57-68 (2016).

AU Serial No. 2019356497 Examination Report dated Sep. 3, 2024.

JP Serial No. 2021-505775 Decision of Rejection dated Jun. 24, 2024.

EP Serial No. 19870688.9 Search Report dated Mar. 13, 2025.

SG Serial No. 11202100960R Examination Report dated Dec. 14, 2022.

CA3107948 Office Action dated Feb. 20, 2026.

ULZ, Peter et al. Inferring Expressed Genes by Whole-Genome Sequencing of Plasma DNA. Nature Genetics vol. 48,10: pp. 1273-1278 (2016).

* cited by examiner

FIG. 2A
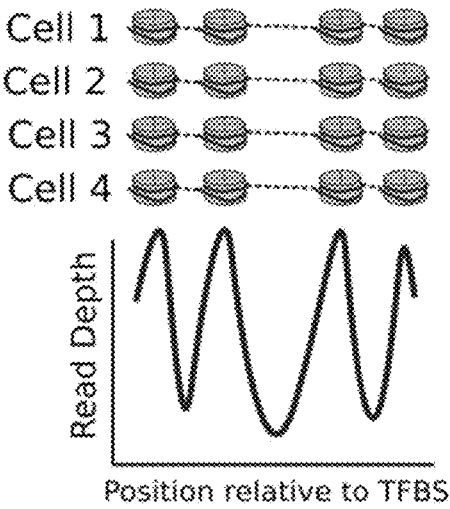 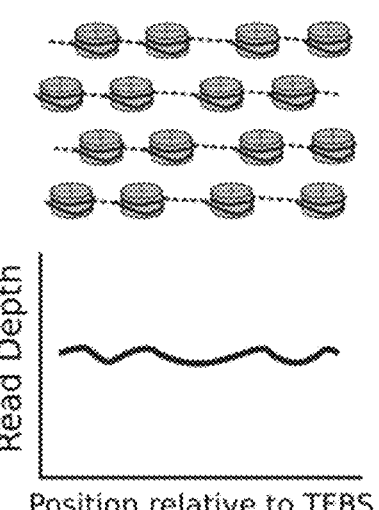
FIG. 2B
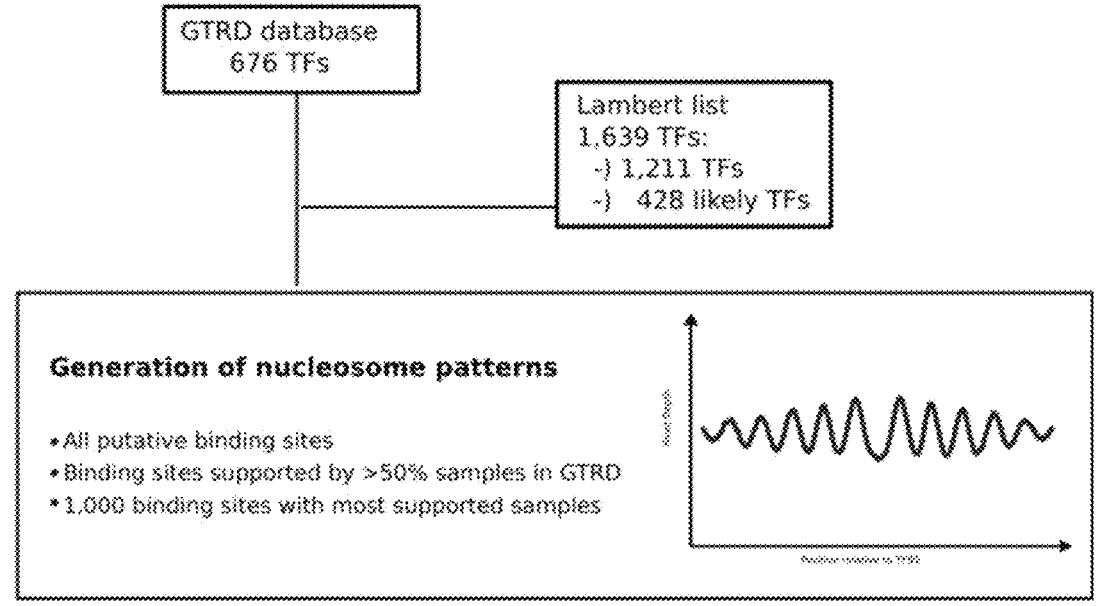

Position relative to TFBS

Sites supported by >50%
samples 1,000 sites supported by
most samples

ATF-3: sites supported by >50% sample

ATH-1: sites supported by >50% sample

CREB: sites supported by >50% sample

Dp-1: sites supported by >50% sample

FIG. 7I
FIG. 7J
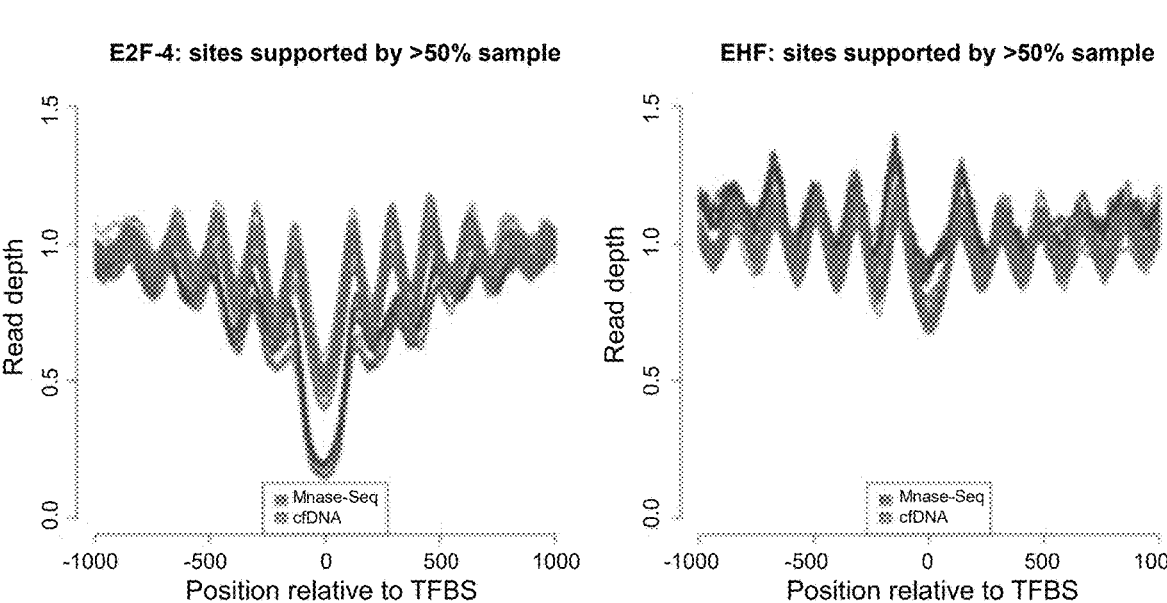
FIG. 7K
FIG. 7L
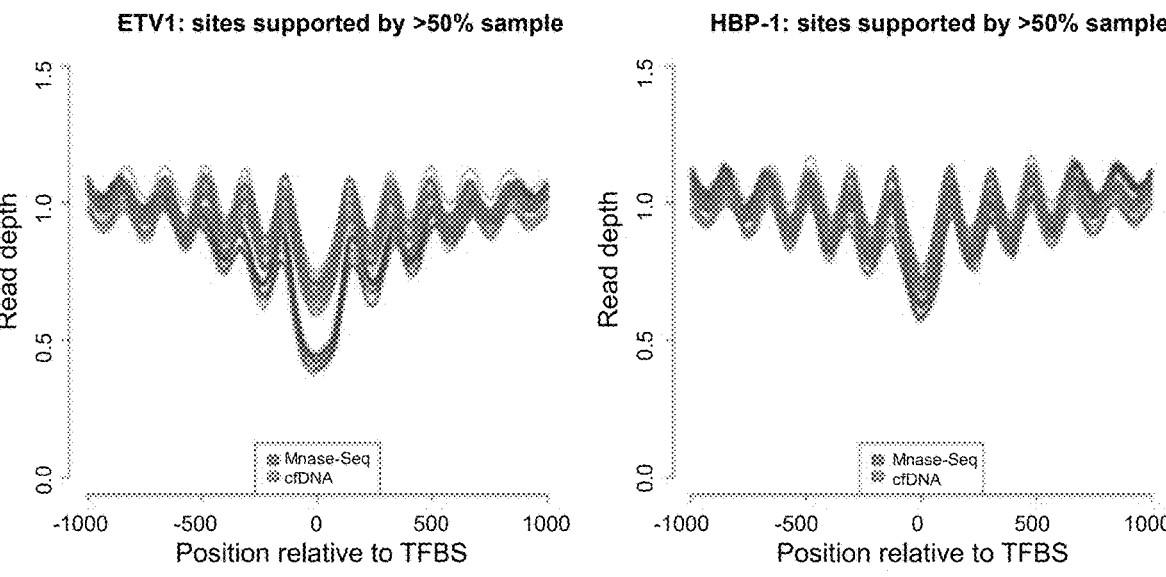

FIG. 7GG                                                    FIG. 7HH
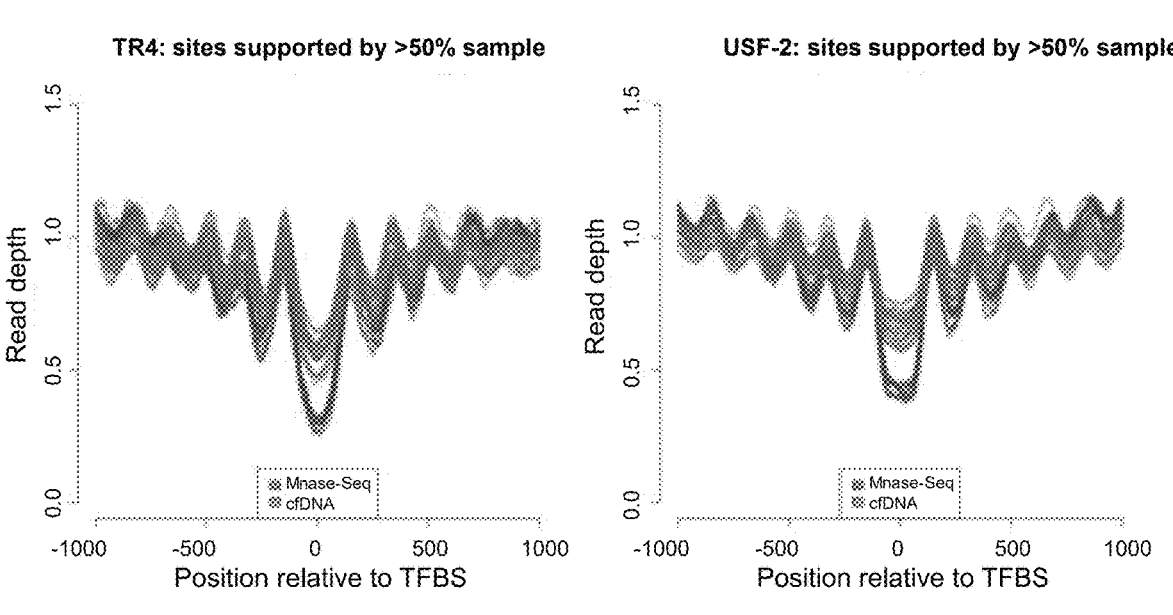
FIG. 7II                                                    FIG. 7JJ
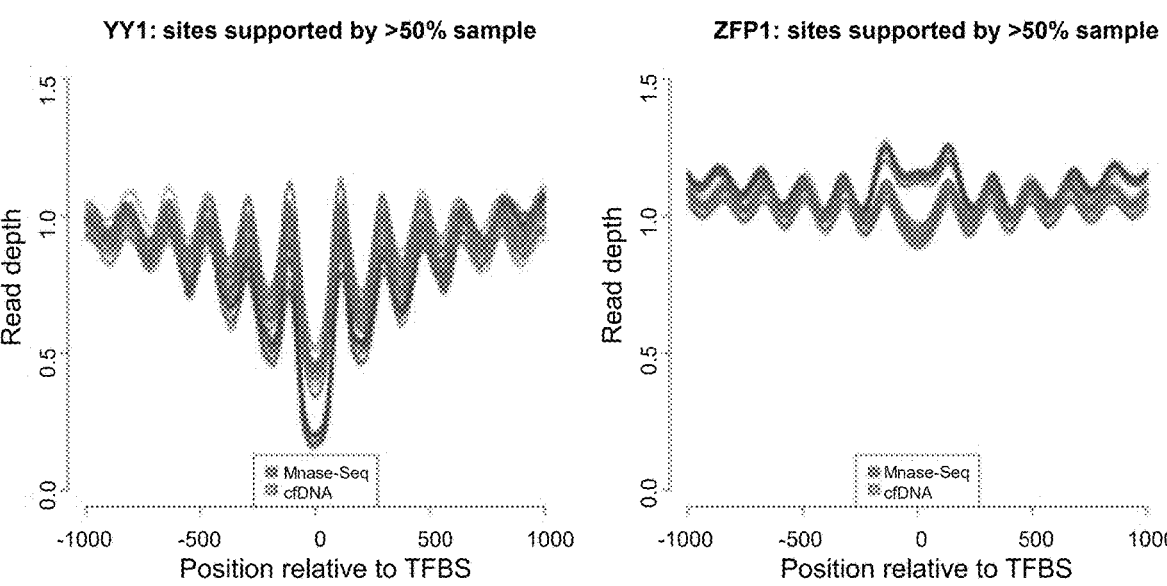

NKX3.1

Pooled prostate cancer cases (n=69)

Position relative to TFBS

FIG. 12A
FIG. 12C
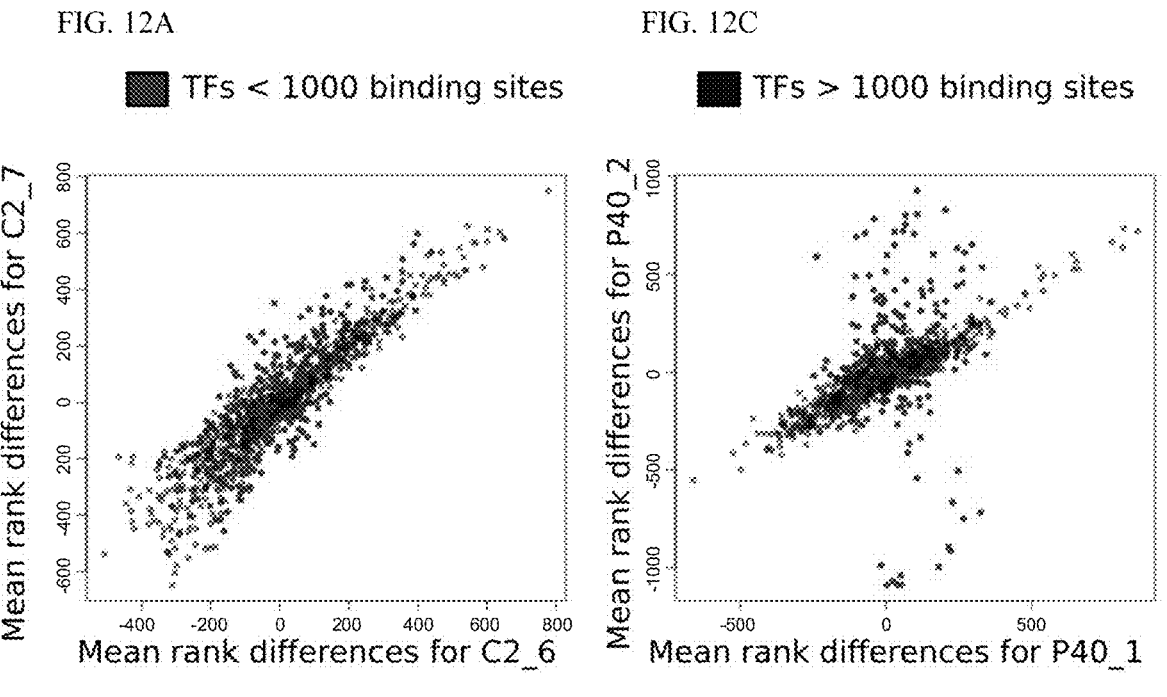
FIG. 12B
FIG. 12D
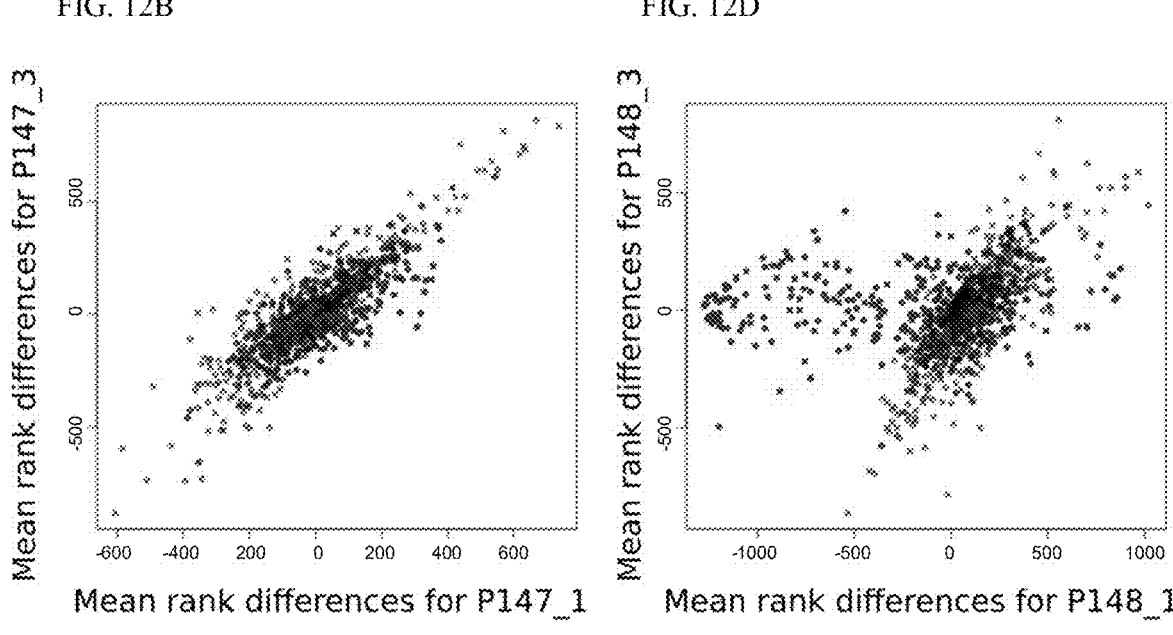

FIG. 13A
FIG. 13B
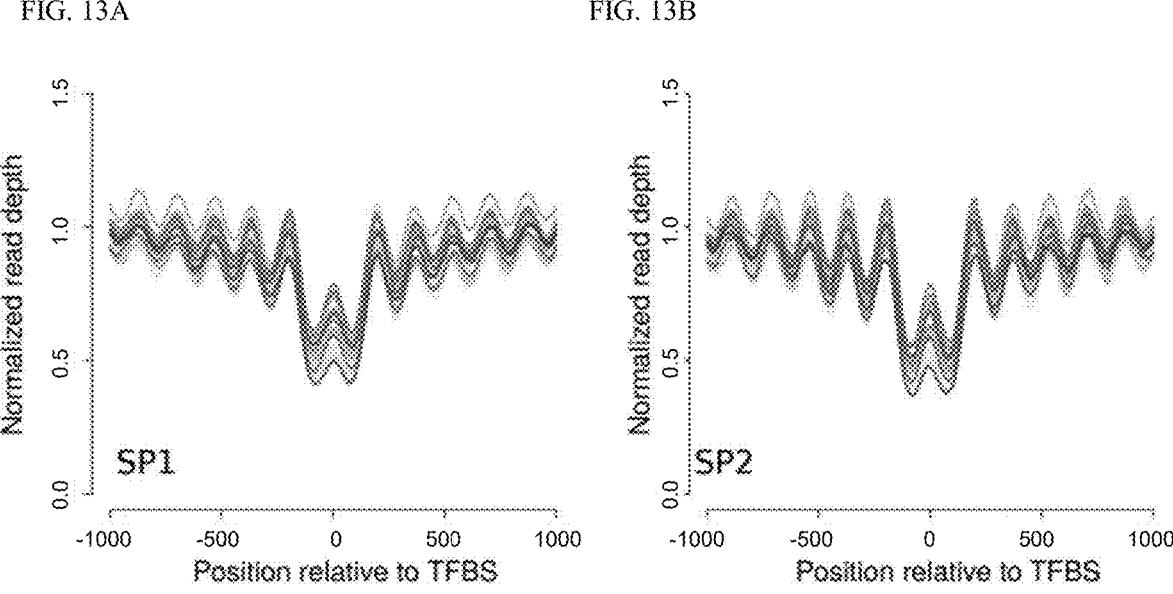
FIG. 13C
FIG. 13D
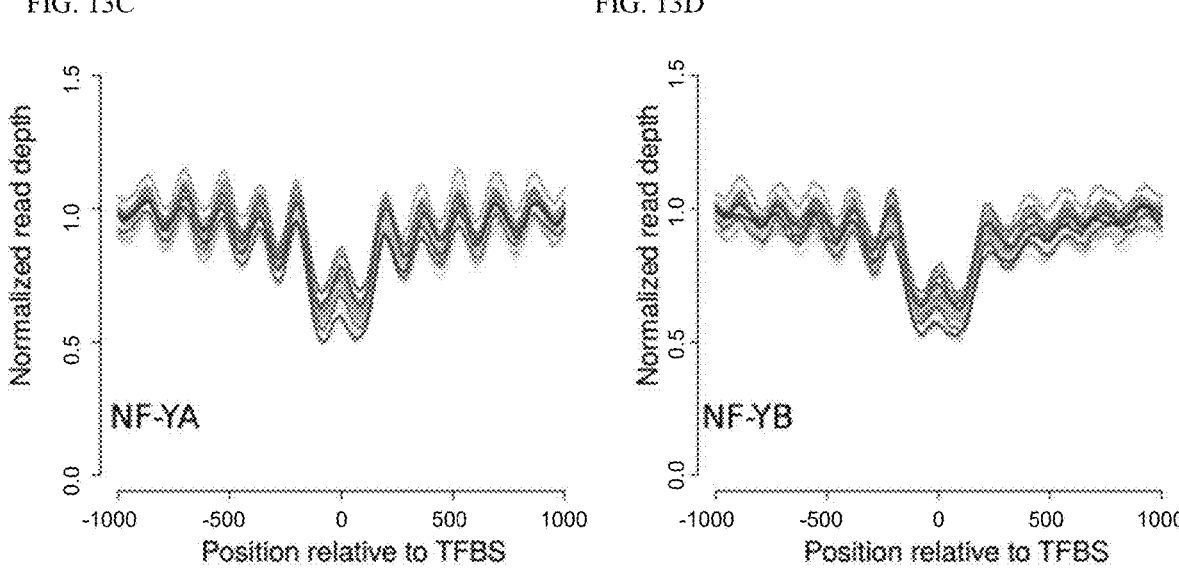

FIG. 13E
FIG. 13H
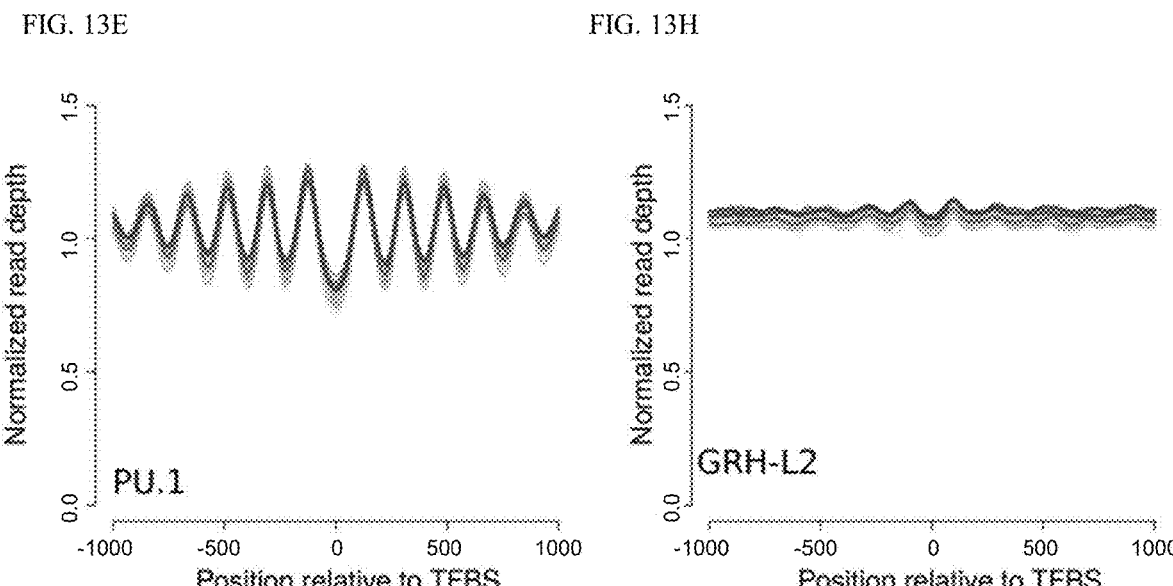
FIG. 13F
FIG. 13G
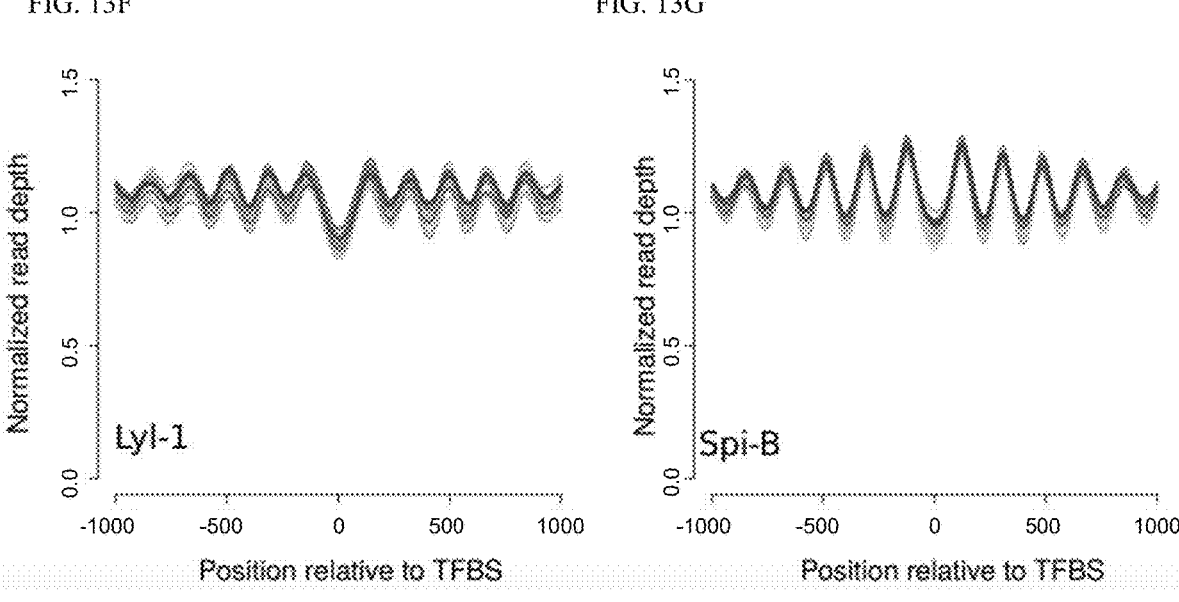

FIG. 14A                            FIG. 14B
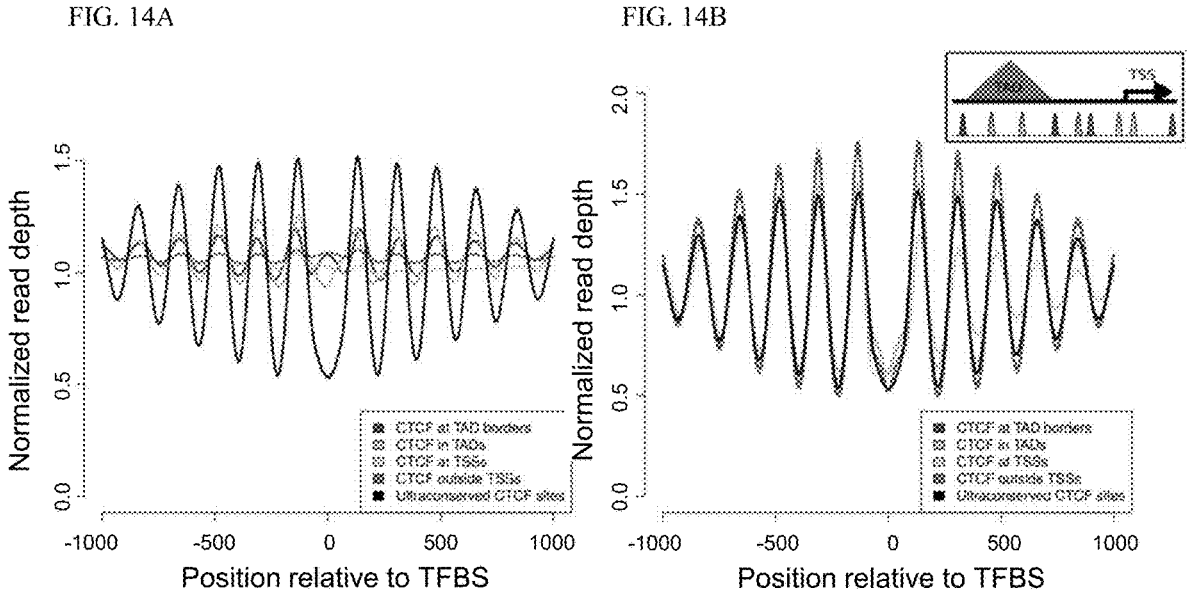
FIG. 14C
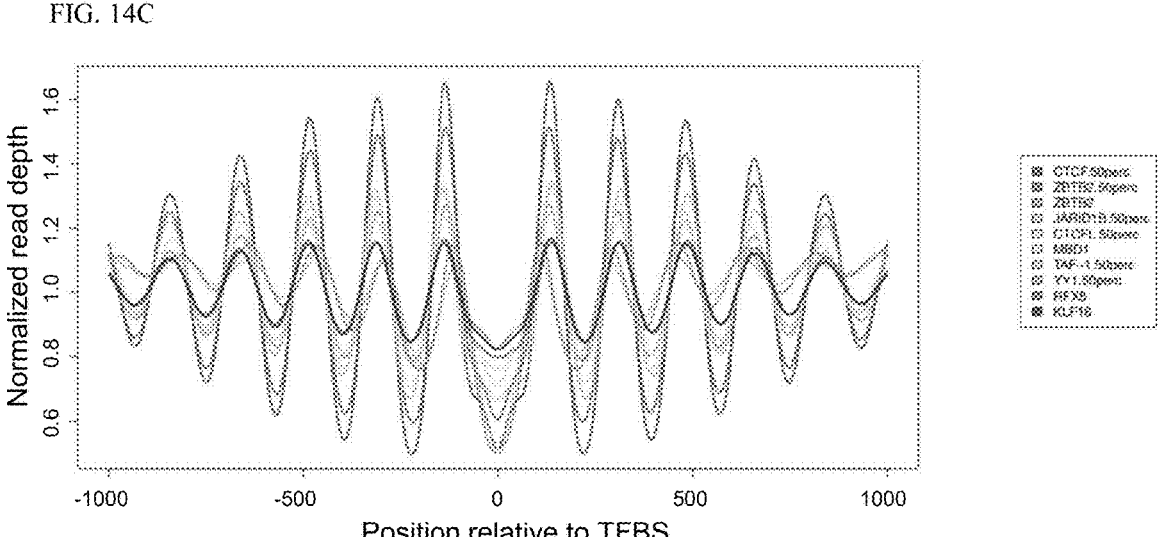

FIG. 17A
FIG. 17B
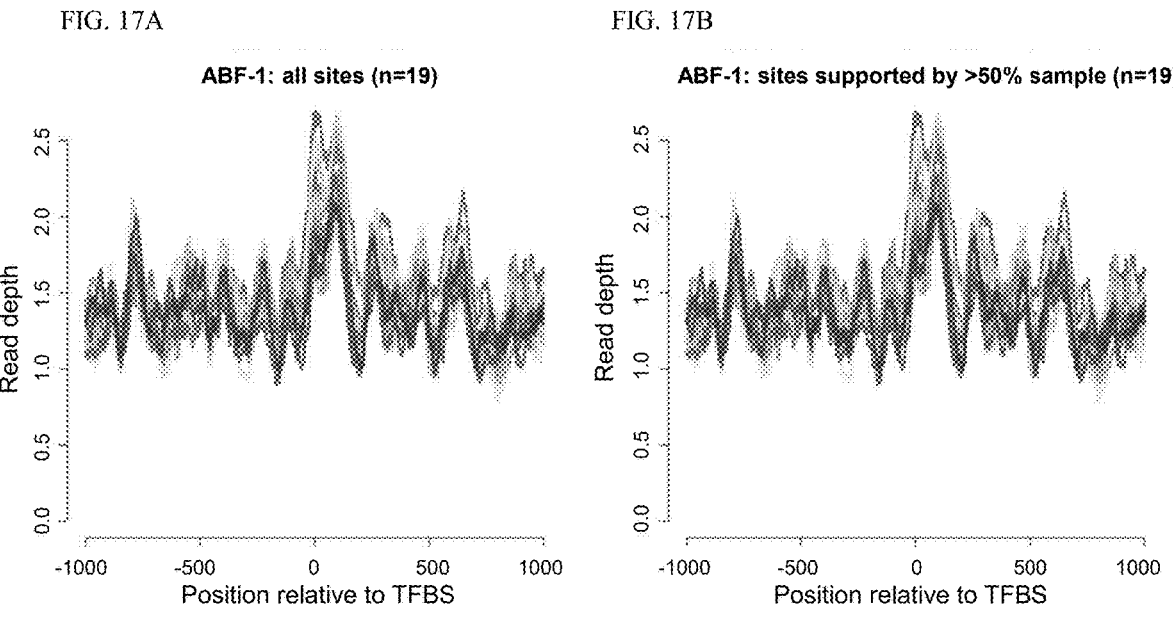
FIG. 17C
FIG. 17D
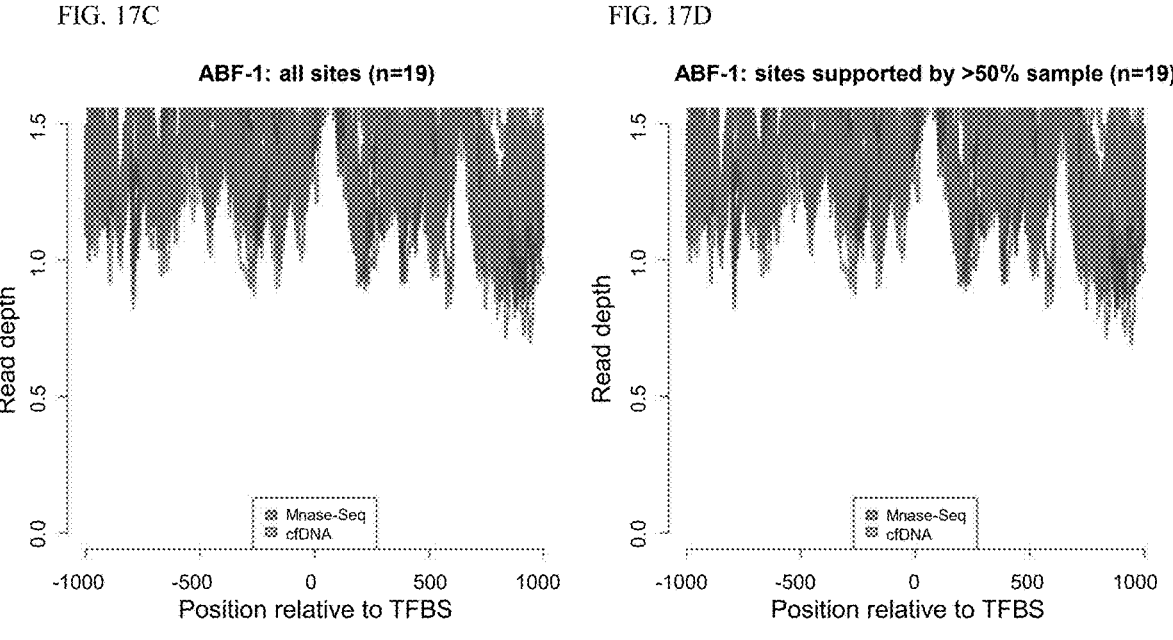

FIG. 20A
FIG. 20B
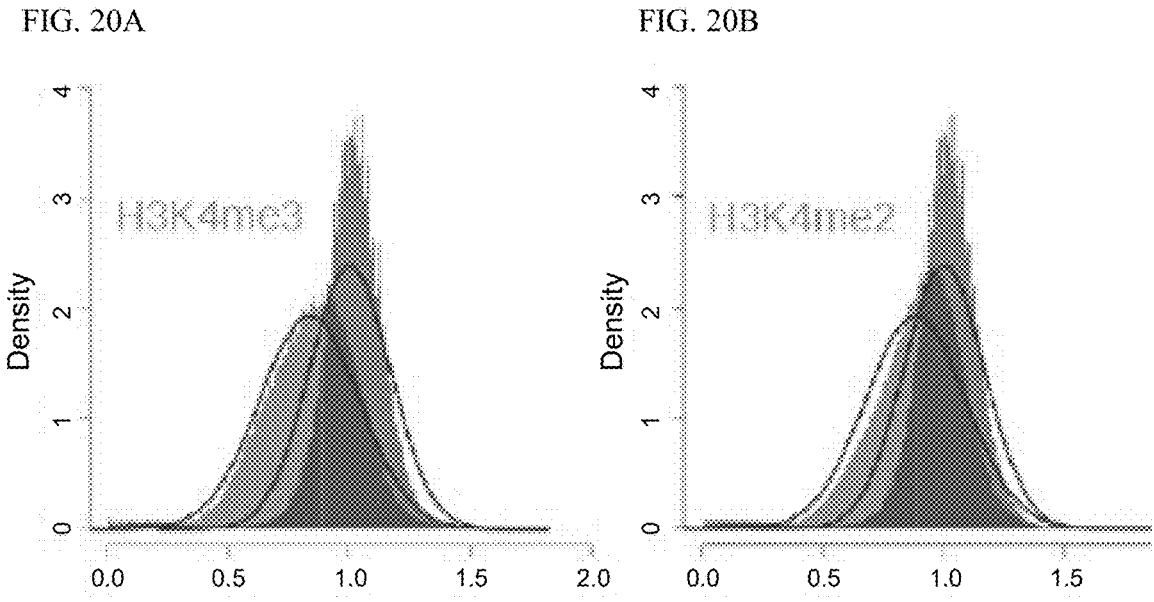
FIG. 20C
FIG. 20D
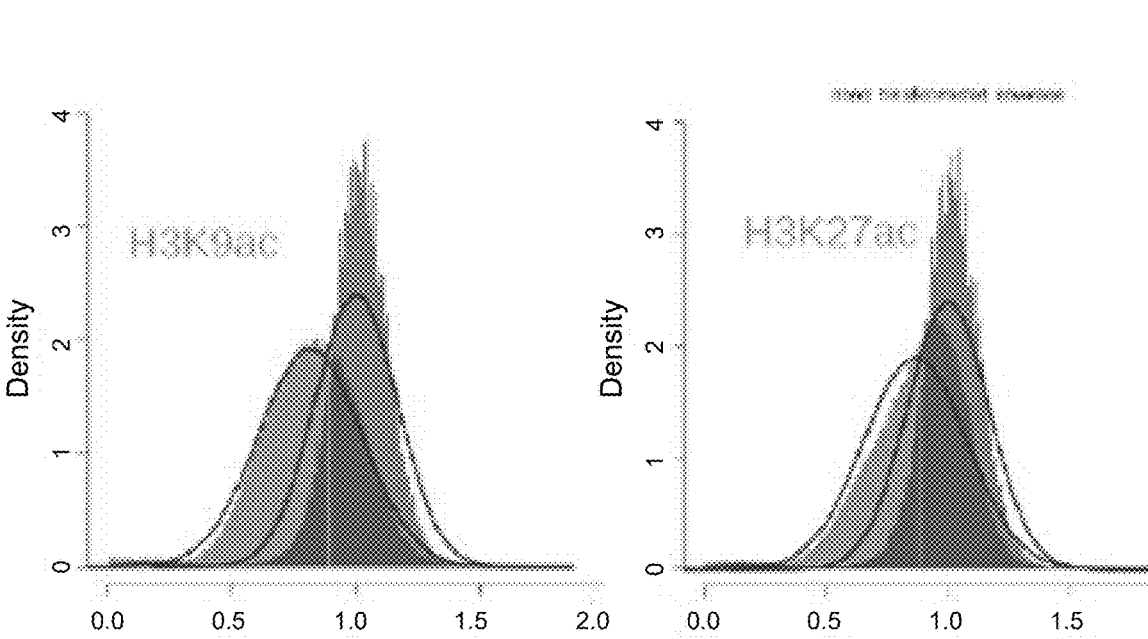

FIG. 20E
FIG. 20F
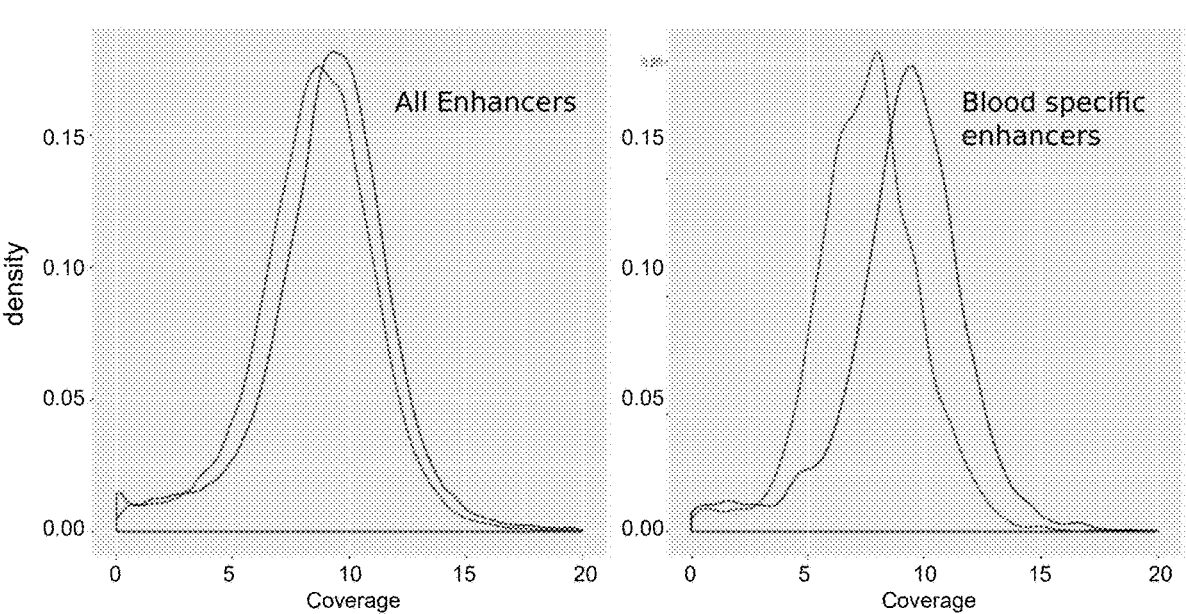
FIG. 20G
FIG. 20H
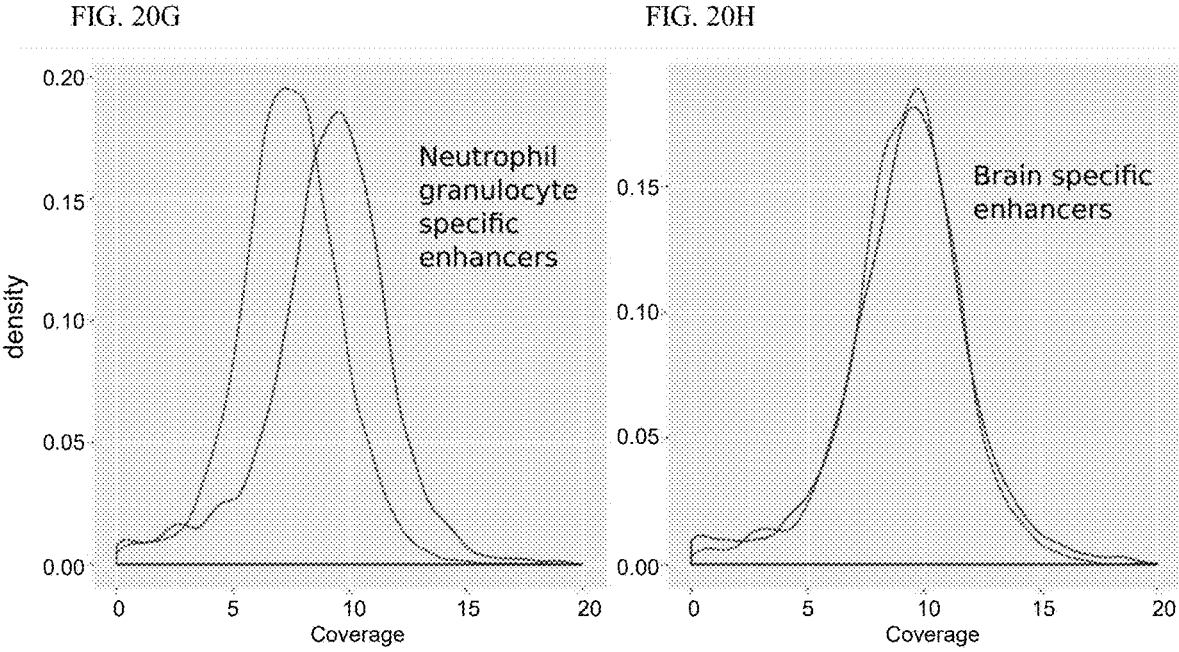

*FIG. 23*

| TF1 | TF2 | Overlap (Fraction of TF1) |
|---|---|---|
| USF-2 | USF-1 | 0.98 |
| ZNF143 | RBAK | 0.95 |
| REST | MIER2 | 0.94 |
| AP-2A | AP-2C | 0.92 |
| ZNF75A | GABPA | 0.91 |
| MafK | MafF | 0.87 |
| MLL2 | MYST1 | 0.86 |
| JunD | Fra-2 | 0.86 |
| HHEX | FOXA3 | 0.86 |
| ZNF238 | ZBTB42 | 0.85 |
| CTCF | ZBTB2 | 0.85 |
| SIX5 | RBAK | 0.84 |
| ZNF143 | ZNF76 | 0.84 |
| c-Myc | Max | 0.83 |
| RERE | FOXA3 | 0.82 |
| FOXA2 | FOXA3 | 0.81 |
| c-Jun | JunB | 0.81 |
| HMG20B | FOXA3 | 0.80 |
| N-Myc | Max | 0.78 |
| HHEX | RERE | 0.78 |

*FIG. 25*
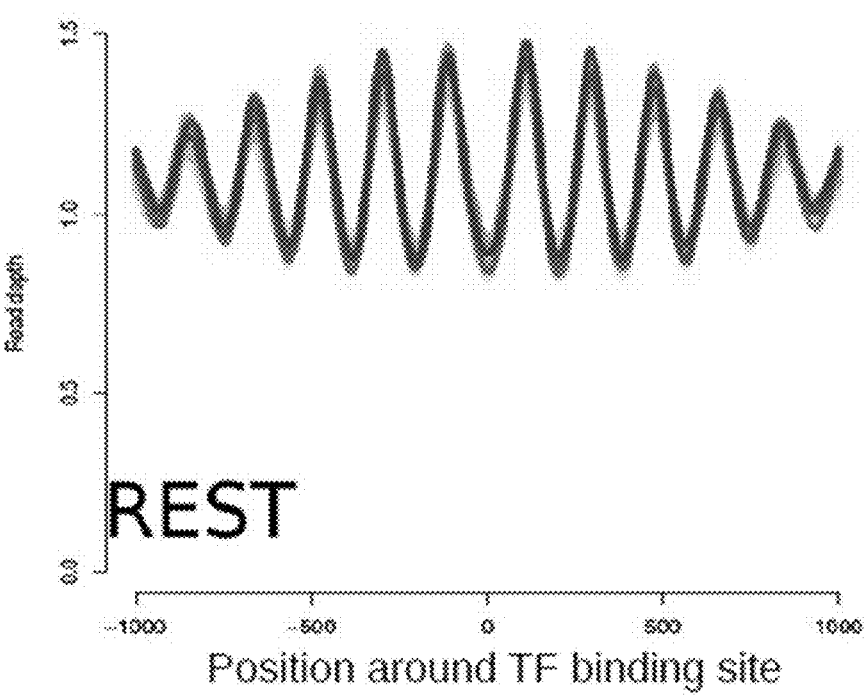
REST
Position around TF binding site
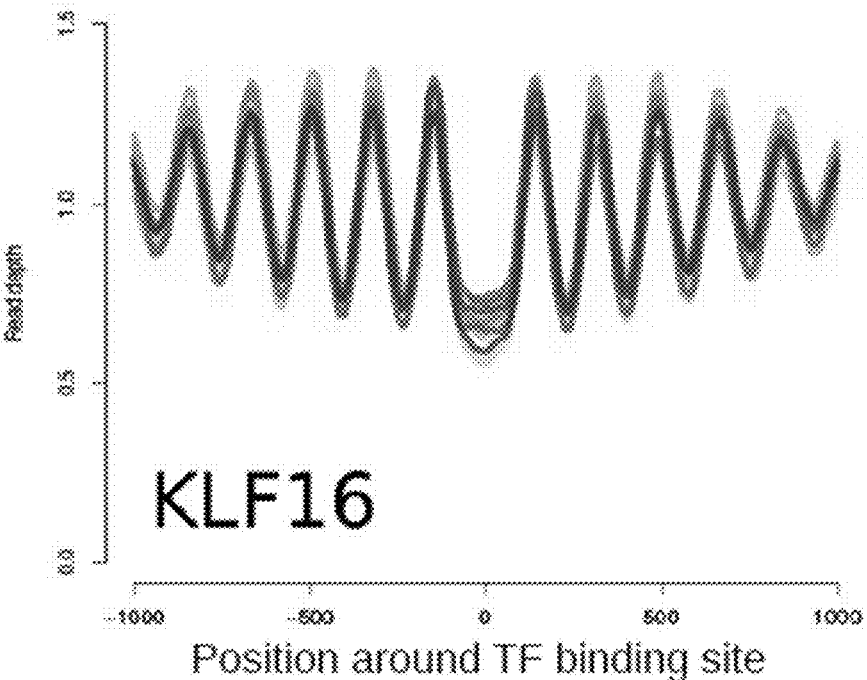
KLF16
Position around TF binding site

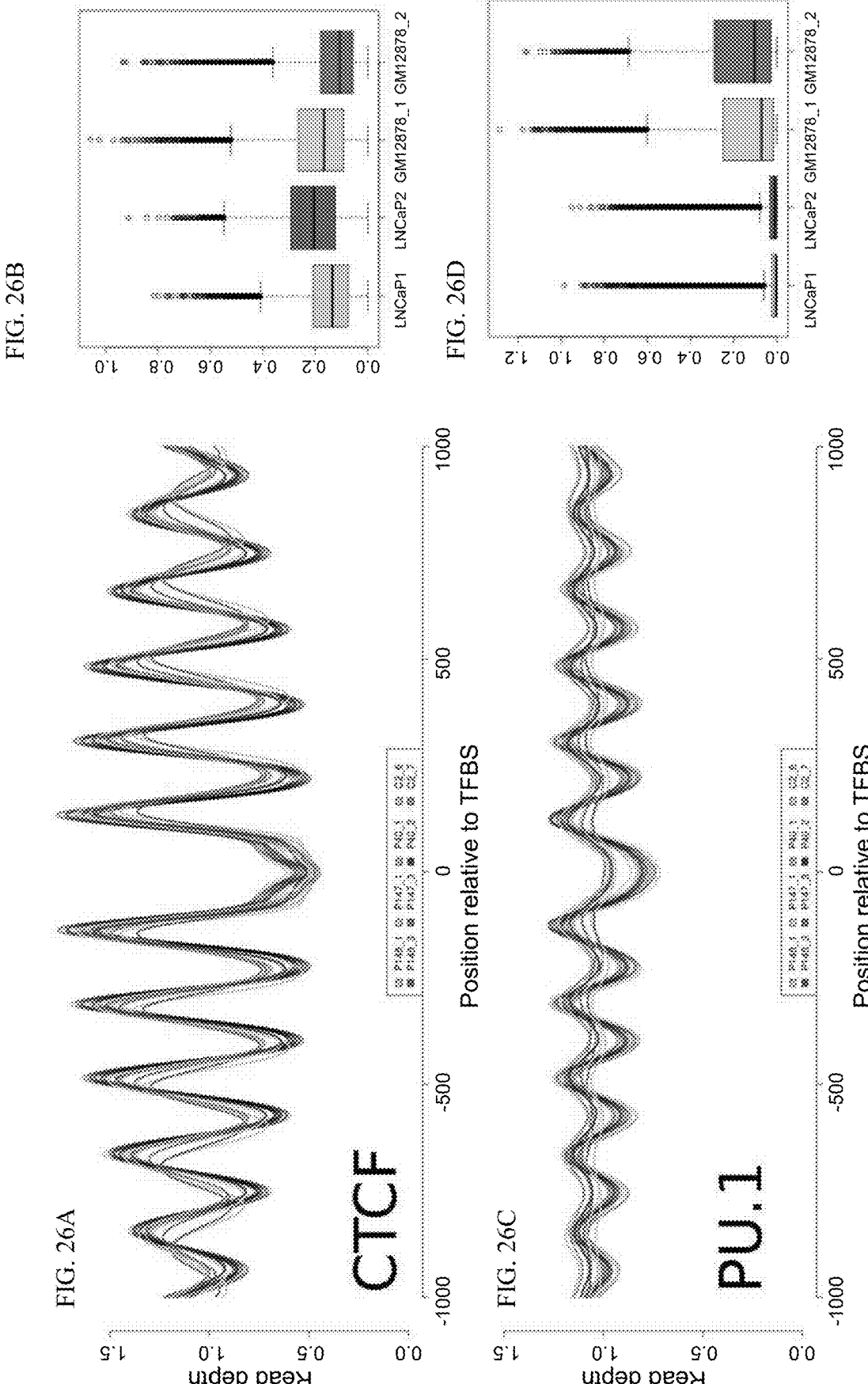

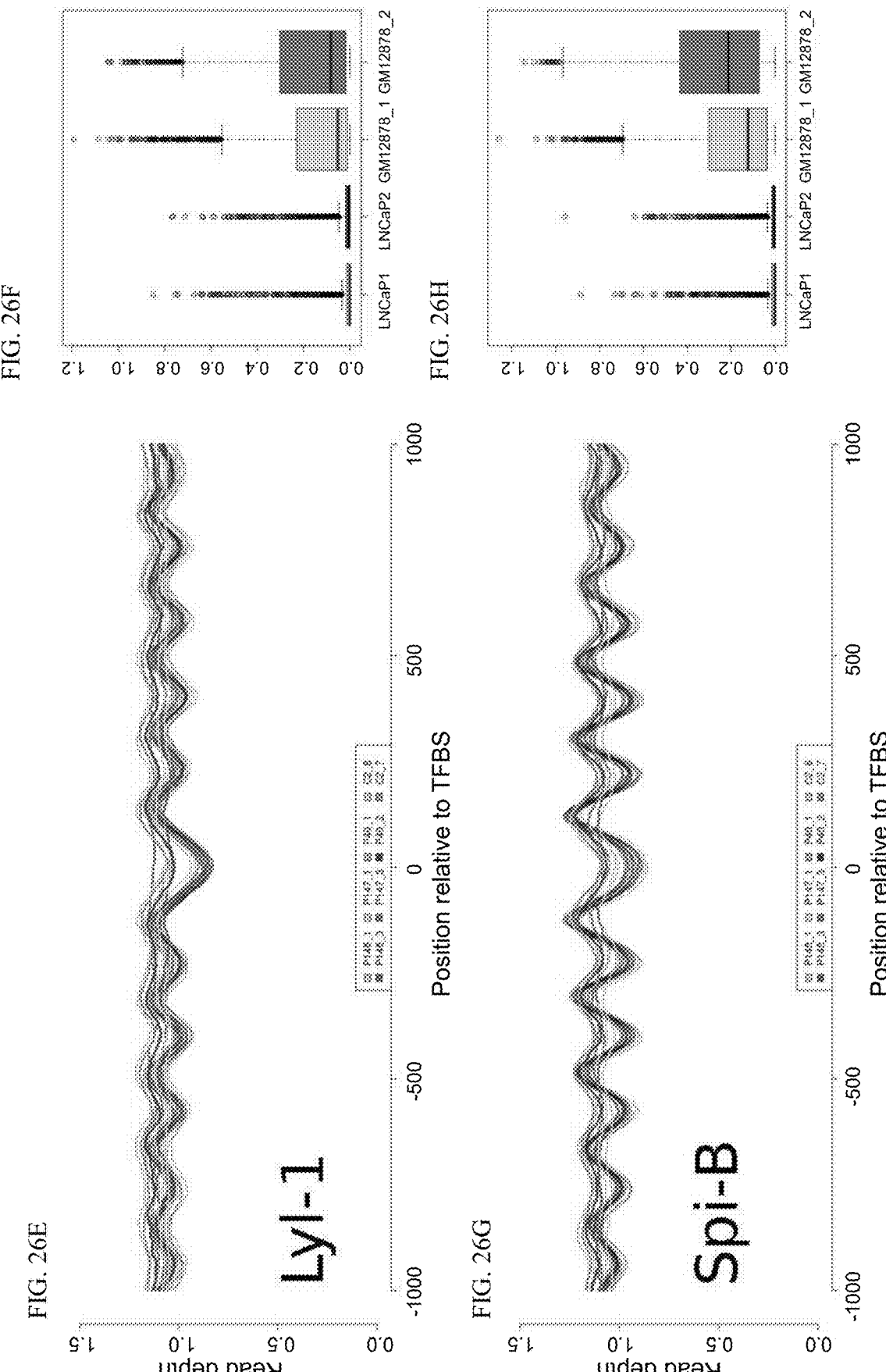

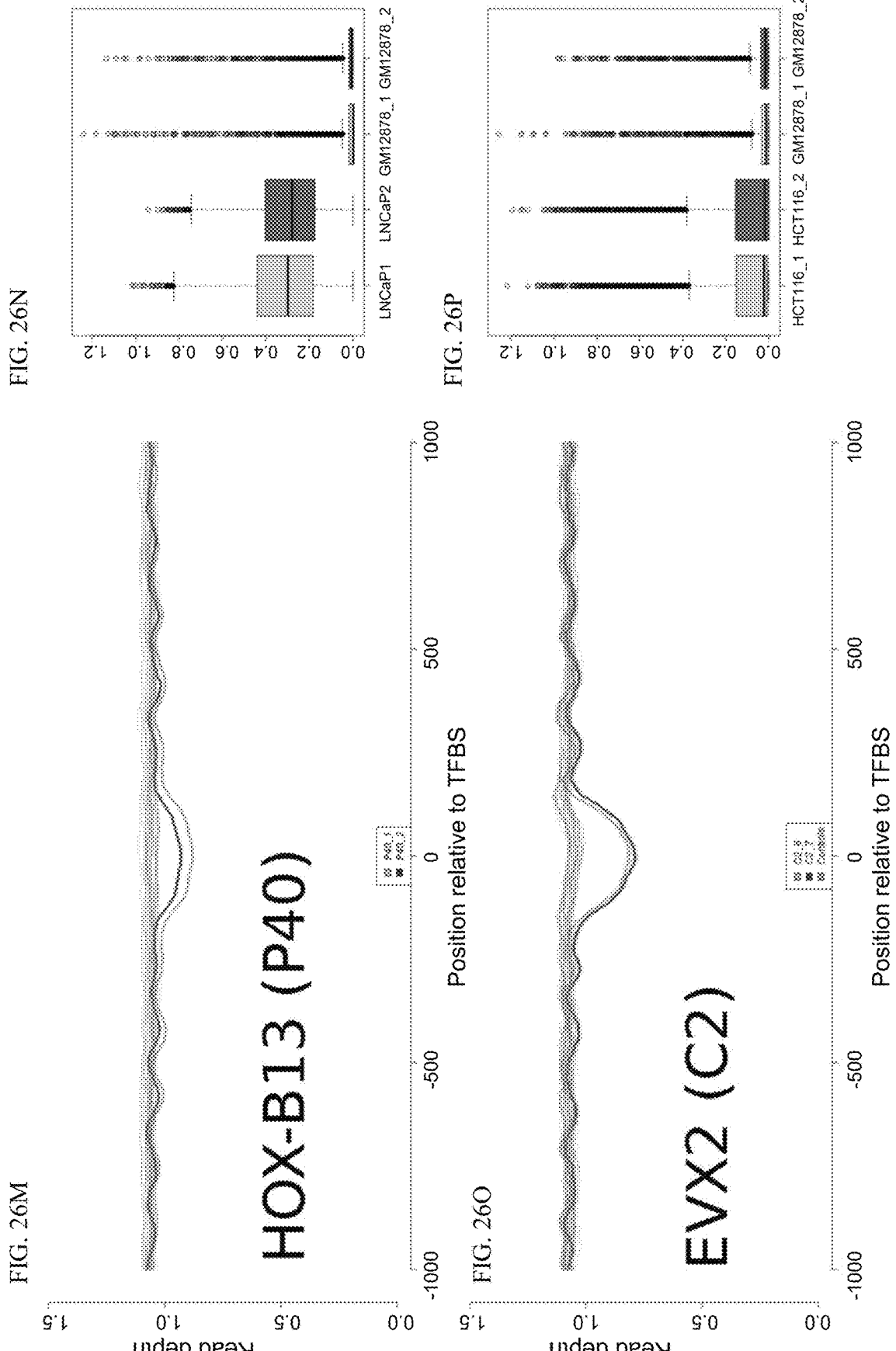

Figure 28A:
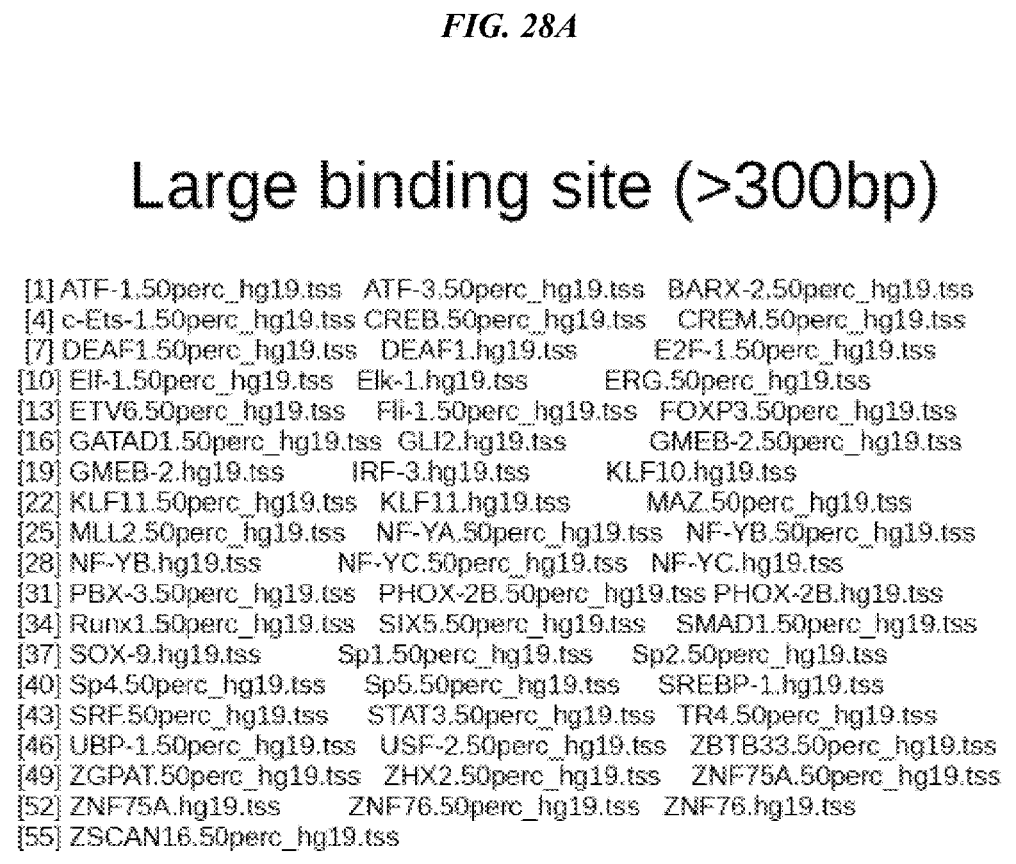

Large binding site (>300bp)

```
[1] ATF-1.50perc_hg19.tss    ATF-3.50perc_hg19.tss    BARX-2.50perc_hg19.tss
[4] c-Ets-1.50perc_hg19.tss CREB.50perc_hg19.tss    CREM.50perc_hg19.tss
[7] DEAF1.50perc_hg19.tss   DEAF1.hg19.tss          E2F-1.50perc_hg19.tss
[10] Elf-1.50perc_hg19.tss   Elk-1.hg19.tss          ERG.50perc_hg19.tss
[13] ETV6.50perc_hg19.tss    Fli-1.50perc_hg19.tss   FOXP3.50perc_hg19.tss
[16] GATAD1.50perc_hg19.tss  GLI2.hg19.tss           GMEB-2.50perc_hg19.tss
[19] GMEB-2.hg19.tss         IRF-3.hg19.tss          KLF10.hg19.tss
[22] KLF11.50perc_hg19.tss   KLF11.hg19.tss          MAZ.50perc_hg19.tss
[25] MLL2.50perc_hg19.tss    NF-YA.50perc_hg19.tss   NF-YB.50perc_hg19.tss
[28] NF-YB.hg19.tss          NF-YC.50perc_hg19.tss   NF-YC.hg19.tss
[31] PBX-3.50perc_hg19.tss   PHOX-2B.50perc_hg19.tss PHOX-2B.hg19.tss
[34] Runx1.50perc_hg19.tss   SIX5.50perc_hg19.tss    SMAD1.50perc_hg19.tss
[37] SOX-9.hg19.tss          Sp1.50perc_hg19.tss     Sp2.50perc_hg19.tss
[40] Sp4.50perc_hg19.tss     Sp5.50perc_hg19.tss     SREBP-1.hg19.tss
[43] SRF.50perc_hg19.tss     STAT3.50perc_hg19.tss   TR4.50perc_hg19.tss
[46] UBP-1.50perc_hg19.tss   USF-2.50perc_hg19.tss   ZBTB33.50perc_hg19.tss
[49] ZGPAT.50perc_hg19.tss   ZHX2.50perc_hg19.tss    ZNF75A.50perc_hg19.tss
[52] ZNF75A.hg19.tss         ZNF76.50perc_hg19.tss   ZNF76.hg19.tss
[55] ZSCAN16.50perc_hg19.tss
```

*FIG. 28B*

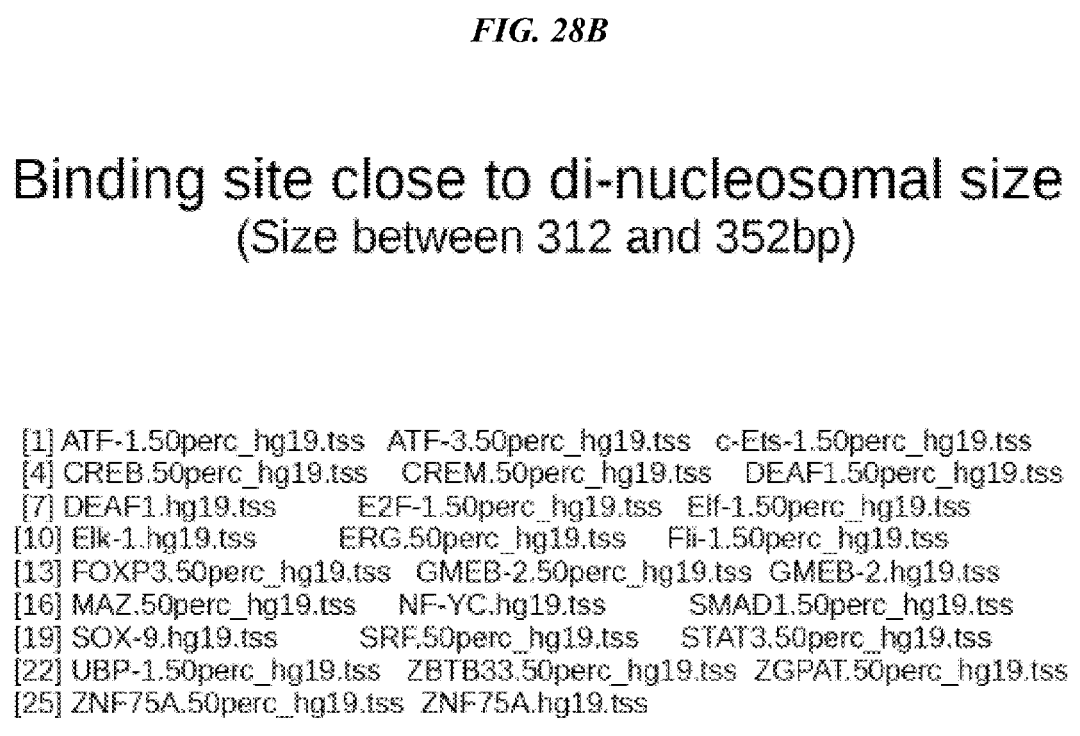

Binding site close to di-nucleosomal size
(Size between 312 and 352bp)

[1] ATF-1.50perc_hg19.tss   ATF-3.50perc_hg19.tss   c-Ets-1.50perc_hg19.tss
[4] CREB.50perc_hg19.tss   CREM.50perc_hg19.tss   DEAF1.50perc_hg19.tss
[7] DEAF1.hg19.tss          E2F-1.50perc_hg19.tss   Elf-1.50perc_hg19.tss
[10] Elk-1.hg19.tss          ERG.50perc_hg19.tss   Fli-1.50perc_hg19.tss
[13] FOXP3.50perc_hg19.tss   GMEB-2.50perc_hg19.tss   GMEB-2.hg19.tss
[16] MAZ.50perc_hg19.tss   NF-YC.hg19.tss          SMAD1.50perc_hg19.tss
[19] SOX-9.hg19.tss          SRF.50perc_hg19.tss   STAT3.50perc_hg19.tss
[22] UBP-1.50perc_hg19.tss   ZBTB33.50perc_hg19.tss   ZGPAT.50perc_hg19.tss
[25] ZNF75A.50perc_hg19.tss   ZNF75A.hg19.tss

TRANSCRIPTION FACTOR PROFILING

CROSS-REFERENCE

This application is a continuation of PCT/US2019/055119, filed Oct. 8, 2019, which claims the benefit of U.S. Provisional Patent Application 62/742,854, filed Oct. 8, 2018, U.S. Provisional Patent Application 62/752,270, filed Oct. 29, 2018, and U.S. Provisional Patent Application 62/849,097, filed May 16, 2019, each of which is entirely incorporated herein by reference.

BACKGROUND

Transcription factors (TFs) may modulate the expression of their target genes and may play a key role in development and differentiation. Genomic alterations can lead to the activation or inactivation of TFs, and the resulting disturbances of gene regulation may contribute to physiologic conditions such as aging or underlie diseases, such as cancer. In order to bind regulatory deoxyribonucleic acid (DNA), TFs often have to interact with nucleosomes, which may affect both their occupancy and positioning.

Alterations in transcription factors may be important drivers of tumorigenesis in cancer, and TF nucleosome interactions remain largely unmapped. However, non-invasive assays for assessing transcription factor activity are lacking.

Given the role of TFs in regulating chromatin accessibility and transcription, understanding the impact of genetic variation on TF binding may provide insights into the non-coding genetic components of development and disease. Major insights into the epigenetic information encoded within the nucleoprotein structure of chromatin may be obtained using high-throughput, genome-wide methods for separately assaying the chromatin accessibility ("open chromatin"), nucleosome positioning, and transcription factor (TF) occupancy.

Deregulation of transcription factors (TFs) may be an important driver of tumorigenesis. For TFs to bind DNA, the binding region may need to be accessible. Hence, TFs and chromatin remodeling complexes shift and position nucleosomes to enhance accessibility. What is therefore needed are methods to profile transcription factor binding sites to infer nucleosome position, and chromatin accessibility. What is also needed are methods of using transcription factor binding site profiling, and transcription factor binding site signatures to infer disease state, disease progression, and treatment responsiveness.

SUMMARY

The present disclosure provides methods and systems for assessing (e.g., modeling) transcription factor (TF) binding sites (TFBSs) and using TFBS information to detect, assess, diagnose, and analyze disease states and identify treatment responsiveness.

Next-generation sequencing-based genome-wide assays may be used to provide TF-binding patterns and the associated chromatin architecture. As nucleosomes and sequence-specific TFs bind regulatory deoxyribonucleic acid (DNA) regions in a mutually exclusive fashion, TFs either compete or interact with nucleosomes, which affects both their occupancy and positioning. In a given population of cells, nucleosome occupancy refers to the average number of nucleosomes measured within a specified genomic region, whereas nucleosome positioning indicates the probability of a reference point on a nucleosome (usually the dyad, e.g., the midpoint of a canonical nucleosome) existing at a specific genomic coordinate.

Cell-free circulating nucleic acid, such as cell-free DNA (cfDNA), may provide an easily-accessible source of nucleic acid for TFBS analysis. Such cfDNA may be the product of a digestion process that preferentially degrades DNA that is not protected by proteins, such as the histone complex. Cell-free DNA coverage patterns may reflect nucleosome positioning and occupancy caused by transcription factors actively binding the genome. These nucleosome occupancy patterns measured through cfDNA may then be used to infer the activity of TFs in the normal and tumor genomes.

TFs may bind preferentially within open chromatin, which may affect nucleosome positioning. Circulating cell-free DNA from blood plasma may represent mono-nucleosomal DNA, and nucleosome plasma footprints may be informative regarding TFBS.

The present disclosure provides methods and systems for charting of nucleosome positions from cfDNA to provide information about TFs for applications relating to disease identification, prediction, staging, and/or identifying treatment responsiveness. Methods and systems are described herein for using transcription factor information determined from nucleosome footprints in nucleic acid molecules (e.g., cfDNA). Information from nucleosome footprints in nucleic acid molecules may be used to evaluate, assess, detect, and diagnose diseases such as cancers. In some examples, the information may be featurized and used as inputs into machine learning models useful in many of these applications such as disease identification, prediction, staging and identifying treatment responsiveness.

In an aspect, the present disclosure provides a computer-implemented method to determine a transcription factor binding profile in a nucleic acid sample from a subject, the method comprising: (a) providing a set of sequence reads from deoxyribonucleic acid (DNA) extracted from the subject; (b) using said set of sequence reads to generate a coverage pattern for a transcription factor; (c) processing the coverage pattern to provide a signal; and (d) processing the signal with a reference signal, wherein the signal and the reference signal have different frequencies, thereby determining a transcription factor binding profile in the sample.

In some examples, the DNA is cell-free DNA.

In some examples, (c) comprises using a low-pass filter. In some examples, (c) comprises using a Savitzky-Golay filter.

In some examples, the subject is a human.

In another aspect, the present disclosure provides a computer-implemented method for detecting a presence or absence of a disease in a subject, the method comprising: (a) providing a set of sequence reads from deoxyribonucleic acid (DNA) extracted from the subject; (b) using said set of sequence reads to generate a coverage pattern for a transcription factor; (c) processing the coverage pattern to provide a signal; and (d) processing the signal with a reference signal, wherein the signal and the reference signal have different frequencies, thereby detecting said presence or absence of said disease in said subject.

In some examples, the DNA is cell-free DNA.

In some examples, the disease is cancer.

In some examples, (b) comprises aligning the set of sequence reads to a reference sequence to provide an aligned sequence pattern, selecting regions of the aligned sequence pattern that correspond to binding sites of the transcription factor, and normalizing the aligned sequence pattern in the regions. In some examples, (d) comprises calculating an accessibility score for each of the binding sites of the transcription factor.

In some examples, (c) comprises using a low-pass filter. In some examples, (c) comprises using a Savitzky-Golay filter.

In some examples, the subject is a human.

In some examples, the transcription factor is a cancer-specific transcription factor. In some examples, the transcription factor is selected from the group consisting of GRH-L2, ASH-2, HOX-B13, EVX2, PU.1, Lyl-1, Spi-B, FOXA1, HNF-1A, HNF-4A, HNF-4G, and DLX-2.

In some examples, the accessibility scores for at least 2, or at least 5, or at least 10, or at least 15, or at least 20, or at least 25 transcription factor binding sites are determined and inputted into a machine learning model to train a classifier capable of distinguishing between healthy subjects and cancer patients, between disease progressors and non-progressors, between a plurality of disease subtypes, between a plurality of disease stages, between disease treatment responders and non-responders, or any combination thereof.

In some examples, the transcription factor is selected from the group consisting of GRH-L2, ASH-2, HOX-B13, EVX2, PU.1, Lyl-1, Spi-B, and FOXA1.

In some examples, patient-specific and/or tumor-specific patterns, including inferred binding patterns for the transcription factors AR, HOXB13, and NKX3-1, are observed.

In some examples, (d) comprises identifying a sign of higher accessibility of the transcription factor. In some examples, the transcription factor is an epithelial transcription factor. In some examples, the transcription factor is GRH-L2.

In some examples, transcription factors GRHL2, FOXA1, and ZNF121 are associated with increased accessibility scores or open chromatin accessibility in patients with breast cancer.

In some examples, an open accessibility of transcription factors GRHL2, FOXA1, and ZNF121 is indicative of breast cancer.

In some examples, transcription factors EVX2, DLX2, HNF1A, HNF4A, GRHL2, and HNF4G are associated with increased accessibility scores or open chromatin accessibility in patients with colon cancer.

In some examples, an open accessibility of transcription factors EVX2, DLX2, HNF1A, GRH-L2, HNF4A, and HNF4G is indicative of colon cancer.

In some examples, transcription factors LYL1 and PU.1 are associated with decreased accessibility scores or closed chromatin accessibility in patients with colon cancer.

In some examples, a closed accessibility of transcription factors LYL1 and PU.1 is indicative of colon cancer.

In one example, open accessibility of transcription factors tbx21 or EOMES is indicative of exhausted CD8$^+$ T cells.

In one example, open accessibility of transcription factors selected from Eomesodermin (EOMES), Ybx21, Gata3, Rora, Bcl6, Blimp-1, von Hippel-Lindau tumor suppressor (VHL), Foxo1, IRF4, BATF, and NFATc1 is indicative of exhausted CD8$^+$ T cells.

In some examples, the method further comprises detecting the presence or absence of the disease in the subject with an accuracy of at least about 70%. In some examples, the method further comprises detecting the presence or absence of the disease in the subject with an accuracy of at least about 80%. In some examples, the method further comprises detecting the presence or absence of the disease in the subject with an accuracy of at least about 90%.

In some examples, the method further comprises detecting the presence of the disease in the subject with a sensitivity of at least about 70%. In some examples, the method further comprises detecting the presence of the disease in the subject with a sensitivity of at least about 80%. In some examples, the method further comprises detecting the presence of the disease in the subject with a sensitivity of at least about 90%.

In some examples, the method further comprises detecting the absence of the disease in the subject with a specificity of at least about 70%. In some examples, the method further comprises detecting the absence of the disease in the subject with a specificity of at least about 80%. In some examples, the method further comprises detecting the absence of the disease in the subject with a specificity of at least about 90%.

In some examples, the method further comprises detecting the presence of the disease in the subject with a positive predictive value (PPV) of at least about 70%. In some examples, the method further comprises detecting the presence of the disease in the subject with a positive predictive value (PPV) of at least about 80%. In some examples, the method further comprises detecting the presence of the disease in the subject with a positive predictive value (PPV) of at least about 90%.

In some examples, the method further comprises detecting the absence of the disease in the subject with a negative predictive value (NPV) of at least about 70%. In some examples, the method further comprises detecting the absence of the disease in the subject with a negative predictive value (NPV) of at least about 80%. In some examples, the method further comprises detecting the absence of the disease in the subject with a negative predictive value (NPV) of at least about 90%.

In some examples, the method further comprises detecting the presence or absence of the disease in the subject with an Area Under the Receiver Operator Characteristic (AUROC) of at least about 0.70. In some examples, the method further comprises detecting the presence or absence of the disease in the subject with an Area Under the Receiver Operator Characteristic (AUROC) of at least about 0.80. In some examples, the method further comprises detecting the presence or absence of the disease in the subject with an Area Under the Receiver Operator Characteristic (AUROC) of at least about 0.90.

In some examples, the method further comprises applying a trained classifier to the signal to detect the presence or absence of the disease in the subject. In some examples, the method further comprises applying a trained classifier to the accessibility scores of the binding sites of the transcription factor to detect the presence or absence of the disease in the subject. In some examples, the trained classifier comprises a trained machine learning classifier. In some examples, the trained machine learning classifier comprises a supervised machine learning algorithm. In some examples, the supervised machine learning algorithm comprises one or more of: a regression, a support vector machine, a tree-based method, a neural network, and a random forest.

In another aspect, the present disclosure provides methods to allow classification of patients by tumor type, including, for example, tumor subtypes (e.g., subtypes of prostate cancer, colorectal cancer, breast cancer, lung cancer), or tumor stage, which may have important clinical implications for patient management including treatment planning and responsiveness. Accordingly, the methods provided herein for mapping tumor-specific transcription factor binding in vivo based on patient samples (e.g., blood, plasma, or serum samples), thereby making a key part of the noncoding genome amenable for clinical analysis.

In some examples, the method comprises distinguishing subtypes of disease.

In some examples, the method comprises distinguishing subtypes of cancer.

In some examples, the method comprises distinguishing subtypes of prostate cancer, colorectal cancer, breast cancer, and lung cancer.

In some examples, the method comprises distinguishing prostate cancer subtype, e.g., among patients having prostate adenocarcinoma or small-cell neuroendocrine prostate cancer.

In some examples, the method comprises distinguishing stage of cancer (e.g., among stage I, II, III, and IV cancers).

In some examples, the method comprises distinguishing stage I and II cancers from stage III and IV cancers.

In some examples, transcription factors GRHL2, FOXA1, HOXB13, AR, and NKX3-1 are associated with increased accessibility scores or open chromatin accessibility in patients with prostate adenocarcinoma.

In some examples, an open accessibility of transcription factors GRHL2, FOXA1, HOXB13, AR, and NKX3-1 is indicative of prostate adenocarcinoma.

In some examples, transcription factors REST, GRHL2, FOXA1, HOXB13, AR, and NKX3-1 is associated with decreased or closed chromatin accessibility in patients with small-cell neuroendocrine prostate cancer.

In some examples, a decreased accessibility of transcription factors REST, GRHL2, GRHL3, FOXA1, FOXA2, GATA2, GATA3, HOXB13, AR, and NKX3-1 is indicative of small-cell neuroendocrine prostate cancer.

In some examples, an increased accessibility of transcription factors GLIS1, SOX2, and SOX11 are indicative of small-cell neuroendocrine prostate cancer.

In another aspect, the present disclosure provides a system comprising a computing device comprising at least one computer processor, an operating system configured to perform executable instructions, a memory, and a computer program including instructions executable by the computing device to provide a computer application for detecting a presence or absence of a disease in a subject, the computer application comprising: a sequence module programmed to obtain a set of sequence reads from deoxyribonucleic acid (DNA) extracted from the subject; a coverage module programmed to use the set of sequence reads to generate a coverage pattern for a transcription factor; a signal module programmed to process the coverage pattern to provide a signal; a detection module programmed to process the signal with a reference signal, wherein the signal and the reference signal have different frequencies, thereby detecting the presence or absence of the disease in the subject.

In another aspect, the present disclosure provides a non-transitory computer-readable medium comprising machine-executable code that, upon execution by one or more computer processors, implements a method for detecting a presence or absence of a disease in a subject, the method comprising: (a) providing a set of sequence reads from deoxyribonucleic acid (DNA) extracted from the subject; (b) using said set of sequence reads to generate a coverage pattern for a transcription factor; (c) processing the coverage pattern to provide a signal; and (d) processing the signal with a reference signal, wherein the signal and the reference signal have different frequencies, thereby detecting said presence or absence of said disease in said subject.

In another aspect, the present disclosure provides a system for detecting a presence or absence of a disease in a subject, the system comprising: a database comprising a set of sequence reads from deoxyribonucleic acid (DNA) extracted from the subject; and one or more computer processors operatively coupled to the database, wherein the one or more computer processors are individually or collectively programmed to: (a) use the set of sequence reads to generate a coverage pattern for a transcription factor; (b) process the coverage pattern to provide a signal; (c) process the signal with a reference signal, wherein the signal and the reference signal have different frequencies, thereby detecting the presence or absence of the disease in the subject.

In another aspect, the present disclosure provides a computer-implemented method for monitoring a progression or regression of a disease in a subject, the method comprising: (a) providing a first set of sequence reads from deoxyribonucleic acid (DNA) extracted from the subject at a first time and a second set of sequence reads from DNA extracted from the subject at a second time that is later than the first time; (b) using the first set of sequence reads to generate a first coverage pattern for a transcription factor and using the second set of sequence reads to generate a second coverage pattern for the transcription factor; (c) processing the first coverage pattern to provide a first signal and processing the second coverage pattern to provide a second signal; (d) processing the first signal with a reference signal, wherein the first signal and the reference signal have different frequencies; (e) processing the second signal with the reference signal, wherein the second signal and the reference signal have different frequencies; and (f) based on the processing of the first signal and the second signal with the reference signal, monitoring the progression or regression of the disease in the subject.

In some examples, the accessibility scores for at least 2, or at least 5, or at least 10, or at least 15, or at least 20, or at least 25 transcription factor binding sites are determined and inputted into a machine learning model to train a classifier capable of distinguishing between disease progressors and non-progressors, between a plurality of disease subtypes, between a plurality of disease stages, or any combination thereof.

In some examples, the accessibility scores for at least 2, or at least 5, or at least 10, or at least 15, or at least 20, or at least 25 transcription factor binding sites are determined and inputted into a machine learning model to train a classifier capable of distinguishing between disease treatment responders and non-responders.

In some examples, the second coverage pattern indicates phenotypic changes of a tumor during a course of the disease.

In some examples, the phenotypic change is a change from androgen-dependent to androgen-independent stage of cancer.

In some examples, the DNA is cell-free DNA.

In some examples, the disease is cancer.

In some examples, (b) comprises aligning the first set of sequence reads and the second set of sequence reads to a reference sequence to provide a first aligned sequence pattern and a second aligned sequence pattern, respectively, selecting regions of the first aligned sequence pattern and the second aligned sequence pattern that correspond to binding sites of the transcription factor, and normalizing the first aligned sequence pattern and second aligned sequence pattern in the regions.

In some examples, (c) comprises using a low-pass filter.

In some examples, (c) comprises using a Savitzky-Golay filter.

In some examples, the subject is a human.

In some examples, the transcription factor is a cancer-specific transcription factor.

In some examples, the transcription factor is selected from the group consisting of GRH-L2, ASH-2, HOX-B13, EVX2, PU.1, Lyl-1, Spi-B, and FOXA1.

In some examples, the transcription factor is selected from the group consisting of HNF-la, HNF-4a, HNF-4g, EVX-2 and DLX-2.

In some examples, the method further comprises, based on (f), adjusting a therapeutic regimen for the disease in the subject.

In another aspect, the present disclosure provides a system comprising a computing device comprising at least one computer processor, an operating system configured to perform executable instructions, a memory, and a computer program including instructions executable by the computing device to provide a computer application for monitoring a progression or regression of a disease in a subject, the computer application comprising: a sequence module programmed to obtain a first set of sequence reads from deoxyribonucleic acid (DNA) extracted from the subject at a first time and a second set of sequence reads from DNA extracted from the subject at a second time that is later than the first time; a coverage module programmed to use the first set of sequence reads to generate a first coverage pattern for a transcription factor and use the second set of sequence reads to generate a second coverage pattern for the transcription factor; a signal module programmed to process the first coverage pattern to provide a first signal, and process the second coverage pattern to provide a second signal; a first processing module programmed to process the first signal with a reference signal, wherein the first signal and the reference signal have different frequencies; a second processing module programmed to process the second signal with the reference signal, wherein the second signal and the reference signal have different frequencies; and a detection module programmed to, based on the processing of the first signal and the second signal with the reference signal, monitor the progression or regression of the disease in the subject.

In another aspect, the present disclosure provides a non-transitory computer-readable medium comprising machine-executable code that, upon execution by one or more computer processors, implements a method for monitoring a progression or regression of a disease in a subject, the method comprising: (a) providing a first set of sequence reads from deoxyribonucleic acid (DNA) extracted from the subject at a first time and a second set of sequence reads from DNA extracted from the subject at a second time that is later than the first time; (b) using the first set of sequence reads to generate a first coverage pattern for a transcription factor and using the second set of sequence reads to generate a second coverage pattern for the transcription factor; (c) processing the first coverage pattern to provide a first signal and processing the second coverage pattern to provide a second signal; (d) processing the first signal with a reference signal, wherein the first signal and the reference signal have different frequencies; (e) processing the second signal with the reference signal, wherein the second signal and the reference signal have different frequencies; and (f) based on the processing of the first signal and the second signal with the reference signal, monitoring the progression or regression of the disease in the subject.

In another aspect, the present disclosure provides a system for monitoring a progression or regression of a disease in a subject, the system comprising: a database comprising a first set of sequence reads from deoxyribonucleic acid (DNA) extracted from the subject at a first time and a second set of sequence reads from DNA extracted from the subject at a second time that is later than the first time; and one or more computer processors operatively coupled to the database, wherein the one or more computer processors are individually or collectively programmed to: (a) use the first set of sequence reads to generate a first coverage pattern for a transcription factor and use the second set of sequence reads to generate a second coverage pattern for the transcription factor; (b) process the first coverage pattern to provide a first signal, and process the second coverage pattern to provide a second signal; (c) process the first signal with a reference signal, wherein the first signal and the reference signal have different frequencies; (d) process the second signal with the reference signal, wherein the second signal and the reference signal have different frequencies; and (e) based on the processing of the first signal and the second signal with the reference signal, monitor the progression or regression of the disease in the subject.

In another aspect, the present disclosure provides a system to determine a transcription factor binding profile in a nucleic acid sample from a subject, the system comprising a processor configured to: (a) analyze a set of sequence reads from deoxyribonucleic acid (DNA) extracted from the subject; (b) using the set of sequence reads to generate a coverage pattern for a transcription factor; (c) processing the coverage pattern to provide a signal; and (d) processing the signal with a reference signal, wherein the signal and the reference signal have different frequencies, thereby determining a transcription factor binding profile.

In some examples, the DNA is cell-free DNA.

In some examples, (c) comprises using a low-pass filter. In some examples, (c) comprises using a Savitzky-Golay filter.

In some examples, the subject is a human.

In another aspect, the present disclosure provides a system for detecting a presence or absence of a disease in a subject, comprising a processor configured to: (i) use a set of sequence reads from deoxyribonucleic acid (DNA) extracted from the subject to generate a coverage pattern for a transcription factor; (ii) process the coverage pattern to provide a signal, wherein the signal has a different frequency than a reference signal; and (iii) processing the signal with the reference signal, thereby detecting the presence or absence of the disease in the subject.

In some examples, the present disclosure provides a system for classifying a tumor by tumor subtype or tumor stage, comprising a processor configured to: (i) use a first set of sequence reads from deoxyribonucleic acid (DNA) extracted from the subject at a first time and a second set of sequence reads extracted from DNA from the subject at a second time that is later than the first time to generate a first coverage pattern for a transcription factor and a second coverage pattern for the transcription factor; (ii) process the first coverage pattern to provide a first signal and process the second coverage pattern to provide a second signal, wherein the first signal and the second signal have different frequencies than a reference signal; and (iii) processing the first signal with the reference signal and processing the second signal with the reference signal, to monitor the progression or regression of the disease in the subject.

In another aspect, the present disclosure provides a system for monitoring progression or regression of a disease in a subject, comprising a processor configured to: (i) use a first set of sequence reads from deoxyribonucleic acid (DNA) extracted from the subject at a first time and a second set of sequence reads extracted from DNA from the subject at a second time that is later than the first time to generate a first coverage pattern for a transcription factor and a second coverage pattern for the transcription factor; (ii) process the first coverage pattern to provide a first signal, and process the second coverage pattern to provide a second signal, wherein the first signal and the second signal have different frequencies than a reference signal; and (iii) processing the first signal with the reference signal and processing the second signal with the reference signal, to monitor the progression or regression of the disease in the subject.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

In another aspect, the present disclosure provides a method for determining a tumor-specific TFBS pattern, the method comprising: (a) providing a first set of sequence reads from deoxyribonucleic acid (DNA) extracted from the subject at a first time and a second set of sequence reads from DNA extracted from the subject at a second time that is later than the first time; (b) using the first set of sequence reads to generate a first coverage pattern for a transcription factor and using the second set of sequence reads to generate a second coverage pattern for the transcription factor; (c) processing the first coverage pattern to provide a first signal and processing the second coverage pattern to provide a second signal; (d) processing the first signal with a reference signal, wherein the first signal and the reference signal have different frequencies; (e) processing the second signal with the reference signal, wherein the second signal and the reference signal have different frequencies; and (f) based on the processing of the first signal and the second signal with the reference signal, determining the tumor-specific TFBS pattern.

In another aspect, the present disclosure provides a system comprising a computing device comprising at least one computer processor, an operating system configured to perform executable instructions, a memory, and a computer program including instructions executable by the computing device to provide a computer application for determining a tumor-specific TFBS pattern, the computer application comprising: a sequence module programmed to obtain a first set of sequence reads from deoxyribonucleic acid (DNA) extracted from the subject at a first time and a second set of sequence reads from DNA extracted from the subject at a second time that is later than the first time; a coverage module programmed to use the first set of sequence reads to generate a first coverage pattern for a transcription factor and use the second set of sequence reads to generate a second coverage pattern for the transcription factor; a signal module programmed to process the first coverage pattern to provide a first signal, and process the second coverage pattern to provide a second signal; a first processing module programmed to process the first signal with a reference signal, wherein the first signal and the reference signal have different frequencies; a second processing module programmed to process the second signal with the reference signal, wherein the second signal and the reference signal have different frequencies; and a detection module programmed to, based on the processing of the first signal and the second signal with the reference signal, determine the tumor-specific TFBS pattern.

In another aspect, the present disclosure provides a non-transitory computer-readable medium comprising machine-executable code that, upon execution by one or more computer processors, implements a method for determining a tumor-specific TFBS pattern, the method comprising: (a) providing a first set of sequence reads from deoxyribonucleic acid (DNA) extracted from the subject at a first time and a second set of sequence reads from DNA extracted from the subject at a second time that is later than the first time; (b) using the first set of sequence reads to generate a first coverage pattern for a transcription factor and using the second set of sequence reads to generate a second coverage pattern sequence reads for the transcription factor; (c) processing the first coverage pattern to provide a first signal and processing the second coverage pattern to provide a second signal; (d) processing the first signal with a reference signal, wherein the first signal and the reference signal have different frequencies; (e) processing the second signal with the reference signal, wherein the second signal and the reference signal have different frequencies; and (f) based on the processing of the first signal and the second signal with the reference signal, determining the tumor-specific TFBS pattern.

In another aspect, the present disclosure provides a system for monitoring a progression or regression of a disease in a subject, the system comprising: a database comprising a first set of sequence reads from deoxyribonucleic acid (DNA) extracted from the subject at a first time and a second set of sequence reads from DNA extracted from the subject at a second time that is later than the first time; and one or more computer processors operatively coupled to the database, wherein the one or more computer processors are individually or collectively programmed to: (a) use the first set of sequence reads to generate a first coverage pattern for a transcription factor and use the second set of sequence reads to generate a second coverage pattern for the transcription factor; (b) process the first coverage pattern to provide a first signal, and process the second coverage pattern to provide a second signal; (c) process the first signal with a reference signal, wherein the first signal and the reference signal have different frequencies; (d) process the second signal with the reference signal, wherein the second signal and the reference signal have different frequencies; and (e) based on the processing of the first signal and the second signal with the reference signal, determine the tumor-specific TFBS pattern.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative examples of the present disclosure are shown and described. As will be realized, the present disclosure is capable of other and different examples, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The features of the invention are set forth with particularity in the appended claims. A better understanding of the features and advantages of the present methods and systems will be obtained by reference to the following detailed description that sets forth illustrative examples, in which the principles of the methods and systems are utilized, and the accompanying drawings (also "figure" and "FIG." herein), of which:

FIGS. 2A-2N show the establishment of TF-nucleosome interactions from cell-free deoxyribonucleic acid (cfDNA). FIG. 2A shows that regions with highly organized, e.g., phased, nucleosomes result in an oscillating read depth pattern where a peak of reads indicate the positions of dyads, e.g., the midpoint of a canonical nucleosome. A less defined positioning of nucleosomes yields a rather flat coverage profile. FIG. 2B shows that TFBS data for 676 TFs were retrieved from the GTRD and aligned with a curated list of known or likely human TFs. Three different calculations, each with increased stringency, were conducted. FIGS. 2M and 2N show accessibility plots and DNase hypersensitivity for TF FOXA1 illustrating the preferential amplitude change in patients with hormone-dependent cancers, e.g., prostate and breast cancer.

FIGS. 3A and 3B show how TF accessibility is determined. To measure TF accessibility, the observed raw coverage signal (purple in FIG. 3A and black in FIG. 3B) was split by Savitzky-Golay filtering into a low-frequency signal (red) and a high-frequency signal (blue) using different window sizes. FIG. 3B illustrates an overlay of the three signals in FIG. 3A. The high-frequency signal is used as a measure for accessibility. FIG. 3C shows that the range of the high-frequency signal (Y-axis) critically depends on the number of TFBSs (X-axis), as TFs with few binding sites have more noise due to lesser averaging. A LOESS model is fitted (blue) in order to correct for this bias. FIGS. 3D and 3E show wavelet analysis of GRHL2: Heatmap of periods along the region surrounding the TFBSs of GRHL2 (FIG. 3D). Color code represents quantiles of the signal power distribution. Average power of periods of transcription factor GRHL2 (FIG. 3E). FIG. 3F shows detrended original (black) and reconstructed (red) nucleosome coverage profiles of transcription factor GRHL2 resulting from wavelet analysis. FIGS. 3G-3I show that all tested procedures (FIG. 3G: >50%-TFBSs, Savitzky-Golay filtering; FIG. 3H: the sum of powers, wavelet analysis; FIG. 3I: 1,000-msTFBSs, Savitzky-Golay filtering), showed increased values as a measure of accessibility for transcription factors that are expressed in blood (more than 10 FPKM), but not in genes that show no or low signs of expression (<0.1 FPKM). FIGS. 3J-3L show that transcription factors with a mean DNase hypersensitivity coverage of more than 2 in GM12878 DNase data from the ENCODE project have higher adjusted ranges and higher sum of powers than factors that have a mean coverage of <1 in all three analyses conducted (FIG. 3J: >50%-TFBSs, Savitzky-Golay filtering; FIG. 3K the sum of powers, wavelet analysis; FIG. 3L: 1,000-msTFBSs, Savitzky-Golay filtering).

FIG. 4A shows that prostate adenocarcinomas are AR dependent and have accordingly frequently increased PSA (prostate-specific antigen) levels and normal NSE (neuron-specific enolase) values. In contrast, t-SCNC are no longer dependent on AR and have usually low PSA and increased NSE levels. Several TFs involved in the transdifferentiation process from an adenocarcinoma to a t-SCNC were identified and are indicated in the arrows. FIGS. 4B and 4C show the accessibility profile of the prostate lineage-specific homeobox TF HOXB13 and the respective DNase hypersensitivity assays of prostate cancer cell line LNCaP. In this and the subsequent panels, the profiles calculated from healthy controls are shown in gray, whereas the patient-derived profiles are displayed in the indicated colors. FIGS. 4D and 4E show the accessibility pattern and DNA hypersensitivity assay of NKX3-1, one of the earliest genes expressed during prostatic epithelium maturation. FIGS. 4F-4H show AR accessibility for all AR binding sites in the GTRD and in addition for AR binding sites with higher binding intensity in tumors (T-ARBSs), and for sites with high binding intensity in normal samples (normal AR binding sites, N-ARBSs) (Pomerantz et al., 2015). The well-established lineage specificity of AR was confirmed by DNA hypersensitivity assays. FIGS. 4I-4K (top two panels) show coverage pattern changes during transdifferentiation from an adenocarcinoma to a neuroendocrine carcinoma established from two plasma samples from patient P148 for hormone-dependent (AR, FOXA1 in FIG. 4I), tissue identity-specific (HOXB13, NKX3-1 in FIG. 4J), and neuroendocrine reprogramming (REST. N-MYC in FIG. 4K) TFs. FIGS. 4I-4K (lower two panels) show] analysis of the same TFs as in FIG. 4A from 4 plasma samples from patients with neuroendocrine prostate cancers.

FIGS. 6A and 6B show TFBS-nucleosome coverage profiles for two representative TFs. CREM in FIG. 6A and GATAD1 in FIG. 6B, established from 24 cfDNA samples from healthy controls, each shown with an individual blue line. The MNase-seq coverage patterns from the lymphoblastoid cell line GM12878 obtained from ENCODE are illustrated in red. Additional MNase plots are illustrated in FIGS. 17C and 17D. FIG. 6C shows a heatmap of fragment sizes around CTCF binding sites displayed as a plot of the length of each sequencing read (Y-axis) as a function of the distance from the fragment midpoint to the center of the site for each annotated feature (X-axis). FIG. 6D shows a heatmap of individual CTCF binding sites and surrounding regions. Regions are ordered by the coverage within the central 50 base pairs (bp) around the TFBS. The spatial density of cfDNA fragments within a 1 kilobase (kb) region centered on the TFBSs were computed and ranked. FIGS. 6E and 6F show matrices of overlaps between TFBSs (FIG. 6E: all 676 GRTD TFs; FIG. 6F: 505 TFs with the 1,000-msTFBSs). Each point represents the percentage of overlaps (within about 50 bp) in binding site definitions. FIGS. 6G-6L show TFBS analyses with high molecular weight DNA, which is not mono-nucleosomal DNA, yields a uniform, non-oscillating pattern (blue) in contrast to plasma DNA (green).

FIGS. 8A and 8B show coverage profiles for TFs AP-4 in FIG. 8A and BCL-3 in FIG. 8B after calculations conducted separately for TFBS within and outside of TSSs. FIGS. 8Q and 8R show boxplots illustrating the percentage of overlap for CpG islands (FIG. 8Q) and TSSs (FIG. 8R).

FIG. 10A shows GRHL2 accessibility in plasma samples P148_1 and P148_3 from patient P148. FIG. 10B shows an analysis of GLIS1 in the two plasma samples from patient P148.

FIGS. 12A-12D show a comparison of TFBS accessibility in serial analysis. Plots of correlation between serial samples from patients C2 in FIG. 12A, P147 in FIG. 12B, P40 in FIG. 12C, and P148 in FIG. 12D. The X-axis represents the first plasma sample, and the Y-axis represents the second plasma sample.

FIGS. 13A-13H show the establishment of TF-nucleosome interactions. FIGS. 13A-13D show TFBS-nucleosome profiles for four TFs, e.g., SP1 in FIG. 13A and SP2 in FIG. 13B, which mostly bind to common sites in the genome and furthermore co-bind with NF-YA in FIG. 13C and NF-YB in FIG. 13D. FIGS. 13E-13H show TF-nucleosome interactions depicted as average nucleosome occupancy profiles established from plasma DNA, shown for the hematopoietic cell lineage-specific TFs PU.1 in FIG. 13E, LYL1 in FIG. 13F, and SPIB in FIG. 13G, and the epithelial cell-specific TF GRHL2 in FIG. 13H. The different amplitudes may reflect the different contributions of DNA released from hematopoietic and epithelial cells to the circulation.

FIGS. 14A-14C demonstrate that CTCF is an extraordinary example for the characterization of different TFBSs and demonstrate accessibility score the characterization of TFBSs. FIGS. 14A and 14B illustrate the various binding sites of CTCF in relation to TADs or TSSs. Coverage patterns of CTCF split into CTCF sites that overlap (red) or are outside of TAD boundaries (orange). CTCF sites in proximity (e.g., within about 2 kbp; green) or distal (more than 2 kbp; blue) to TSSs. and ultra-conserved CTCF sites (black) for the complete GTRD data set (FIG. 14A) and only those peaks that are supported by more than 50% of the maximum number of samples analyzed (FIG. 14B). FIG. 14C shows TF-nucleosome profiles illustrating the variability of their patterns.

FIGS. 16B-16G show coverage patterns change after neuroendocrine differentiation in sample P148. FIGS. 16B and 16C show that nucleosome phasing changes notably in Androgen Receptor binding sites in sites defined by GTRD in FIG. 16B and tumor-specific AR-binding sites (defined by Pomerantz et al.) in FIG. 16C. FIGS. 16D and 16E show that nucleosome phasing also is drastically reduced in other transcription factors of the AR-axis, namely FOXA1 in FIG. 16D and HOX-B13 in FIG. 16E. The phasing is prominent in sample 1, but mostly disappears in sample 3. FIGS. 16F and 16G show that repressive factors that play a role in neurogenesis (ZNF644 in FIG. 16F, REST in FIG. 16G) are largely deactivated in sample 3.

FIGS. 17A-17D show a TF-nucleosome interaction map for 676 high-confidence TFs with reliable binding site information. The TF-nucleosome profiles are sorted according to their accessibility score and the number of TFBSs.

FIGS. 20A-20H show plots demonstrating how epigenetic control regions influence nucleosome positioning. Histone modifications (FIGS. 20A-20D) and enhancers (FIGS. 20E-20H) are exemplified.

FIG. 23 shows overlap of different TFs. These overlap values correspond to the heatmap of FIG. 2C.

FIG. 25 shows nucleosome patterns for REST and KLF16 for samples from 24 healthy individuals. Each line represents a different individual. In the 24 healthy individuals, the patterns appear nearly identical in an identical setting for transcription factors that are active in blood cells.

FIG. 27 includes a list of TFs that may be used in the methods and systems provided herein.

FIGS. 28A-28B include TFs that may be used in the methods and systems provided herein. FIG. 28A includes TFs with binding sites of more than 300 bp, while FIG. 28B includes TFs with binding sites close to di-nucleosomal size (between 312-352 bp).

FIG. 29A provides a TFBS analysis of a plasma sample from a health donor (NPH001). Each point represents a TF, the y-axis displays the accessibility values, and the x-axis illustrates the overall z-score, as a measure of deviation in accessibility from normal control samples. In the samples from healthy donors (compared to every remaining healthy donor), only a few TFs exceeded a z-score of ±3 (dotted gray lines) and no TFs exceeded the ±5%-score (red lines) threshold. FIG. 29B provides an overall z-score plot, as in FIG. 29A, but with a plasma sample derived from a patient with prostate cancer (P40). FIG. 29C provides an overall z-score plot as in FIG. 29A, for plasma sample C2_6. FIG. 29D provides nucleosome position profiles from plasma DNA of healthy controls (gray profiles) and two plasma samples derived from a patient C2 with colon cancer (blue and red) for TF EVX2. FIG. 29E provides bar charts of overall z-score plots for merged breast, prostate, and colon cancer pools. The left panel displays TFs with increased accessibility in at least one tumor entity; the right panel summarized the accessibilities of hematopoietic related TFs.

FIG. 30A provides graphs showing comparisons of accessibilities for selected TFs in subsamples of the COAD cohort based on their tumor fraction. FIG. 30B provides graphs showing logistic regression with all 504 TFs for samples from the colon cancer cohort with stage I (left panel) and stage II (right panel), respectively. All presented results are cross-validated test-set values.

DETAILED DESCRIPTION

Figure 1:
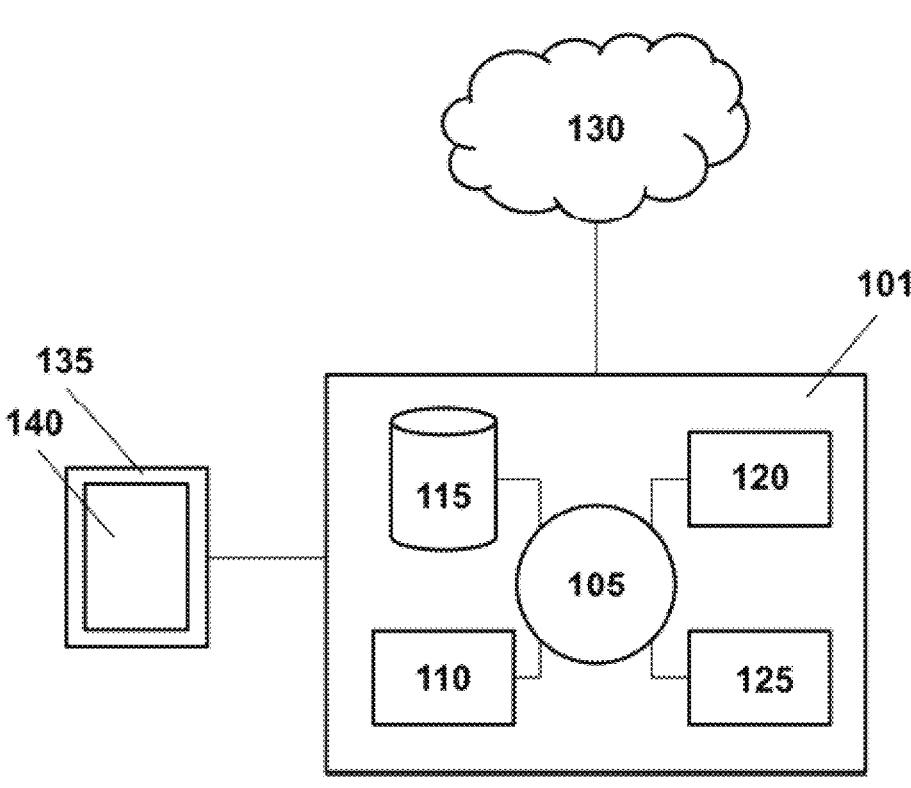
FIG. 1 shows a computer system that is programmed or otherwise configured to perform methods of the present disclosure, such as storing, processing, identifying, or interpreting subject (e.g., patient) data, biological data, biological sequences, reference sequences, transcription factor (TF) binding site (TFBS) data, or TFBS features such as z-scores or TFBS accessibility scores.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

As used herein, the term "accessibility score" generally refers to a measure for the accessibility of each transcription factor (TF) binding site. Since transcription factor binding may open or "prime" its target enhancers, without necessarily activating them per se, the rank values are termed "accessibility score." The accessibility score may be used to objectively compare the accessibility of TFBSs in serial analyses from the same person or among different individuals. This score provides a robust assessment of TFBS accessibility with particular utility to use cfDNA in clinical diagnostics, cancer detection and treatment monitoring.

As used herein, the term "aligned sequence pattern" generally refers to a spatial pattern of sequence reads after alignment to a reference genome.

As used herein, the term "circulating free DNA" or "cell-free DNA" (cfDNA) generally refers to deoxyribonucleic acid (DNA) that was first detected in human blood plasma in 1948. (Mandel, P. Metais, P., C R Acad. Sci. Paris, 142, 241-243 (1948)) Since then, its connection to disease has been established in several areas. (Tong, Y. K. Lo, Y. M., Clin Chim Acta, 363, 187-196 (2006)) Studies reveal that much of the circulating nucleic acids in blood arise from necrotic or apoptotic cells (Giacona, M. B., et al., Pancreas, 17, 89-97 (1998)) and greatly elevated levels of nucleic acids from apoptosis is observed in diseases such as cancer. (Giacona, M. B., et al., Pancreas, 17, 89-97 (1998); Fournie, G. J., et al., Cancer Lett, 91, 221-227 (1995)). Particularly for cancer, where the circulating DNA bears hallmark signs of the disease including mutations in oncogenes, microsatellite alterations, and, for certain cancers, viral genomic sequences, DNA or RNA in plasma has become increasingly studied as a potential biomarker for disease. 16266-16271 (2008)).

The cell-free fraction may be blood serum or blood plasma. The term "cell-free fraction" of a biological sample, as used herein, generally refers to a fraction of the biological sample that is substantially free of cells. As used herein, the term "substantially free of cells" generally refers to a preparation from the biological sample comprising fewer than about 20,000 cells per mL, fewer than about 2,000 cells per mL, fewer than about 200 cells per mL, or fewer than about 20 cells per mL. Genomic DNA may not be excluded from the acellular sample and typically comprises from about 50% to about 90% of the nucleic acids that are present in the sample.

As used herein, the term "coverage pattern" generally refers to a spatial arrangement of sequencing reads after alignment to a reference genome. The coverage pattern identifies the extent and depth of coverage of next-generation sequencing methods.

As used herein, the term "derived from" generally refers to an origin or source, and may include naturally occurring, recombinant, unpurified or purified molecules. A nucleic acid derived from an original nucleic acid may comprise the original nucleic acid, in part or in whole, and may be a fragment or variant of the original nucleic acid. A nucleic acid derived from a biological sample may be purified from that sample.

As used herein, the term "diagnose" or "diagnosis" of a status or outcome generally refers to predicting or diagnosing the status or outcome, determining predisposition to a status or outcome, monitoring treatment of a subject (e.g., a patient), diagnosing a therapeutic response of a subject (e.g., a patient), and prognosis of status or outcome, progression, and response to particular treatment.

As used herein, the term "nucleic acid" generally refers to a polynucleotide comprising two or more nucleotides. It may be DNA or RNA. The nucleic acid may be a polymeric form of nucleotides of any length, either deoxyribonucleotides (dNTPs) or ribonucleotides (rNTPs), or analogs thereof. Nucleic acids may have any three-dimensional structure, and may perform any function, known or unknown. Non-limiting examples of nucleic acids include deoxyribonucleic (DNA), ribonucleic acid (RNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation or binding with a reporter agent. A "variant" nucleic acid is a polynucleotide having a nucleotide sequence identical to that of its original nucleic acid except having at least one nucleotide modified, for example, deleted, inserted, or replaced, respectively. The variant may have a nucleotide sequence at least about 80%, 90%, 95%, or 99%, identity to the nucleotide sequence of the original nucleic acid.

As used herein, the term "target nucleic acid" generally refers to a nucleic acid molecule in a starting population of nucleic acid molecules having a nucleotide sequence whose presence, amount, and/or sequence, or changes in one or more of these, are desired to be determined. A target nucleic acid may be any type of nucleic acid, including DNA, RNA, and analogs thereof. As used herein, a "target ribonucleic acid (RNA)" generally refers to a target nucleic acid that is RNA. As used herein, a "target deoxyribonucleic acid (DNA)" generally refers to a target nucleic acid that is DNA.

As used herein, the terms "amplifying" and "amplification" generally refer to increasing the size or quantity of a nucleic acid molecule. The nucleic acid molecule may be single-stranded or double-stranded. Amplification may include generating one or more copies or "amplified product" of the nucleic acid molecule. Amplification may be performed, for example, by extension (e.g., primer extension) or ligation. Amplification may include performing a primer extension reaction to generate a strand complementary to a single-stranded nucleic acid molecule, and in some cases generate one or more copies of the strand and/or the single-stranded nucleic acid molecule. The term "DNA amplification" generally refers to generating one or more copies of a DNA molecule or "amplified DNA product." The term "reverse transcription amplification" generally refers to the generation of deoxyribonucleic acid (DNA) from a ribonucleic acid (RNA) template via the action of a reverse transcriptase.

The term "transcription factor" generally refers to a protein that controls the rate of transcription of genetic information from DNA to messenger RNA by binding to a specific DNA sequence. Transcription factors are proteins that bind to DNA-regulatory sequences (e.g., enhancers and silencers), usually localized in the 5'-upstream region of target genes, to modulate the rate of gene transcription. This may result in increased or decreased gene transcription, protein synthesis, and subsequent altered cellular function, (for example, cells changing in response to the environment (normal or pathological), for example during atrophy, hypertrophy, hyperplasia, metaplasia, or dysplasia). As used herein, specific transcription factors are referred to by a nomenclature although other synonyms may also be used for the transcription factors recited herein.

The term "transcription factor binding profile" generally refers to a multi-factor information profile for a given transcription factor that includes both tissue contributions and biological processes. The TFBP also includes an "accessibility score," and a z-score statistic to objectively compare across different plasma samples significant changes in TFBS accessibility. The profile may allow identification of lineage-specific TFs suitable for both tissue-of-origin and tumor-of-origin identification.

As used herein, the term "subject" generally refers to an individual, entity or a medium that has or is suspected of having testable or detectable genetic information or material. A subject can be a person, individual, or patient. The subject can be a vertebrate, such as, for example, a mammal. Non-limiting examples of mammals include humans, simians, farm animals, sport animals, rodents, and pets. The subject may be displaying a symptom(s) indicative of a health or physiological state or condition of the subject, such as a cancer or a stage of a cancer of the subject. As an alternative, the subject can be asymptomatic with respect to such health or physiological state or condition.

As used herein, the term "sample" generally refers to a biological sample obtained from or derived from one or more subjects. Biological samples may be cell-free biological samples or substantially cell-free biological samples, or may be processed or fractionated to produce cell-free biological samples. For example, cell-free biological samples may include cell-free ribonucleic acid (cfRNA), cell-free deoxyribonucleic acid (cfDNA), cell-free protein and/or cell-free polypeptides. A biological sample may be tissue (e.g., tissue obtained by biopsy), blood (e.g., whole blood), plasma, serum, sweat, urine, saliva, or a derivative thereof. Cell-free biological samples may be obtained or derived from subjects using an ethylenediaminetetraacetic acid (EDTA) collection tube, a cell-free RNA collection tube (e.g., Streck), or a cell-free DNA collection tube (e.g., Streck). Cell-free biological samples may be derived from whole blood samples by fractionation. Biological samples or derivatives thereof may contain cells. For example, a biological sample may be a blood sample or a derivative thereof (e.g., blood collected by a collection tube or blood drops), a tumor sample, a tissue sample, a urine sample, or a cell (e.g., tissue) sample.

The present disclosure provides methods and systems for modeling transcription factor (TF) binding sites (TFBSs) and using TFBS information to detect, assess, diagnose, and analyze disease states. cfDNA represents a unique analyte generated by endogenous physiological processes to generate in vivo maps of nucleosomal occupancy by whole-genome sequencing. Nucleosomal occupancy at transcription factor binding sites (TFBSs) may be leveraged to infer expressed genes from cells releasing their DNA into the circulation. cfDNA nucleosome occupancy may reflect footprints of TFs.

I. Transcription Factor Binding Site/Nucleosome Occupancy Analysis

Though next-generation sequencing can provide significant information regarding TFs, there is a need for non-invasive ways to measure TF activity or their modulations under therapies (e.g., from blood). Cell-free DNA (cfDNA) (e.g., from plasma), which in patients with cancer also contains circulating tumor DNA (ctDNA), may offer opportunities for non-invasive diagnostic strategies in patients with cancer. As cfDNA may be released after enzymatic digestion from apoptotic cells, it may circulate mostly as mononucleosomal DNA. Hence, whole-genome sequencing of cfDNA fragments may enable the generation of nucleosome maps where dyads, e.g., the midpoint of a canonical nucleosome, of sites with high nucleosome preferences, resulted in a strong peak of reads whereas dyads of less preferentially positioned nucleosomes showed reduced peaks or none at all.

As the inference of TF binding from cfDNA has tremendous diagnostic potential in cancer and beyond, an improved and optimized bioinformatics pipeline was developed. This process is capable of resolving those constituents involved in nucleosome signatures at TFBSs to objectively assess and to compare TFBS accessibility in different plasma samples. Deep whole-genome sequencing (WGS) data may be obtained from plasma samples from healthy donors and from plasma samples of patients with cancer (for example, metastatic prostate, colon, or breast cancer). In some examples, cfDNA also includes circulating tumor DNA (ctDNA). Furthermore, shallow WGS data may also be obtained from plasma samples from patients with the aforementioned tumor entities. This approach may be used to profile individual TFs, instead of establishing general tissue-specific patterns using mixtures of cfDNA signals resulting from multiple cell types and analyses by Fourier transformation as per other approaches. The methods and system provided herein also beneficially provide a more nuanced view of both tissue contributions and biological processes, which allows identification of lineage-specific TFs suitable for both tissue-of-origin and tumor-of-origin analyses.

Certain lineage-specific TFs may be suitable for determining the tissue-of-origin of plasma DNA. However, determining which TFs may be useful in such an application requires evaluating the accessibility of the TFs, e.g., at their binding sites in cfDNA. Conventional methods may lack the ability to evaluate TF accessibility at their binding sites in cfDNA as proxy for their activity. Calculations are conducted separately for TFBSs within and outside of transcription start sites (TSSs). Average TFBS patterns comprise two signals: a TSS-proximal (within about 2 kb of TSS resulting in a "low frequency pattern") and a TSS-distal (more than 2 kb away from TSS peak, resulting in a "high-frequency pattern"), corresponding to the more evenly spaced peak signal. To suppress effects on the coverage not contributed by preferential nucleosomal positioning and to remove local biases from the nucleosome data, filters may be used for detrending (for example, a Savitzky-Golay filter). The obtained low-frequency signal may then be used to normalize the high-frequency signal and subsequently the data range (maximum of the data values minus the minimum, corresponds to the amplitude) of the high-frequency signal may be recorded. As the range of high-frequency signals depends on the number of TFBSs (with the exception of the 1,000-msTFBSs), these range values may be corrected by smoothing as they depend on the number of TFBSs and then used to calculate ranks as measure for the accessibility of each TFBS.

A metric developed for this analysis, termed the "accessibility score," may be used to objectively compare the accessibility of TFBSs in serial analyses of samples obtained from the same person or among different individuals. As TF binding opens or "primes" its target enhancers, without necessarily activating them per se, the rank values may be termed "accessibility score." These results demonstrate robust approaches for assessing TFBS accessibility with particular utility to use cfDNA in clinical diagnostics.

In contrast to other analyses, which may use general tissue-specific patterns using mixtures of cfDNA signals resulting from multiple cell types and analyses by Fourier transformation, methods and system of the present disclosure may profile individual TFs and thereby established lineage-specific TFs for clinical applications. Due to the improved resolution of TFBS analyses, monitoring the accessibility of TFBSs from cfDNA may be possible, and in some examples is demonstrated to be useful for revealing TF plasticity during a disease course, for example, reprogramming to a different cell lineage.

FIGS. 20A-20H show plots demonstrating how epigenetic control regions influence nucleosome positioning. Histone modifications and enhancers are exemplified.

Figures 21A, 21B:
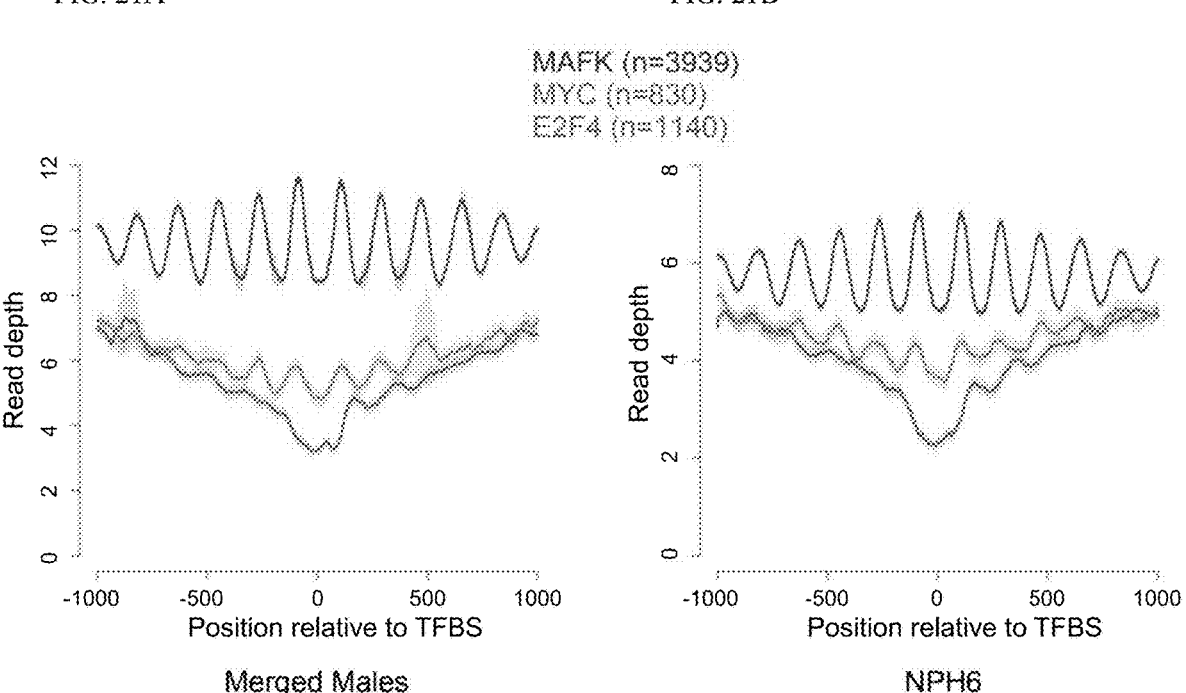
FIGS. 21A and 21B show nucleosome positioning of selected TFs.

FIGS. 21A and B show nucleosome positioning of selected TFs.

Figure 22:
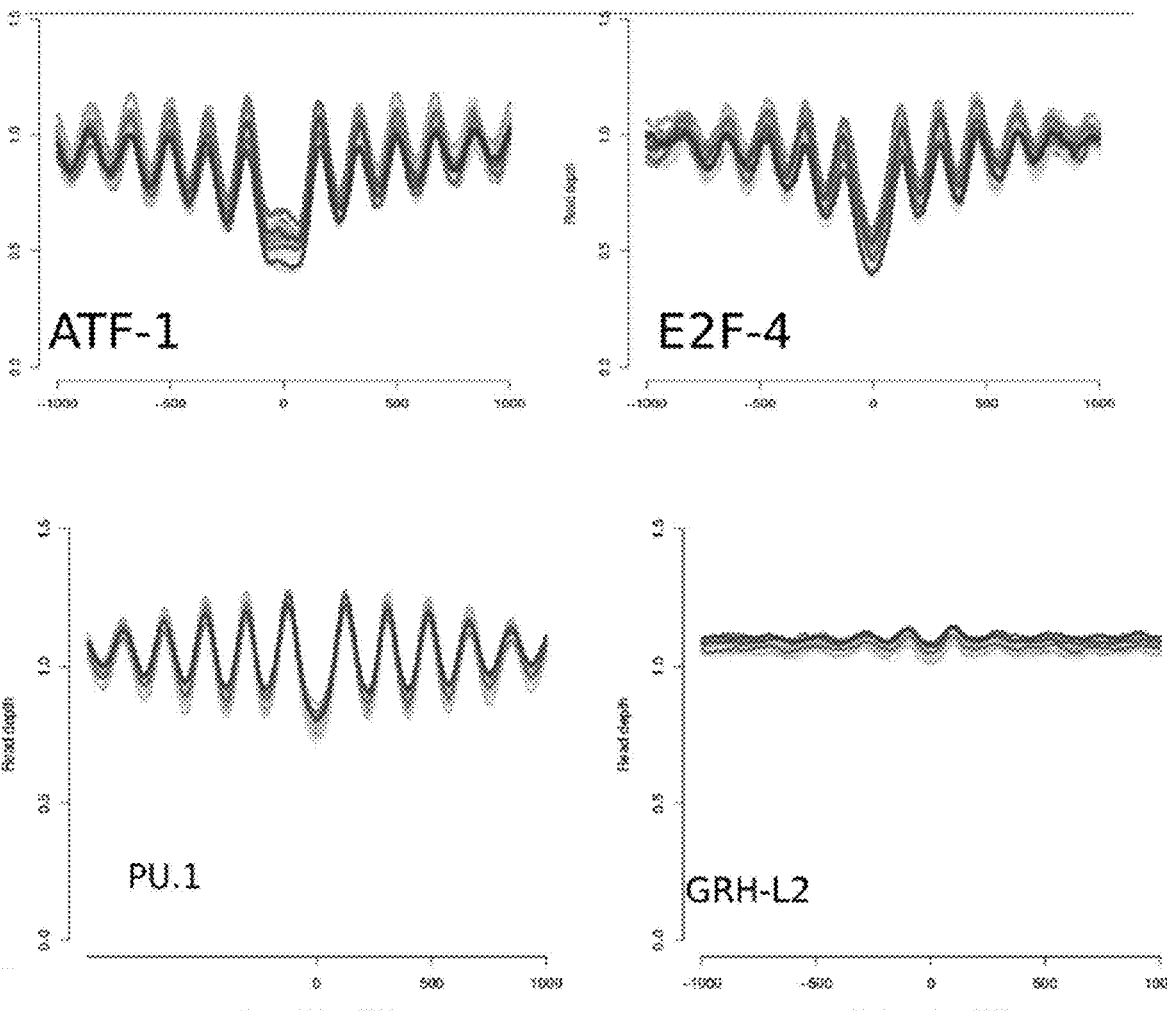
FIG. 22 shows coverage patterns for selected TFs.
Figure 24A:
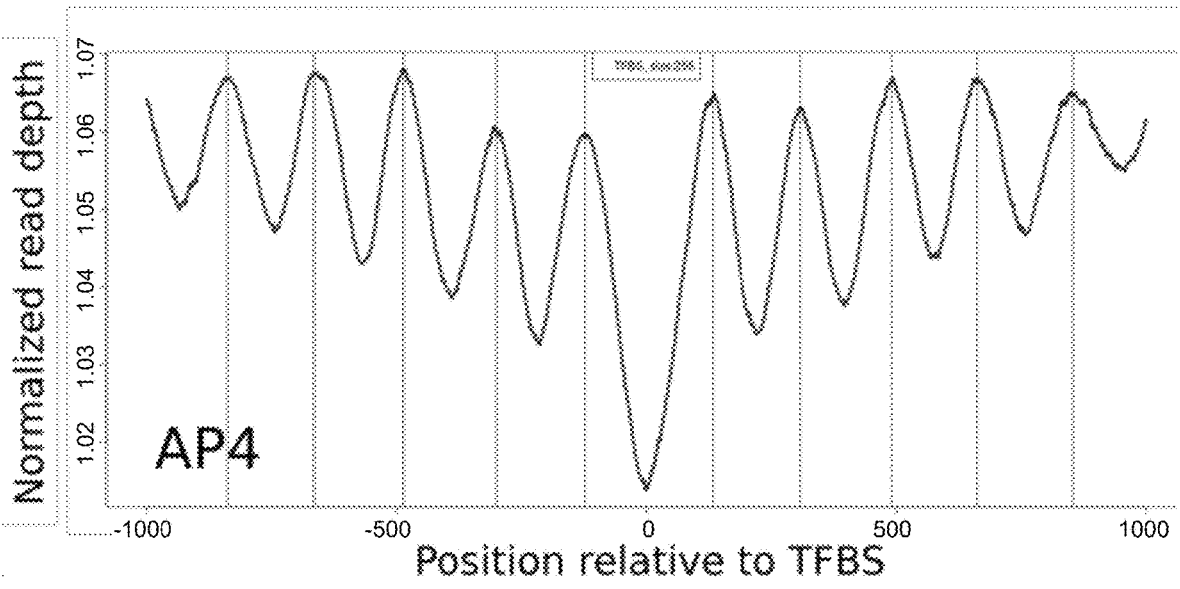
FIGS. 24A-24D show the effect of TFBS size.
Figure 24B:
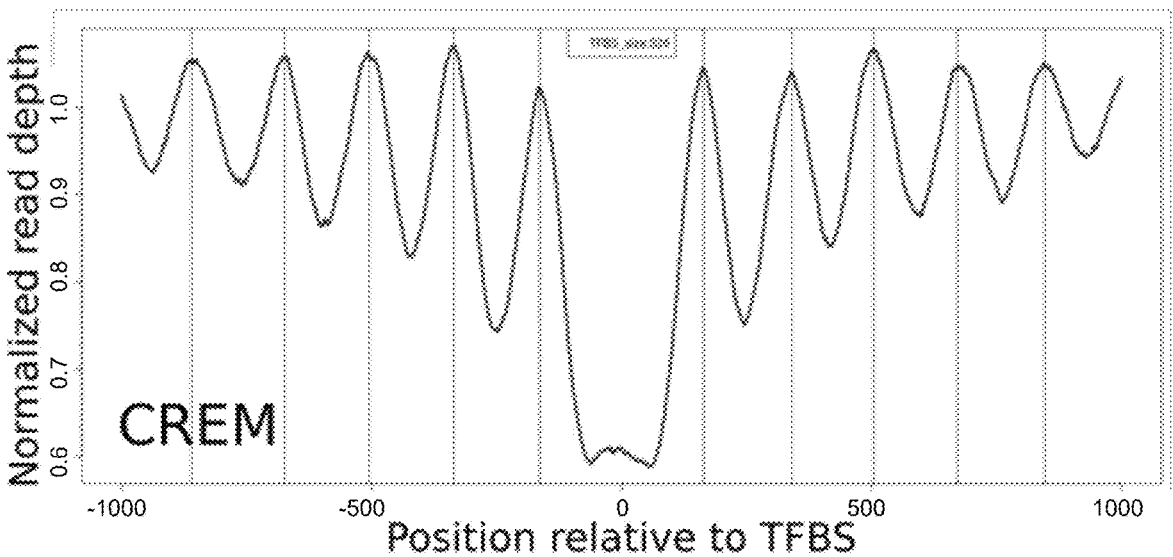
Figure 24C:
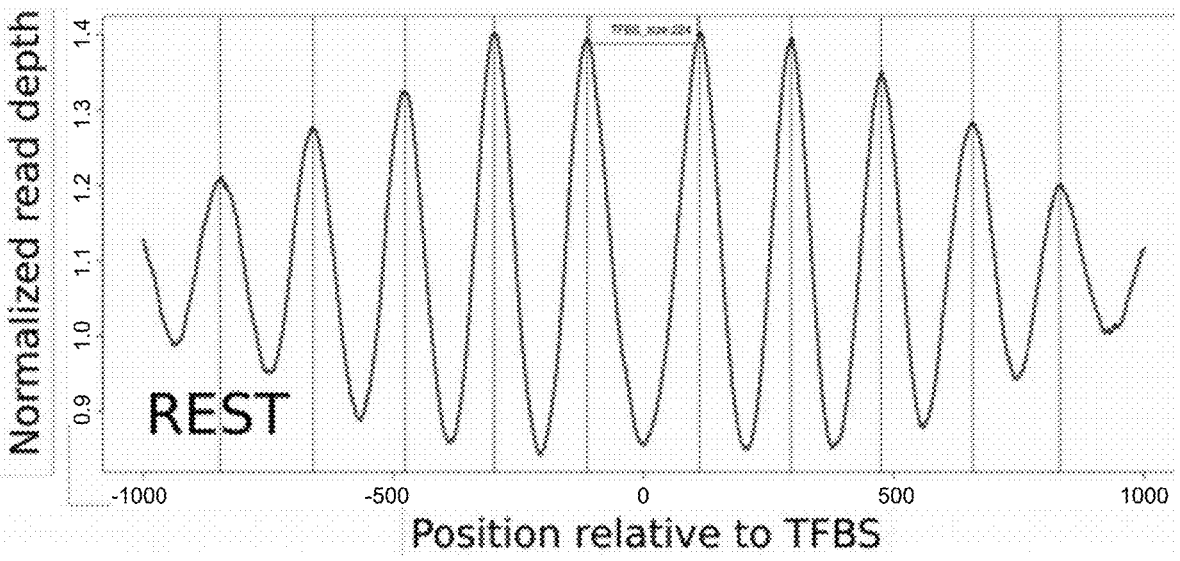
Figure 24D:
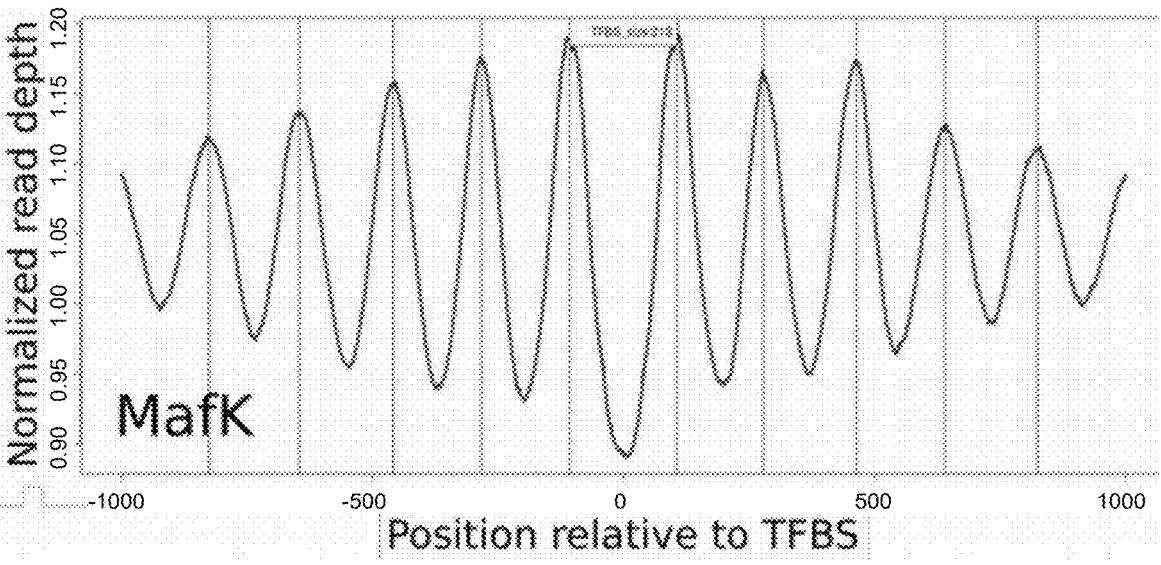

FIG. 22 shows coverage patterns for selected TFs.

FIG. 23 shows overlap of different TFs. These overlap values correspond to the heatmap of FIG. 2C.

FIGS. 20A-20H the effect of TFBS size.

FIG. 25 shows nucleosome patterns for REST and KLF16 for samples from 24 healthy individuals. Each line represents a different individual. In the 24 healthy individuals, the patterns appear nearly identical in an identical setting for transcription factors that are active in blood cells.

Figures 26I, 26J, 26K, 26L:
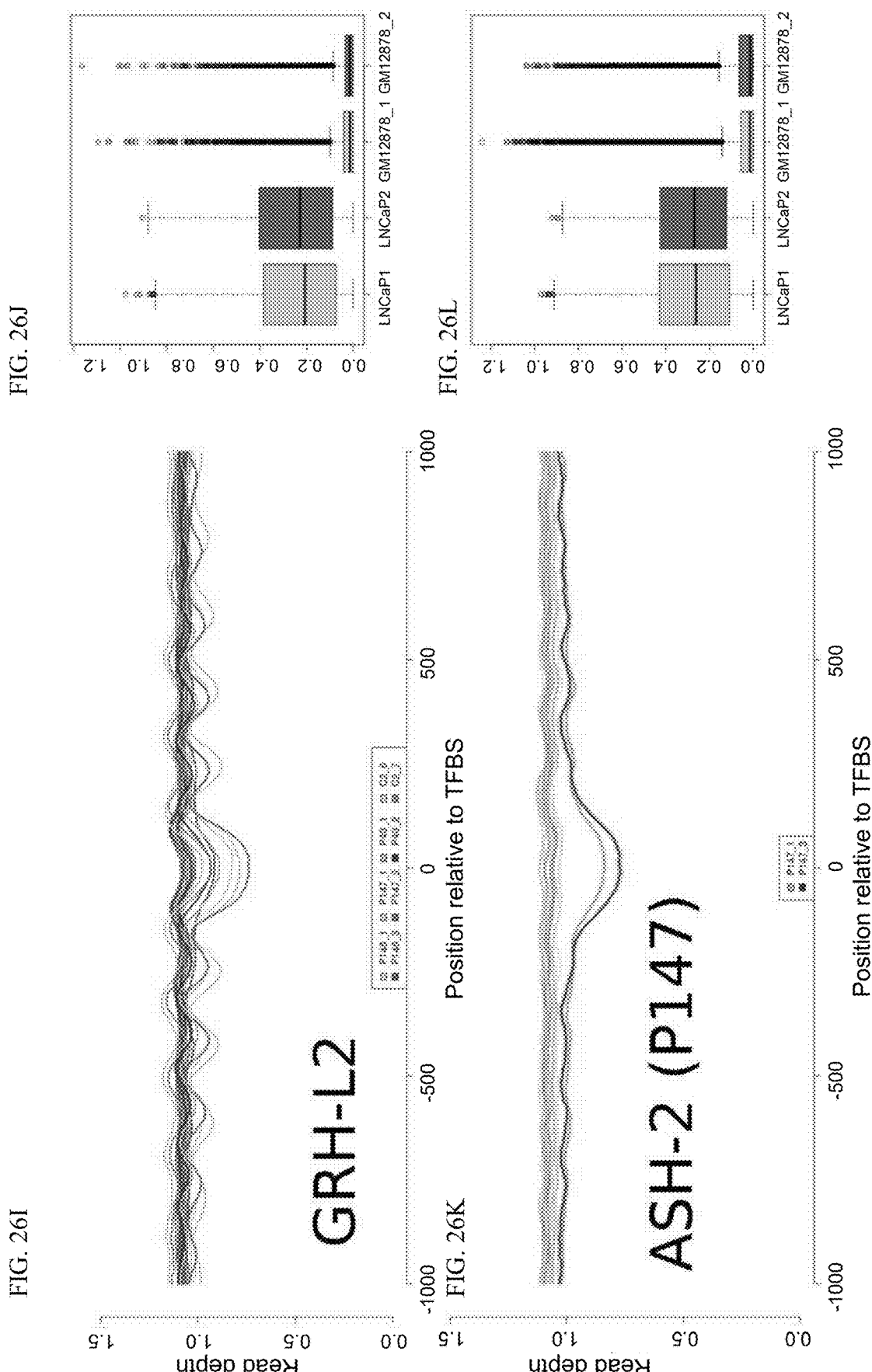
FIGS. 26A-26P show nucleosome positioning for selected TFs for late-stage cancer samples. CTCF patterns look alike in all samples (FIGS. 26A and 26B). Activity of blood-specific TFs including PU.1 (FIGS. 26C and 26D), Lyl-1 (FIGS. 26E and 26F), and Spi-B (FIGS. 26G and 26H) are reduced in cancer samples. Cancer-specific TFs including GRH-L2 (epithelial marker) (FIGS. 26I and 26J), ASH-2 (FIGS. 26K and 26L) and HOX-B13 (prostate cancer markers of the Androgen receptor axis) (FIGS. 26M and 26N), and EVX2 (colon cancer marker) (FIGS. 26O and 26P) are more active.

FIGS. 26A-26P show nucleosome positioning for selected TFs for late-stage cancer samples. CTCF patterns look alike in all samples (FIGS. 26A and 26B). Activity of blood-specific TFs including PU.1 (FIGS. 26C and 26D), Lyl-1 (FIGS. 26E and 26F), and Spi-B (FIGS. 26G and 26H) are reduced in cancer samples. Cancer-specific TFs including GRH-L2 (epithelial marker) (FIGS. 26I and 26J), ASH-2 (FIGS. 26K and 26L) and HOX-B13 (prostate cancer markers of the Androgen receptor axis) (FIGS. 26M and 26N), and EVX2 (colon cancer marker) (FIGS. 26O and 26P) are more active.

II. Transcription Factor Binding Sites

Transcription factor binding sites are identified from the Gene Transcription Regulation Database (GTRD: a database on gene transcription regulation—2019 update. I. S. Yevshin, R. N. Sharipov. S. K. Kolmykov, Y. V. Kondrakhin, F. A. Kolpakov. Nucleic Acids Res. 2019 Jan. 8; 47(D1): D100-D105) using statistical thresholds for use in the present methods and systems and are informative for machine learning models and classifier generation. In some examples, the associated pathways and classes of transcription factors are similarly useful and informative for machine learning models and classifier generation.

Statistical thresholds are used to identify differential TFs between two or more patient groups for analysis (for example, healthy vs. cancer, progressor vs. non-progressor, a stage among a plurality of stages (e.g., I, II, III, or IV), a subtype among a plurality of subtypes, or treatment responder vs. non-responder).

In some examples, transcription factors such as those listed in FIGS. 27A, 27B, 28A, and 28B may be analyzed using the methods and systems described herein.

In some examples, the transcription factor is selected from the group consisting of GRH-L2, ASH-2, HOX-B13, EVX2, PU.1, Lyl-1, Spi-B, and FOXA1.

In some examples, patient-specific as well as tumor-specific patterns, including inferred binding patterns for the transcription factors AR, HOXB13, and NKX3-1, are observed.

In some examples, the transcription factor is an epithelial transcription factor. In some examples, the transcription factor is GRHL2.

In some examples, transcription factors GRHL2, FOXA1, and ZNF121 are associated with increased accessibility scores or open chromatin accessibility in patients with breast cancer.

In some examples, an open accessibility of at least one transcription factor selected from GRHL2, FOXA1, and ZNF121 is indicative of breast cancer.

In some examples, transcription factors EVX2, DLX2, HNF1A, HNF4A, GRHL2, and HNF4G are associated with increased accessibility scores or open chromatin accessibility in patients with colon cancer.

In some examples, an open accessibility of at least one transcription factor selected from EVX2, DLX2, HNF1A, GRHL2, HNF4A, and HNF4G is indicative of colon cancer.

In some examples, transcription factors LYL1, EVI1, TAL1, Spi-B, TBX21, and PU.1 are associated with decreased accessibility scores or closed chromatin accessibility in patients with colon cancer.

In some examples, a closed accessibility of at least one transcription factor selected from LYL1, EVI1, TAL1, Spi-B, TBX21, and PU.1 is indicative of colon cancer.

In some examples, transcription factors GRHL2, FOXA1, HOXB13, AR, and NKX3-1 are associated with increased accessibility scores or open chromatin accessibility in patients with prostate adenocarcinoma.

In some examples, an open accessibility of at least one transcription factor selected from GRHL2, FOXA1, HOXB13, AR and NKX3-1 is indicative of prostate adeno-carcinoma.

In some examples, transcription factors REST, GRHL2, FOXA1, HOXB13, AR, and NKX3-1 are associated with decreased or closed chromatin accessibility in patients with small-cell neuroendocrine prostate cancer.

In some examples, a decreased accessibility of at least one transcription factor selected from REST, GRHL2, FOXA1, HOXB13, AR, and NKX3-1 is indicative of small-cell neuroendocrine prostate cancer.

In one example, the correlation between the accessibility of hematopoietic transcription factors and tissue specific TFs is associated with the presence of diseases such as cancer.

In one example, the hematopoietic transcription factors are selected from LYL1, SCL, Bcl11a, Hhex, Lmo2, Spi1, and PU.1. In one example, the hematopoietic transcription factors are selected from LYL1 or PU.1.

In some examples, a low accessibility of hematopoietic transcription factors, such as LYL1, SPIB, and EVIL (transcriptional regulator ecotropic viral integration site 1), is associated with prostate cancer.

In some examples, the transcription factor is selected from the group consisting of GRH-L2, ASH-2, HOX-B13, EVX2, PU.1, Lyl-1, Spi-B, and FOXA1.

In some examples, the transcription factor is selected from the group consisting of HNF-la, HNF-4A, HNF-4G, EVX-2, and DLX-2.

In some examples, a low accessibility of hematopoietic-related TFs, for example LYL1, TAL1 (SCL/TAL1 (stem cell leukemia/T-cell acute lymphoblastic leukemia [T-ALL] 1, EVI1, TBX21 (T-bet), and PU.1, is associated with cancer.

During persistent exposure to antigens in chronic viral infection or cancer, effector CD8$^+$ T cells acquire an alternative cell differentiation fate termed T cell exhaustion. They fail to undergo antigen-independent self-renewal like memory cells and lose their effector functions in a hierarchical manner, which hinders viral clearance and tumor control by these antigen-specific CD8$^+$ T cells.

In one example, open accessibility of transcription factors tbx21 or EOMES is indicative of exhausted CD8$^+$ T cells.

In one example, open accessibility of transcription factors Eomesodermin (EOMES), Blimp-1, von Hippel-Landau tumor suppressor (VHL), Foxo1, IRF4, BATF, and NFATc1 is indicative of exhausted CD8$^+$ T cells.

III. Machine Learning Systems and Models

A. Sample Features

In some examples, TFBS accessibility scores are used as input features in machine learning models to find correlations between sequence composition and subject (e.g., patient) groups. Examples of such patient groups include presence of diseases or conditions, stages, subtypes, responders vs. non-responders, and progressors vs. non-progressors. In some examples, feature matrices are generated to compare samples obtained from individuals with known conditions or characteristics. In some examples, samples are obtained from healthy individuals or individuals who do not have any of the known indications, and samples from patients known to have cancer.

As used herein, as it relates to machine learning and pattern recognition, the term "feature" refers to an individual measurable property or characteristic of a phenomenon being observed. Features are usually numeric, but structural features such as strings and graphs may be used in syntactic pattern recognition. The concept of "feature" is related to that of explanatory variable used in statistical techniques such as for example, but not limited to, linear regression. In some examples, the feature is a transcription factor binding profile. In some examples, the feature is an accessibility score calculated from a transcription factor binding profile.

In some examples, the features are inputted into a feature matrix for machine learning analysis.

In some examples, the accessibility scores of at least 2, or at least 5, or at least 10, or at least 15, or at least 20, or at least 25 transcription factor binding sites are determined and inputted into a machine learning model to train a classifier capable of distinguishing between healthy subjects and cancer patients, or between disease progressors and non-progressors.

In some examples, the accessibility scores of at least 2, or at least 5, or at least 10, or at least 15, or at least 20, or at least 25 transcription factor binding sites are determined and inputted into a machine learning model to train a classifier capable of distinguishing between a plurality of disease subtypes, or a plurality of disease stages.

In some examples, the accessibility scores of at least 2, or at least 5, or at least 10, or at least 15, or at least 20, or at least 25 transcription factor binding sites are determined and inputted into a machine learning model to train a classifier capable of distinguishing between disease treatment responders and non-responders.

For a plurality of assays, the system identifies feature sets to accept as inputs to a machine learning model. The system performs an assay on each molecule class and forms a feature vector from the measured values. The system accepts as inputs the feature vector into the machine learning model and generates an output classification of whether the biological sample has a specified property.

In some examples, the machine learning model generates a classifier capable of distinguishing between two or more groups or classes of individuals or features in a population of individuals or features of the population. For example, the classifier may be a binary classifier capable of distinguishing between two groups or classes of individuals or features in a population of individuals or features of the population. As another example, the classifier may be a multi-class classifier capable of distinguishing between more than two groups or classes of individuals or features in a population of individuals or features of the population. In some examples, the classifier is a trained machine learning classifier.

In some examples, the informative loci or features of biomarkers in a cancer tissue are assayed to form a profile. In the case of a binary classifier, receiver operating characteristic (ROC) curves may be generated for plotting the performance of a particular feature (e.g., any of the biomarkers described herein and/or any item of additional biomedical information) in distinguishing between two populations (e.g., individuals responding and not responding to a therapeutic agent). In some examples, the feature data across the entire population (e.g., the cases and controls) are sorted in ascending order based on the value of a single feature.

In some examples, the specified property is selected from healthy vs. cancer, a disease subtype among a plurality of disease subtypes, a disease stage among a plurality of disease stages, progressor vs. non-progressor, responder vs. non-responder, or a combination thereof.

B. Data Analysis

In some examples, the present disclosure provides a system, method, or kit having data analysis realized in software application, computing hardware, or both. In some examples, the analysis application or system includes at least a data receiving module, a data pre-processing module, a data analysis module (which can operate on one or more types of genomic data), a data interpretation module, or a data visualization module. In some examples, the data receiving module can comprise computer systems that connect laboratory hardware or instrumentation with computer systems that process laboratory data. In some examples, the data pre-processing module can comprise hardware systems or computer software that performs operations on the data in preparation for analysis. Examples of operations that can be applied to the data in the pre-processing module include affine transformations, denoising operations, data cleaning, reformatting, or subsampling. A data analysis module, which can be specialized for analyzing genomic data from one or more genomic materials, can, for example, take assembled genomic sequences and perform probabilistic and statistical analysis to identify abnormal patterns related to a disease, pathology, state, risk, condition, or phenotype. A data interpretation module can use analysis methods, for example, drawn from statistics, mathematics, or biology, to support understanding of the relation between the identified abnormal patterns and health conditions, functional states, prognoses, or risks. A data visualization module can use methods of mathematical modeling, computer graphics, or rendering to create visual representations of data that can facilitate the understanding or interpretation of results (e.g., by a user such as a subject (e.g., a patient) or a physician or other health care provider).

In some examples, machine learning methods are applied to distinguish samples in a population of samples. In some examples, machine learning methods are applied to distinguish samples between healthy and cancer (e.g., advanced adenoma) samples.

In some examples, the one or more machine learning operations used to train the prediction engine include one or more of: a generalized linear model, a generalized additive model, a non-parametric regression operation, a random forest classifier, a spatial regression operation, a Bayesian regression model, a time series analysis, a Bayesian network, a Gaussian network, a decision tree learning operation, an artificial neural network, a recurrent neural network, a reinforcement learning operation, linear or non-linear regression operations, a support vector machine, a clustering operation, and a genetic algorithm operation.

In some examples, computer processing methods are selected from logistic regression, multiple linear regression (MLR), dimension reduction, partial least squares (PLS) regression, principal component regression, autoencoders, variational autoencoders, singular value decomposition, Fourier bases, wavelets, discriminant analysis, support vector machine, decision tree, classification and regression trees (CART), tree-based methods, random forest, gradient boost tree, logistic regression, matrix factorization, multidimensional scaling (MDS), dimensionality reduction methods, t-distributed stochastic neighbor embedding (t-SNE), multilayer perceptron (MLP), network clustering, neuro-fuzzy, and artificial neural networks.

In some examples, the methods disclosed herein can include computational analysis on nucleic acid sequencing data of samples from an individual or from a plurality of individuals.

C. Classifier Generation

In an aspect, the present disclosure provides systems and methods comprising a classifier generated based on feature information derived from sequence analysis from biological samples of cfDNA. The classifier forms part of a predictive engine for distinguishing groups in a population based on sequence features identified in biological samples such as cfDNA.

In some examples, a classifier is created by normalizing the sequence information by formatting similar portions of the sequence information into a unified format and a unified scale; storing the normalized sequence information in a columnar database; training a prediction engine by applying one or more one machine learning operations to the stored normalized sequence information, the prediction engine mapping, for a particular population, a combination of one or more features; applying the prediction engine to the accessed field information to identify an individual associated with a group; and classifying the individual into a group.

The trained classifier may be configured to accept a plurality of input variables and to produce one or more output values based on the plurality of input variables. The plurality of input variables may comprise one or more datasets indicative of a disease, disorder, or abnormal condition (e.g., a cancer). For example, an input variable may comprise a number of nucleic acid sequences corresponding to or aligning to a set of disease-associated genomic loci. The plurality of input variables may also include clinical health data of a subject.

For example, the clinical health data may comprise one or more quantitative measures of the subject, such as age, weight, height, body mass index (BMI), blood pressure, heart rate, and glucose levels. As another example, the clinical health data can comprise one or more categorical measures, such as race, ethnicity, history of medication or other clinical treatment, history of tobacco use, history of alcohol consumption, daily activity or fitness level, genetic test results, blood test results, and imaging results.

A trained algorithm provided herein may comprise a classifier, such that each of the one or more output values comprises one of a fixed number of possible values (e.g., a linear classifier, a logistic regression classifier, etc.) indicating a classification of a sample by the classifier. The trained algorithm may comprise a binary classifier, such that each of the one or more output values comprises one of two values (e.g., {0, 1}, {positive, negative}, or {high-risk, low-risk}) indicating a classification of the sample by the classifier. The trained algorithm may be another type of classifier, such that each of the one or more output values comprises one of more than two values (e.g., {0, 1, 2}, {positive, negative, or indeterminate}, or {high-risk, intermediate-risk, or low-risk}) indicating a classification of the sample by the classifier. The output values may comprise descriptive labels, numerical values, or a combination thereof. Some of the output values may comprise descriptive labels. Such descriptive labels may provide an identification or indication of an assessment of a disease, disorder, or abnormal condition of the subject, and may comprise, for example, positive, negative, high-risk, intermediate-risk, low-risk, or indeterminate. Such descriptive labels may provide an identification of a treatment for the subject's assessment of the disease, disorder, or abnormal condition, and may comprise, for example, a therapeutic intervention, a duration of the therapeutic intervention, and/or a dosage of the therapeutic intervention suitable to treat the disease, disorder, or abnormal condition. Such descriptive labels may provide an identification of secondary clinical tests that may be appropriate to perform on the subject, and may comprise, for example, an imaging test, a blood test, a computed tomography (CT) scan, a magnetic resonance imaging (MRI) scan, an ultrasound scan, a chest X-ray, a positron emission tomography (PET) scan, a PET-CT scan, a cytology assay, or any combination thereof. For example, such descriptive labels may provide a prognosis of the disease, disorder, or abnormal condition of the subject. As another example, such descriptive labels may provide a relative assessment of the disease, disorder, or abnormal condition of the subject. Some descriptive labels may be mapped to numerical values, for example, by mapping "positive" to 1 and "negative" to 0.

Some of the output values may comprise numerical values, such as binary, integer, or continuous values. Such binary output values may comprise, for example, {0, 1}, {positive, negative}, or {high-risk, low-risk}. Such integer output values may comprise, for example, {0, 1, 2}. Such continuous output values may comprise, for example, a probability value of at least 0 and no more than 1. Such continuous output values may comprise, for example, an un-normalized probability value of at least 0. Such continuous output values may indicate a prognosis of the disease, disorder, or abnormal condition of the subject. Some numerical values may be mapped to descriptive labels, for example, by mapping 1 to "positive" and 0) to "negative."

Some of the output values may be assigned based on one or more cutoff values. For example, a binary classification of samples may assign an output value of "positive" or 1 if the sample indicates that the subject has at least a 50% probability of having a disease, disorder, or abnormal condition. For example, a binary classification of samples may assign an output value of "negative" or 0 if the sample indicates that the subject has less than a 50% probability of having a disease, disorder, or abnormal condition. In this case, a single cutoff value of 50% is used to classify samples into one of the two possible binary output values. Examples of single cutoff values may include about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%.

As another example, a classification of samples may assign an output value of "positive" or 1 if the sample indicates that the subject has a probability of having a disease, disorder, or abnormal condition of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more. The classification of samples may assign an output value of "positive" or 1 if the sample indicates that the subject has a probability of having a disease, disorder, or abnormal condition of more than about 50%, more than about 55%, more than about 60%, more than about 65%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, or more than about 99%.

The classification of samples may assign an output value of "negative" or 0 if the sample indicates that the subject has a probability of having a disease, disorder, or abnormal condition of less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%. The classification of samples may assign an output value of "negative" or 0 if the sample indicates that the subject has a probability of having a disease, disorder, or abnormal condition of no more than about 50%, no more than about 45%, no more than about 40%, no more than about 35%, no more than about 30%, no more than about 25%, no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1%.

The classification of samples may assign an output value of "indeterminate" or 2 if the sample is not classified as "positive," "negative," 1, or 0. In this case, a set of two cutoff values is used to classify samples into one of the three possible output values. Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify samples into one of n+1 possible output values, where n is any positive integer.

The trained classifier may be trained with a plurality of independent training samples. Each of the independent training samples may comprise a sample from a subject, associated datasets obtained by assaying the sample (as described elsewhere herein), and one or more known output values corresponding to the sample (e.g., a clinical diagnosis, prognosis, absence, or treatment efficacy of a disease, disorder, or abnormal condition of the subject). Independent training samples may comprise samples and associated datasets and outputs obtained or derived from a plurality of different subjects. Independent training samples may comprise samples and associated datasets and outputs obtained at a plurality of different time points from the same subject (e.g., on a regular basis such as weekly, biweekly, or monthly). Independent training samples may be associated with presence of the disease, disorder, or abnormal condition (e.g., training samples comprising samples and associated datasets and outputs obtained or derived from a plurality of subjects known to have the disease, disorder, or abnormal condition). Independent training samples may be associated with absence of the disease, disorder, or abnormal condition (e.g., training samples comprising samples and associated datasets and outputs obtained or derived from a plurality of subjects who are known to not have a previous diagnosis of the disease, disorder, or abnormal condition or who have received a negative test result for the disease, disorder, or abnormal condition).

The trained classifier may be trained with at least about 5, at least about 10, at least about 15, at least about 20, at least about 25, at least about 30, at least about 35, at least about 40), at least about 45, at least about 50, at least about 100, at least about 150, at least about 200, at least about 250), at least about 300, at least about 350, at least about 400, at least about 450, or at least about 500 independent training samples. The independent training samples may comprise samples associated with presence of the disease, disorder, or abnormal condition and/or samples associated with absence of the disease, disorder, or abnormal condition. The trained classifier may be trained with no more than about 500), no more than about 450, no more than about 400, no more than about 350), no more than about 300, no more than about 250), no more than about 200, no more than about 150, no more than about 100, or no more than about 50 independent training samples associated with presence of the disease, disorder, or abnormal condition. In some embodiments, the sample is independent of samples used to train the trained classifier.

The trained classifier may be trained with a first number of independent training samples associated with presence of the disease, disorder, or abnormal condition and a second number of independent training samples associated with absence of the disease, disorder, or abnormal condition. The first number of independent training samples associated with presence of the disease, disorder, or abnormal condition may be no more than the second number of independent training samples associated with absence of the disease, disorder, or abnormal condition. The first number of independent training samples associated with presence of the disease, disorder, or abnormal condition may be equal to the second number of independent training samples associated with absence of the disease, disorder, or abnormal condition. The first number of independent training samples associated with presence of the disease, disorder, or abnormal condition may be greater than the second number of independent training samples associated with absence of the disease, disorder, or abnormal condition.

The trained classifier may be configured to identify a presence or absence of the disease, disorder, or abnormal condition at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more; for at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The accuracy of identifying the presence or absence of the disease, disorder, or abnormal condition by the trained algorithm may be calculated as the percentage of independent test samples (e.g., subjects known to have the disease, disorder, or abnormal condition or subjects with negative clinical test results for the disease, disorder, or abnormal condition) that are correctly identified or classified as having or not having the disease, disorder, or abnormal condition.

The trained classifier may be configured to identify the presence of the disease, disorder, or abnormal condition with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the presence of the disease, disorder, or abnormal condition using the trained classifier may be calculated as the percentage of samples identified or classified as having the disease, disorder, or abnormal condition that correspond to subjects that truly have the disease, disorder, or abnormal condition.

The trained classifier may be configured to identify the absence of the disease, disorder, or abnormal condition with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the disease, disorder, or abnormal condition using the trained classifier may be calculated as the percentage of samples identified or classified as not having the disease, disorder, or abnormal condition that correspond to subjects that truly do not have the disease, disorder, or abnormal condition. The trained classifier may be configured to identify the absence of the disease, disorder, or abnormal condition with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. As used herein, specificity refers to "the probability of a negative test among those who are free from the disease." It equals number of disease-free persons who tested negative divided by the total number of disease-free individuals. The clinical specificity of identifying the absence of the disease, disorder, or abnormal condition using the trained classifier may be calculated as the percentage of independent test samples associated with absence of the disease, disorder, or abnormal condition (e.g., subjects with negative clinical test results for the disease, disorder, or abnormal condition) that are correctly identified or classified as not having the disease, disorder, or abnormal condition. In some examples, the model, classifier, or predictive test has a specificity of at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%.

The trained classifier may be configured to identify the presence of the disease, disorder, or abnormal condition with a clinical sensitivity at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. As used herein, sensitivity refers to "the probability of a positive test among those who have the disease." It equals number of diseased individuals who tested positive divided by the total number of diseased individuals.

In some examples, the model, classifier, or predictive test has a sensitivity of at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99%. The clinical sensitivity of identifying the presence of the disease, disorder, or abnormal condition using the trained classifier may be calculated as the percentage of independent test samples associated with presence of the disease, disorder, or abnormal condition (e.g., subjects known to have the disease, disorder, or abnormal condition) that are correctly identified or classified as having the disease, disorder, or abnormal condition.

The trained classifier may be configured to identify the presence or absence of the disease, disorder, or abnormal condition with an Area Under the Receiver Operator Characteristic (AUROC) of at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, at least about 0.99, or more. The AUROC may be calculated as an integral of the Receiver Operator Characteristic (ROC) curve (e.g., the area under the ROC curve, or AUC) associated with the trained classifier in classifying samples as having or not having the disease, disorder, or abnormal condition.

The trained classifier may be adjusted or tuned to improve one or more of the performance, accuracy, PPV, NPV, clinical sensitivity, clinical specificity, or AUC of identifying the disease, disorder, or abnormal condition. The trained classifier may be adjusted or tuned by adjusting parameters of the trained classifier (e.g., a set of cutoff values used to classify a sample as described elsewhere herein, or weights of a neural network). The trained classifier may be adjusted or tuned continuously during the training process or after the training process has completed.

After the trained classifier is initially trained, a subset of the inputs may be identified as most influential or most important to be included for making high-quality classifications. For example, a subset of the plurality of input variables may be identified as most influential or most important to be included for making high-quality classifications or identifications of assessments of a disease, disorder, or abnormal condition. The plurality of input variables or a subset thereof may be ranked based on classification metrics indicative of each input variable's influence or importance toward making high-quality classifications or identifications of assessments of the disease, disorder, or abnormal condition. Such metrics may be used to reduce, in some cases significantly, the number of input variables (e.g., predictor variables) that may be used to train the trained classifier to a desired performance level (e.g., based on a desired minimum accuracy, PPV. NPV, clinical sensitivity, clinical specificity. AUC, or a combination thereof). For example, if training the trained classifier with a plurality comprising several dozen or hundreds of input variables in the trained classifier results in an accuracy of classification of more than 99%, then training the trained classifier instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable accuracy of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%). The subset may be selected by rank-ordering the entire plurality of input variables and selecting a predetermined number (e.g., no more than about 5, no more than about 10, no more than about 15, no more than about 20, no more than about 25, no more than about 30, no more than about 35, no more than about 40, no more than about 45, no more than about 50), or no more than about 100) of input variables with the best classification metrics.

D. Digital Processing Device

In some examples, the subject matter described herein can include a digital processing device or use of the same. In some examples, the digital processing device can include one or more hardware central processing units (CPU), graphics processing units (GPU), or tensor processing units (TPU) that carry out the device's functions. In some examples, the digital processing device can include an operating system configured to perform executable instructions. In some examples, the digital processing device may be connected a computer network. In some examples, the digital processing device may be connected to the Internet. In some examples, the digital processing device may be connected to a cloud computing infrastructure. In some examples, the digital processing device may be connected to an intranet. In some examples, the digital processing device may be connected to a data storage device.

Non-limiting examples of suitable digital processing devices include server computers, desktop computers, laptop computers, notebook computers, sub-notebook computers, netbook computers, netpad computers, set-top computers, handheld computers, Internet appliances, mobile smartphones, and tablet computers. Suitable tablet computers can include, for example, those with booklet, slate, and convertible configurations.

In some examples, the digital processing device can include an operating system configured to perform executable instructions. For example, the operating system can include software, including programs and data, which manages the device's hardware and provides services for execution of applications. Non-limiting examples of operating systems include Ubuntu, FreeBSD, OpenBSD, NetBSD®, Linux, Apple® Mac OS X Server®, Oracle® Solaris®, Windows Server®, and Novell® NetWare®. Non-limiting examples of suitable personal computer operating systems include Microsoft® Windows®, Apple® Mac OS XR, UNIX®, and UNIX-like operating systems such as GNU/Linux®. In some examples, the operating system can be provided by cloud computing, and cloud computing resources can be provided by one or more service providers.

In some examples, the device can include a storage and/or memory device. The storage and/or memory device can be one or more physical apparatuses used to store data or programs on a temporary or permanent basis. In some examples, the device can be volatile memory and require power to maintain stored information. In some examples, the device can be non-volatile memory and retain stored information when the digital processing device is not powered. In some examples, the non-volatile memory can include flash memory. In some examples, the non-volatile memory can include dynamic random-access memory (DRAM). In some examples, the non-volatile memory can include ferroelectric random access memory (FRAM). In some examples, the non-volatile memory can include phase-change random access memory (PRAM). In some examples, the device can be a storage device including, for example, CD-ROMs, DVDs, flash memory devices, magnetic disk drives, magnetic tapes drives, optical disk drives, and cloud computing-based storage. In some examples, the storage and/or memory device can be a combination of devices such as those disclosed herein. In some examples, the digital processing device can include a display to send visual information to a user. In some examples, the display can be a cathode ray tube (CRT). In some examples, the display can be a liquid crystal display (LCD). In some examples, the display can be a thin film transistor liquid crystal display (TFT-LCD). In some examples, the display can be an organic light emitting diode (OLED) display. In some examples, on OLED display can be a passive-matrix OLED (PMOLED) or active-matrix OLED (AMOLED) display. In some examples, the display can be a plasma display. In some examples, the display can be a video projector. In some examples, the display can be a combination of devices such as those disclosed herein.

In some examples, the digital processing device can include an input device to receive information from a user. In some examples, the input device can be a keyboard. In some examples, the input device can be a pointing device including, for example, a mouse, trackball, track pad, joystick, game controller, or stylus. In some examples, the input device can be a touch screen or a multi-touch screen. In some examples, the input device can be a microphone to capture voice or other sound input. In some examples, the input device can be a video camera to capture motion or visual input. In some examples, the input device can be a combination of devices such as those disclosed herein.

E. Non-Transitory Computer-Readable Storage Medium

In some examples, the subject matter disclosed herein can include one or more non-transitory computer-readable storage media encoded with a program including instructions executable by the operating system. The operating system may be part of a networked digital processing device. In some examples, a computer-readable storage medium can be a tangible component of a digital processing device. In some examples, a computer-readable storage medium may be removable from a digital processing device. In some examples, a computer-readable storage medium can include, for example, CD-ROMs, DVDs, flash memory devices, solid state memory, magnetic disk drives, magnetic tape drives, optical disk drives, cloud computing systems and services, and the like. In some examples, the program and instructions can be permanently, substantially permanently, semi-permanently, or non-transitorily encoded on the media.

F. Computer Systems

The present disclosure provides computer systems that are programmed to implement methods described herein. FIG. 1 shows a computer system 101 that is programmed or otherwise configured to perform methods of the present disclosure, such as storing, processing, identifying, or interpreting subject (e.g., patient) data, biological data, biological sequences, reference sequences, TFBS data, or TFBS features such as z-scores or TFBS accessibility scores. The computer system 101 can process various aspects of subject (e.g., patient) data, biological data, biological sequences, or reference sequences of the present disclosure. The computer system 101 can be an electronic device of a user or a computer system that is remotely located with respect to the electronic device. The electronic device can be a mobile electronic device.

The computer system 101 includes a central processing unit (CPU, also "processor" and "computer processor" herein) 105, which can be a single core or multi core processor, or a plurality of processors for parallel processing. The computer system 101 also includes memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 can be a data storage unit (or data repository) for storing data. The computer system 101 can be operatively coupled to a computer network ("network") 130 with the aid of the communication interface 120. The network 130 can be the Internet, an internet and/or extranet, or an intranet and/or extranet that is in communication with the Internet. The network 130 in some examples is a telecommunication and/or data network. The network 130 can include one or more computer servers, which can enable distributed computing, such as cloud computing. The network 130, in some examples with the aid of the computer system 101, can implement a peer-to-peer network, which may enable devices coupled to the computer system 101 to behave as a client or a server.

The CPU 105 can execute a sequence of machine-readable instructions, which can be embodied in a program or software. The instructions may be stored in a memory location, such as the memory 110. The instructions can be directed to the CPU 105, which can subsequently program or otherwise configure the CPU 105 to implement methods of the present disclosure. Examples of operations performed by the CPU 105 can include fetch, decode, execute, and writeback.

The CPU 105 can be part of a circuit, such as an integrated circuit. One or more other components of the system 101 can be included in the circuit. In some examples, the circuit is an application specific integrated circuit (ASIC).

The storage unit 115 can store files, such as drivers, libraries and saved programs. The storage unit 115 can store user data, e.g., user preferences and user programs. The computer system 101 in some examples can include one or more additional data storage units that are external to the computer system 101, such as located on a remote server that is in communication with the computer system 101 through an intranet or the Internet.

The computer system 101 can communicate with one or more remote computer systems through the network 130. For instance, the computer system 101 can communicate with a remote computer system of a user. Examples of remote computer systems include personal computers (e.g., portable PC), slate or tablet PC's (e.g., Apple® iPad, Samsung® Galaxy Tab), telephones. Smart phones (e.g., Apple® iPhone, Android-enabled device, Blackberry®), or personal digital assistants. The user can access the computer system 101 via the network 130.

Methods as described herein can be implemented by way of machine (e.g., computer processor) executable code stored on an electronic storage location of the computer system 101, such as, for example, on the memory 110 or electronic storage unit 115. The machine executable or machine readable code can be provided in the form of software. During use, the code can be executed by the processor 105. In some examples, the code can be retrieved from the storage unit 115 and stored on the memory 110 for ready access by the processor 105. In some examples, the electronic storage unit 115 can be precluded, and machine-executable instructions are stored on memory 110.

The code can be pre-compiled and configured for use with a machine having a processer adapted to execute the code or can be interpreted or compiled during runtime. The code can be supplied in a programming language that can be selected to enable the code to execute in a pre-compiled, interpreted, or as-compiled fashion.

Aspects of the systems and methods provided herein, such as the computer system 101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 101 can include or be in communication with an electronic display 135 that comprises a user interface (UI) 140 for providing, for example, a nucleic acid sequence, an enriched nucleic acid sample, a transcription factor binding profile, an accessibility score, an expression profile, and an analysis of an expression profile. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 105. The algorithm can, for example, probe a plurality of regulatory elements, sequence a nucleic acid sample, enrich a nucleic acid sample, determine an expression profile of a nucleic acid sample, analyze an expression profile of a nucleic acid sample, and archive or disseminate results of analysis of an expression profile.

In some examples, the subject matter disclosed herein can include at least one computer program or use of the same. A computer program can a sequence of instructions, executable in the digital processing device's CPU, GPU, or TPU, written to perform a specified task. Computer-readable instructions can be implemented as program modules, such as functions, objects, Application Programming Interfaces (APIs), data structures, and the like, that perform particular tasks or implement particular abstract data types. For example, a computer program can be written in various versions of various languages.

The functionality of the computer-readable instructions can be combined or distributed as desired in various environments. In some examples, a computer program can include one sequence of instructions. In some examples, a computer program can include a plurality of sequences of instructions. In some examples, a computer program can be provided from one location. In some examples, a computer program can be provided from a plurality of locations. In some examples, a computer program can include one or more software modules. In some examples, a computer program can include, in part or in whole, one or more web applications, one or more mobile applications, one or more standalone applications, one or more web browser plug-ins, extensions, add-ins, or add-ons, or combinations thereof.

In some examples, the computer processing can be a method of statistics, mathematics, biology, or any combination thereof. In some examples, the computer processing method includes a dimension reduction method including, for example, logistic regression, dimension reduction, principal component analysis, autoencoders, singular value decomposition, Fourier bases, singular value decomposition, wavelets, discriminant analysis, support vector machine, tree-based methods, random forest, gradient boost tree, logistic regression, matrix factorization, network clustering, and neural network.

In some examples, the computer processing method is a supervised machine learning method including, for example, a regression, support vector machine, tree-based method, and network.

In some examples, the computer processing method is an unsupervised machine learning method including, for example, clustering, network, principal component analysis, and matrix factorization.

G. Databases

In some examples, the subject matter disclosed herein can include one or more databases, or use of the same to store subject (e.g., patient) data, biological data, biological sequences, or reference sequences. Reference sequences can be derived from a database. For example, many databases can be suitable for storage and retrieval of the sequence information. In some examples, suitable databases can include, for example, relational databases, non-relational databases, object-oriented databases, object databases, entity-relationship model databases, associative databases, and XML databases. In some examples, a database can be internet-based. In some examples, a database can be web-based. In some examples, a database can be cloud computing-based. In some examples, a database can be based on one or more local computer storage devices.

Figure 6A:
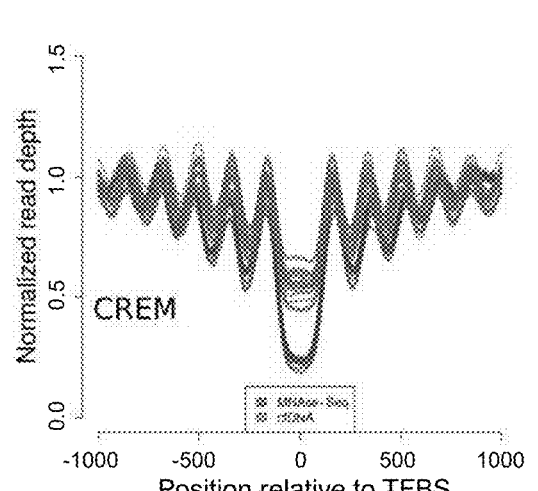
FIGS. 6A-6L show TF-nucleosome interaction map for 676 high-confidence TFs with reliable binding site information.
Figure 6B:
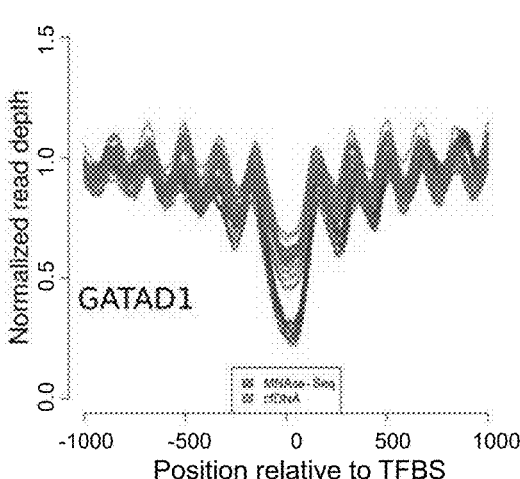

The 676 TFs from the Gene Transcription Regulation Database (GTRD; version 18.01); were used as these contain detailed TFBS information based on ChIP-seq data for a variety of tissue samples. The TFs were annotated with an up-to-date curated list of 1,639 known or likely human TFs (FIGS. 6A and 6B). Because of the potentially high number of TFBSs to which TFs bind with variable frequencies, three different stringency criteria were defined (FIGS. 6A and 6B): first, all TFBSs for all tissue samples in the GTRD; second, those peaks supported by more than 50% of the maximum number of samples (subsequently referred to as ">50%-TFBSs"; in these two analyses all 676 GTRD TFs were included); third, the 1,000 TFBSs per TFs that were supported by the majority of samples ("1,000-msTFBSs"; 505 TFs fulfilled this criterion).

In some examples, the reference genome is selected from GrCH38, GrCH37, hg19, or hg38.

In some examples, the reference genome database is used for alignment and mapping steps of the methods disclosed herein.

IV. Methods of Use

A. Diagnostic and Subject Characterization Methods and Systems

Methods and systems provided herein may perform predictive analytics using artificial intelligence-based approaches to analyze acquired TFBS data from a subject (e.g., patient) to generate an output of an assessment (e.g., a diagnosis, a prognosis, a treatment selection, a treatment monitoring, a staging, or a sub-typing) of the subject having a cancer (e.g., colorectal cancer, breast cancer, prostate cancer). For example, the application may apply a prediction algorithm to the acquired TFBS data to generate the assessment (e.g., a diagnosis, a prognosis, a treatment selection, a treatment monitoring, a staging, or a sub-typing) of the subject having the cancer. The prediction algorithm may comprise an artificial intelligence-based predictor, such as a machine learning-based model, configured to process the acquired TFBS data to generate the assessment (e.g., a diagnosis, a prognosis, a treatment selection, a treatment monitoring, a staging, or a sub-typing) of the subject having the cancer.

The machine learning predictor may be trained using datasets e.g., datasets generated by performing TFBS assays of biological samples of individuals) from one or more sets of cohorts of patients having cancer as inputs and known diagnosis (e.g., staging and/or tumor fraction, subtype, treatment responder vs. non-responder, progressor vs. non-progressor) outcomes of the subjects as outputs to the machine learning predictor.

Training datasets (e.g., datasets generated by performing multi-analyte assays of biological samples of individuals) may be generated from, for example, one or more sets of subjects having common characteristics (features) and outcomes (labels). Training datasets may comprise a set of features and labels corresponding to the features relating to diagnosis. Features may comprise characteristics such as, for example, certain ranges or categories of cfDNA assay measurements, such as z-scores, accessibility scores, etc. For example, a set of features collected from a given subject at a given time point may collectively serve as a diagnostic signature, which may be indicative of an identified cancer of the subject at the given time point. Characteristics may also include labels indicating the subject's diagnostic outcome, such as for one or more cancers.

Labels may comprise outcomes such as, for example, a known diagnosis outcome of the subject (e.g., staging, subtype, tumor fraction, or progressor vs. non-progressor). Outcomes may include a characteristic associated with the cancers in the subject. For example, characteristics may be indicative of the subject having one or more cancers.

Training sets (e.g., training datasets) may be selected by random sampling of a set of data corresponding to one or more sets of subjects (e.g., retrospective and/or prospective cohorts of subjects (e.g., patients) having or not having one or more cancers). Alternatively, training sets (e.g., training datasets) may be selected by proportionate sampling of a set of data corresponding to one or more sets of subjects (e.g., retrospective and/or prospective cohorts of subjects (e.g., patients) having or not having one or more cancers). Training sets may be balanced across sets of data corresponding to one or more sets of subjects (e.g., patients from different clinical sites or trials). The machine learning predictor may be trained until certain predetermined conditions for accuracy or performance are satisfied, such as having minimum desired values corresponding to diagnostic accuracy measures. For example, the diagnostic accuracy measure may correspond to prediction of a diagnosis, staging, or subtype of one or more cancers in the subject.

Examples of diagnostic accuracy measures may include sensitivity, specificity, positive predictive value (PPV), negative predictive value (NPV), accuracy, and area under the curve (AUC) of a Receiver Operating Characteristic (ROC) curve corresponding to the diagnostic accuracy of detecting or predicting the cancer (e.g., colorectal cancer).

In an aspect, the present disclosure provides a computer-implemented method for detecting a presence or absence of a disease or diagnosing a disease in a subject, the method comprising: (a) providing a set of sequence reads from deoxyribonucleic acid (DNA) extracted from the subject; (b) using the set of sequence reads to generate a coverage pattern for a transcription factor; (c) processing the coverage pattern to provide a signal; (d) processing the signal with a reference signal, wherein the signal and the reference signal have different frequencies, thereby detecting the presence or absence of the disease or diagnosing the disease in the subject.

In some examples, the DNA is cell-free DNA.

In some examples, the disease is cancer.

In some examples, (b) comprises aligning the sequence reads to a reference sequence to provide an aligned sequence pattern, selecting regions of the aligned sequence pattern that correspond to binding sites of the transcription factor, and normalizing the aligned sequence pattern in the regions.

In some examples, (c) comprises using a low-pass filter.

In some examples, (c) comprises using a Savitzky-Golay filter.

In some examples, the subject is a human.

In some examples, the transcription factor is a cancer-specific transcription factor.

In some examples, the accessibility score of at least 2, or at least 5, or at least 10, or at least 15, or at least 20, or at least 25 transcription factor binding sites are determined and inputted into a machine learning model to train a classifier capable of distinguishing between healthy subjects vs. cancer patients.

In some examples, the accessibility score of at least 2, or at least 5, or at least 10, or at least 15, or at least 20, or at least 25 transcription factor binding sites are determined and inputted into a machine learning model to train a classifier capable of distinguishing between disease progressors and non-progressors, between disease subtypes among a plurality of disease subtypes, between disease stages among a plurality of disease stages, or any combination thereof.

In some examples, the accessibility score of at least 2, or at least 5, or at least 10, or at least 15, or at least 20, or at least 25 transcription factor binding sites is determined and inputted into a machine learning model to train a classifier capable of distinguishing between disease treatment responders and non-responders.

In an aspect, the methods described herein allow classification of patients by tumor type, including, for example, tumor subtypes (e.g., subtypes of prostate cancer, colorectal cancer, breast cancer, lung cancer), which may have important clinical implications for patient management including treatment planning and responsiveness. Accordingly, the methods provided herein for mapping tumor-specific transcription factor binding in vivo based on patient samples (e.g., blood, plasma or serum samples) make a key part of the noncoding genome amenable for clinical analysis.

In some examples, the method distinguishes subtypes of disease.

In some examples, the method distinguishes subtypes of cancer.

In some examples, the method distinguishes subtypes of prostate cancer, colorectal cancer, breast cancer, and lung cancer.

In some examples, the method distinguishes prostate cancer subtype patients having prostate adenocarcinoma or small-cell neuroendocrine prostate cancer.

In another aspect, the present disclosure provides a computer-implemented method for monitoring a progression or regression of a disease in a subject, the method comprising: (a) providing a first set of sequence reads from deoxyribonucleic acid (DNA) extracted from the subject at a first time and a second set of sequence reads from DNA extracted from the subject at a second time that is later than the first time; (b) using the first set of sequence reads to generate a first coverage pattern for a transcription factor and using the second set of sequence reads to generate a second coverage pattern for the transcription factor; (c) processing the first coverage pattern to provide a first signal and processing the second coverage pattern to provide a second signal; (d) processing the first signal with a reference signal, wherein the first signal and the reference signal have different frequencies; (e) processing the second signal with the reference signal, wherein the second signal and the reference signal have different frequencies; and (f) based on the processing of the first signal and the second signal with the reference signal, monitoring the progression or regression of the disease in the subject.

In some examples, the DNA is cell-free DNA.

In some examples, the disease is cancer.

In some examples, (b) comprises aligning the first set of sequence reads and second sets of sequence reads to a reference sequence to provide a first aligned sequence pattern and a second aligned sequence pattern, respectively, selecting regions of the first aligned sequence pattern and the second aligned sequence pattern that correspond to binding sites of the transcription factor, and normalizing the first aligned sequence pattern and second aligned sequence pattern in the regions.

In some examples, (c) comprises using a low-pass filter. In some examples, (c) comprises using a Savitzky-Golay filter.

In some examples, the subject is a human.

In some examples, the transcription factor is a cancer-specific transcription factor.

In a further aspect, the present disclosure provides a system for detecting or diagnosing a disease in a subject, comprising a processor configured to: (i) use sequence reads from deoxyribonucleic acid (DNA) extracted from the subject to generate a coverage pattern for a transcription factor; (ii) process the coverage pattern to provide a signal, wherein the signal has a different frequency than a reference signal; and (iii) based on the signal, provide a detection or diagnosis of the disease for the subject.

In another aspect, the present disclosure provides a system for monitoring a progression or regression of a disease during or after a course of treatment in a subject, comprising a processor configured to: (i) use a first set of sequence reads from deoxyribonucleic acid (DNA) extracted from the subject at a first time and a second set of sequence reads from DNA extracted from the subject at a second time during or after treatment that is later than the first time to generate a first coverage pattern for a transcription factor corresponding to the first set of sequence reads and a second coverage pattern for the transcription factor corresponding to the second set of sequence reads; (ii) process the first coverage pattern to provide a first signal and process the second coverage pattern to provide a second signal, wherein the first signal and the second signal have different frequencies than a reference signal; and (iii) based on the processing of the first signal and the second signal with the reference signal, monitor the progression or regression of the disease during or after the course of treatment in the subject.

In a further aspect, the present disclosure provides a system for detecting or diagnosing a disease in a subject, comprising a processor configured to: (i) use sequence reads from deoxyribonucleic acid (DNA) extracted from the subject to generate a coverage pattern for a transcription factor; (ii) process the coverage pattern to provide a signal, wherein the signal has a different frequency than a reference signal; and (iii) based on the signal, provide a detection or diagnosis of the disease for the subject.

In some embodiments, the trained classifier may determine that the subject is at risk of a disease, disorder, or abnormal condition (e.g., cancer) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more.

The trained classifier may determine that the subject is at risk of a disease, disorder, or abnormal condition at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more.

Upon identifying the subject as having a disease, disorder, or abnormal condition, the subject may be provided with a therapeutic intervention (e.g., prescribing an appropriate course of treatment to treat the disease, disorder, or abnormal condition of the subject). The therapeutic intervention may comprise a prescription of an effective dose of a drug, a further testing or evaluation of the disease, disorder, or abnormal condition, a further monitoring of the disease, disorder, or abnormal condition, or a combination thereof. If the subject is currently being treated for the disease, disorder, or abnormal condition with a course of treatment, then the therapeutic intervention may comprise a subsequent different course of treatment (e.g., to increase treatment efficacy due to non-efficacy of the current course of treatment).

The therapeutic intervention may comprise recommending the subject for a secondary clinical test to confirm a diagnosis or other assessment of the disease, disorder, or abnormal condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cytology assay, or any combination thereof.

A plurality of input variables (e.g., TFBS information) may be assessed over a duration of time to monitor a patient (e.g., subject who has a disease, disorder, or abnormal condition or who is being treated for a disease, disorder, or abnormal condition). In such cases, the input variables (e.g., TFBS information) of the samples of the patient may change during the course of treatment. For example, the TFBS information of a patient with decreasing risk of the disease, disorder, or abnormal condition due to an effective treatment may shift toward the profile or distribution of a healthy subject (e.g., a subject without a disease, disorder, or abnormal condition). Conversely, for example, the TFBS information of a patient with increasing risk of the disease, disorder, or abnormal condition due to an ineffective treatment may shift toward the profile or distribution of a subject with higher risk of the disease, disorder, or abnormal condition or a more advanced state of the disease, disorder, or abnormal condition.

The disease, disorder, or abnormal condition of the subject may be monitored by monitoring a course of treatment for treating the disease, disorder, or abnormal condition of the subject. The monitoring may comprise assessing the TFBS information of the subject at two or more time points. The assessing may be based at least on the TFBS information determined at each of the two or more time points.

In some examples, a difference in the TFBS information determined between the two or more time points may be indicative of one or more clinical indications, such as (i) a detection or diagnosis of the disease, disorder, or abnormal condition of the subject, (ii) a prognosis of the disease, disorder, or abnormal condition of the subject, (iii) an increased risk of the disease, disorder, or abnormal condition of the subject, (iv) a decreased risk of the disease, disorder, or abnormal condition of the subject, (v) an efficacy of the course of treatment for treating the disease, disorder, or abnormal condition of the subject, and (vi) a non-efficacy of the course of treatment for treating the disease, disorder, or abnormal condition of the subject.

In some examples, a difference in the TFBS information determined between the two or more time points may be indicative of a diagnosis of the disease, disorder, or abnormal condition of the subject. For example, if the disease, disorder, or abnormal condition was not detected in the subject at an earlier time point but was detected in the subject at a later time point, then the difference is indicative of a detection or diagnosis of the disease, disorder, or abnormal condition of the subject. A clinical action or decision may be made based on this indication of detection or diagnosis of the disease, disorder, or abnormal condition of the subject, such as, for example, prescribing a new therapeutic intervention for the subject. The clinical action or decision may comprise recommending the subject for a secondary clinical test to confirm the diagnosis of the disease, disorder, or abnormal condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cytology assay, or any combination thereof.

In some examples, a difference in the TFBS information determined between the two or more time points may be indicative of a prognosis of the disease, disorder, or abnormal condition of the subject.

In some examples, a difference in the TFBS information determined between the two or more time points may be indicative of the subject having an increased risk of the disease, disorder, or abnormal condition. For example, if the disease, disorder, or abnormal condition was detected in the subject both at an earlier time point and at a later time point, then the difference may be indicative of the subject having an increased risk of the disease, disorder, or abnormal condition. A clinical action or decision may be made based on this indication of the increased risk of the disease, disorder, or abnormal condition, e.g., prescribing a new therapeutic intervention or switching therapeutic interventions (e.g., ending a current treatment and prescribing a new treatment) for the subject. The clinical action or decision may comprise recommending the subject for a secondary clinical test to confirm the increased risk of the disease, disorder, or abnormal condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cytology assay, or any combination thereof.

In some examples, a difference in the TFBS information determined between the two or more time points may be indicative of the subject having a decreased risk of the disease, disorder, or abnormal condition. For example, if the disease, disorder, or abnormal condition was detected in the subject both at an earlier time point and at a later time point, then the difference may be indicative of the subject having a decreased risk of the disease, disorder, or abnormal condition. A clinical action or decision may be made based on this indication of the decreased risk of the disease, disorder, or abnormal condition, e.g., prescribing a new therapeutic intervention or switching therapeutic interventions (e.g., continuing or ending a current treatment) for the subject. The clinical action or decision may comprise recommending the subject for a secondary clinical test to confirm the increased risk of the disease, disorder, or abnormal condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cytology assay, or any combination thereof.

In some examples, a difference in the TFBS information determined between the two or more time points may be indicative of an efficacy of the course of treatment for treating the disease, disorder, or abnormal condition of the subject. For example, if the disease, disorder, or abnormal condition was detected in the subject at an earlier time point but was not detected in the subject at a later time point, then the difference may be indicative of an efficacy of the course of treatment for treating the disease, disorder, or abnormal condition of the subject. A clinical action or decision may be made based on this indication of the efficacy of the course of treatment for treating the disease, disorder, or abnormal condition of the subject, e.g., continuing or ending a current therapeutic intervention for the subject. The clinical action or decision may comprise recommending the subject for a secondary clinical test to confirm the efficacy of the course of treatment for treating the disease, disorder, or abnormal condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cytology assay, or any combination thereof.

In some examples, a difference in the TFBS information determined between the two or more time points may be indicative of a non-efficacy of the course of treatment for treating the disease, disorder, or abnormal condition of the subject. For example, if the disease, disorder, or abnormal condition was detected in the subject both at an earlier time point and at a later time point, and if an efficacious treatment was indicated at an earlier time point, then the difference may be indicative of a non-efficacy of the course of treatment for treating the disease, disorder, or abnormal condition of the subject. A clinical action or decision may be made based on this indication of the non-efficacy of the course of treatment for treating the disease, disorder, or abnormal condition of the subject, e.g., ending a current therapeutic intervention and/or switching to (e.g., prescribing) a different new therapeutic intervention for the subject. The clinical action or decision may comprise recommending the subject for a secondary clinical test to confirm the non-efficacy of the course of treatment for treating the disease, disorder, or abnormal condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, a cytology assay, or any combination thereof.

B. Indications

Non-limiting examples of cancers that can be inferred by the disclosed methods include acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloepithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chronic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom macroglobulinemia, and Wilms Tumor.

In various examples, the tumor is a colorectal disease selected from the group consisting of colorectal cancer, advanced adenoma, ulcerative colitis, Crohn's disease, irritable bowel syndrome (IBS).

In some examples, the colorectal cancer is classified by stages such as stage 0, stage I, stage IIA, stage IIB, stage IIC, stage IIIA, stage IIIB, stage IIIC, stage IVA, stage IVB, or stage IVC.

EXAMPLES

Example 1: Inference of Cell-Specific Transcription Factor Binding from Cell-Free DNA Enables Tumor Subtype Prediction and Early Detection of Cancer In accordance with methods and systems of the present disclosure, an analysis program was developed to determine accessibility of transcription factor binding sites, and the program was applied to 244 cfDNA samples from patients with prostate cancer, breast cancer, or colon cancer.

The inference of TF binding from cfDNA has tremendous diagnostic potential in cancer and beyond, and an improved and optimized bioinformatics pipeline was developed. This process is capable of resolving those constituents involved in nucleosome signatures at TFBSs to objectively assess and to compare TFBS accessibility in different plasma samples. To validate this pipeline for clinical purposes, deep whole-genome sequencing (WGS) data was obtained from 24 plasma samples from healthy donors and from 15 plasma samples of patients with metastatic prostate, colon, or breast cancer, where cfDNA also comprises circulating tumor DNA (ctDNA). Furthermore, shallow WGS data were generated for 229 plasma samples from patients with the aforementioned tumor entities (more than 18.5 billion mapped plasma sequence reads in total). An additional 769 plasma samples from patients with colon cancer (n=592) and health controls (n=177) were also included (providing about 238 billion mapped plasma sequence reads). This approach profiles individual TFs, instead of establishing general tissue-specific patterns using mixtures of cfDNA signals resulting from multiple cell types and analyses by Fourier transformation as per other approaches. The methods and systems provided herein provides insight into both tissue contributions and biological processes, which allows identification of lineage-specific TFs suitable for both tissue-of-origin and tumor-of-origin analyses. Furthermore, TFBS plasticity in cfDNA from patients with cancer and the potential of TFs for classifying prostate cancer subtypes are demonstrated through two examples of relevant clinical applications. First, these TF-based cfDNA assays are capable of distinguishing between prostate adenocarcinoma and small-cell neuroendocrine prostate cancer, a distinction that has important therapeutic implications. Second, the large colon cancer cohort enabled the accurate establishment of resolution limits and exploration of the use of TF-based plasma analyses for detection of early cancer stages.

Analyses of a small panel of individuals with advanced cancers (n=5) demonstrated that cfDNA fragmentation patterns can be used to detect non-hematopoietic signatures. In order to explore the potential of TF-nucleosome interactions mapping from cfDNA in greater detail, known hematopoietic TF-nucleosome footprints were confirmed in plasma samples from healthy controls. A curated list of TFBSs from the Gene Transcription Regulation Database (GTRD) was annotated with a recently published list of known or likely human TFs to generate from cfDNA comprehensive TFBS-nucleosome occupancy maps for 676 TFs. Using the bioinformatics pipeline provided herein, different stringency criteria were evaluated to measure nucleosome signatures at TFBSs, and to establish a metric, which is termed an "accessibility score." and a z-score statistic to objectively compare across different plasma samples significant changes in TFBS accessibility. For clinical purposes, a set of lineage-specific TFs was used for identifying the tissue-of-origin of cfDNA or in patients with cancer the tumor-of-origin. Finally, the accessibility score and z-score statistics were used to elucidate changing TFBS accessibilities from cfDNA of patients with cancer.

Knowing the precise locations of nucleosomes in a genome relative to TF binding sites (TFBSs) is useful to understanding how genes are regulated. To this end, the analysis of cell-free DNA (cfDNA) from plasma, which contains in patients with cancer also circulating tumor DNA (ctDNA), offers improved opportunities to study non-invasively TFBSs in vivo in humans. As cfDNA is mainly released after enzymatic digestion from apoptotic cells, it circulates mostly as mononucleosomal DNA. Hence, sequencing of cfDNA fragments allows the generation of nucleosome maps where dyads of "perfectly positioned"

nucleosomes, e.g., sites with high nucleosome preferences, results in a strong peak of reads reflecting the phasing of nucleosomes whereas dyads of less preferentially positioned nucleosomes showed reduced peaks or none at all. Therefore, cfDNA represents a unique analyte generated by endogenous physiological processes allowing the generation of in vivo maps of nucleosomal occupancy by whole-genome sequencing. This can be leveraged to infer expressed genes by detailed analyses of nucleosomal occupancy at transcription start sites (TSSs). cfDNA nucleosome occupancy can reflect footprints of TFs. In a small panel of individuals with cancer (n=5) cfDNA fragmentation patterns were matched against reference datasets to detect non-hematopoietic signatures. However, TF-nucleosome interactions remain largely unmapped, and there is a need to obtain measurements of TF real-time dynamics on genome-scale in vivo in humans.

Nucleosome position mapping strategies from cfDNA and bioinformatics pipelines are used to address the following issues: (1) whether cfDNA accurately reflects known TF-nucleosome interactions; (2) to generate the most comprehensive TF-nucleosome interaction maps comprising data on 676 TFs; (3) to establish an improved metric, termed an "accessibility score." to objectively compare the accessibility of TFBSs in serial analyses from the same person or among different individuals; and (4) to define a set of lineage-specific TFs suitable for identifying the tissue-of-origin of cfDNA or in patients with cancer the tumor-of-origin. In addition, this study also examined whether TFBS tracking from cfDNA of patients with cancer is capable of elucidating changing TFBSs accessibility and associated pathways. To this end, high-coverage whole-genome sequencing (WGS) data was obtained from 24 plasma samples from healthy donors (12 males and 12 females) and from 16 plasma samples of patients with metastatic prostate cancer, colon cancer, or breast cancer. Furthermore, for confirmatory purposes cfDNA shallow-coverage sequencing data from 229 patients was employed with the aforementioned tumor entities to generate altogether more than 18.3 billion mapped plasma sequence reads to provide a broad in vivo view on an important part of the noncoding genome.

Figure 5:
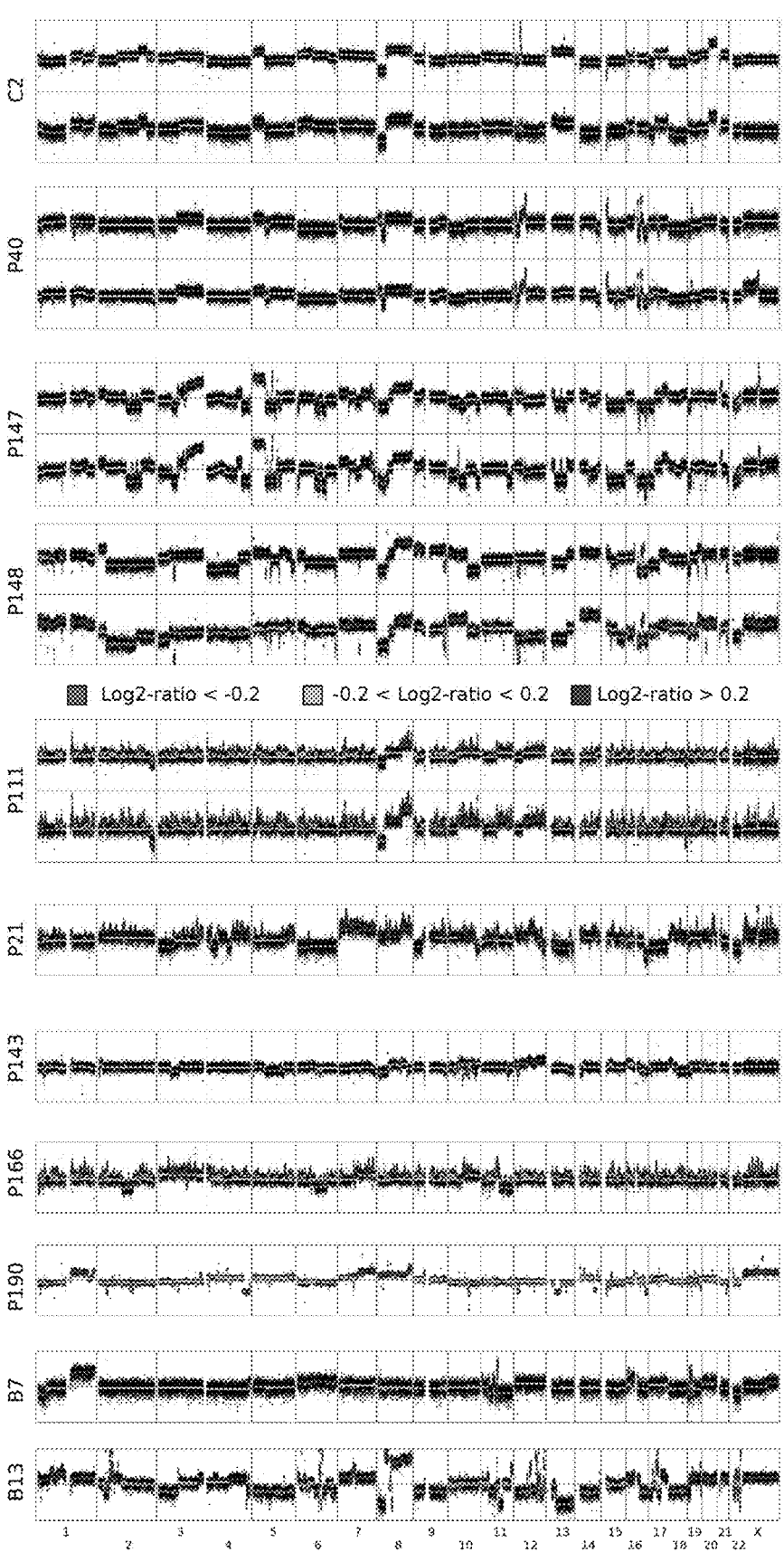
FIG. 5 shows somatic copy number alterations (SCNAs) in plasma samples from patients with cancer. SCNAs were identified after whole-genome sequencing of 8 plasma samples from four patients (C2, P40, P147, and P148).

Nucleosome Occupancy Inferred from cfDNA Shows Characteristic TF Binding Footprints Nucleosome occupancy maps at TFBSs were prepared and tested for similarities and differences among healthy individuals and cancer patients. To this end, high-coverage cfDNA samples were obtained from 24 healthy controls (males and females, 12 each), where the vast majority (more than 90%) of cfDNA is derived from apoptosis of white blood cells with minimal contribution from other tissues, and 11 plasma samples derived from 7 patients with 3 common tumor entities, e.g., four cases with prostate cancer (P40, P147, P148, and P190), one case with colorectal cancer (CRC; C2), and two cases with breast cancers (B7 and B13) with ctDNA fractions ranging from 18-78% (FIG. 5).

The 676 TFs from the Gene Transcription Regulation Database (GTRD; version 18.01); were used as these contain detailed TFBS information based on ChIP-seq data for a variety of tissue samples. The TFs were annotated with an up-to-date curated list of 1,639 known or likely human TFs (FIGS. 6A and 6B). Because of the potentially high number of TFBSs to which TFs bind with variable frequencies, three different stringency criteria were defined (FIGS. 6A and 6B): first, all TFBSs for all tissue samples in the GTRD; second, those peaks supported by more than 50% of the maximum number of samples (subsequently referred to as ">50%-

TFBSs"; in these two analyses all 676 GTRD TFs were included); third, the 1,000 TFBSs per TFs that were supported by the majority of samples ("1,000-msTFBSs"; 505 TFs fulfilled this criterion).

Establishment of TF-Nucleosome Interactions

Figure 2C:
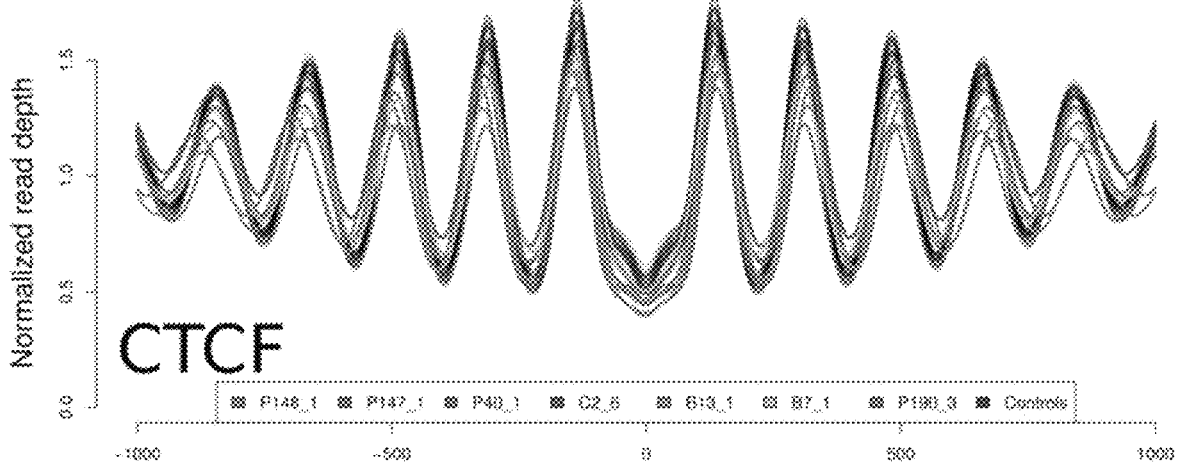
FIG. 2C shows that the coverage pattern of CCCTC-binding factor (CTCF) is similar across all analyzed cfDNAs, which is consistent with DNase hypersensitivity data in FIG. 2D showing approximately equal accessibility in blood (GM12878) and epithelial tissues, e.g., prostate (LNCaP) and colon (HCT116). In this panel and in the respective subsequent panels, the profiles calculated from healthy controls are shown in gray, whereas the patient-derived profiles are displayed in the indicated colors.
Figure 2D:
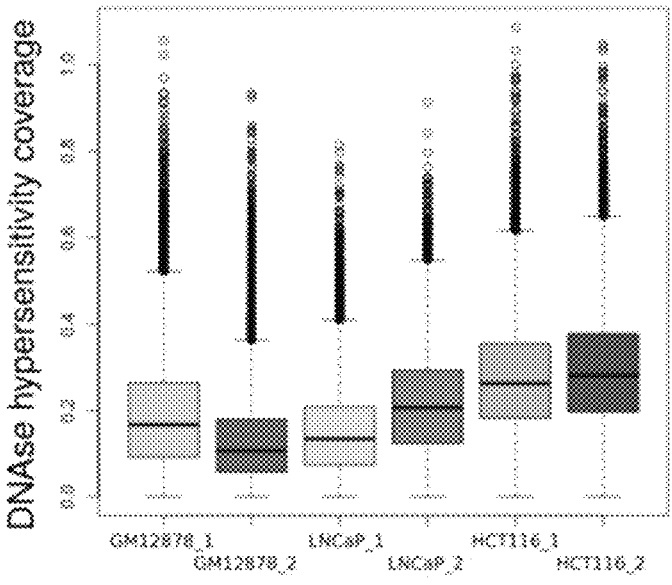
Figure 2E:
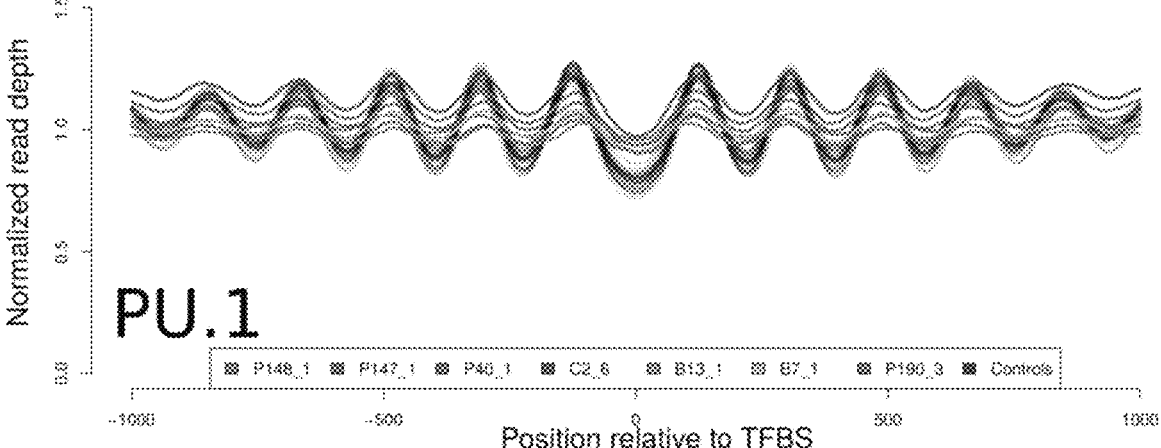
FIGS. 2E-2J show that the hematopoietic lineage-specificity of TFs (PU.1 in FIGS. 2E and 2F), LYL1 in FIGS. 2G and 2H, SPIB in FIGS. 2I and 2J) was confirmed by DNA hypersensitivity assays and their amplitude is reduced in plasma from cancer patients compared to healthy controls. In contrast.
Figure 2F:
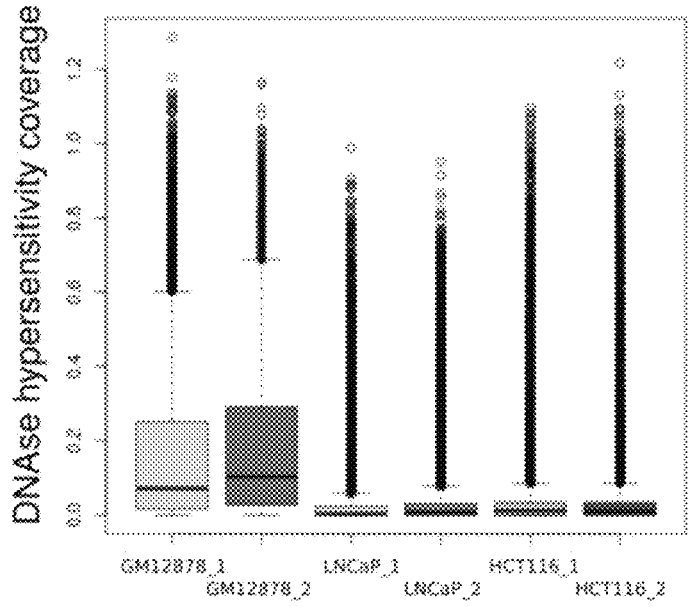
Figure 2G:
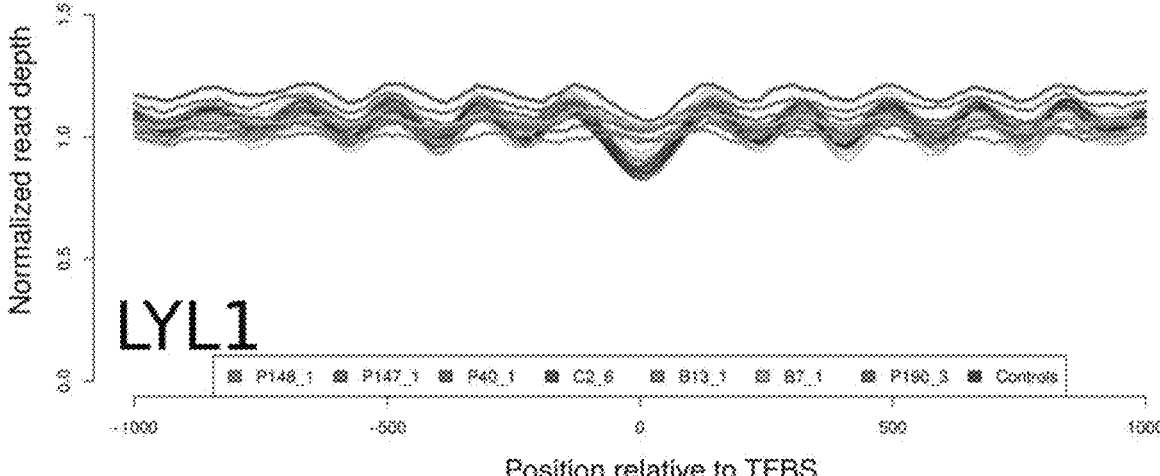
Figure 2H:
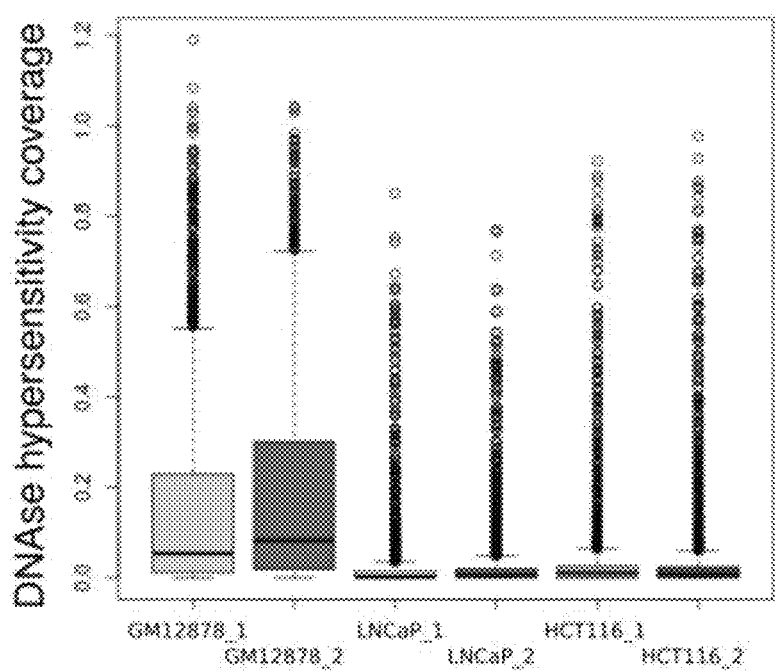
Figure 2I:
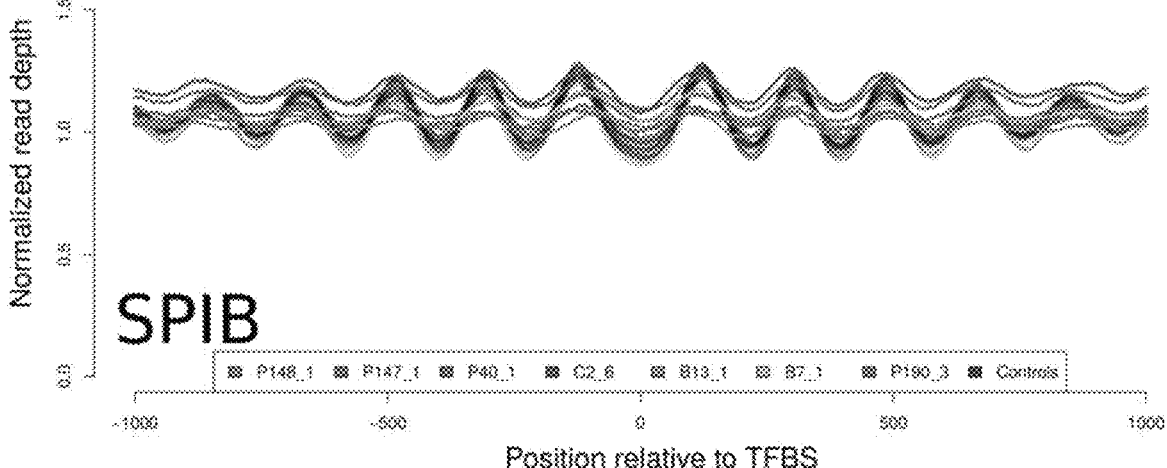
Figure 2J:
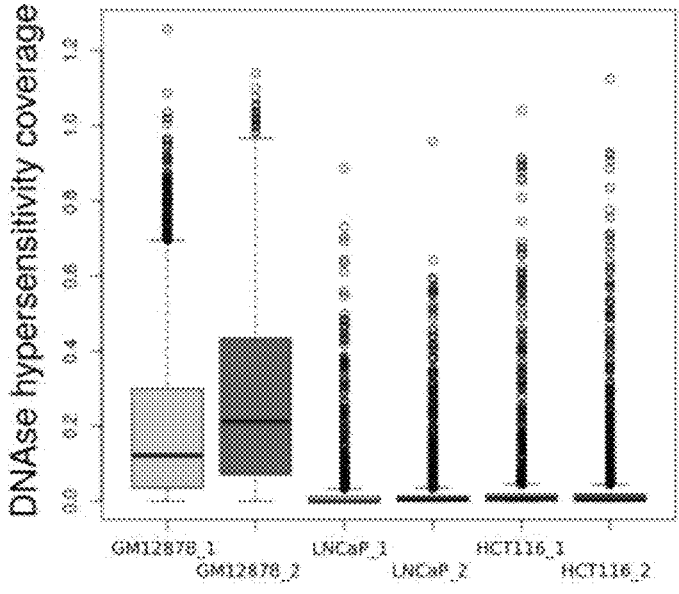
Figure 2K:
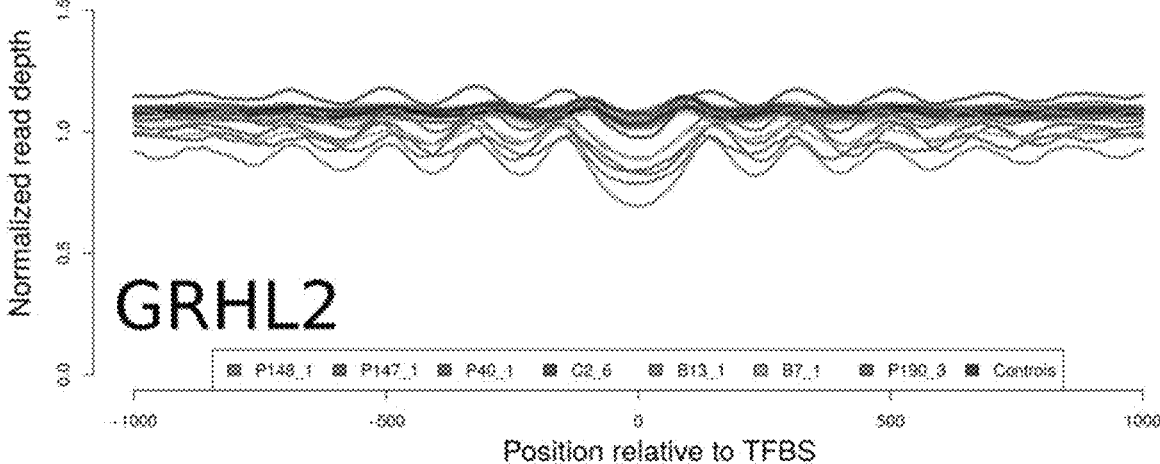
FIGS. 2K and 2L show the amplitudes for the epithelial TF GRHL2 increase in cfDNA from patients with cancer.
Figure 2L:
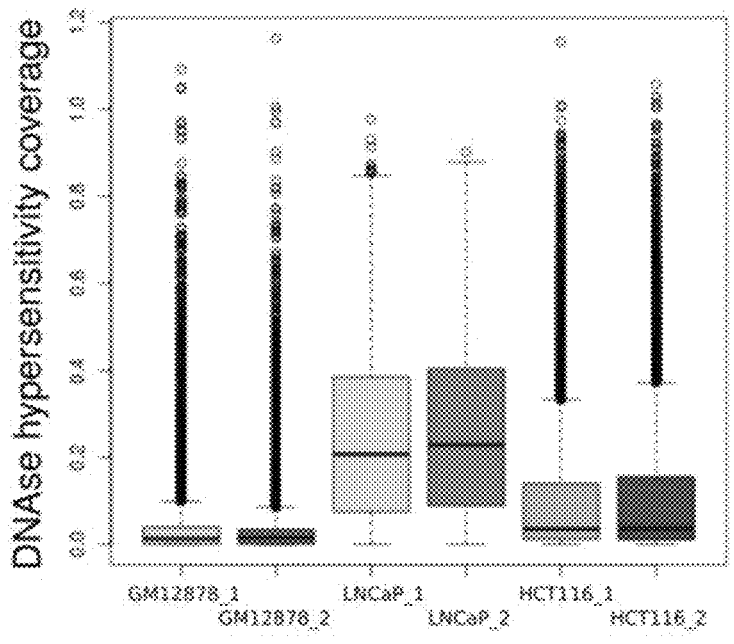
Figure 2M:
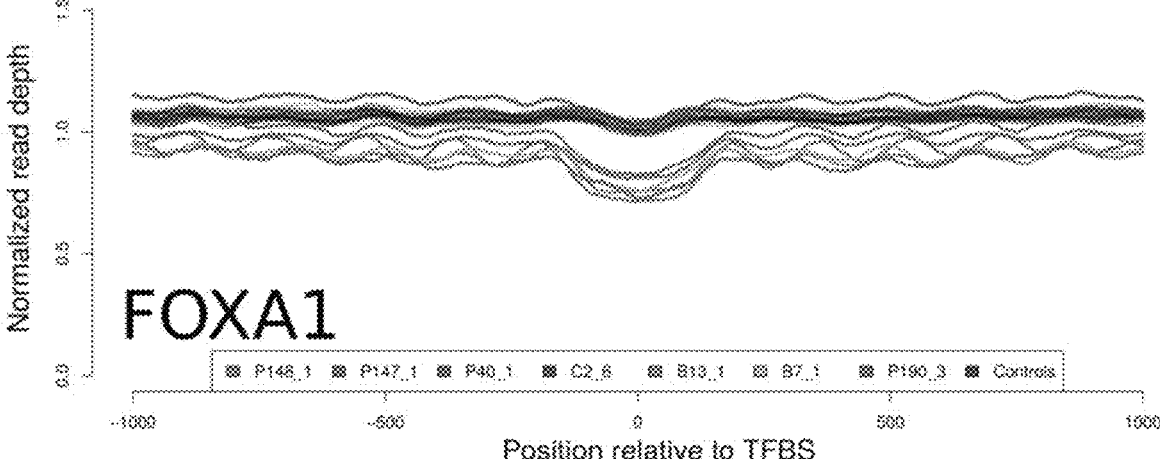
Figure 2N:
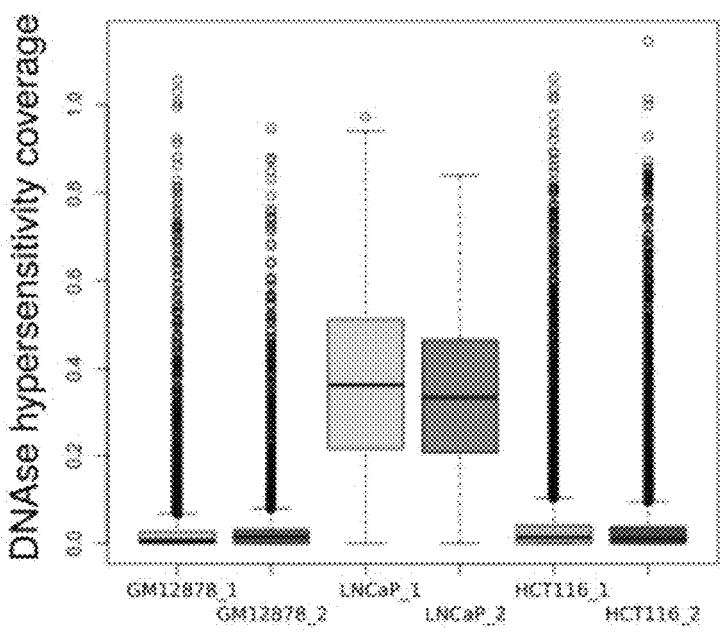

FIGS. 2A-2N show the establishment of TF-nucleosome interactions from cell-free deoxyribonucleic acid (cfDNA). FIG. 2A shows that regions with highly organized, e.g., phased, nucleosomes result in an oscillating read depth pattern where a peak of reads indicate the positions of dyads. e.g., the midpoint of a canonical nucleosome. A less defined positioning of nucleosomes yields a rather flat coverage profile. FIG. 2B shows that TFBS data for 676 TFs were retrieved from the GTRD and aligned with a curated list of known or likely human TFs. Three different calculations, each with increased stringency, were conducted. FIG. 2C shows that the coverage pattern of CCCTC-binding factor (CTCF) is similar across all analyzed cfDNAs, which is consistent with DNase hypersensitivity data in FIG. 2D showing approximately equal accessibility in blood (GM12878) and epithelial tissues. e.g., prostate (LNCaP) and colon (HCT116). In this panel and in the respective subsequent panels, the profiles calculated from healthy controls are shown in gray, whereas the patient-derived profiles are displayed in the indicated colors. FIGS. 2E-2J show that the hematopoietic lineage-specificity of TFs (PU.1 in FIGS. 2E and 2F), LYL1 in FIGS. 2G and 2H. SPIB in FIGS. 2I and 2J) was confirmed by DNA hypersensitivity assays and their amplitude is reduced in plasma from cancer patients compared to healthy controls. In contrast. FIGS. 2K and 2L show the amplitudes for the epithelial TF GRHL2 increase in cfDNA from patients with cancer. FIGS. 2M and 2N show accessibility plots and DNase hypersensitivity for TF FOXA1 illustrating the preferential amplitude change in patients with hormone-dependent cancers. e.g., prostate and breast cancer.

Figure 6C:
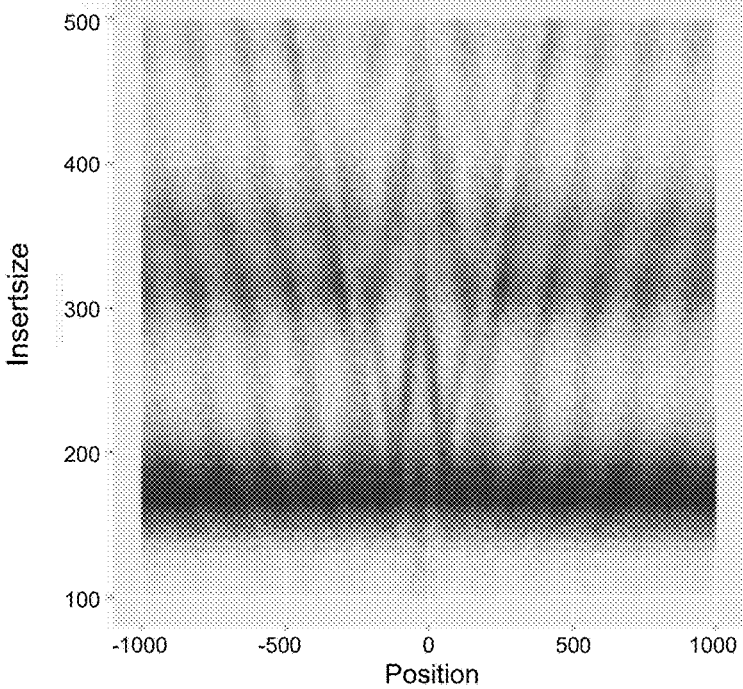
Figures 6D, 6E, 6F:
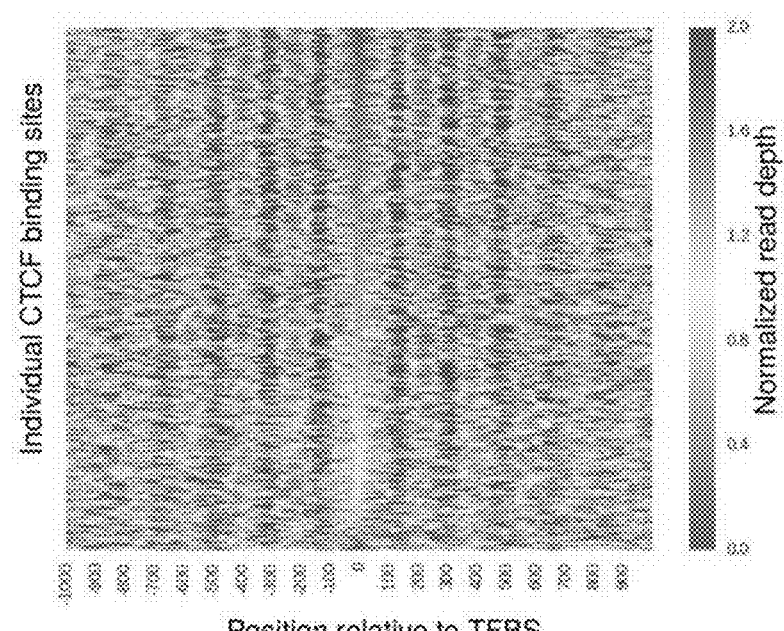
Figures 6G, 6H, 6I:
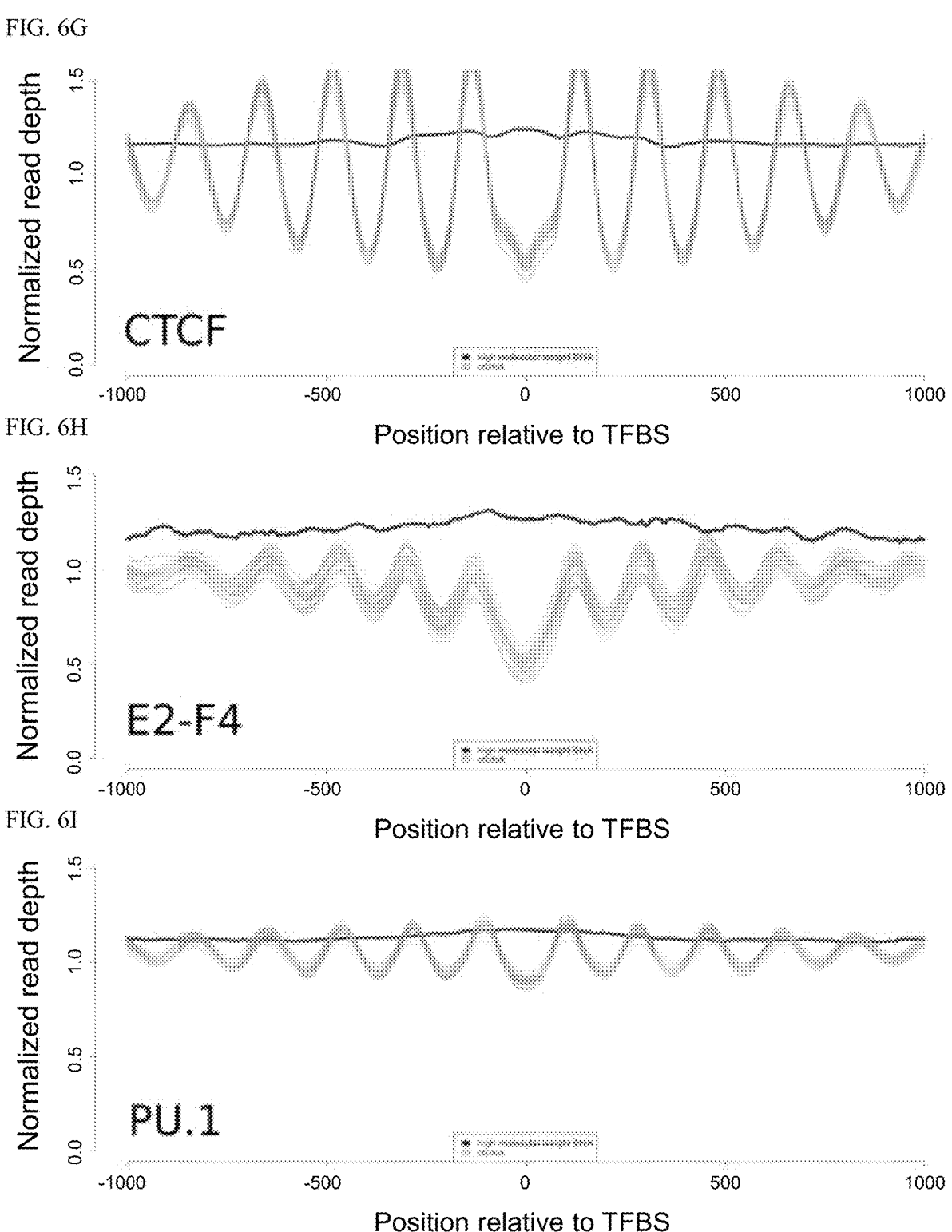
Figures 6J, 6K, 6L:
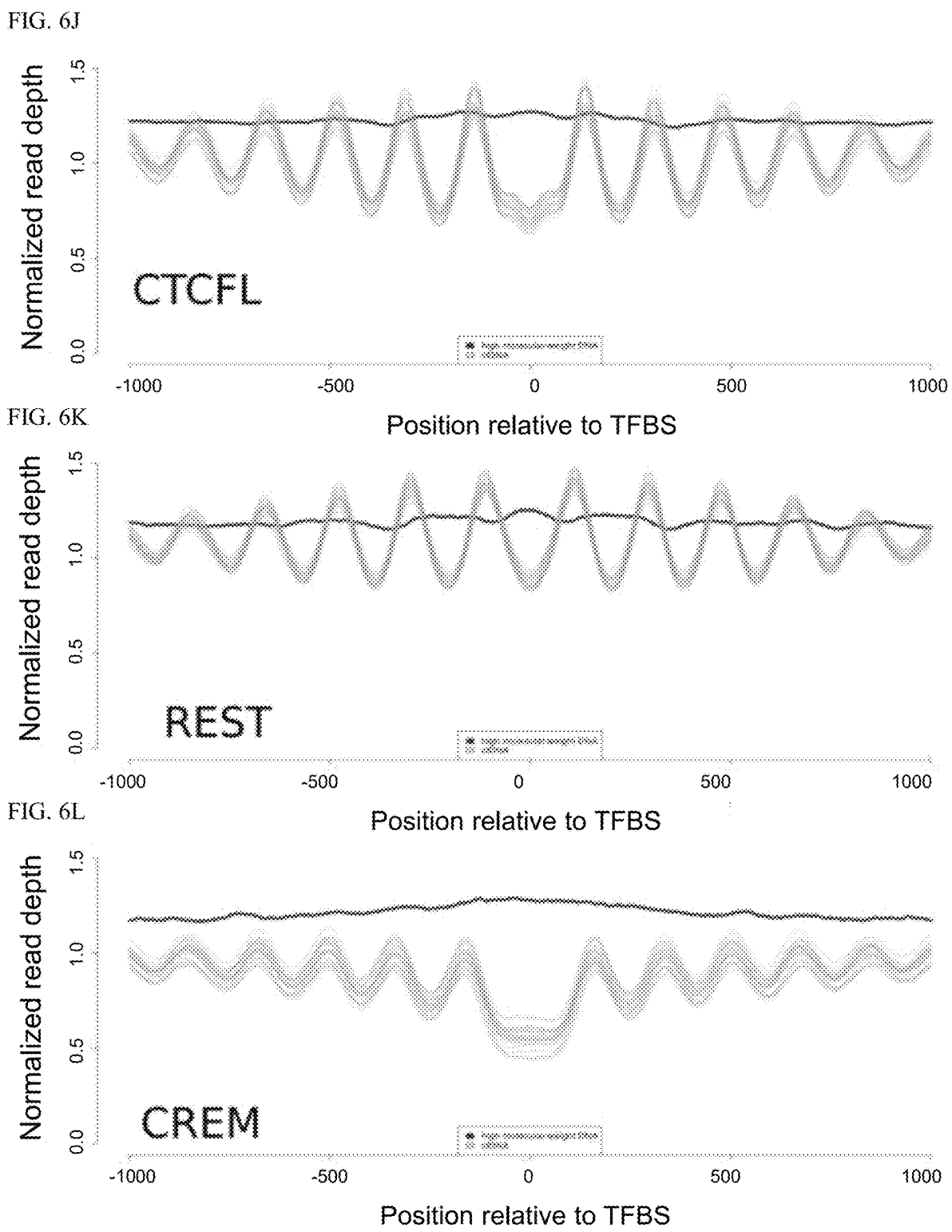
Figure 7A:
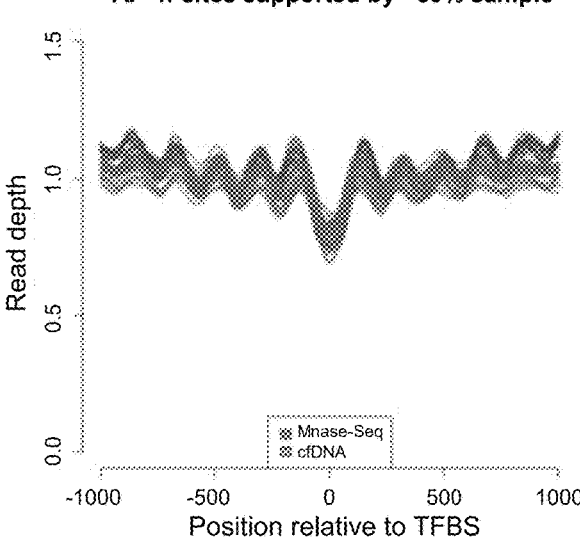
FIGS. 7A-7JJ show TF-nucleosome interaction maps for various TFs. Additional comparisons between coverage profiles of cfDNA and MNase-seq around transcription factor binding sites are shown.
Figure 7B:
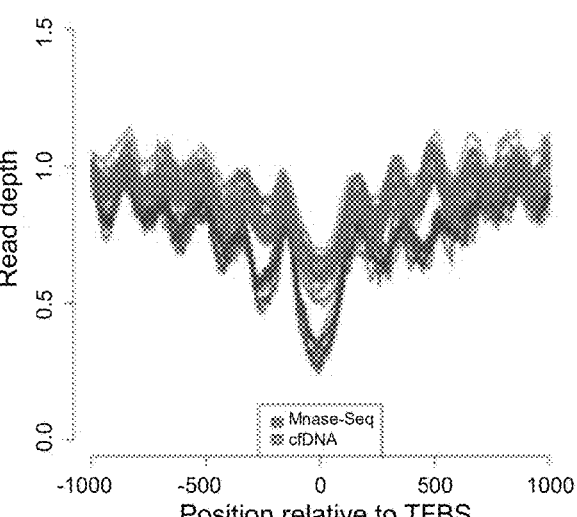
Figure 7C:
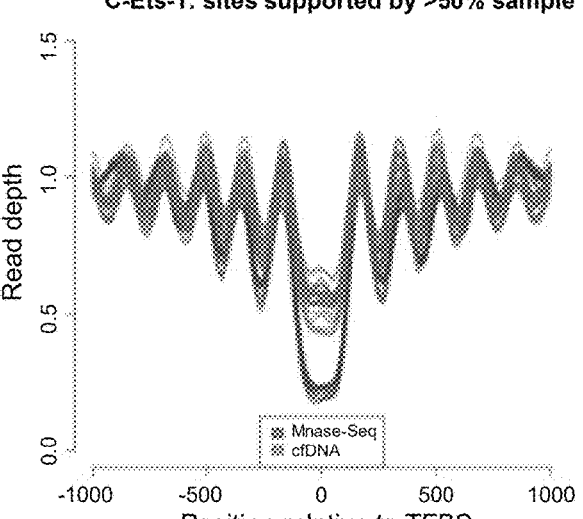
Figure 7D:
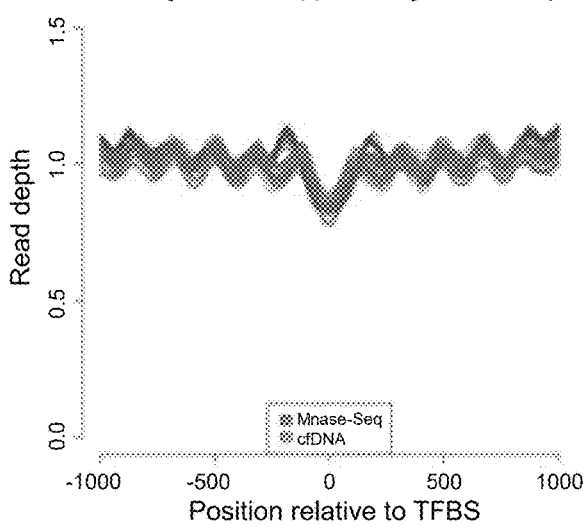
Figure 7E:
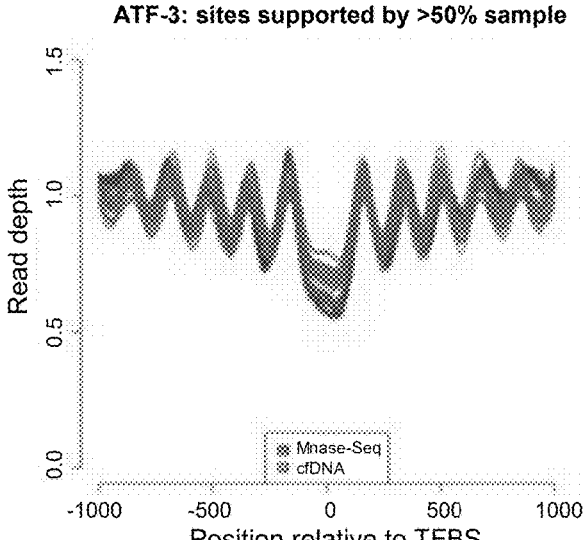
Figure 7F:
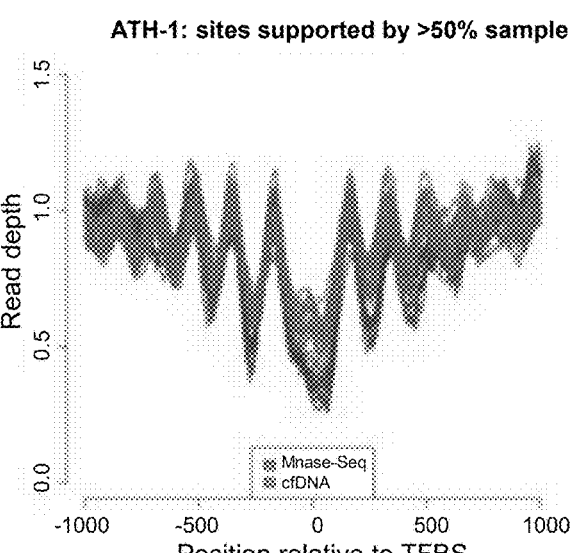
Figure 7G:
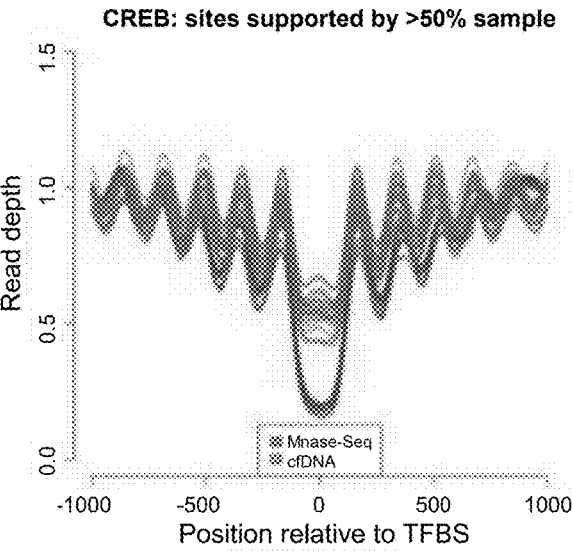
Figure 7H:
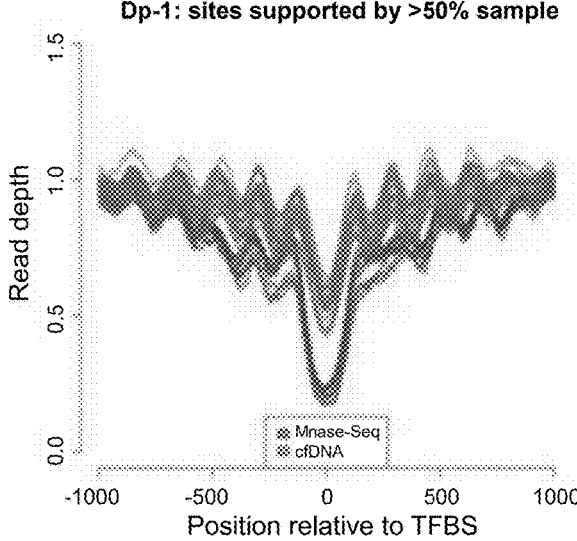
Figure 7M:
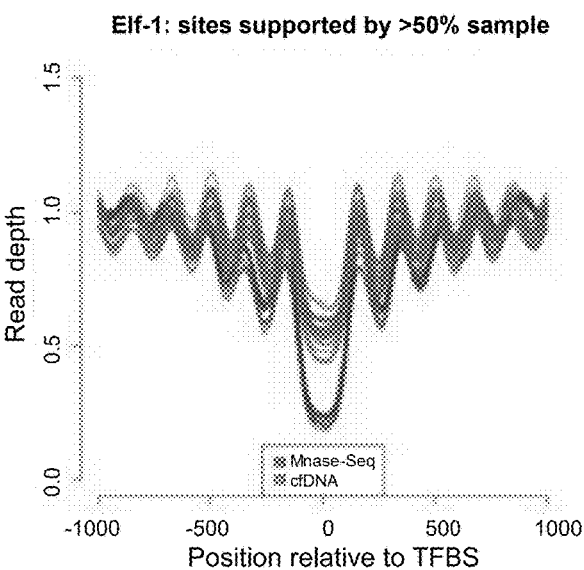
Figure 7N:
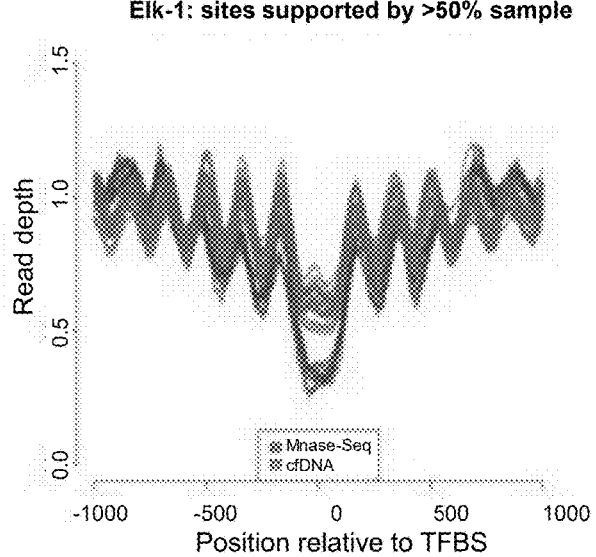
Figure 7O:
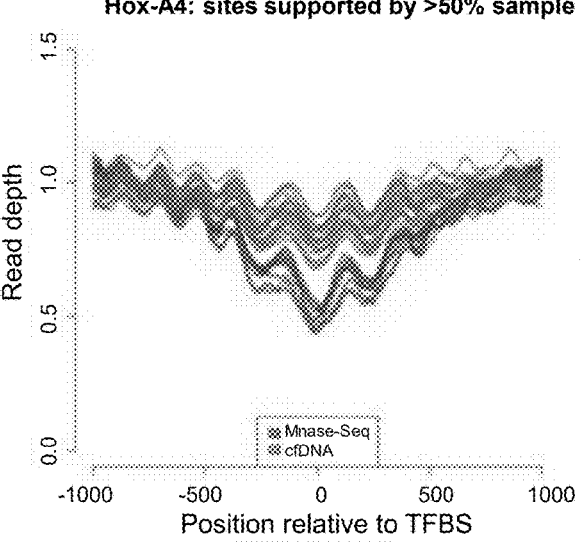
Figure 7P:
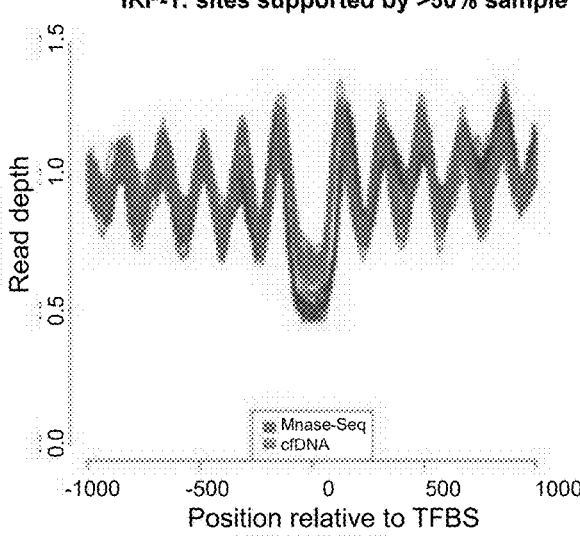
Figure 7Q:
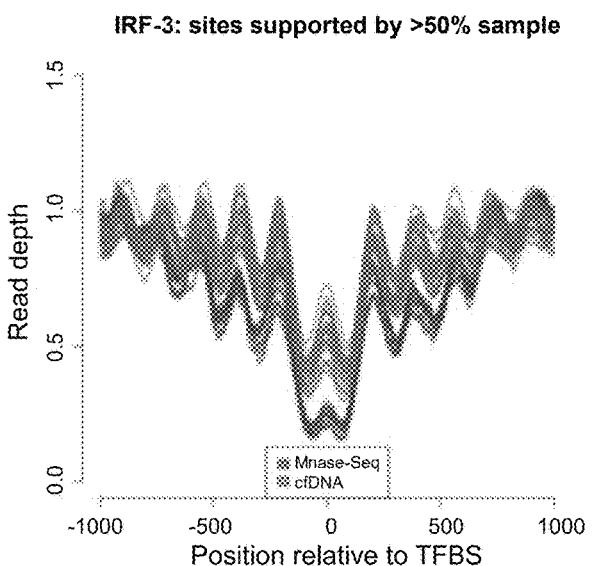
Figure 7R:
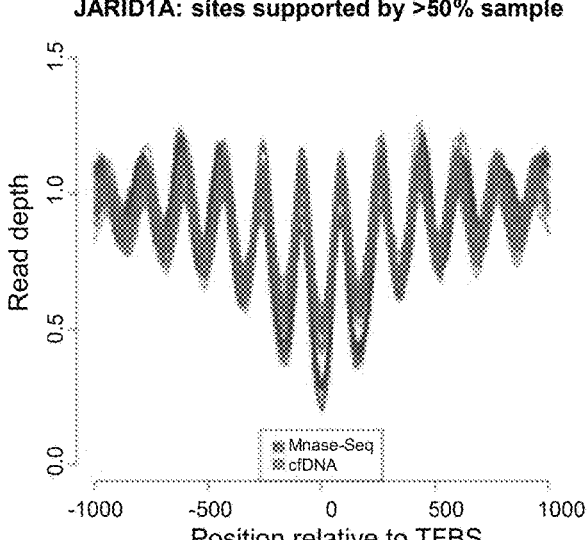
Figure 7S:
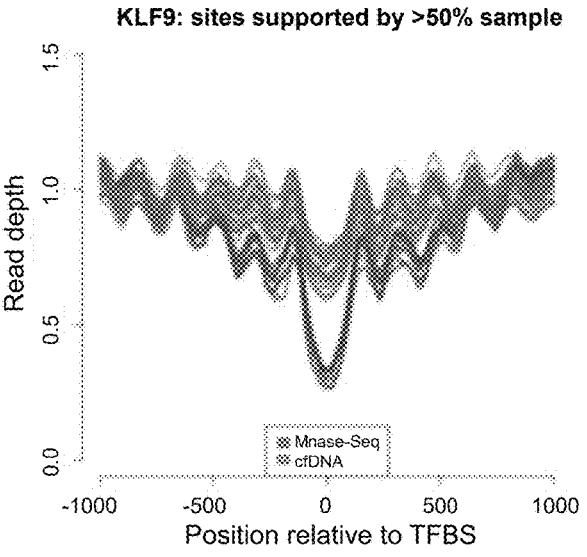
Figure 7T:
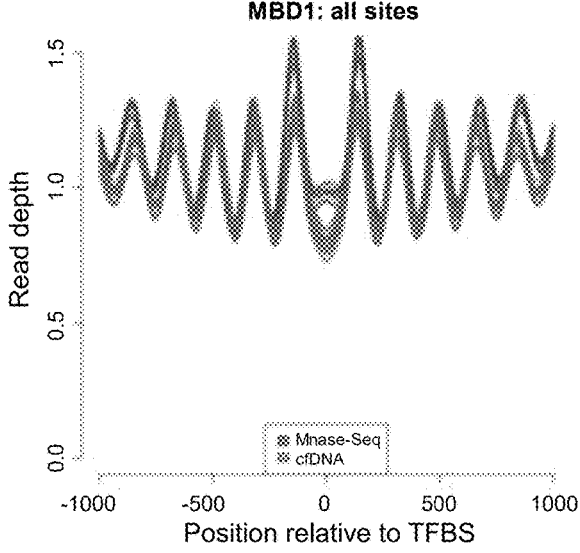
Figure 7U:
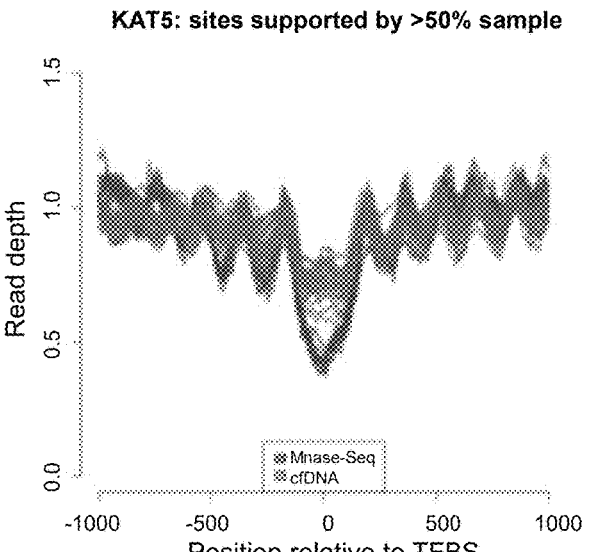
Figure 7V:
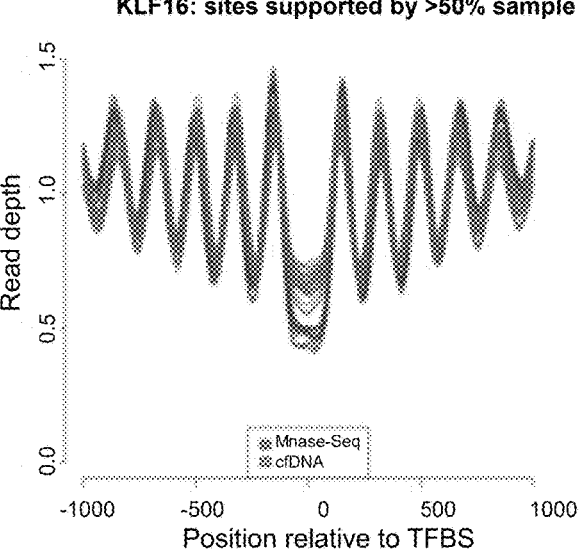
Figure 7W:
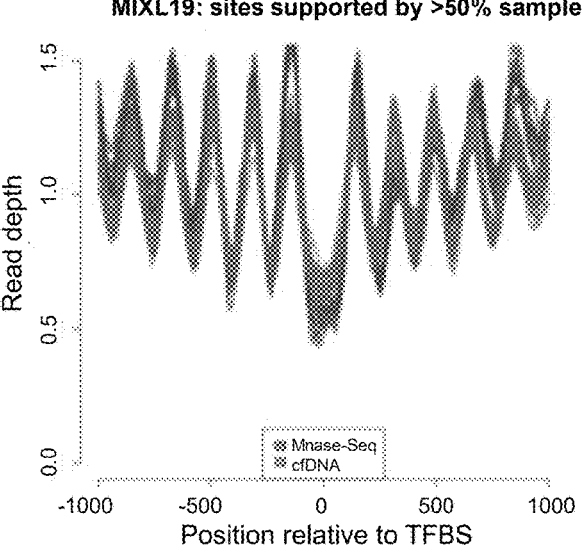
Figure 7X:
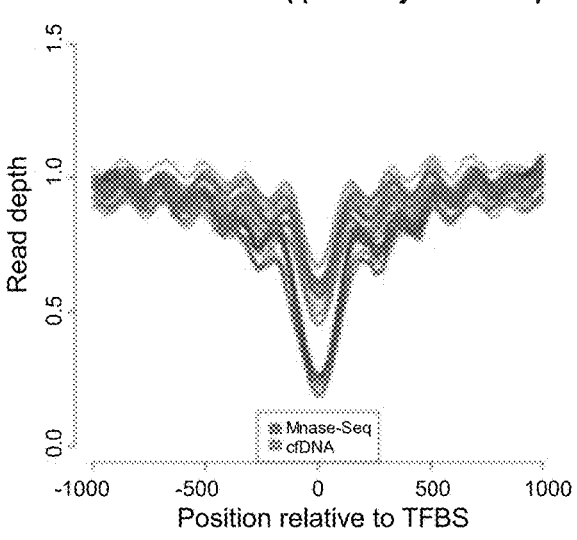
Figure 7Y:
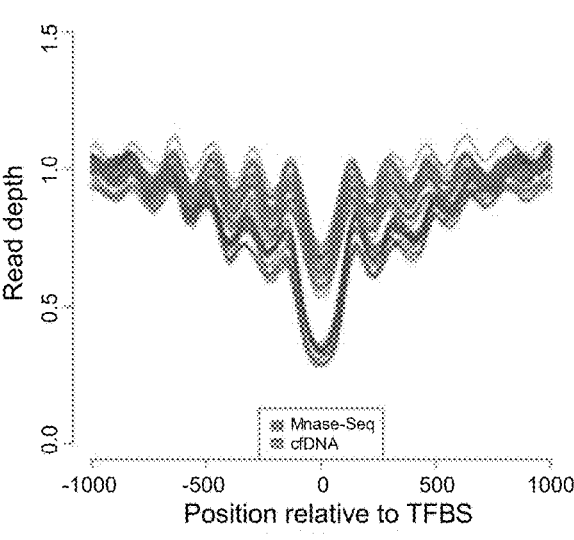
Figure 7Z:
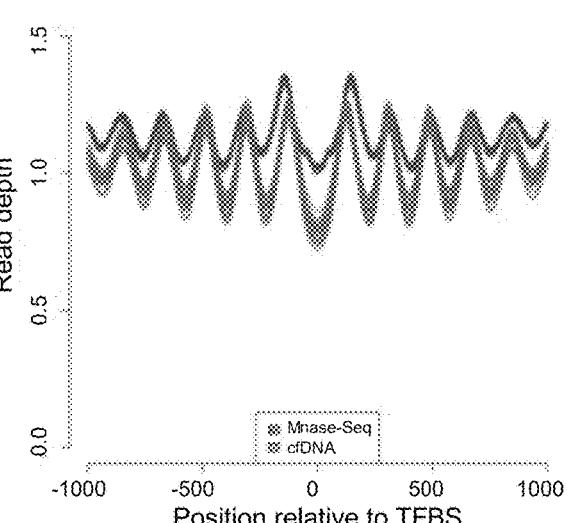
Figure 7A:
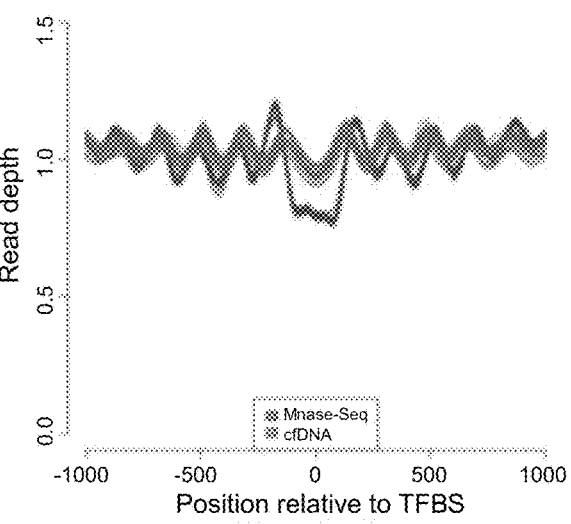
Figure 7B:
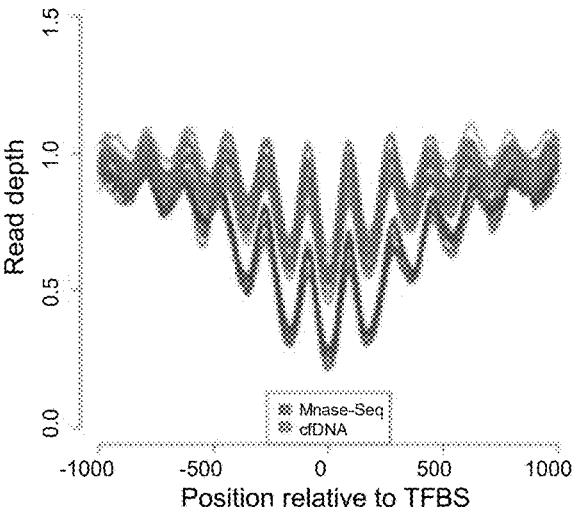
Figure 7C:
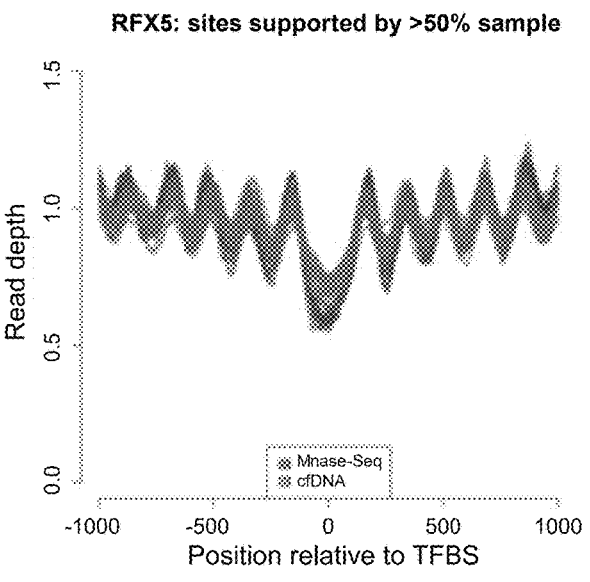
Figure 7D:
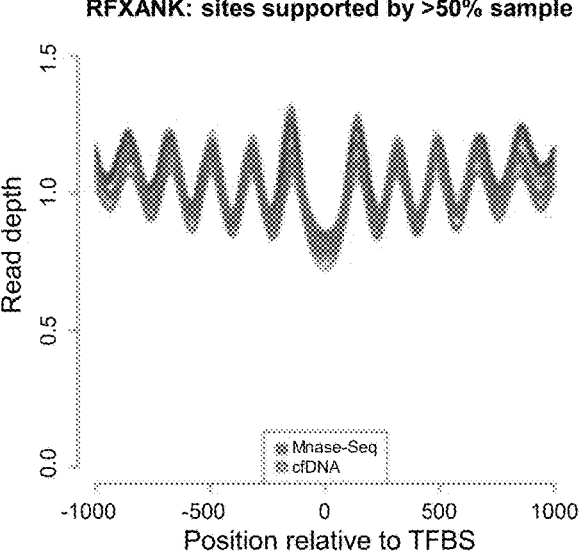
Figure 7E:
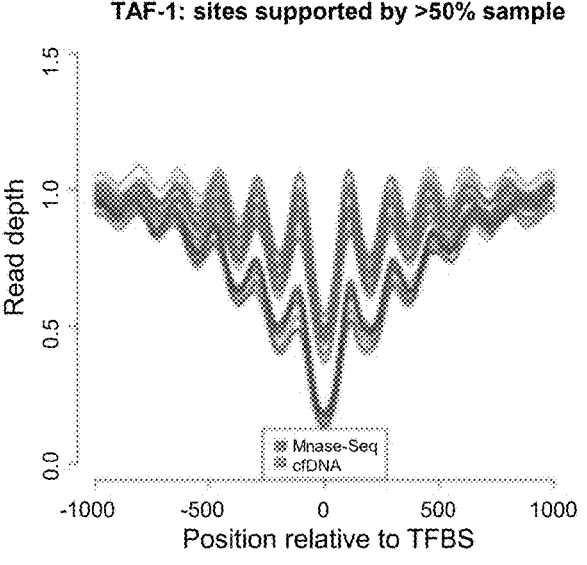
Figure 7F:
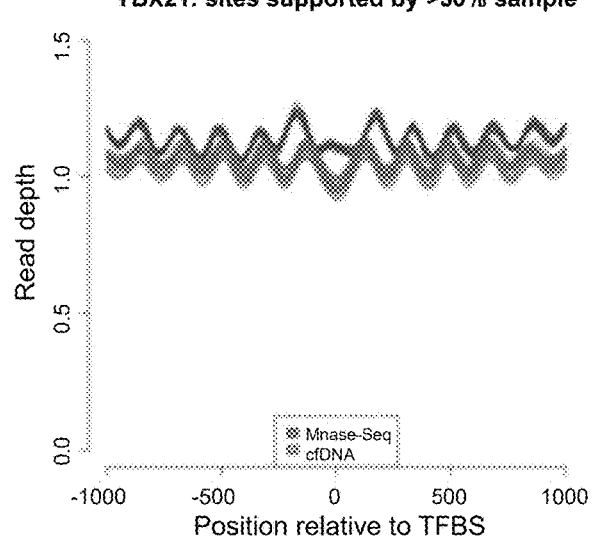
Figure 8A:
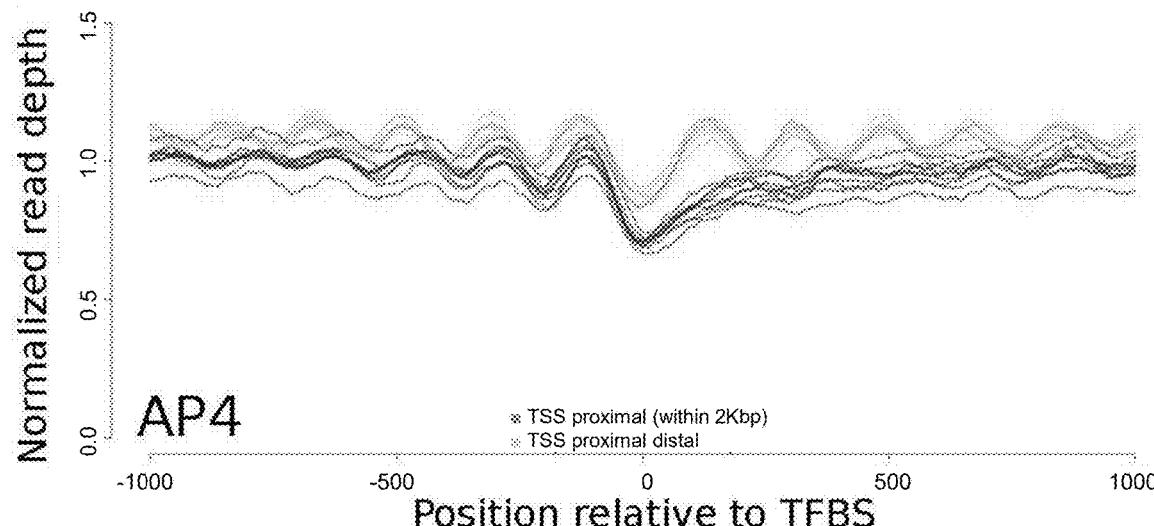
FIGS. 8A-8R show the shape of TFBSs.
Figure 8B:
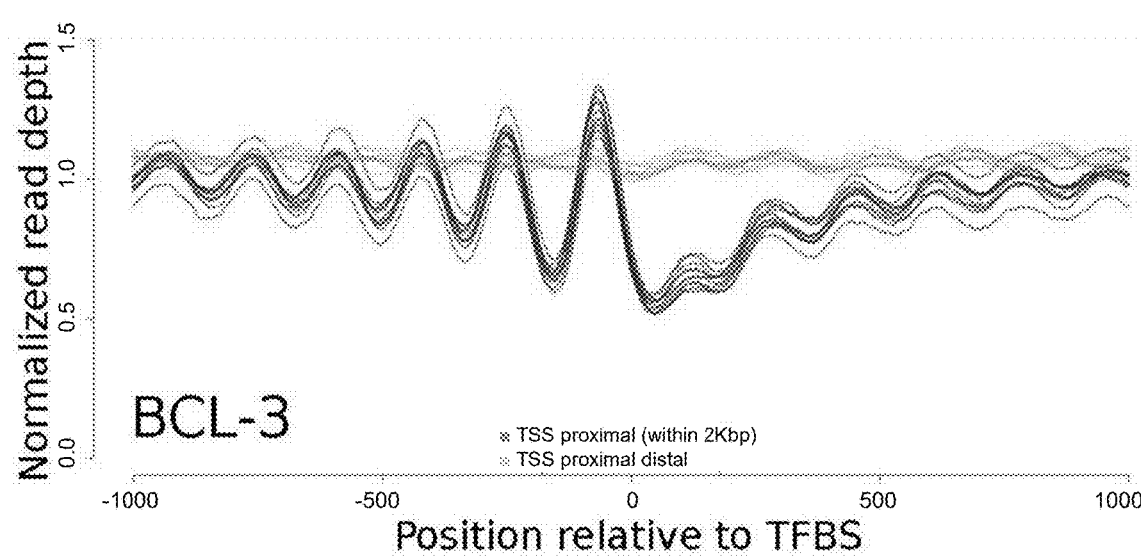
Figure 8C:
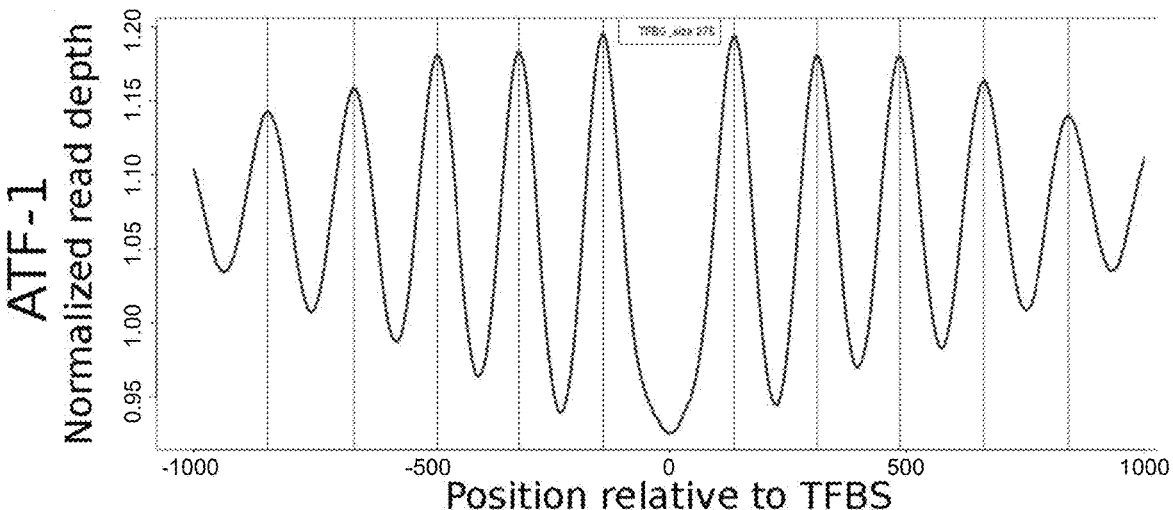
FIGS. 8C-8J show analyses of TFBSs for TFs ATF1 in FIGS. 8C and 8D, CREB in FIGS. 8E and 8F, CREM in FIGS. 8G and 8H, and ATF-3 in FIGS. 8I and 8J may result in evenly spaced or in TSS-like coverage patterns, dependent on whether all tissues in the GTRD were included or whether, more strictly, only those peaks that are supported by more than 50% of the maximum number of samples (>50%-TFBSs) were included.
Figure 8D:
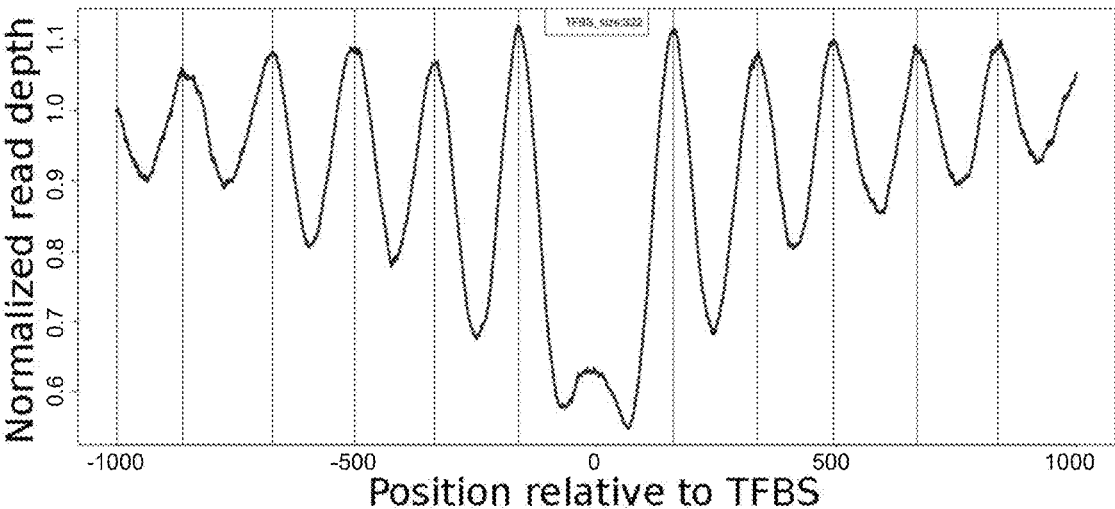
Figure 8E:
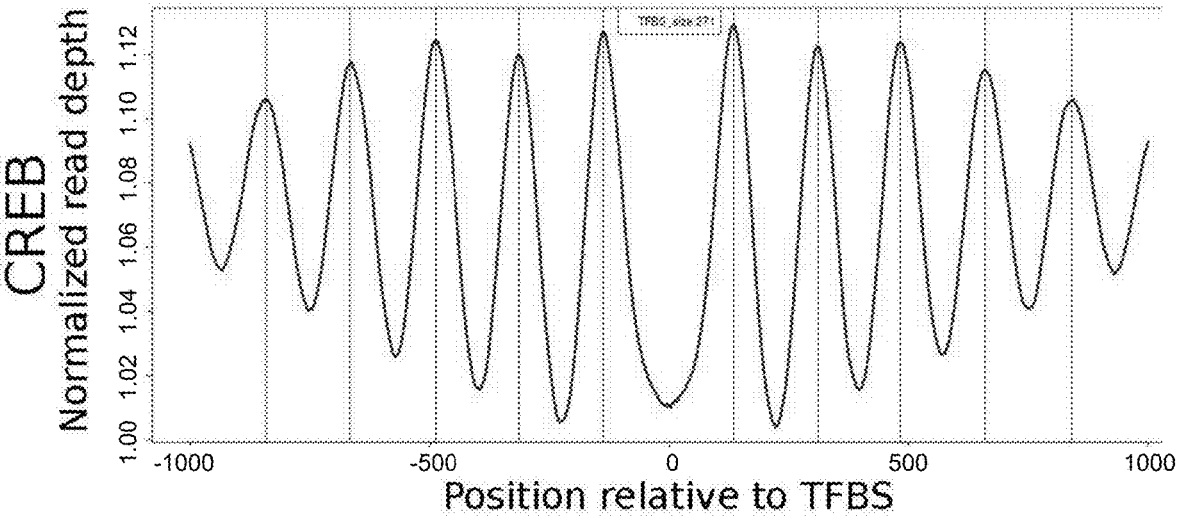
Figure 8F:
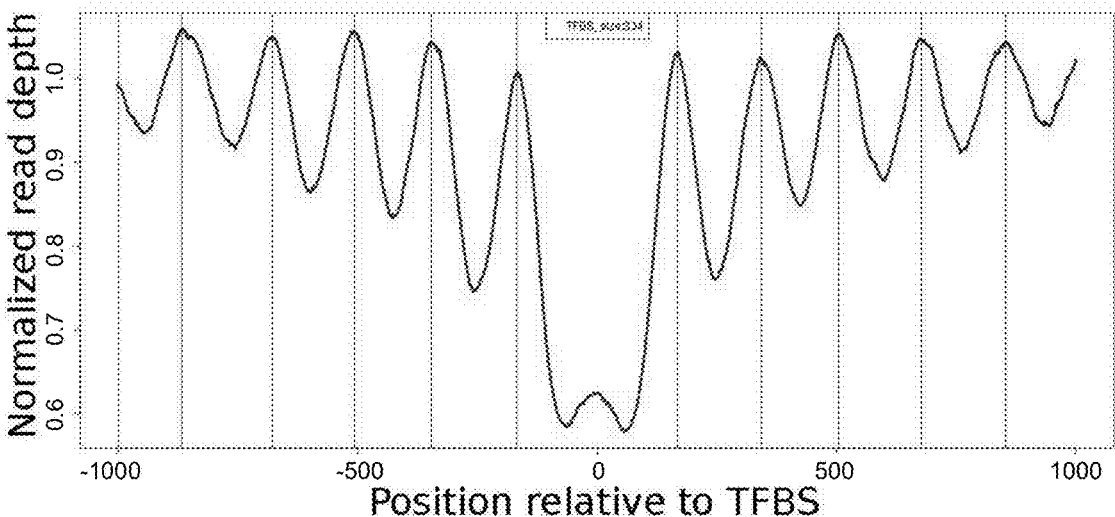
Figure 8G:
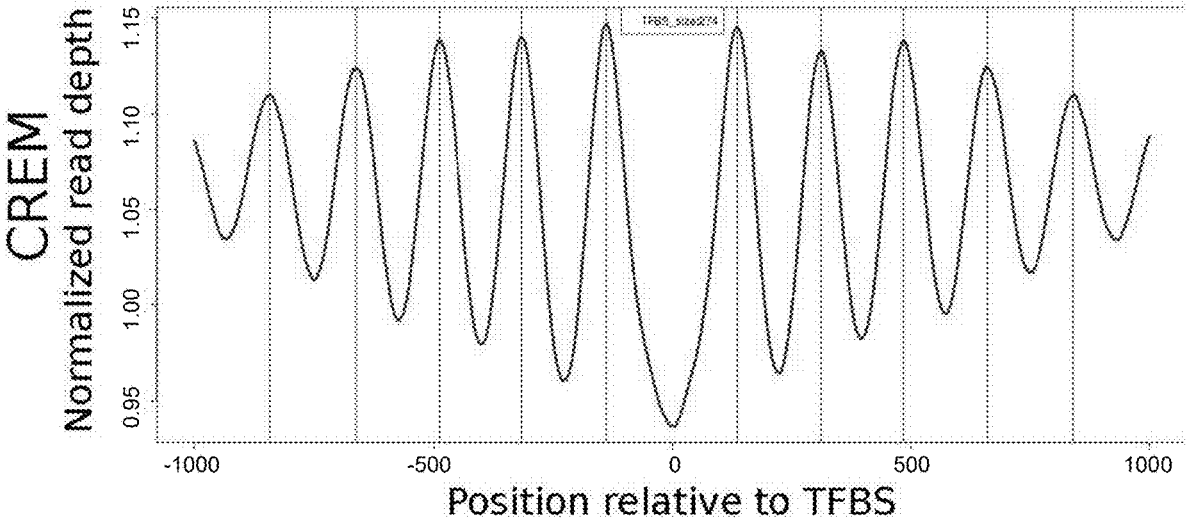
Figure 8H:
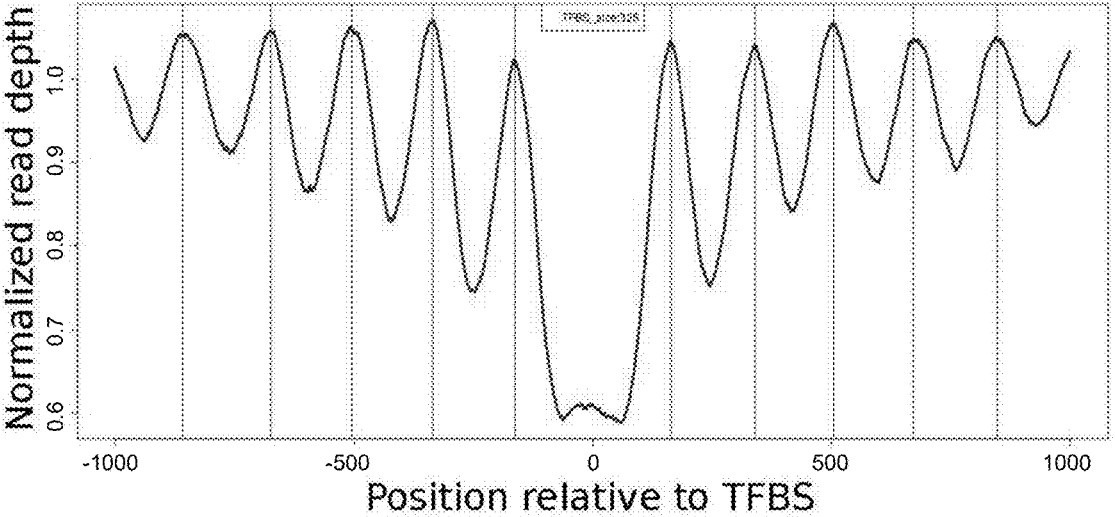
Figure 8I:
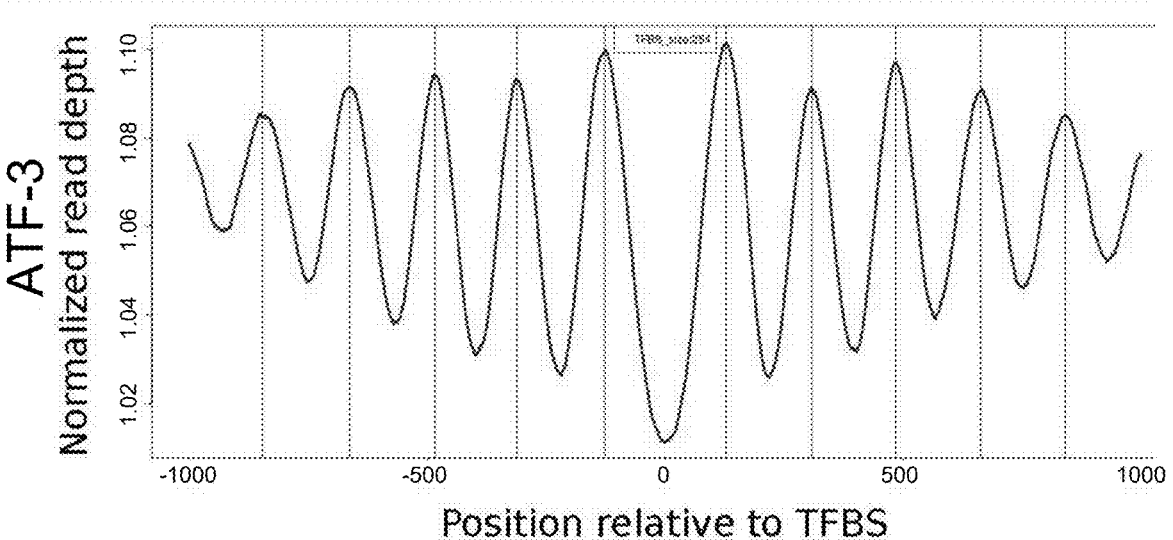
Figure 8J:
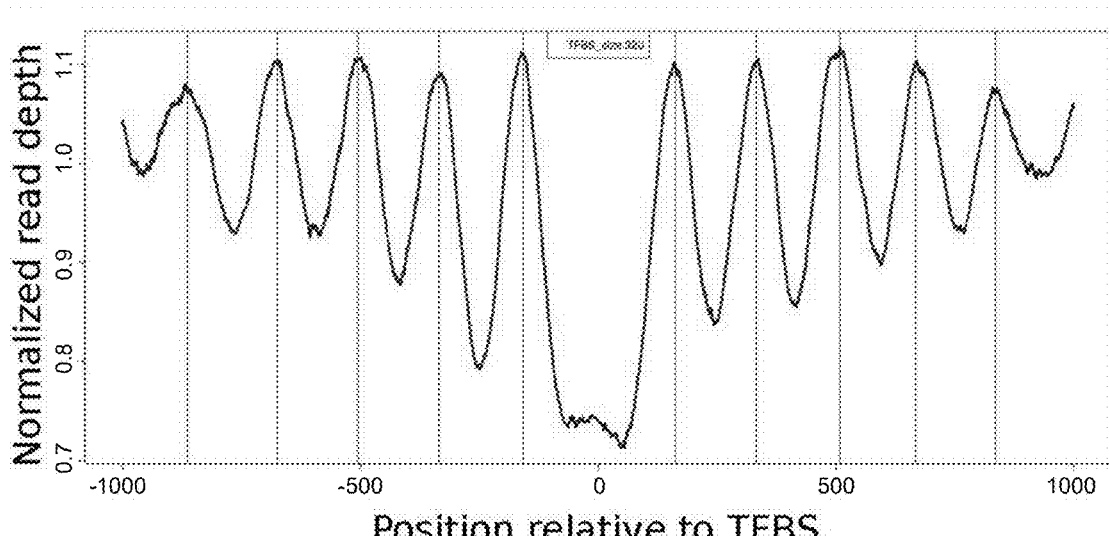
Figure 8K:
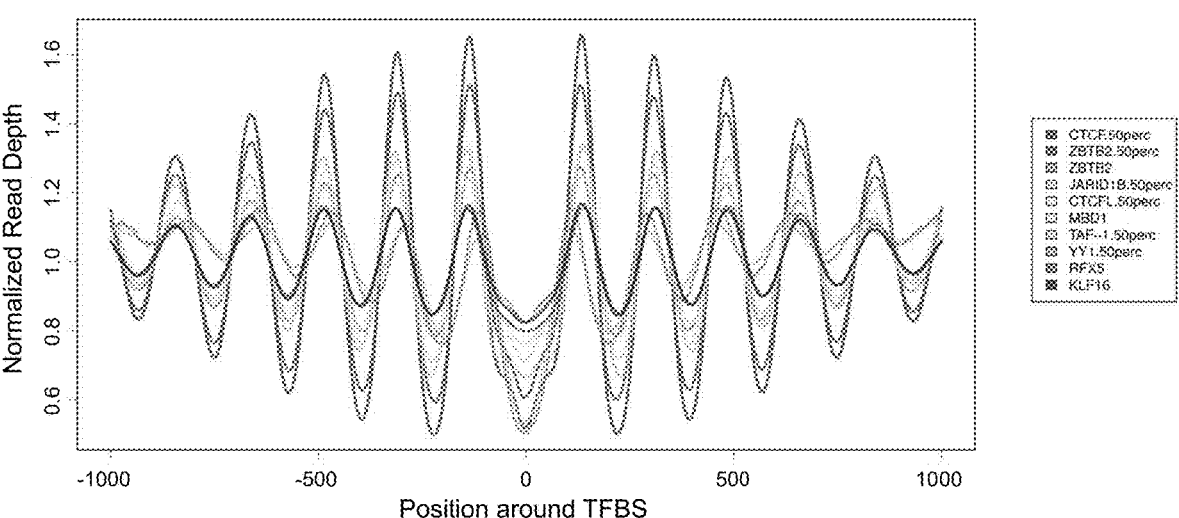
FIGS. 8K and 8L show examples of TF-nucleosome profiles calculated for all and >50%-TFBS (FIG. 8K) and for 1,000-msTFBSs (FIG. 8L), illustrating the variable nucleosome patterns of different TFs in cfDNA.
Figure 8L:
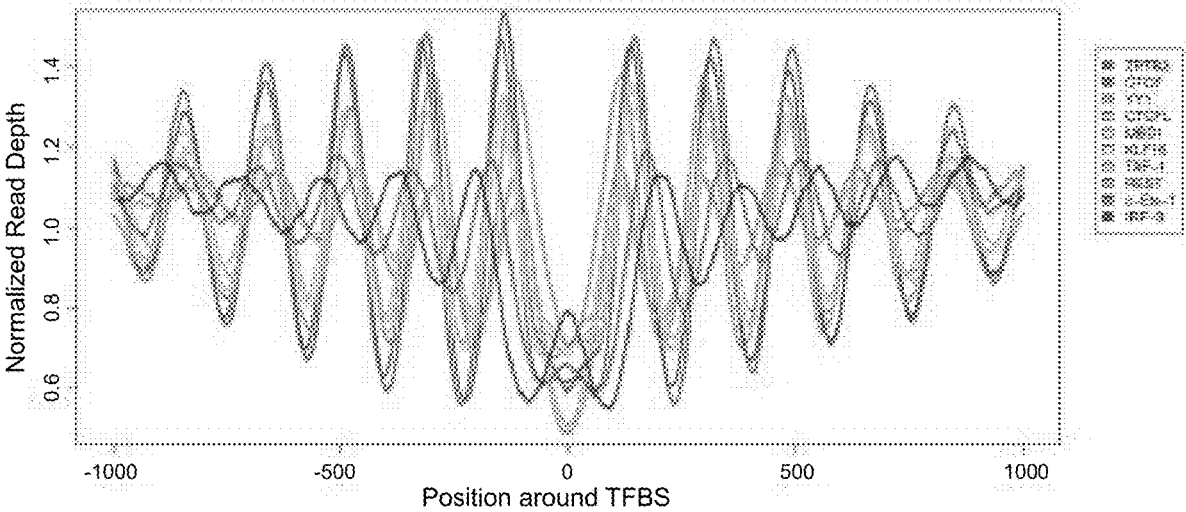
Figure 8M:
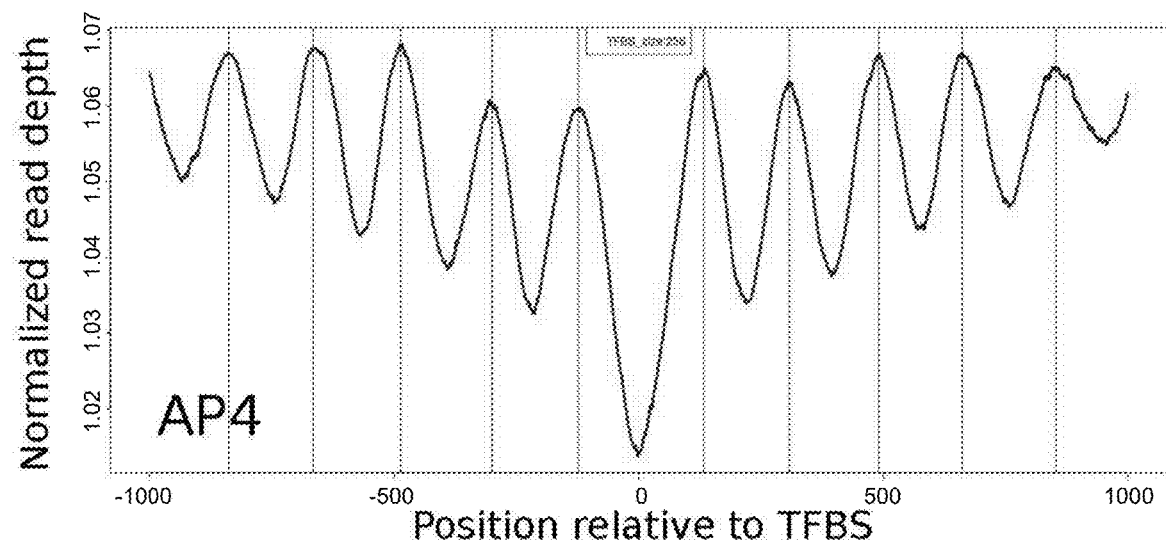
FIGS. 8M-8P show that measurements of TFBS widths revealed substantial differences among various TFBSs.
Figure 8N:
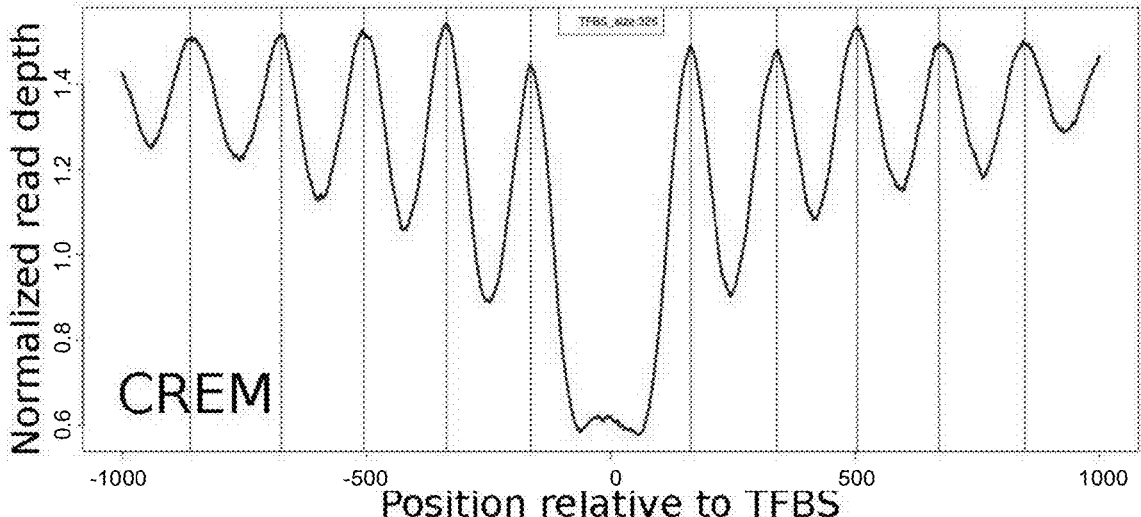
Figure 8O:
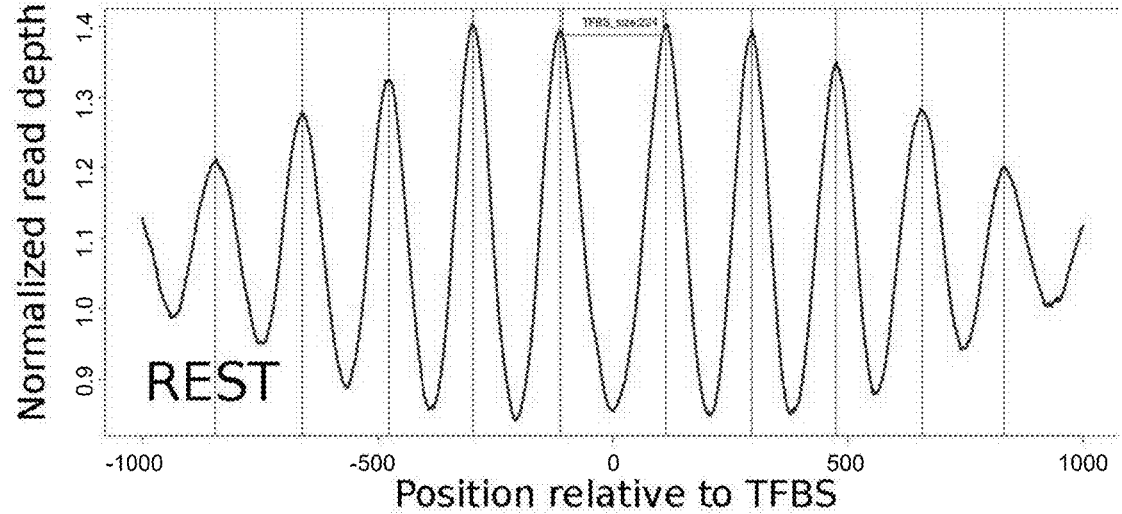
Figure 8P:
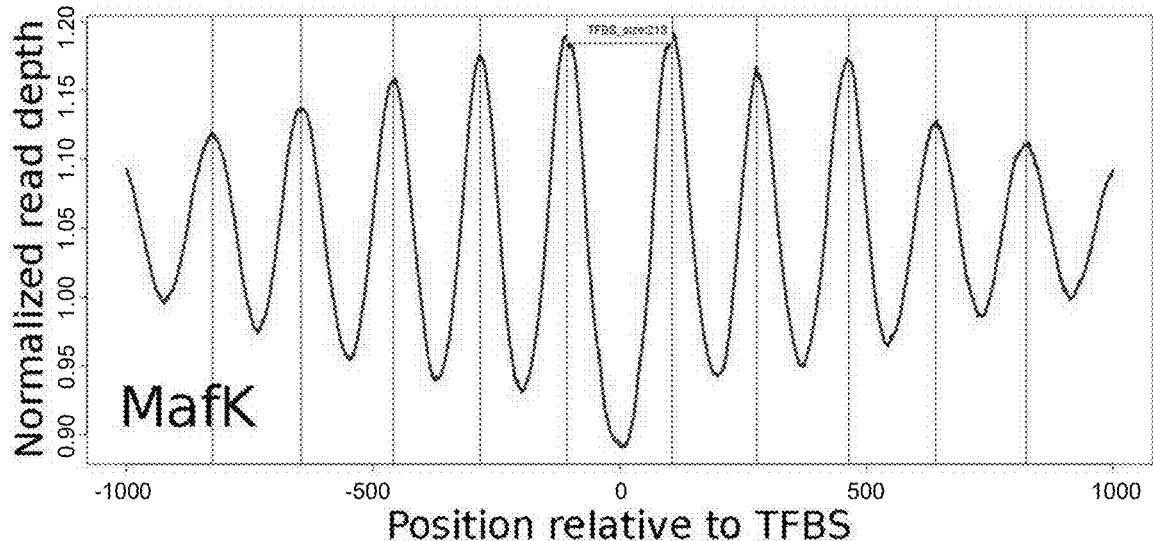
Figure 8Q:
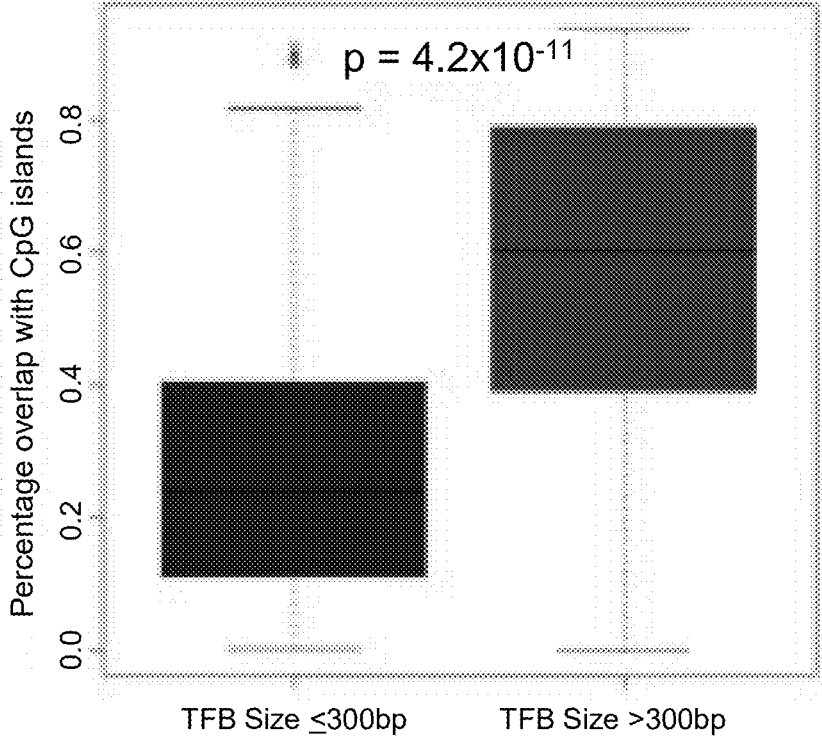
Figure 8R:
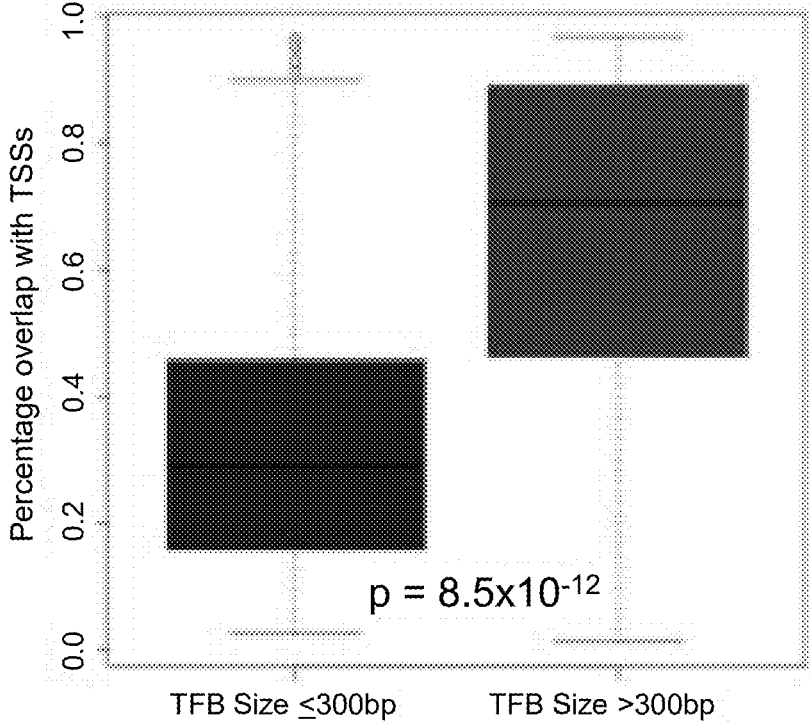
Figure 9A:
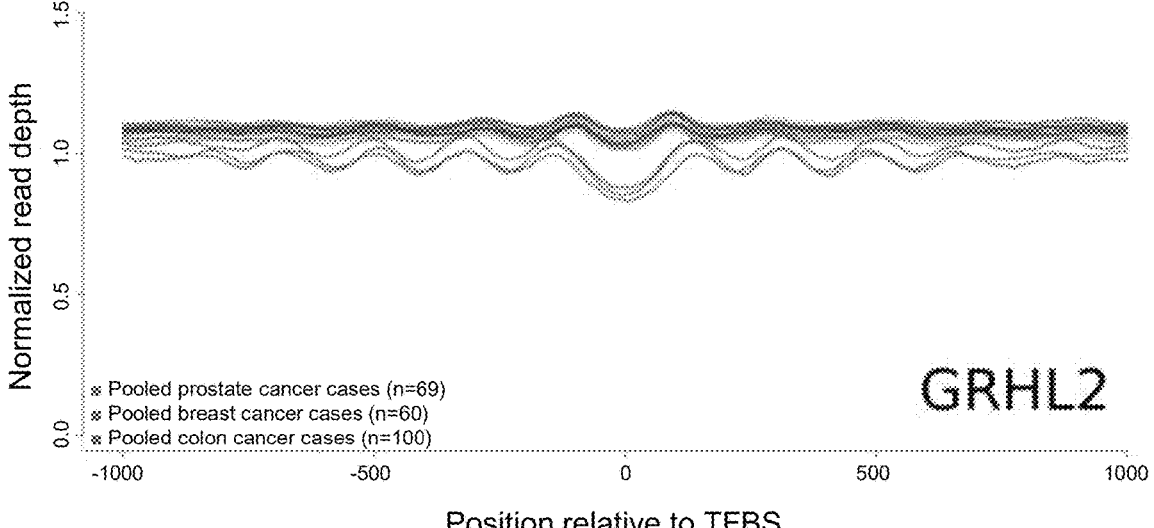
FIGS. 9A-9G show analyses of pooled shallow-coverage cfDNA. Accessibility is shown for pooled cfDNA samples from prostate (n=69), colon (n=100), and breast (n=60) cancer cases of the epithelial TF GRHL2 in FIG. 9A and of hematopoietic TFs (PU.1 in FIG. 9B. LYL1 in FIG. 9C, and SPIB in FIG. 9D). Accessibility is also shown within the prostate cancer cfDNA pool of the lineage-specific TFs AR in FIG. 9E, HOXB13 in FIG. 9F, and NKX3-1 in FIG. 9G.
Figure 9B:
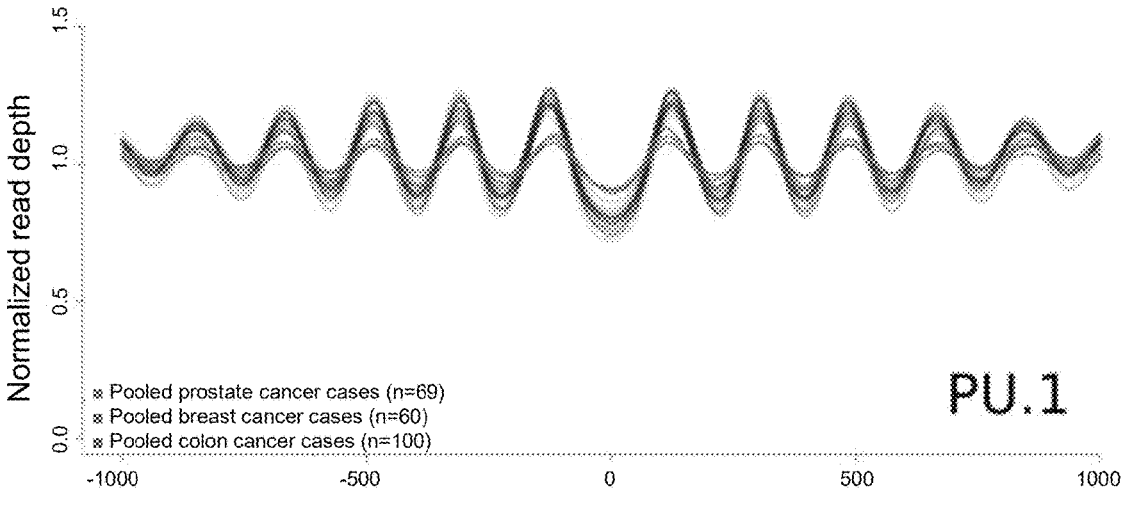
Figure 9C:
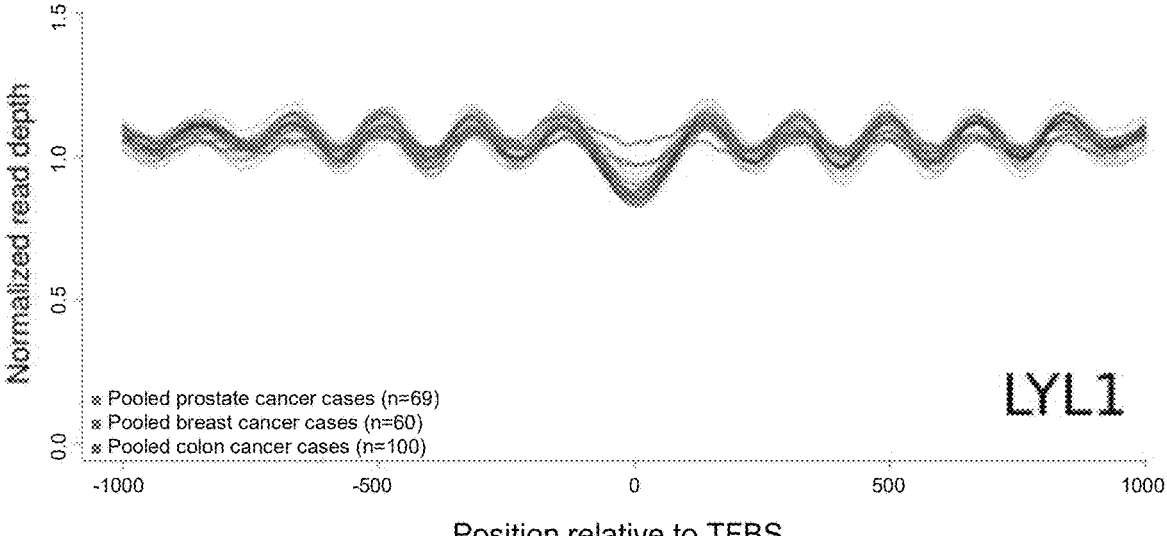
Figure 9D:
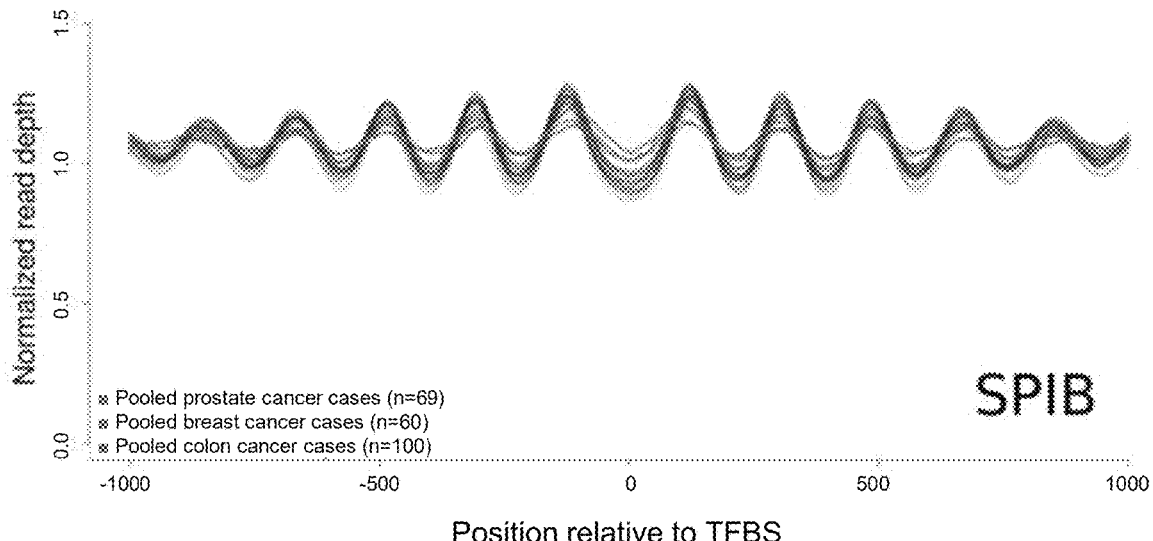
Figure 9E:
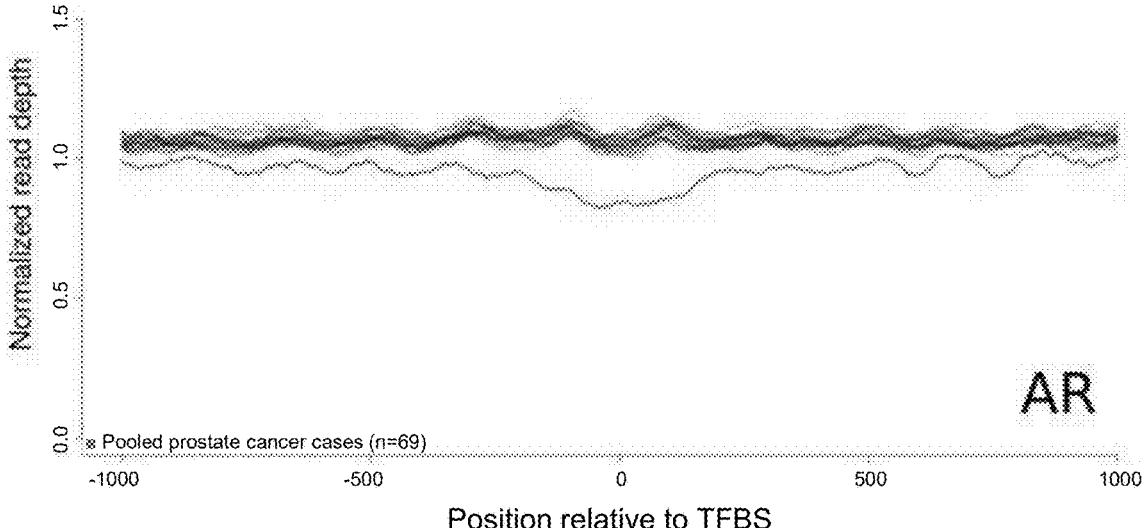
Figure 9F:
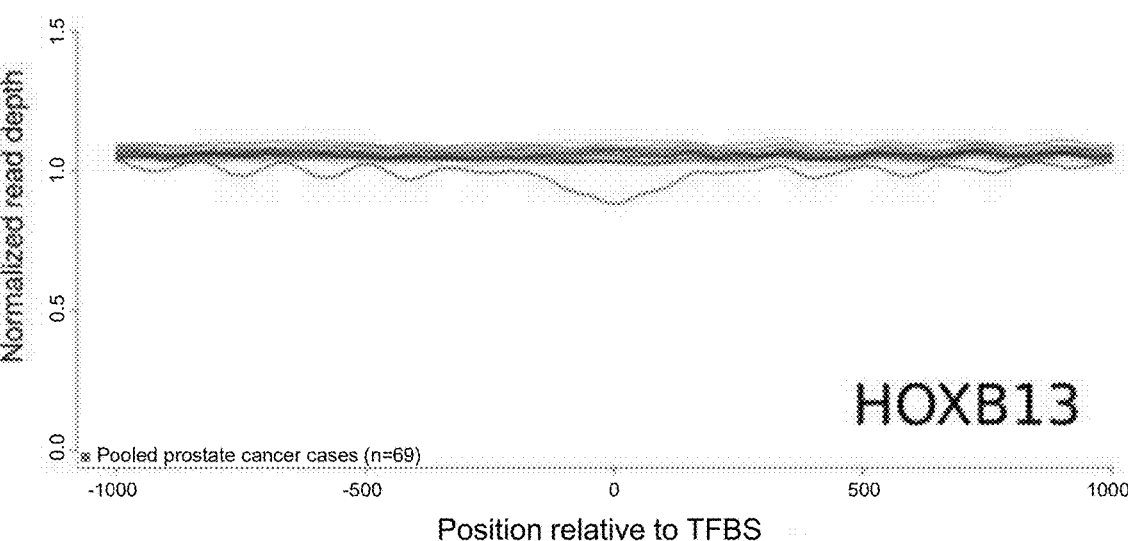
Figure 9G:
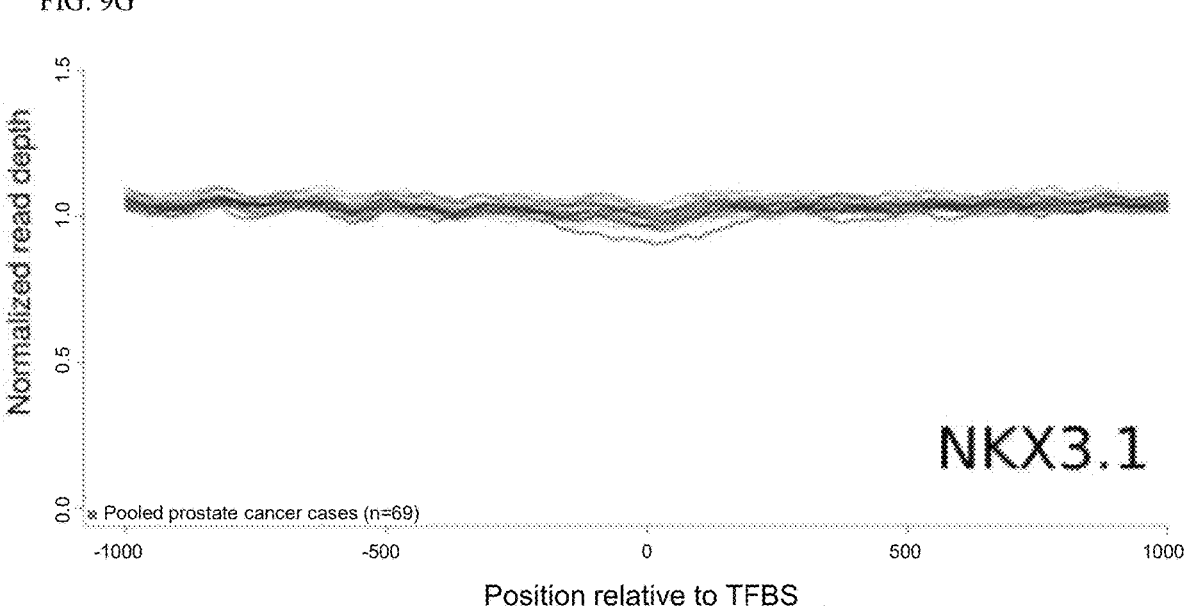

Samples of 24 cfDNAs from healthy controls were used, obtaining a mean of 435,135,450 (range: 352,904,231-556, 303,420) sequencing reads per sample. TF binding sites were often flanked by an array of strongly positioned nucleosomes, visible as a periodic oscillatory pattern (FIGS. 6A-6L). In contrast, a negative control normal, high-molecular weight DNA was used to observe an even coverage over TFBSs (FIGS. 8A-8R). CTCF binding sites, which are surrounded by arrays of strongly positioned nucleosomes, yielded oscillating coverage patterns that remained similar throughout all analyzed samples, regardless of whether the cfDNA was derived from healthy controls or from patients with cancer (FIGS. 2C and 2D). These results were consistent with DNase hypersensitivity assays from the Encyclopedia of DNA Elements (ENCODE) database for cell lines GM12878 (B-lymphocyte cell line from a female donor with European ancestry). LNCaP (androgen-sensitive human prostate adenocarcinoma cell line), and HCT116 (human colon cancer cell line) (FIGS. 2C and 2D).

ctDNA in plasma from patients with cancer altered the balance between DNA from hematopoietic versus epithelial cells compared to the healthy controls, for example, resulting in the cancer-derived samples in decreased amplitudes for the lineage-restricted hematopoietic TFs purine-rich box1 (PU.1 in FIGS. 2E and 2F). LYL1 (lymphoblastic leukemia 1) in FIGS. 2G and 2H, and the lymphocyte lineage-restricted transcription factor SPIB in FIGS. 2I and 2J and an increased amplitude for TF GRHL2, a pioneer TF for epithelial cells (FIGS. 2K and 2L). It is also confirmed that the lineage-specificity of these TFs with data of publicly available DNase hypersensitivity assays (FIGS. 2D, 2F, 2H, 2J, 2L, and 2N). As another example for a well-established TF, FOXA1, which cooperates with nuclear hormone receptors in endocrine-driven tumors of the breast and prostate, was analyzed. Consistent with DNase hypersensitivity assays, preferentially increased accessibility of FOXA1 in the plasma samples of prostate and breast cancer patients was observed as shown in FIGS. 2M and 2N. Comparisons with ENCODE data, where mononucleosome-bound DNA fragments were generated by micrococcal nuclease (MNase) digestion, were also conducted (FIGS. 6A-6L and 7A-7JJ). Coverage-independent analyses were performed (FIG. 6C), and spatial density of cfDNA fragments related to the single recognition sequences were computed (FIG. 6D). Sequence-specific TFs may have canonical motifs and significant secondary motifs, which may correspond to those of other TFs. Catalogs of TFBSs were also generated, which may be affected by co-binding of more than one TF for all 676 TFs and the 505 TTFs from the 1,000-msTFBSs (FIGS. 6E and 6F). Furthermore, using purified, high molecular weight DNA as a negative control, an even coverage was observed over TFBSs (FIGS. 6G-6L). Accordingly, these results showed that the corresponding TFBS coverage profiles closely resembled each other, thereby demonstrating a high accuracy of the approach and that the obtained patterns for any given TF are reproducible throughout all samples.

Figure 27A:
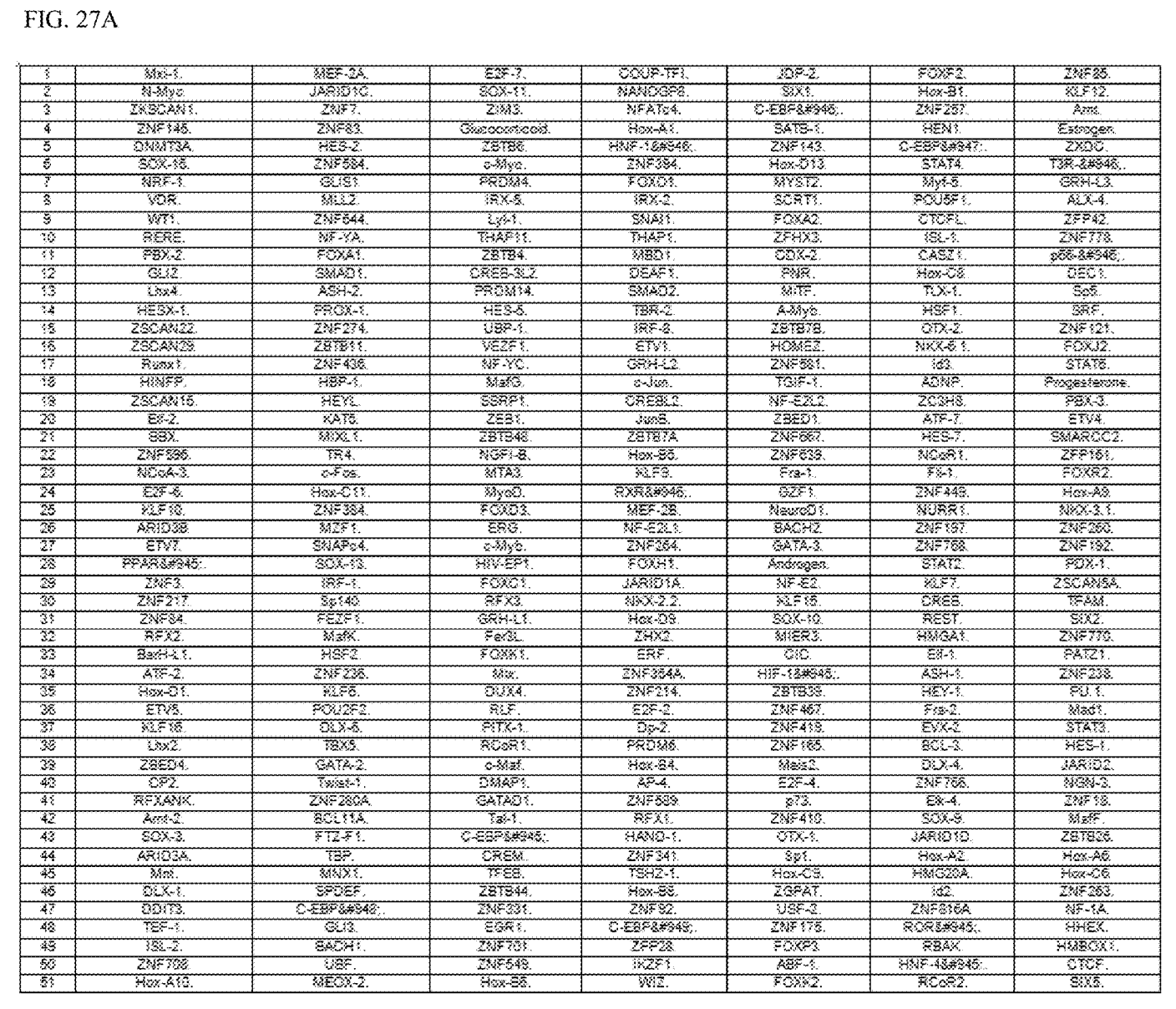
Figure 27B:
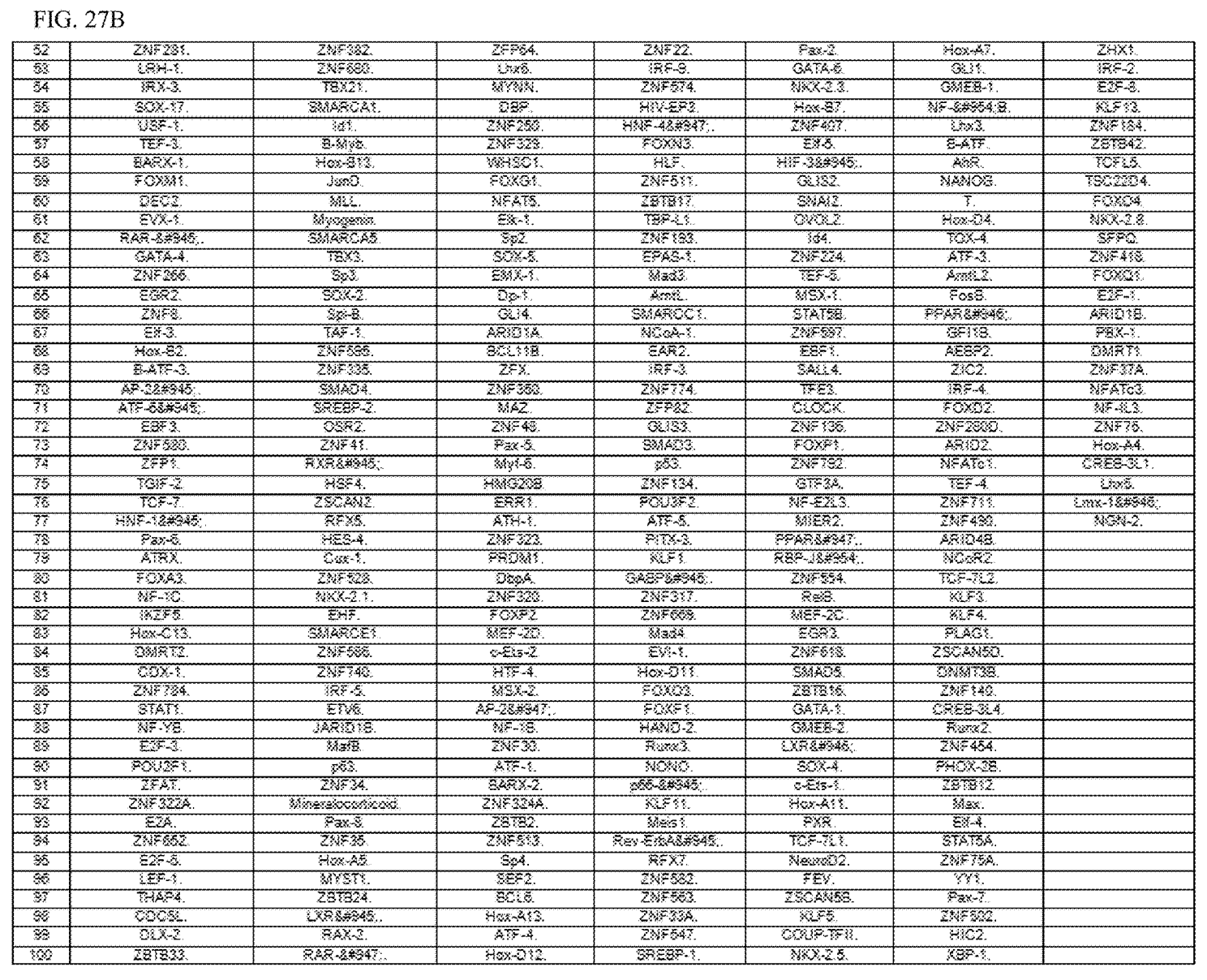

As sequence-specific TFs may have canonical motifs and significant secondary motifs, which may correspond to those of other TFs, overlaps were calculated between various TFBSs (FIGS. 6E and 6F). A list of TFBSs was generated, which may be affected by co-binding of more than one TF (FIGS. 27A and 27B). An example for the effects of such overlaps are the TFs SP1, SP2, NF-YA, and NF-YB with overlap ranges between 10 to 36% where the TFBS-nucleosome profiles were indeed similar (FIGS. 13A-13D). The predominant origin of cfDNA from blood was particularly mirrored in the well positioned nucleosomes flanking the binding sites of lineage-restricted hematopoietic TFs, such as purine-rich box1 (PU.1), LYL1 (lymphoblastic leukemia 1), and the lymphocyte lineage-restricted transcription factor SPI-B (FIGS. 13A-13D). In contrast, the TFBS profile of GRHL2, a pioneer TF for epithelial cells, showed substantially reduced amplitudes (FIGS. 13A-13D).

The CTCF binding sites were evaluated, which are surrounded by arrays of strongly positioned nucleosomes applying the aforementioned three different stringency criteria and observed the expected oscillating pattern preferentially for the >50%-TFBSs and 1,000-msTFBSs (FIGS. 2C-2N). Furthermore, CTCF was used to evaluate distinct binding sites separately (FIGS. 17A-17D) and as additional confirmation coverage independent analyses was conducted (FIGS. 17A-17D) and computed the spatial density of cfDNA fragments related to the single recognition sequences. The resulting heatmap showed that the nucleosome phasing in most analyzed sites is even, which is consistent with the coverage profiles.

FIGS. 7A-7JJ show TF-nucleosome interaction maps for various TFs. Additional comparisons between coverage profiles of cfDNA and MNase-seq around transcription factor binding sites are shown.

CTCF as Extraordinary Example for a TF with Multiple Different Binding Sites

To explore different TFBSs of the same TF, CCCTC-binding factor (CTCF) was used. CTCF is present at 55,000-65,000 binding sites in mammalian genomes. Of these sites, about 5,000 are ultraconserved, about 50% are in intergenic regions, about 15% are located near promoters, and about 40% are intragenic. Furthermore, chromosomes are partitioned into evolutionary conserved higher-order chromosome structures, named topologically associating domains (TADs), and their boundaries are enriched for binding sites of CTCF and cohesin. In mammals, 15% of genomic CTCF-binding sites are present at TAD borders, whereas the other 85% are inside TADs.

CTCF sites that overlap or are outside of TAD boundaries were separately analyzed, in proximity (e.g., within about 2 kbp) or distal (more than 2 kbp) to TSSs, as well as ultra-conserved sites. Analysis was conducted with all tissue types in the GTRD, and different CTCF coverage patterns were obtained, with ultraconserved CTCF sites having the largest amplitude (FIG. 14A). When the analyses were confined to those binding sites that were called in more than 50% of all samples in the GTRD, the resulting profiles became more similar to each other (FIG. 14B). As a coverage-independent confirmation of TFBS signals, the length of each cfDNA fragment was plotted as a function of the distance of the fragment midpoint to the CTCF binding site. The resulting heatmap confirmed the signal periodicity consistent with the coverage-based oscillating pattern (FIG. 6C). In addition, to analyze more closely the landscape of fragments related to the single recognition sequences, the spatial density of cfDNA fragments was computed within a 2 kb region centered on the TFBSs, and the sites were ranked according to the coverage of the central 40 bp. The resulting heatmap showed that nucleosome phasing in most sites analyzed is even (FIG. 6D), which is again consistent with the coverage profiles.

The "Accessibility Score" Enables Accurate Inference of TF Binding from cfDNA

Binding sites, where nucleosomes are repositioned by intervening TF binding, ensure that the respective DNA is accessible to proteins and the transcription and replication machineries. Some TFs showed evenly spaced nucleosome peaks including their binding sites (e.g. PU.1 in FIG. 13E and GRHL2 in FIG. 13H), whereas other TFs had at their binding sites wider troughs (e.g. FIGS. 13A-13D) resembling those for TSSs. For the latter. TFs substantial binding site width differences were measured (FIGS. 8M-8P). This measurement identified 55 TFBSs where the TFBS exceeded 300 bp, of which 26 had binding sites close to di-nucleosomal sizes (312-352 bp) (FIGS. 28A-28B). To test whether these patterns are a side effect of binding to CpG island promoters, a plot was generated for the CpG density (boxplot) and the co-localization with CpG islands (bar chart/pie chart) for the 55 wide TFs vs. those with a narrowly defined binding site.

Certain lineage-specific TFs are suitable for determining the tissue-of-origin of plasma DNA. However, determining which TFs may be useful in such an application requires evaluating the accessibility of the TFs. e.g., at their binding sites in cfDNA. Conventional methods may not evaluate TF accessibility at their binding sites in cfDNA as a proxy for their activity. To implement such an approach. TF-specific nucleosome coverage profiles were investigated. Calculations were conducted separately for TFBSs within and outside of transcription start sites (TSSs) (FIGS. 8A and 8B) and for all GTRD tissues versus the >50%-TFBSs (FIGS. 8C-8J). These analyses demonstrated that average TFBS patterns comprise two signals: a TSS-proximal (within 2 kb of TSS resulting in a "low frequency pattern") and a TSS-distal (more than 2 kb away from TSS peak resulting in a "high-frequency pattern"), corresponding to the more evenly spaced peak signal. To suppress effects on the coverage not contributed by preferential nucleosomal positioning and to remove local biases from the nucleosome data.

Figure 3A:
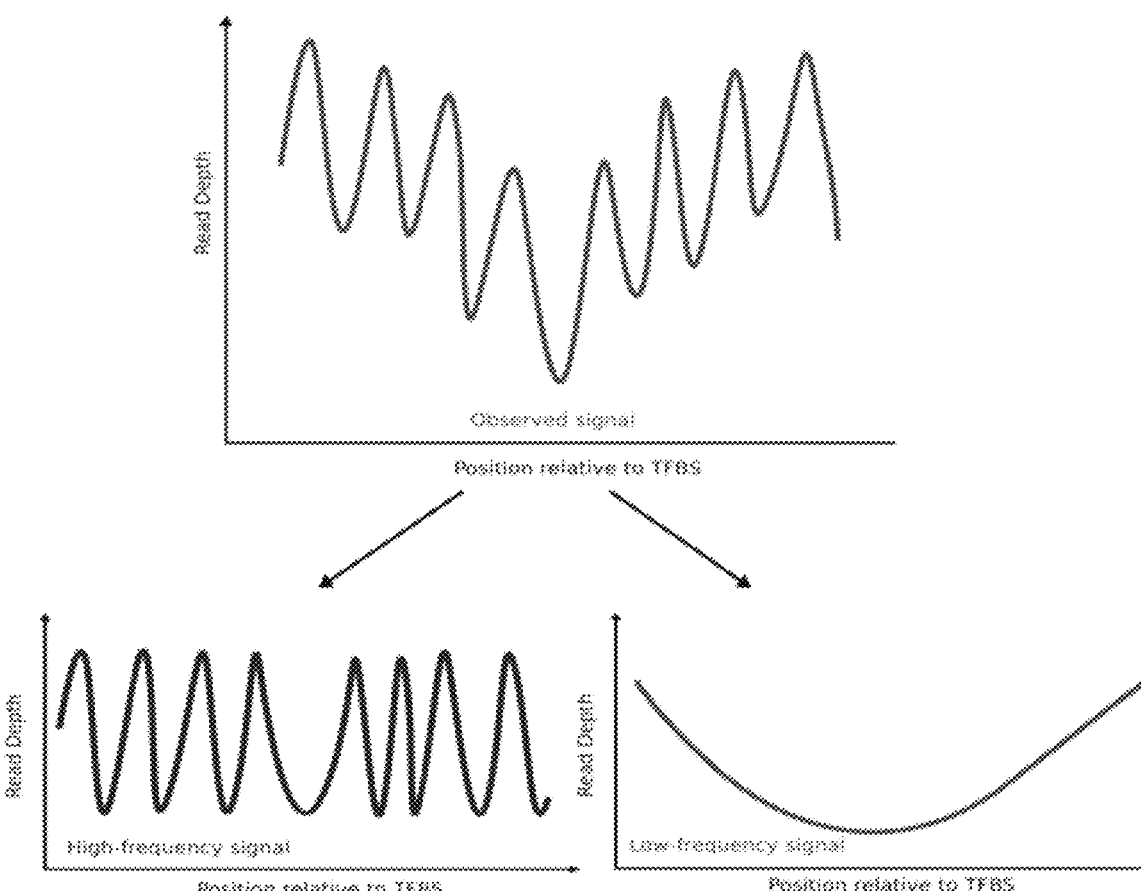
FIGS. 3A-3L show accessibility scores for the characterization of TFBSs.
Figure 3B:
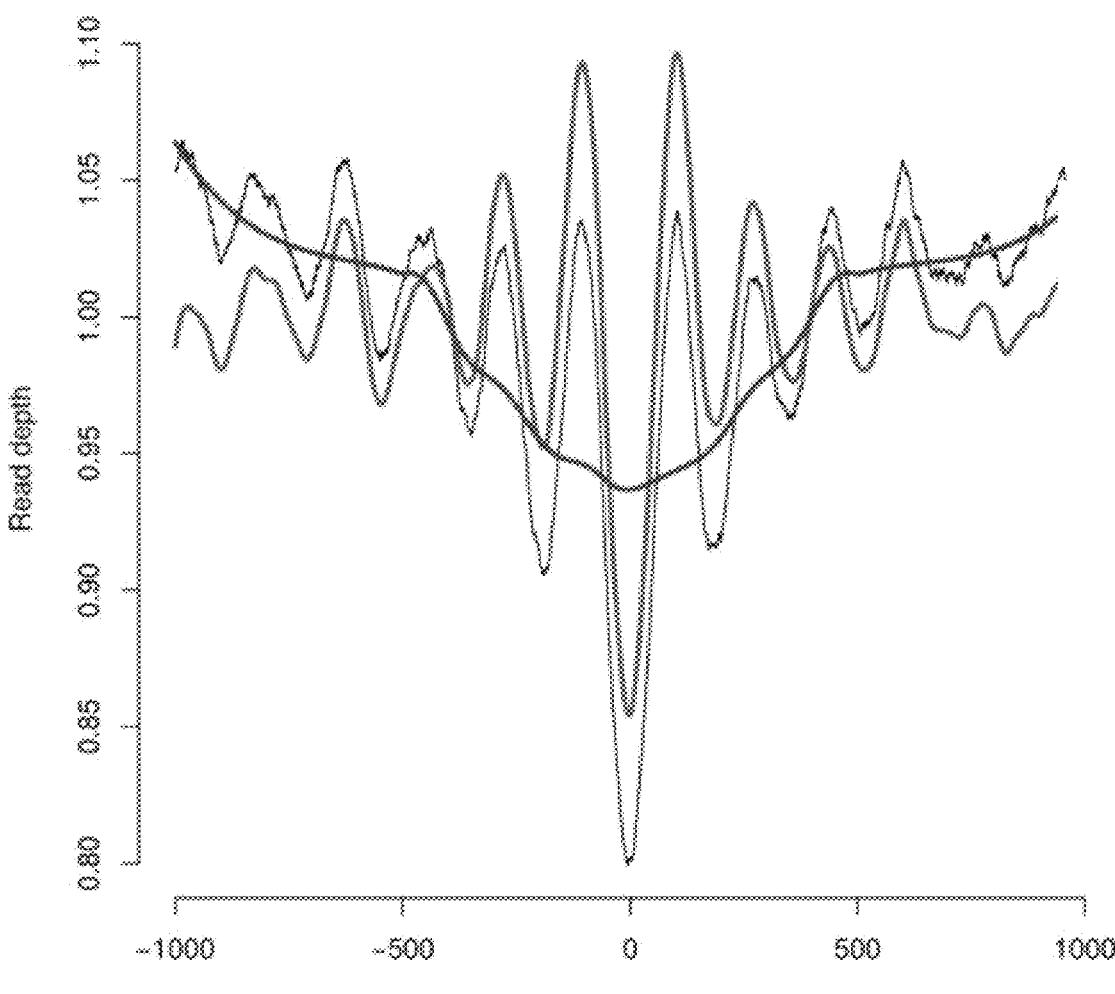
Figure 3C:
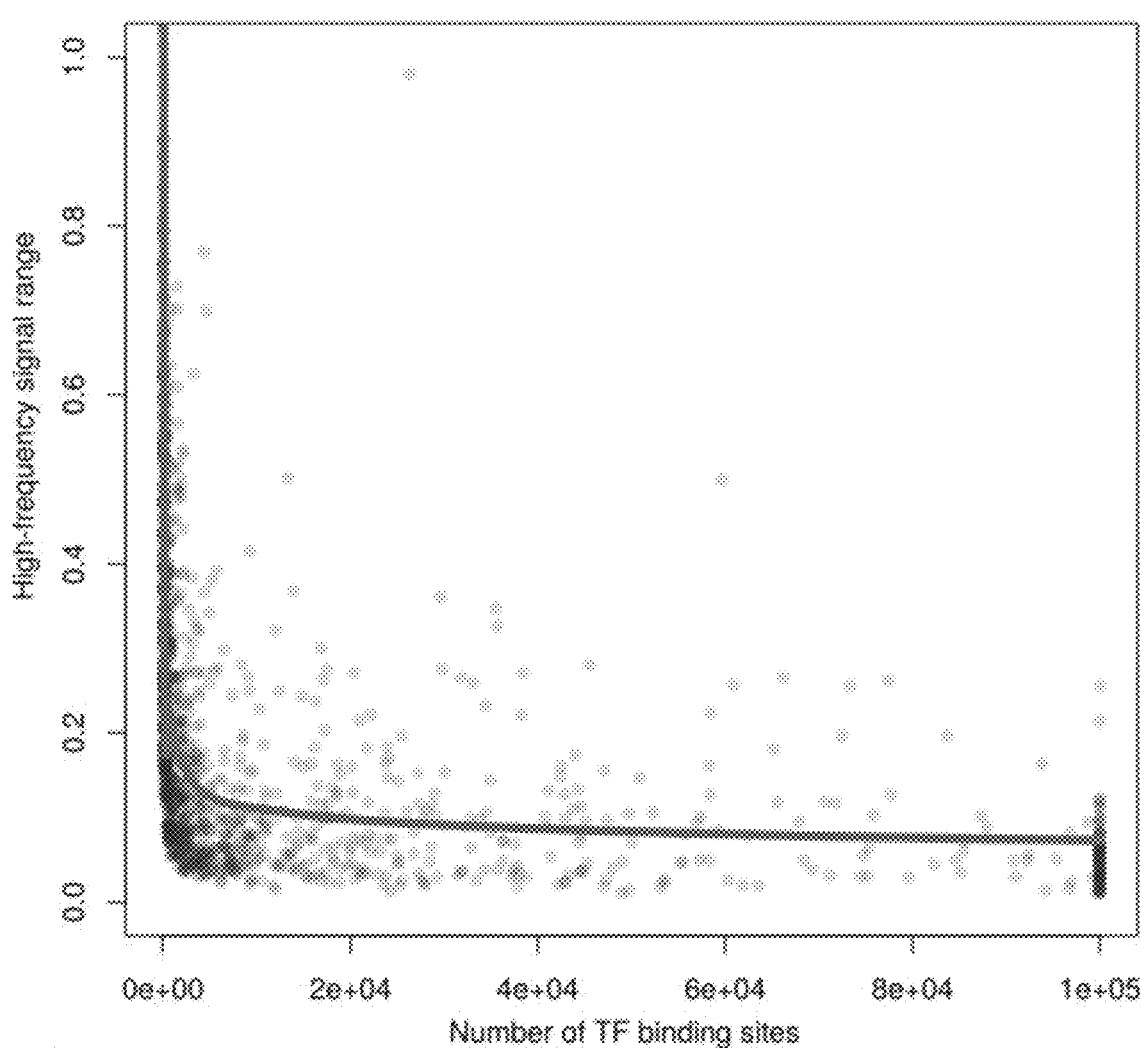
Figure 3D:
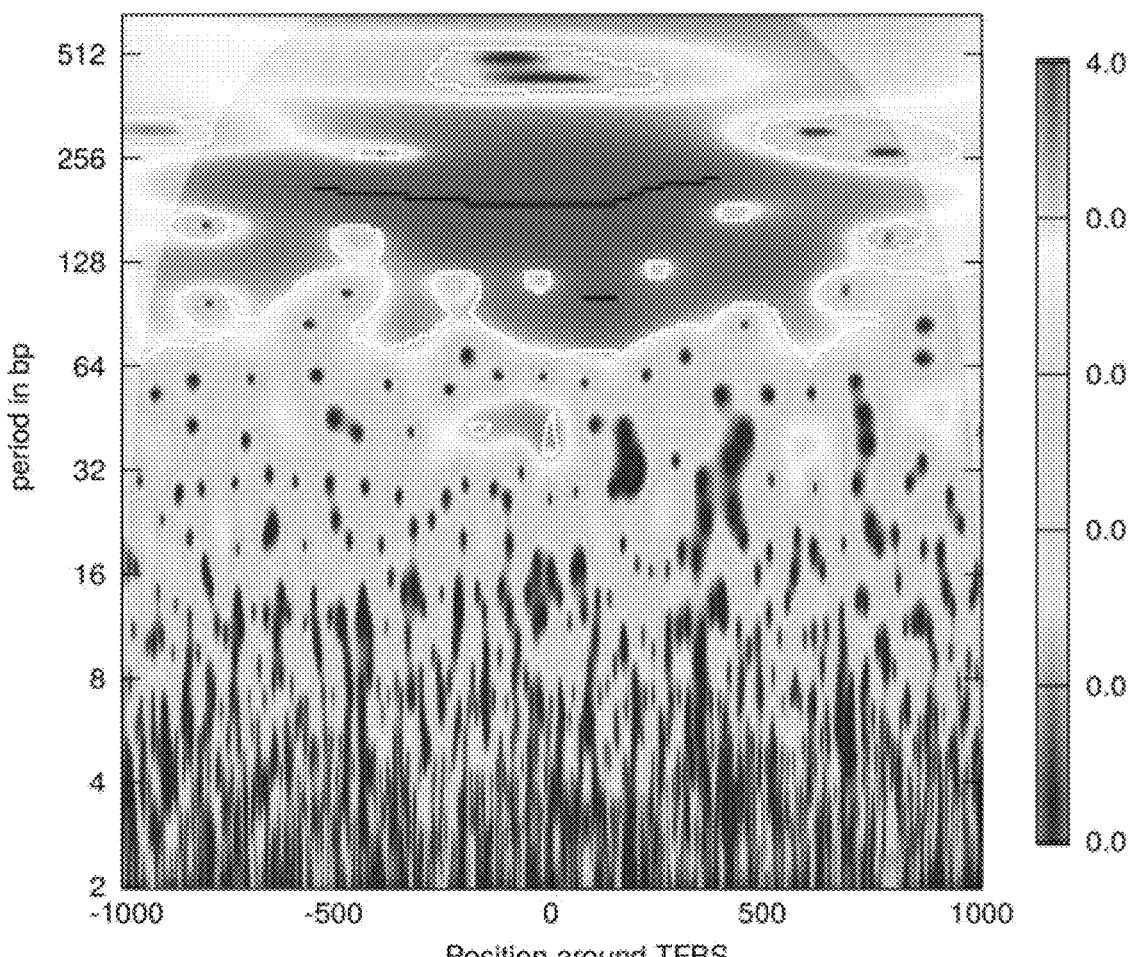
Figure 3E:
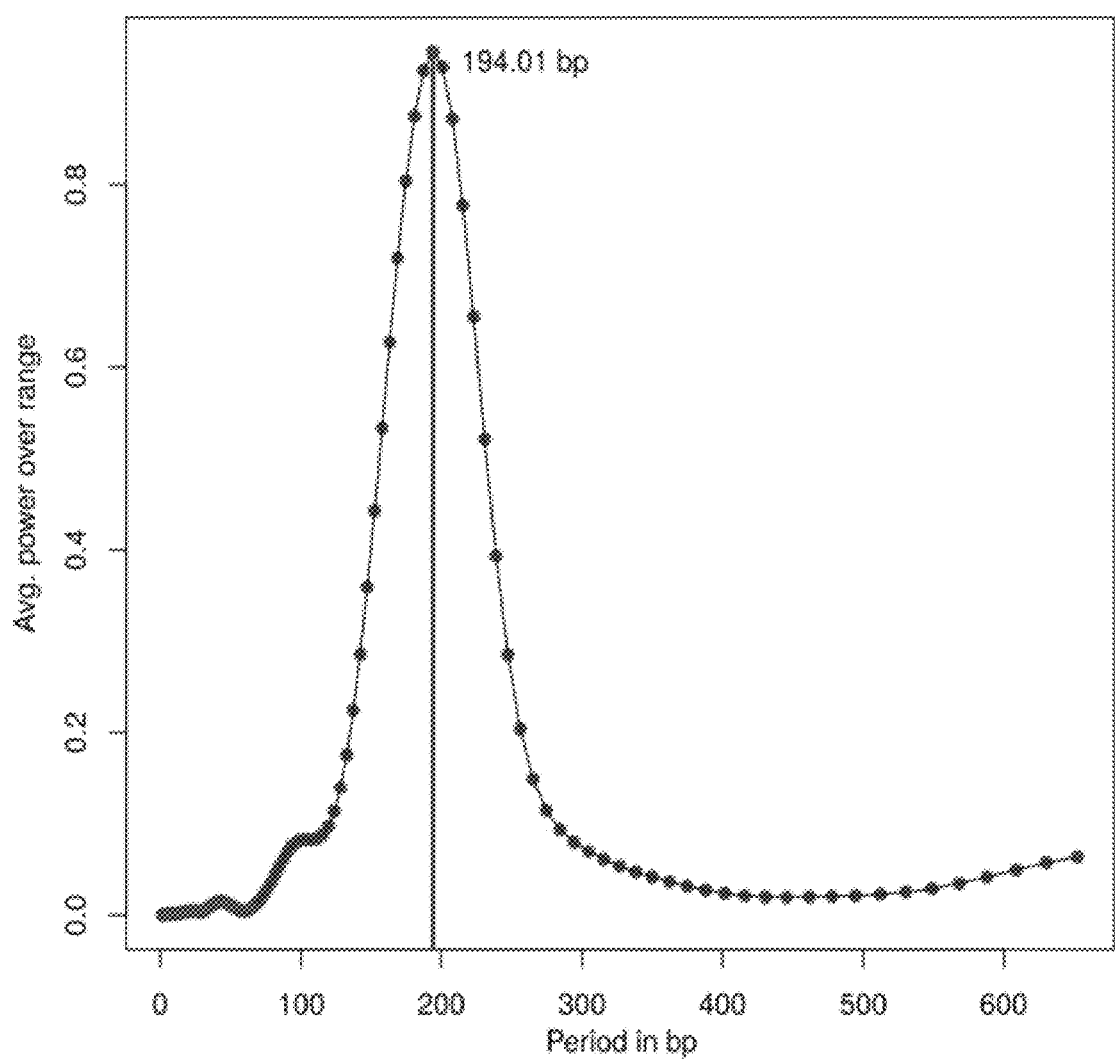
Figure 3F:
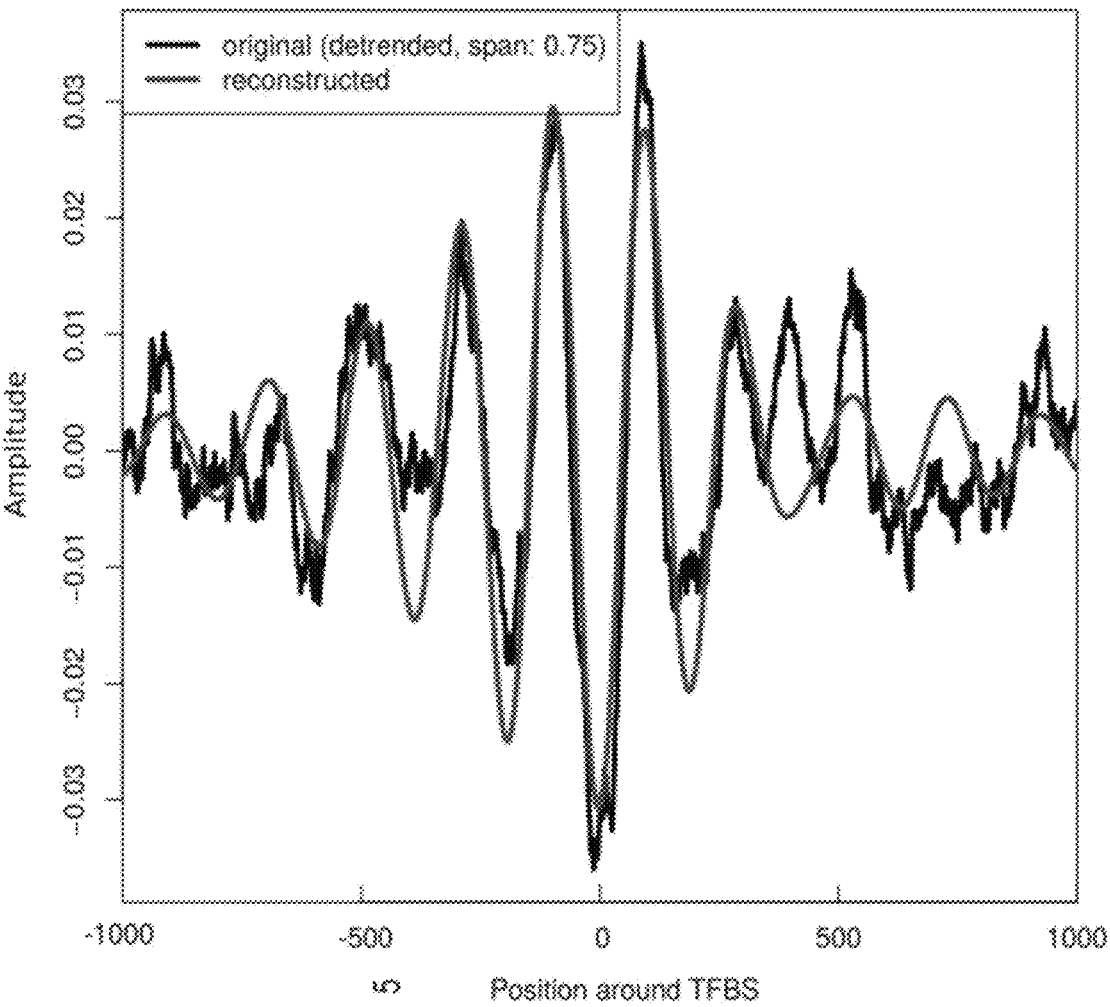
Figure 3G:
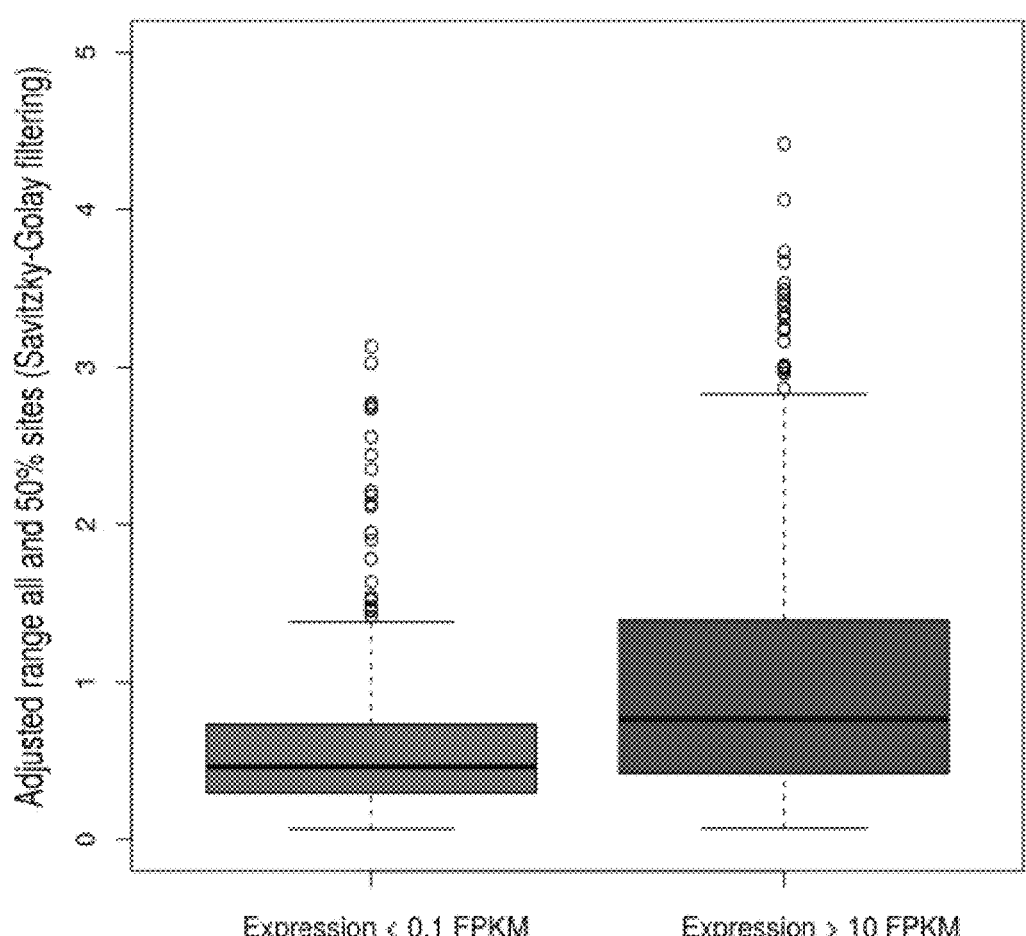
Figure 3H:
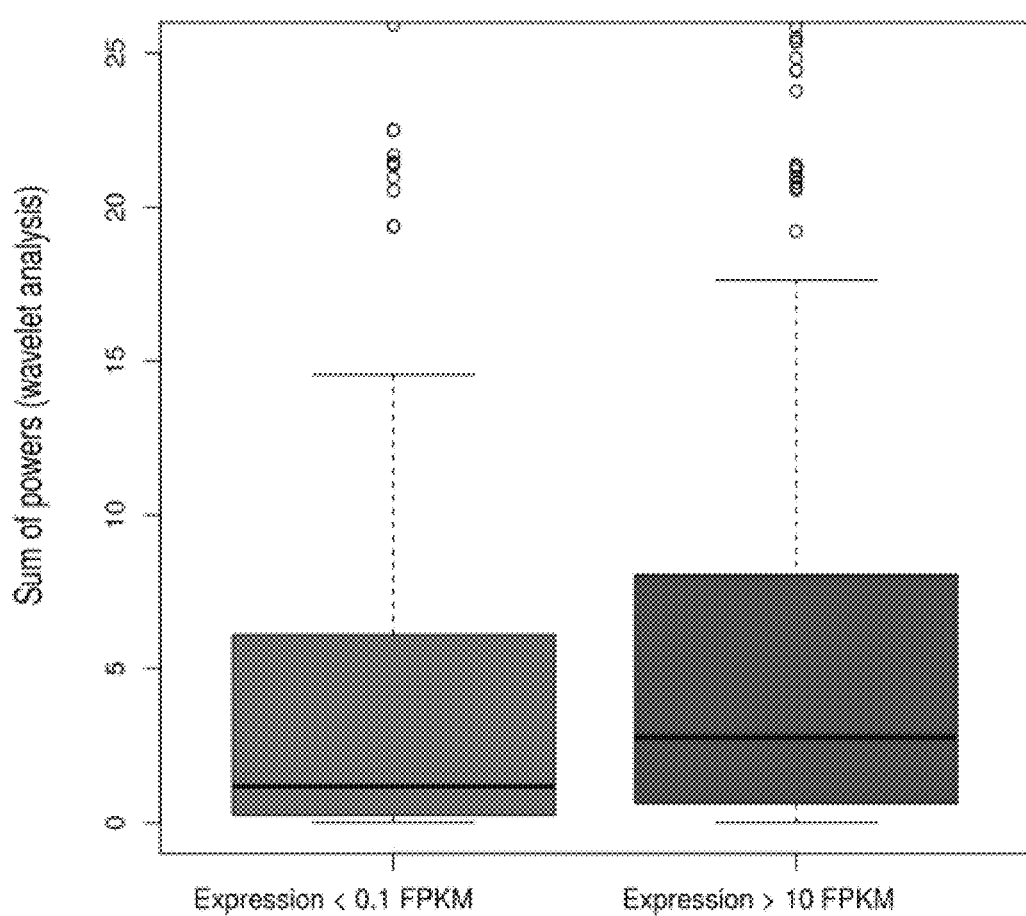
Figure 3I:
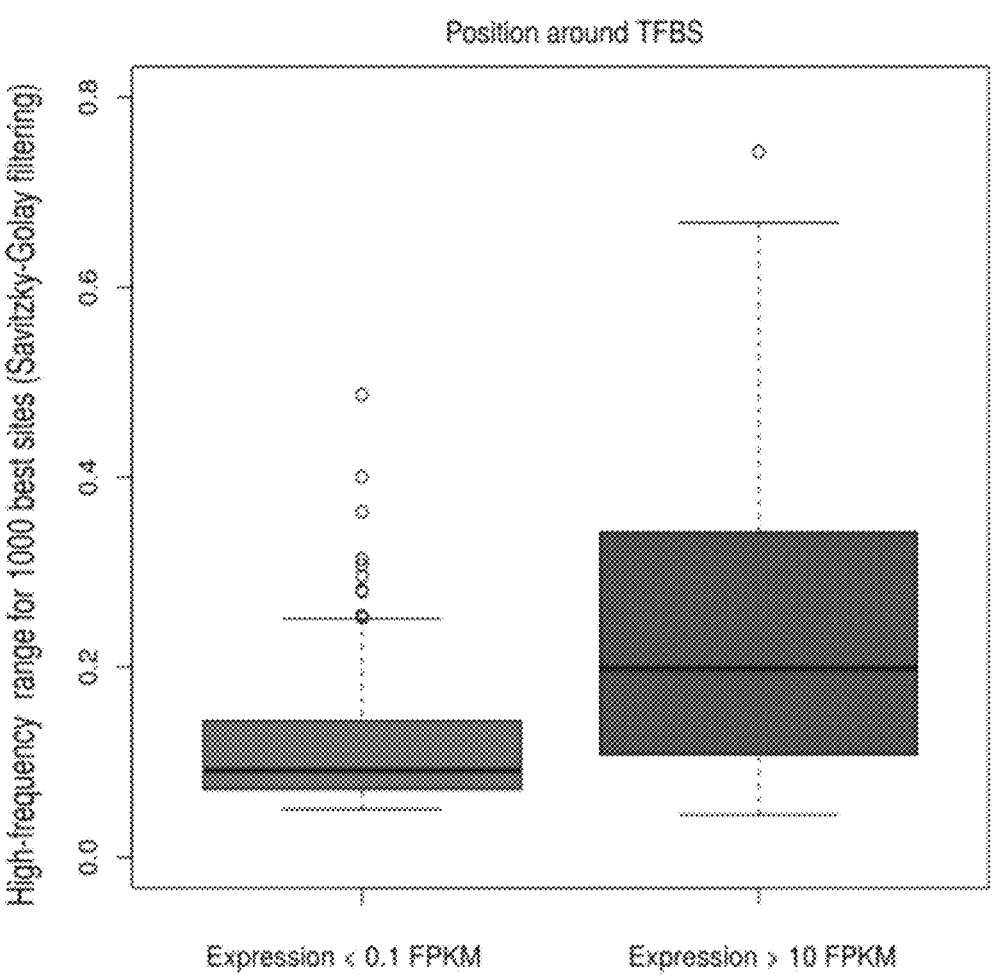
Figure 3J:
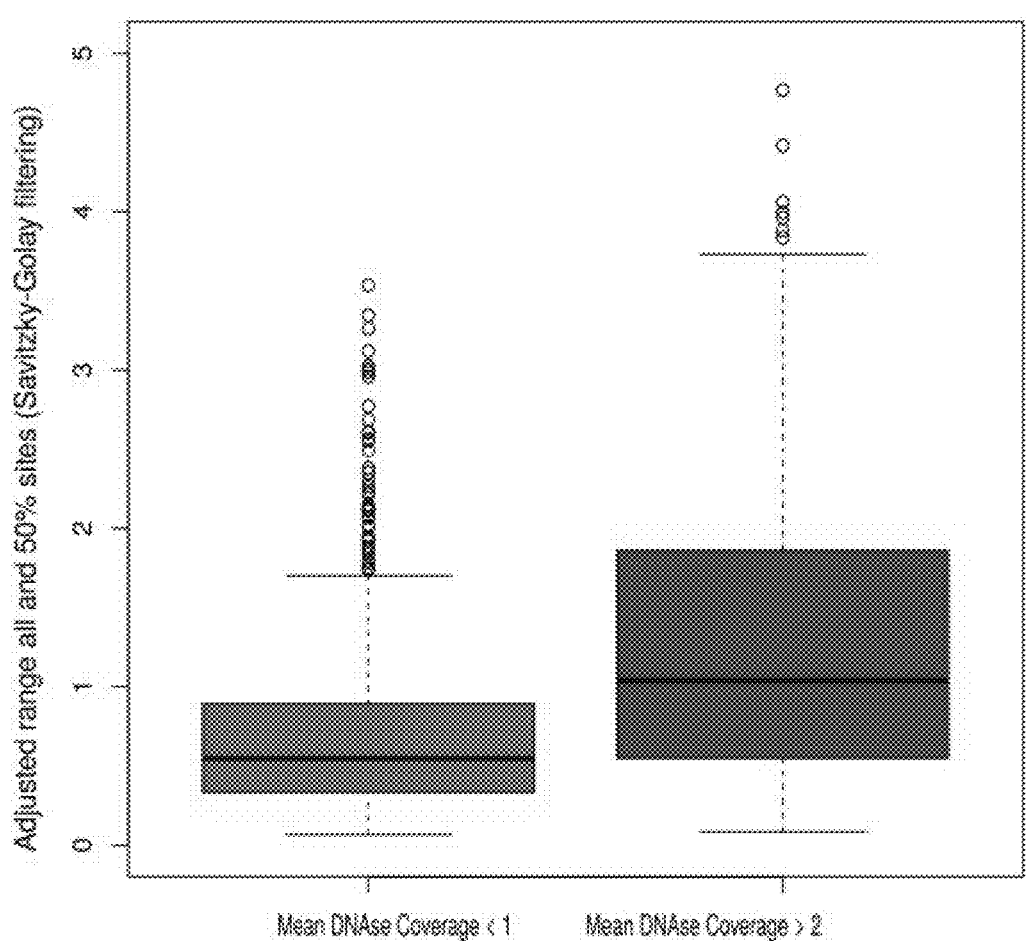
Figure 3K:
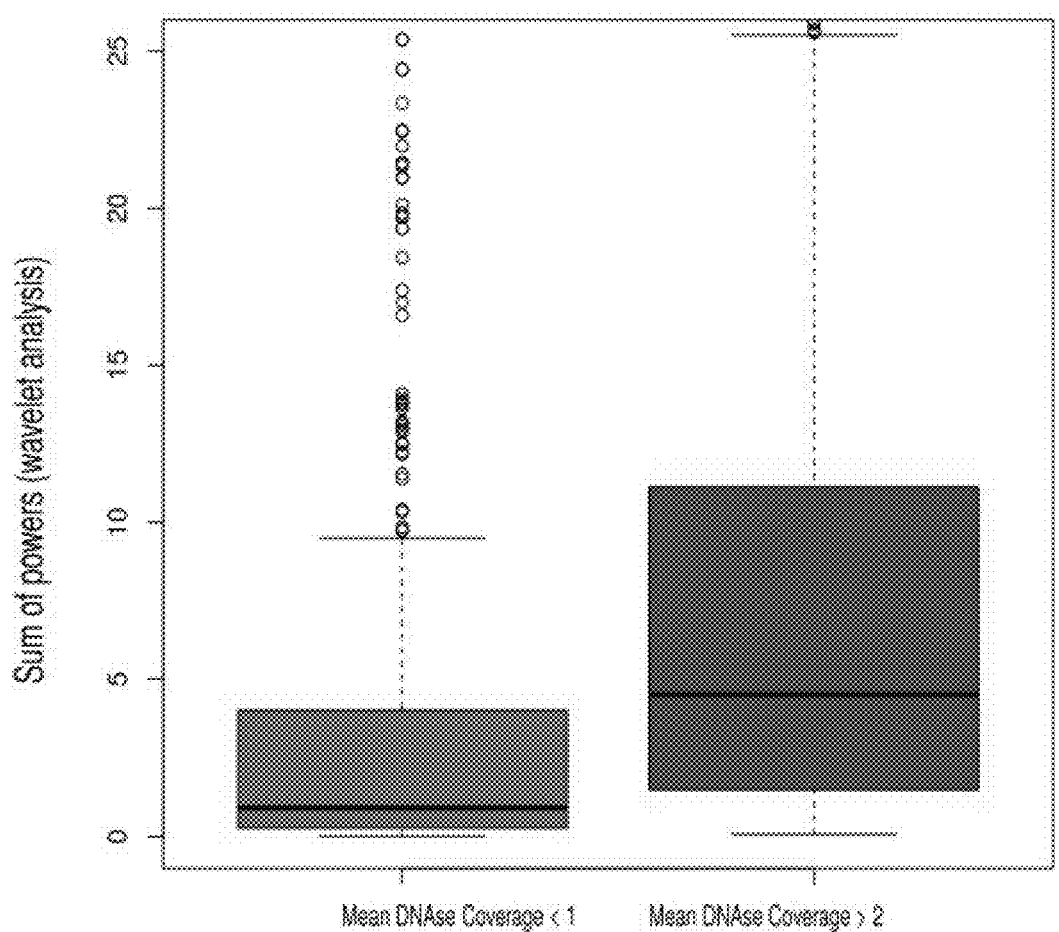
Figure 3L:
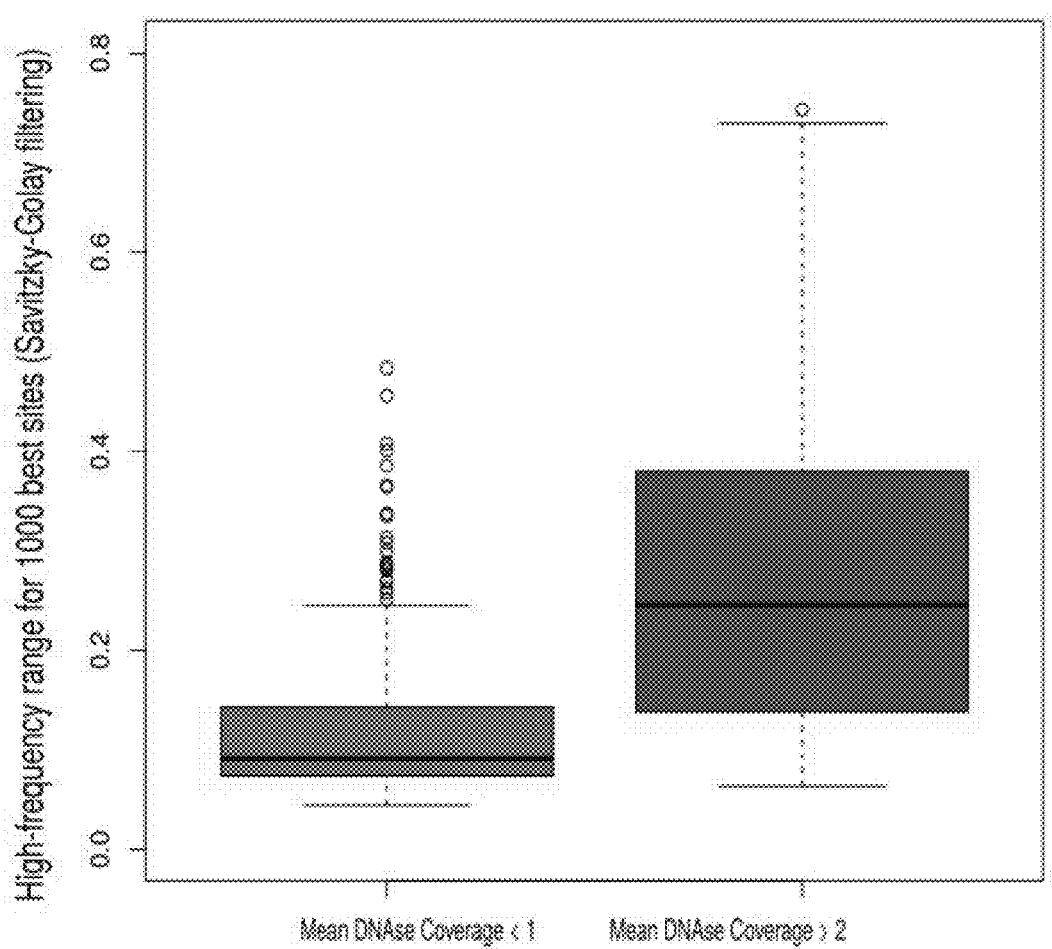

Savitzky-Golay filters were used for detrending (FIGS. 3A and 3B). The obtained low-frequency signal was then used to normalize the high-frequency signal, and subsequently the data range (maximum of the data values minus the minimum, corresponds to the amplitude) of the high-frequency signal was recorded. As the range of high-frequency signals depends on the number of TFBSs (FIG. 3C) (with the exception of the 1,000-msTFBSs), these range values were corrected by LOESS smoothing, as they depend on the number of TFBSs (FIG. 3C) and then ranks were calculated as a measure for the accessibility of each TFBS. FIGS. 3D and 3E shows wavelet analysis of GRHL2: Heatmap of periods along the region surrounding the TFBSs of GRHL2 (left panel). Color code represents quantiles of the signal power distribution. Average power of periods of transcription factor GRHL2 (right panel). FIG. 3F shows detrended original (black) and reconstructed (red) nucleosome coverage profiles of transcription factor GRHL2 resulting from wavelet analysis.

To test potential alternatives for TF accessibility assessment, an unbiased, a detrended signal at a period between 135 and 235 bp was reconstructed by wavelet analysis and the powers of the signal were summed across the 2,000 bp flanking TFBSs (FIGS. 3G-3L). To benchmark the performance of Savitzky-Golay filtering and wavelet analysis, cfRNA data was used, and significantly reduced accessibility was observed for unexpressed TFs (e.g., <0.01 FPKM [Fragments Per Kilobase Million]) as compared to the accessibility of expressed (e.g., more than 10 FPKM) TFs (>50%-TFBSs; Savitzky-Golay filtering: $p=1.75\times10^{-13}$; the sum of powers (wavelet analysis): $p=0.0004049$; 1,000-msTFBSs; Savitzky-Golay filtering: $p=1.254\chi10^{-11}$; Mann-Whitney-U test each) (FIG. 14C). These differences were also significant when the adjusted ranges were compared to mean DNase coverage (>50%-TFBSs; Savitzky-Golay filtering: $p<2.2\times10^{-16}$; the sum of powers (wavelet analysis): $p<2.2\times10^{-16}$; 1,000-msTFBSs; Savitzky-Golay filtering: $p<2.2\times10^{-16}$; Mann-Whitney-U test each). As Savitzky-Golay filtering performed slightly better, this approach was favored, and then detection thresholds were defined for TFBS accessibilities deviating from the normal samples as ±3 mean of the standard deviation (as a z-score of 3). For assessments based on all or >50%-TFBSs, the detection thresholds for normalized accessibility score were ±253 and ±88 for the 1,000-msTFBSs, which have fewer analyzable TFs (FIGS. 8K and 8L).

In addition, a comprehensive TF-nucleosome interaction map was generated for the 676 GTRD TFs from cfDNA (FIG. 14C; FIGS. 17A-17D). TF-nucleosome interactions may be mapped by, for example, using ChIP-seq data sets from the ENCODE Consortium, chromatin structures around 119 human TF were characterized. From these efforts resulted the TF-centric web repository Factorbook which contains data on 167 TFs. However, these data are based on ex vivo tissue samples, whereas in vivo accessibilities generated by an endogenous process are investigated herein.

These results demonstrate a robust approach to assess TFBS accessibility with particular utility to use cfDNA in clinical diagnostics.

TFBSs Accessibility in cfDNA Across Several Cell Types

Plasma samples from 3 common tumor entities were used to demonstrate clinical application. This study started with the analysis of 11 plasma samples derived from 7 patients, e.g., four cases with prostate cancer (P40, P147, P148, and P190), one colorectal cancer (CRC; C2), and two breast cancers (B7 and B13) (FIGS. 4A-4K). The cfDNA from C2, P40, P147, and P148 were sequenced on an Illumina NovaSeq platform with a mean of 688,482,254 (range: 541,216,395-870,285,698) sequencing reads, whereas B7 (328,515,075 reads) and B13 (379,733,061 reads) had been sequenced on an Illumina NextSeq platform.

CTCF is a special transcription factor that is active in every tissue as it regulates chromosome 3D architecture, which is conserved throughout tissues. The amplitude of CTCF remained similar throughout all analyzed samples regardless whether the cfDNA was derived from healthy controls or from patients with cancer (FIGS. 2C and 2D). This was consistent with DNase hypersensitivity assays from the ENCODE database for cell lines GM12878. LNCaP (androgen-sensitive human prostate adenocarcinoma cell line) and HCT116 (human colon cancer cell line) showing the increased accessibility of CTCF binding sites across various tissues (FIGS. 2C and 2D). However, patients with cancer have an increased fraction of ctDNA, which alters the balance between DNA from hematopoietic versus epithelial cells within cfDNA.

Accordingly, the amplitudes for the hematopoietic TFs (PU.1, Lyl-1, and Spi-B) decreased whereas the amplitude for the epithelial TF GRH-L2 increased, illustrating that the contribution of the hematopoietic system is diluted and of epithelial cells increased (FIGS. 2E, 2G, 2I, and 2K). These observations were again consistent with DNase hypersensitivity assays (FIGS. 2D, 2F, 2H, 2J, 2L, and 2N).

As another example for a well-established TF, FOXA1 was analyzed, which is a TF widely expressed in different tissues where it controls cellular differentiation and organ function. Furthermore. FOXA1 cooperates with nuclear hormone receptors in endocrine-driven tumors of the breast and prostate and in prostate its expression has been associated with castration-resistant prostate cancer (CRPC). Indeed, consistent with the DNase hypersensitivity assays, preferentially increased accessibility of FOXA1 was observed in the plasma samples of prostate and breast cancer patients (FIGS. 2M and 2N).

Figure 4A:
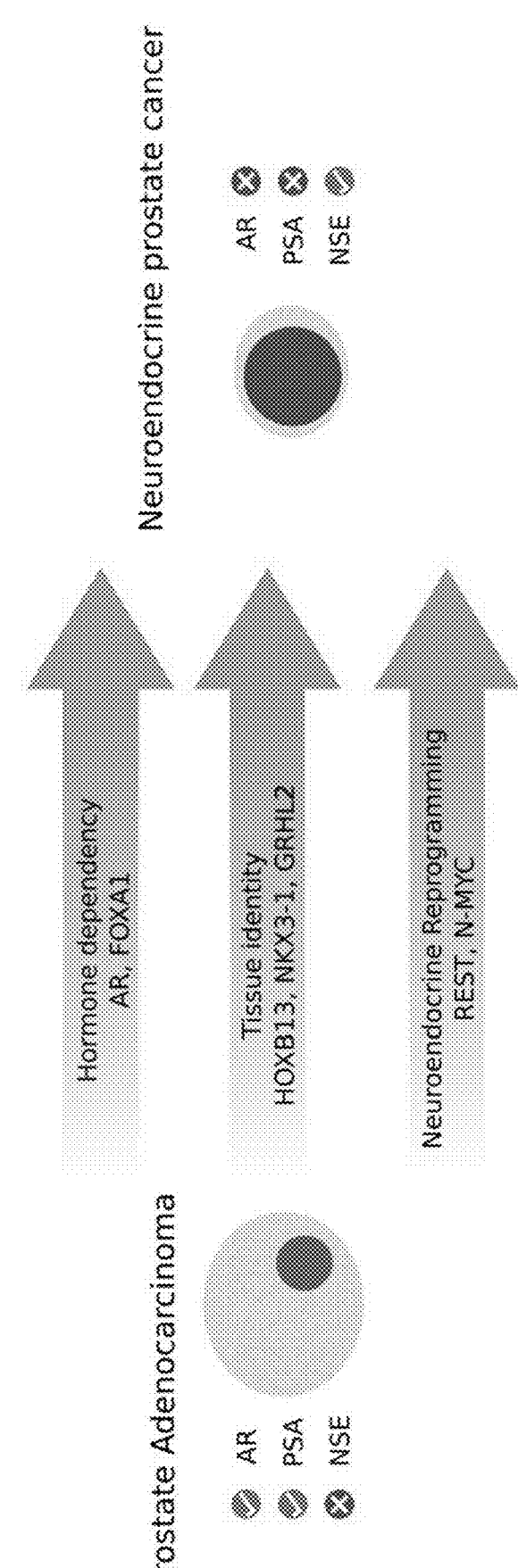
FIGS. 4A-4K show prostate lineage-specific TFs, their plasticity, and suitability for tumor classification.

Inference of TF Binding from cfDNA Supports Molecular Subtyping in Prostate Cancer In some cases, it may be important to assess the extent tissue-specific TFs are suitable for the identification of tumor-of-origin and molecular subtyping. To this end, prostate cancer is a particularly interesting tumor entity because a frequent (about 20%) mechanism in the development of treatment-resistance to novel agents targeting the AR pathway, such as abiraterone or enzalutamide, is the transdifferentiation of an adenocarcinoma to a treatment-emergent small-cell neuroendocrine prostate cancer (t-SCNC). This transdifferentiation has enormous clinical implication because it requires change of therapy, and the involvement of several TFs in such a transdifferentiation process may be studied (FIG. 4A).

Several TFs were detected with an increased accessibility in one but not the other tumor entities. For example, plasma samples from patient C2 with CRC showed an increased accessibility for the c-Jun and JunD (FIGS. 15A-15D) oncogenes, and confirmed with the colon predilection with DNA hypersensitivity assays (FIGS. 15A-15D).

Another analysis was performed on prostate cancer samples. Data was screened for expression of human TFs across tissues and various cell types provided by (Lambert et al., 2018) and the publicly available human protein atlas, and confirmed the well-established prostate lineage specificity of TFs AR, HOXB13, and NKX3-1, which was also reflected in the DNase hypersensitivity assays of the prostate cancer cell line LNCaP (FIGS. 4B-4H).

Figure 4B:
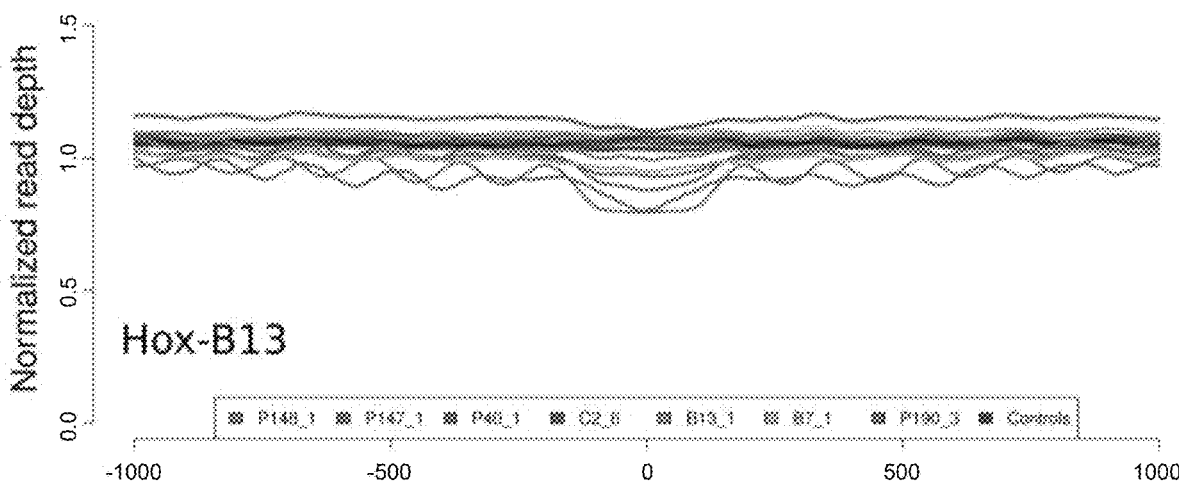
Figure 4C:
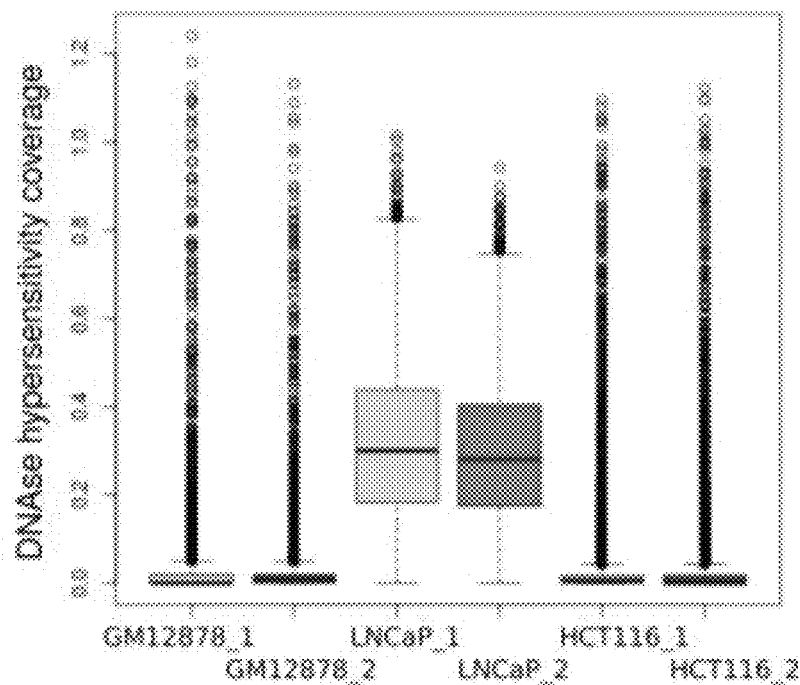
Figure 4D:
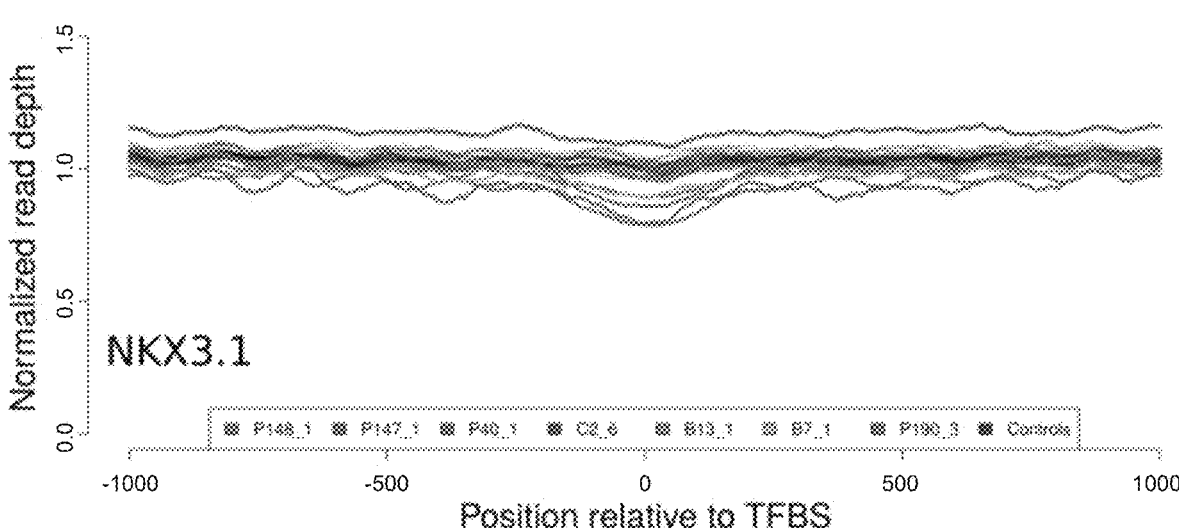
Figure 4E:
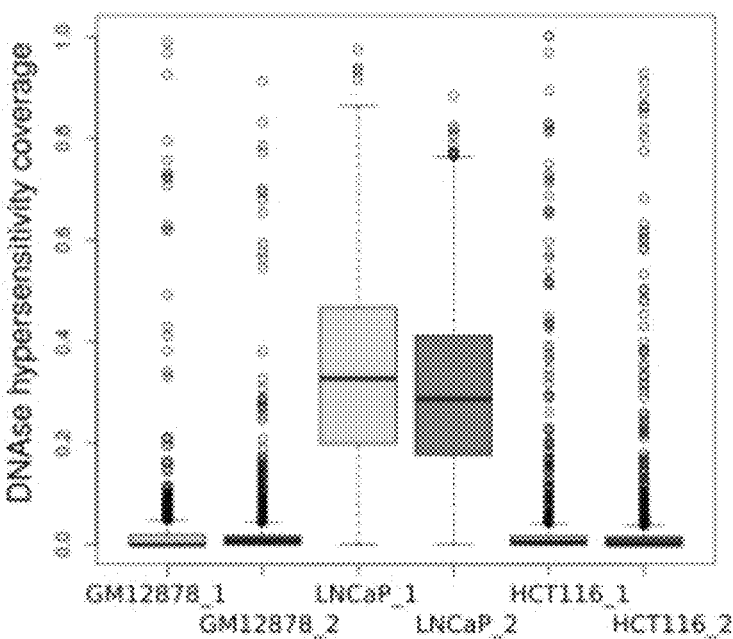

HOXB13 is a highly lineage-specific homeobox TF gene that is important in prostate development and which maintains a high expression level into adulthood in normal prostate (FIGS. 4B and 4C). The NKX3-1 homeobox gene is one of the earliest genes expressed during the prostatic epithelium maturation and is critical for the differentiation of the prostate epithelium and is required for prostate tumor progression (FIGS. 4D and 4E). Both TFs displayed increased accessibility at their binding sites only in the cfDNA of patients with prostate cancer, and furthermore the tissue specificity was confirmed with DNase hypersensitivity assays (FIGS. 15A-15D and 4B-4H).

Figures 4F, 4G:
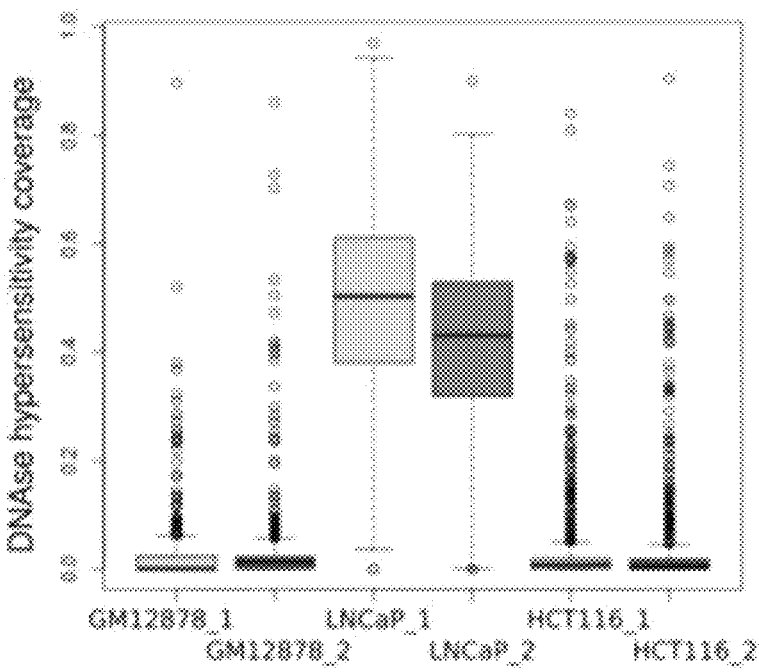
Figure 4H:
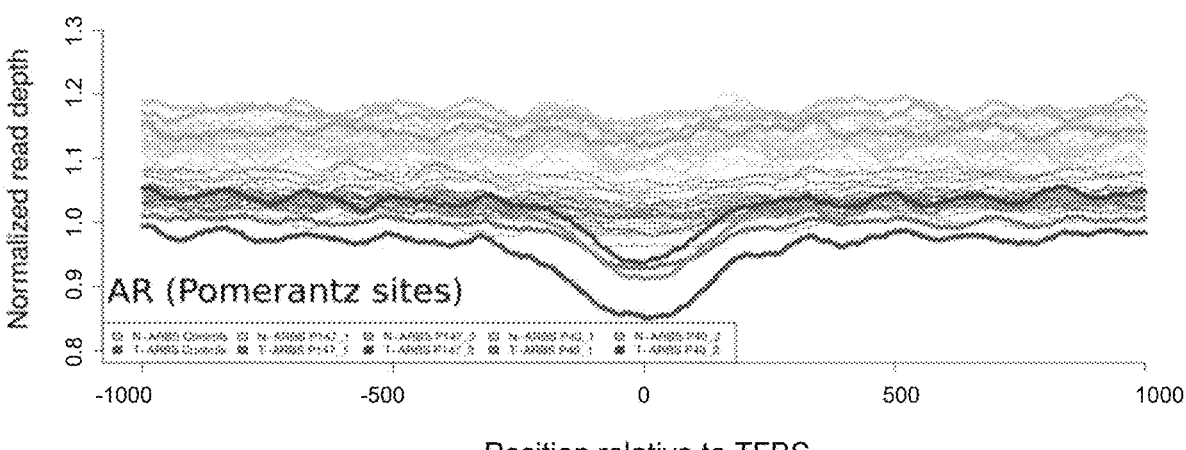

Accordingly, these TFs displayed increased accessibility at their binding sites only in the cfDNA of patients with prostate cancer. Because of the extraordinary relevance of AR in prostate cancer, not only were the AR binding sites as defined by the GTRD used, but those reported by (Pomerantz et al., 2015) were also employed, whereby analyzing the AR cistrome identified 9,179 tumor AR binding sites with higher binding intensity in tumors (tumor AR binding sites, T-ARBSs), and 2,690 normal AR binding sites with high binding intensity in normal samples (normal AR binding sites, N-ARBSs). Indeed, whereas N-ARBSs were not accessible from both controls and patients, the T-ARBS showed increased accessibility in the patients' plasma samples (FIGS. 4F-4H).

Confirmation of Lineage-Specific Transcription Factors in Pooled Samples

This approach can also be applied to samples sequenced with a lesser coverage and which are heavily rearranged. To test this, the TF analysis was repeated after down-sampling P148_1 (819,607,690 reads) and P148_3 (768,763,081 reads) to about 50 million reads. This comparison revealed that the same TFs were identified as increased or decreased accessible, demonstrating that samples with lesser sequencing reads are amenable to these analyses. Subsequently, 4 cfDNA samples were analyzed (P21_2, P111_1, P111_4, P166_1) with a tandem duplicator phenotype (Viswanathan et al., 2018) and one case (P143_3) with chromothripsis on chromosome 10 (mean: 52,869,911; range: 41,780,819-84,049,593) (FIGS. 18A-18F). In these cases, the epithelial TFs FOXA1, GRHL1, and GRHL2, as well as the prostate lineage specific TFs AR, HOXB13, and NKX3-1, showed again increased accessibility (FIGS. 18A-18F indicating that results can be achieved even under impeded requirements and furthermore that alterations of accessibility of these TFs appears to be a universal feature in prostate cancer.

As a further confirmation for the robustness and reproducibility of lineage-specific TFs in cfDNA, pools of multiple cfDNA samples generated by shallow-coverage (<0.2×) were analyzed, showing that those TFs with increased accessibility in the majority or all samples, e.g., lineage-specific TFs, have an increased accessibility score whereas others are averaged out. To this end, cfDNA samples were pooled separately for prostate cancer cases (n=69), colon cancer cases (n=100) and breast cancer cases (n=60) and repeated the analyses. The epithelial TF GRHL2 persisted with increased accessibility, whereas hematopoietic TFs had decreased accessibility (FIGS. 8A-8R). Within the prostate cancer cfDNA pool, the lineage-specific TFs AR (340; 4.0), HOXB13 (712; 8.4), and NKX3-1 (253; 3.0) showed increased accessibilities, demonstrating that alterations of accessibility of these TFs are a universal feature in prostate cancer (FIGS. 8A-8R), and that these features are universally present in prostate cancer and may be suitable for the identification of tumor-of-origin from cfDNA.

FIGS. 9A-9G shows analyses of pooled shallow-coverage cfDNA. Accessibility is shown for pooled cfDNA samples from prostate (n=69), colon (n=100), and breast (n=60) cancer cases of the epithelial TF GRHL2 and of hematopoietic TFs (PU.1, LYL1, and SPIB). Accessibility is also shown within the prostate cancer cfDNA pool of the lineage-specific TFs AR, HOXB13, and NKX3-1.

These analyses demonstrated that accessibility at binding sites of these TFs in cfDNA may also be utilized for the identification of tumor of origin as some lineage-specific TFs are generally changed in epithelial and prostate cancer, respectively.

Figure 4I:
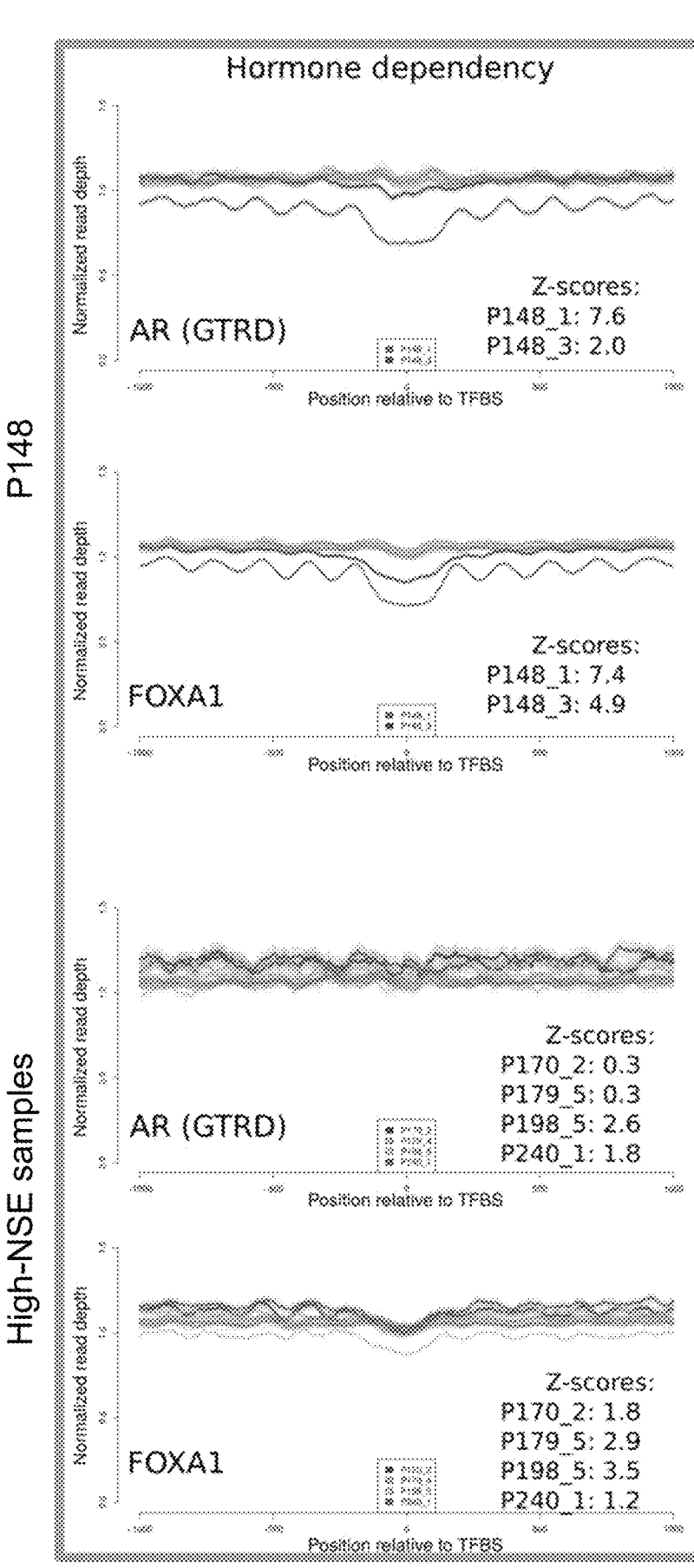
Figure 4J:
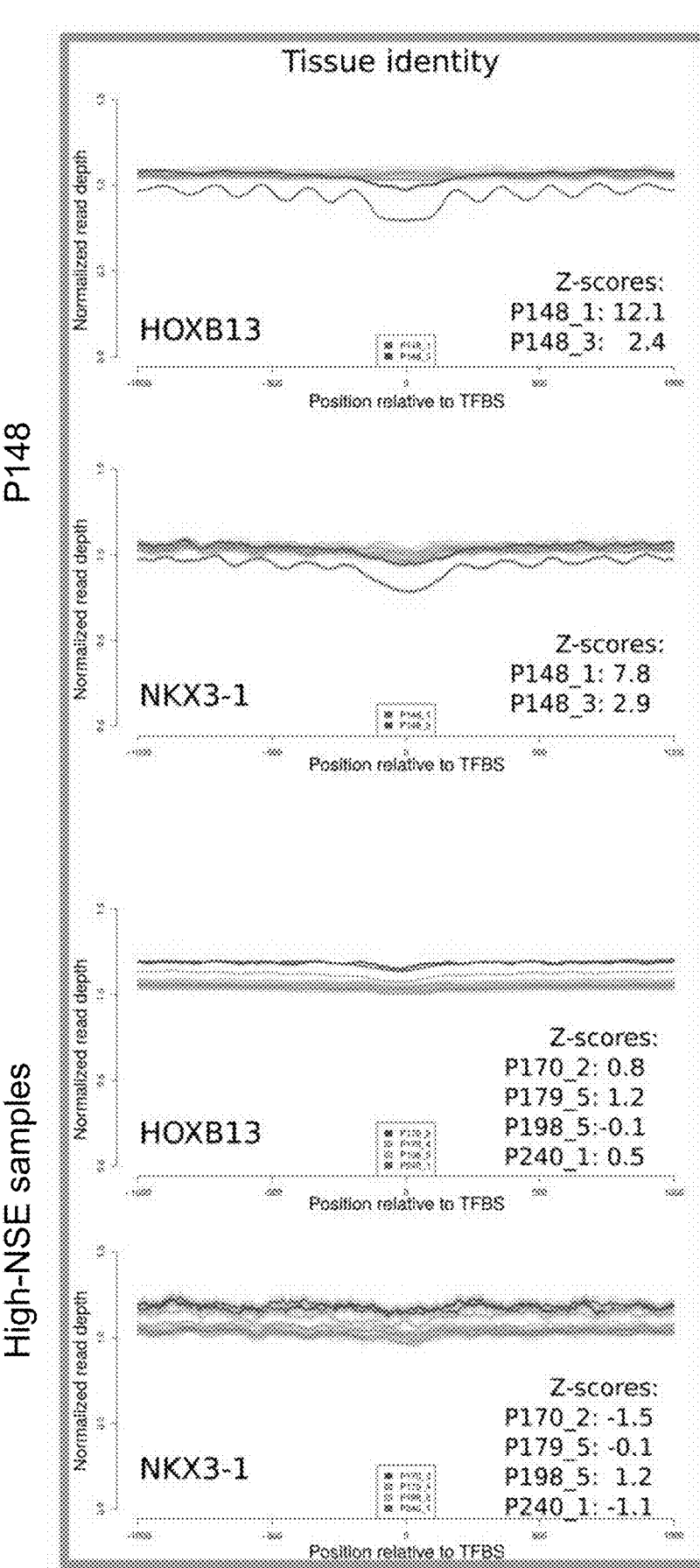
Figure 4K:
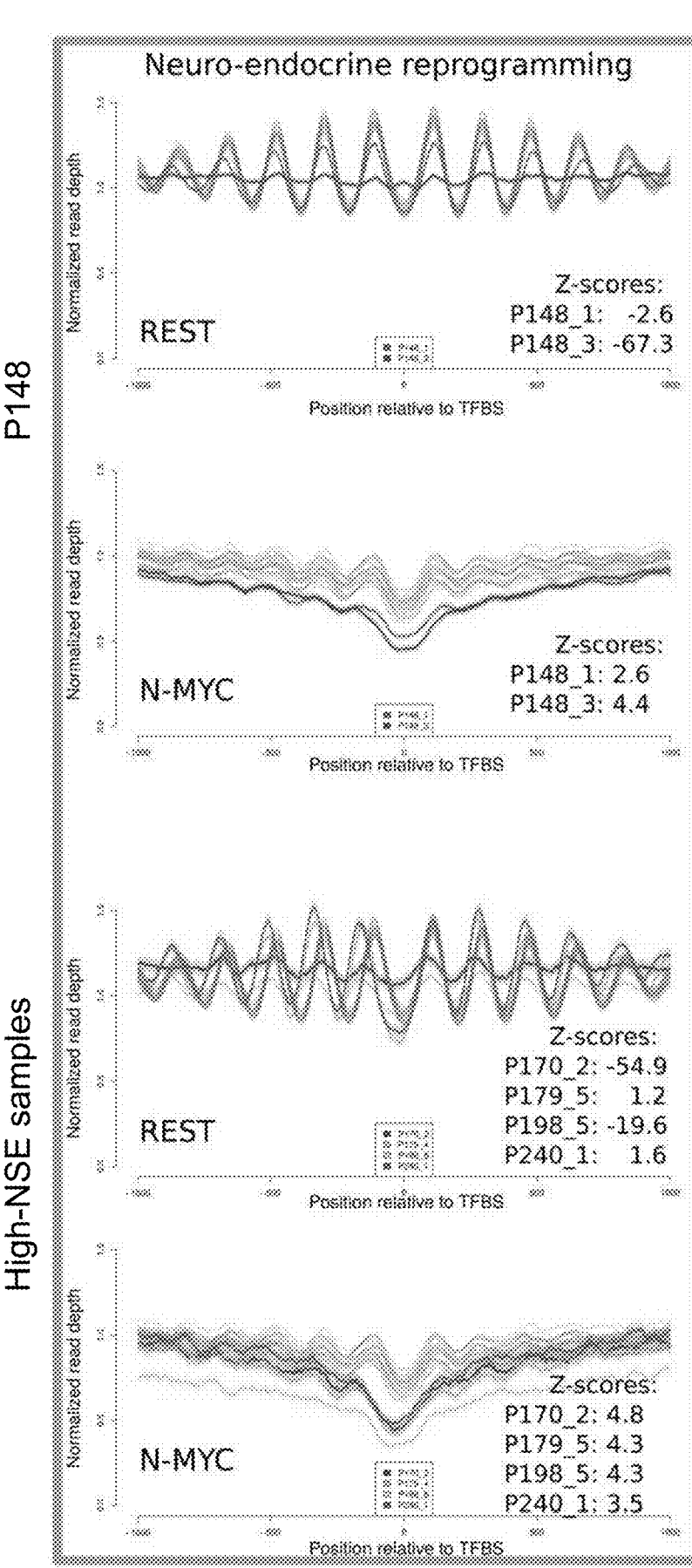
Figures 10A, 10B:
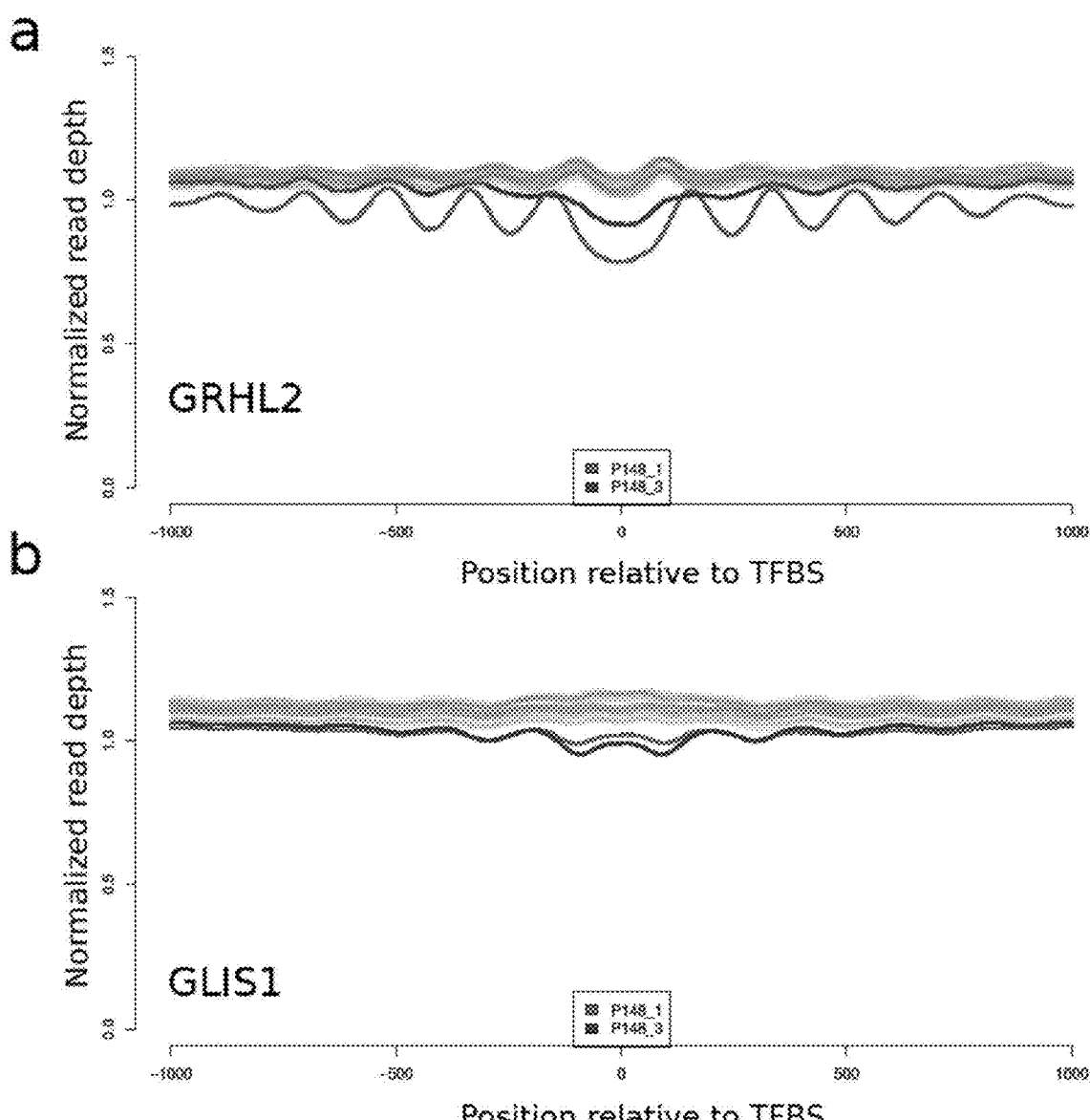
FIGS. 10A-10B show transcription factors involved in transdifferentiation from an adenocarcinoma to a t-SCNC.
Figures 11A, 11B, 11C, 11D:
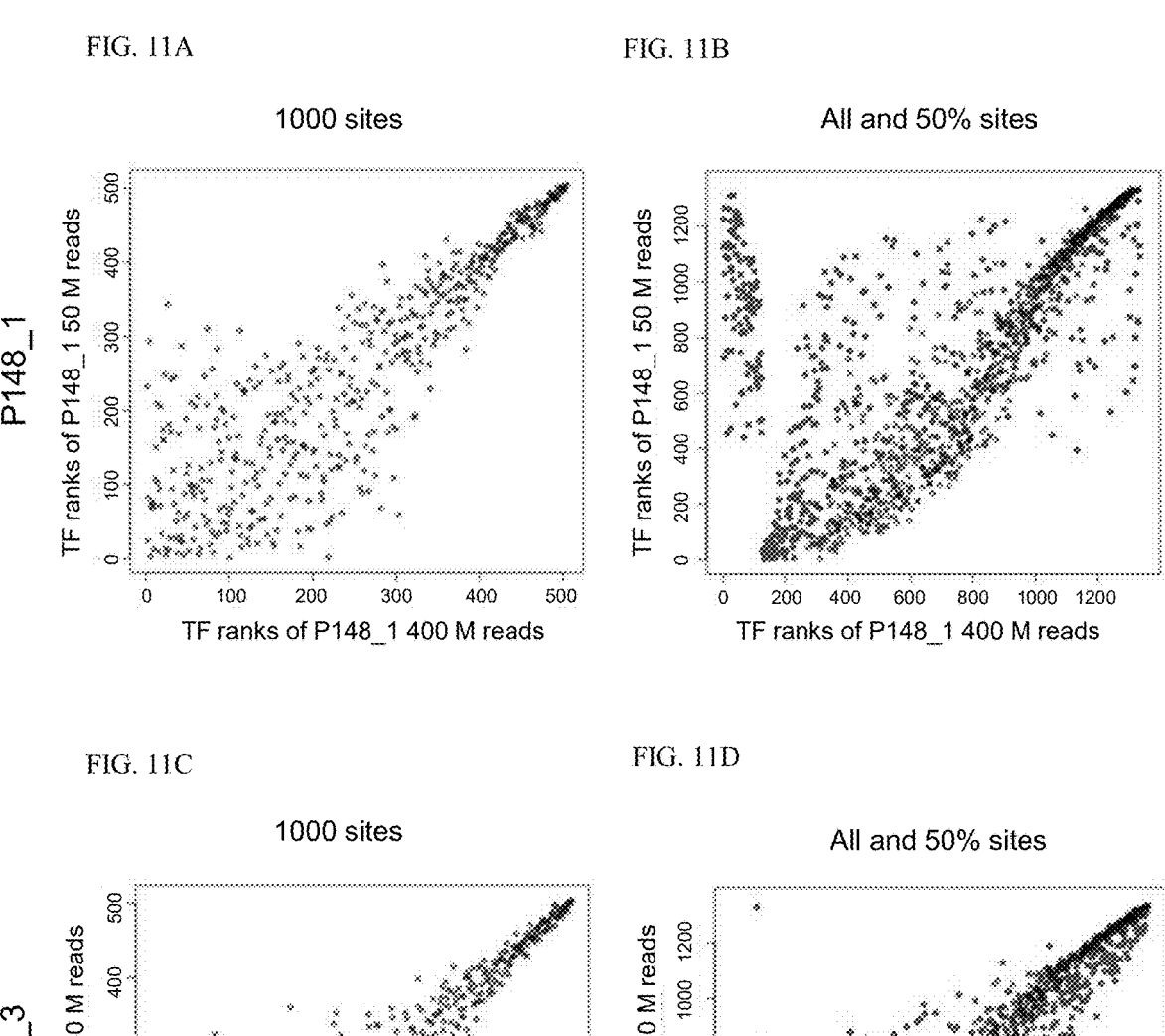
FIGS. 11A-11D show down-sampling of plasma samples P148_1 in FIGS. 11A and 11B, and P148_3 in FIGS. 11C and 11D from patient P148. Plasma samples P148_1 (819, 607,690 reads) and P148_3 (768,763,081 reads) were down-sampled to about 50 million reads and analyzed for 1,000-msTFBSs (FIGS. 11A and 11C) and all and >50%-TFBSs (FIGS. 11B and 11D). The analysis indicates that preferentially TFs with a low number of TFBSs are affected by increased noise.
Figure 15A:
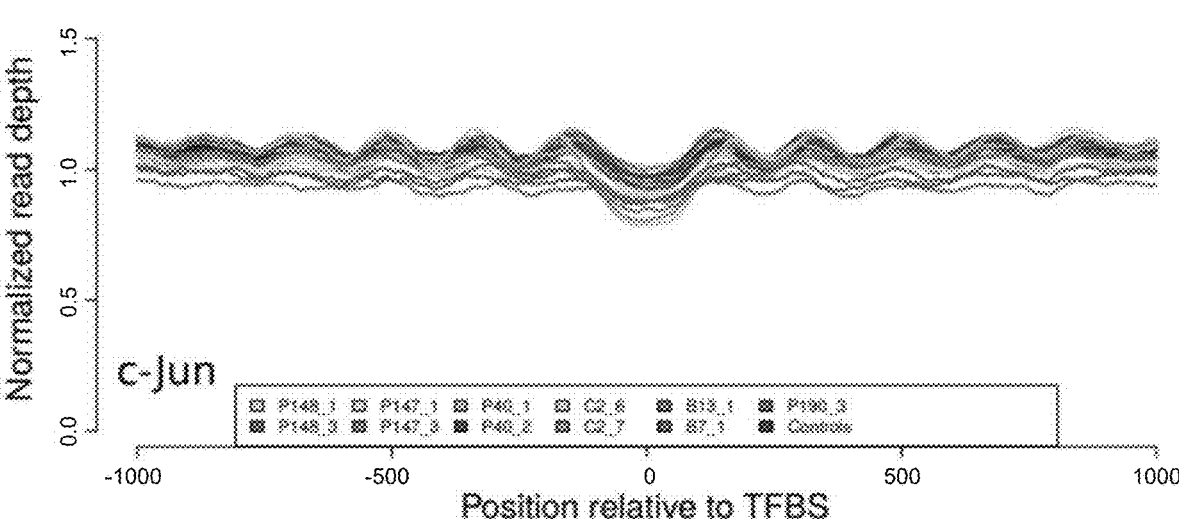
FIGS. 15A-15D show that the oncogenes c-Jun (FIGS. 15A and 15B) and JunD (FIGS. 15C and 15D) showed an increased accessibility only in the CRC patient C2 and the relative colon specificity was confirmed by DNA hypersensitivity assays.
Figure 15B:
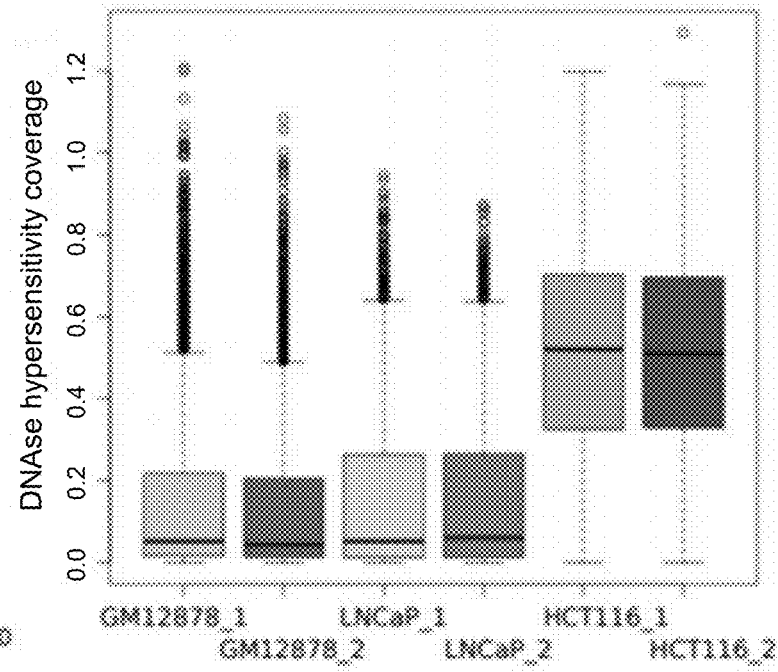
Figure 15C:
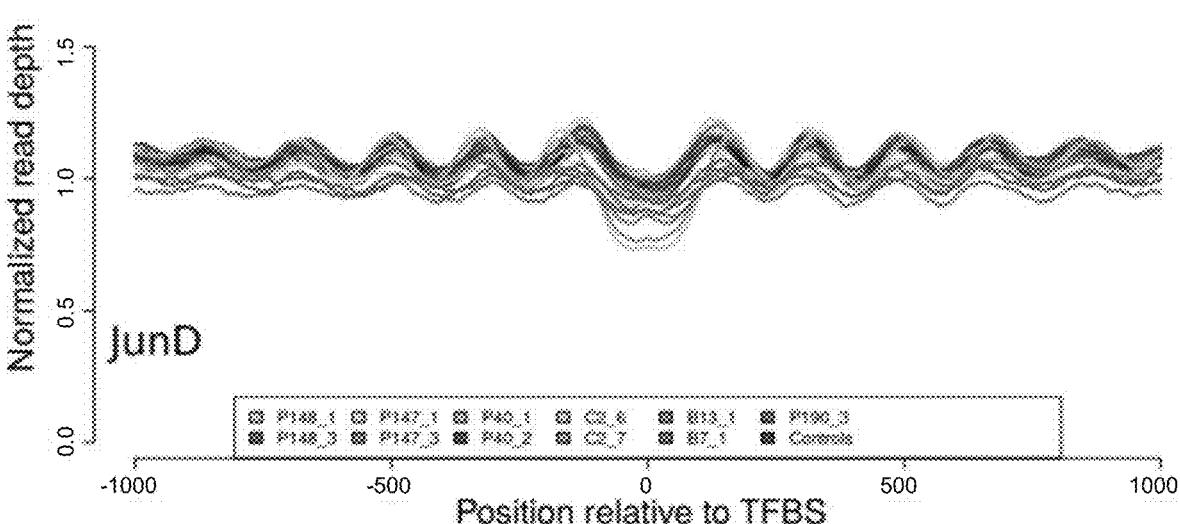
Figure 15D:
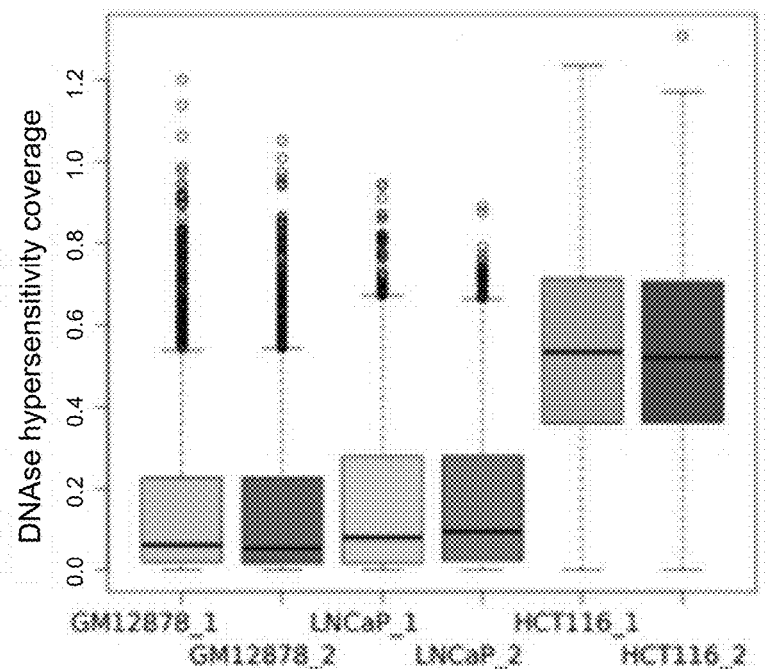
Figure 16A:
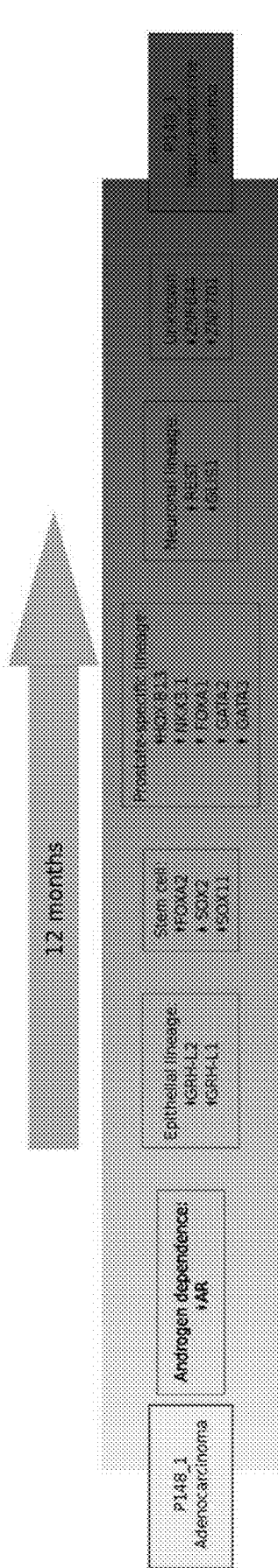
FIGS. 16A-16G show changing accessibility of TFs during transdifferentiation of a prostate cancer. In particular.
Figure 16B:
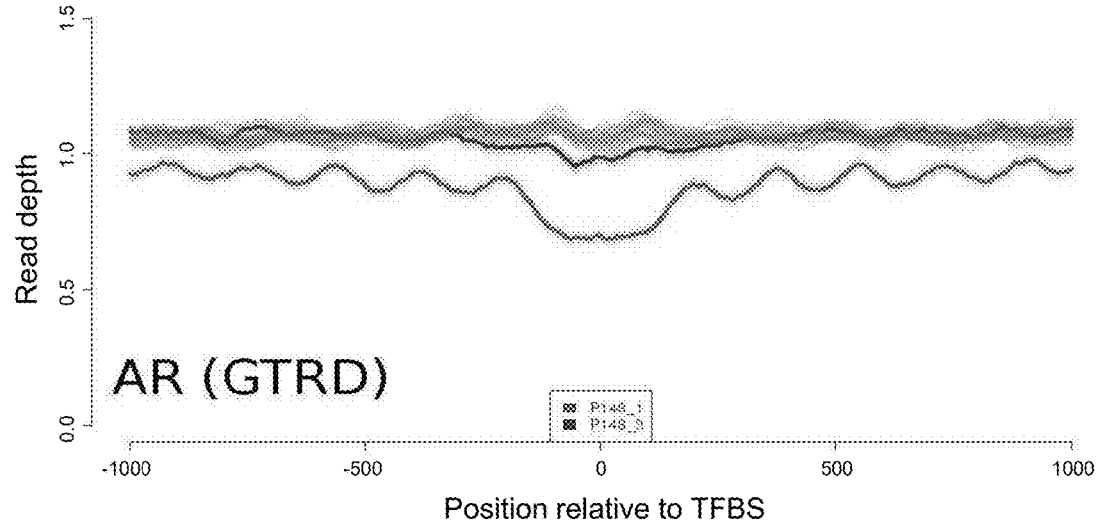
Figure 16C:
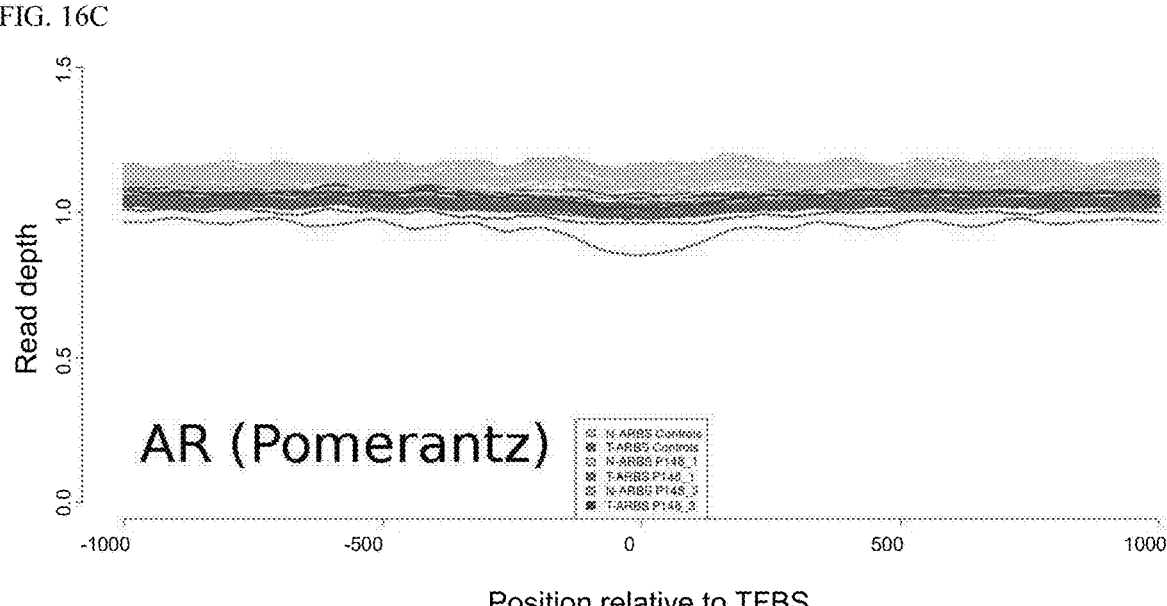
Figure 16D:
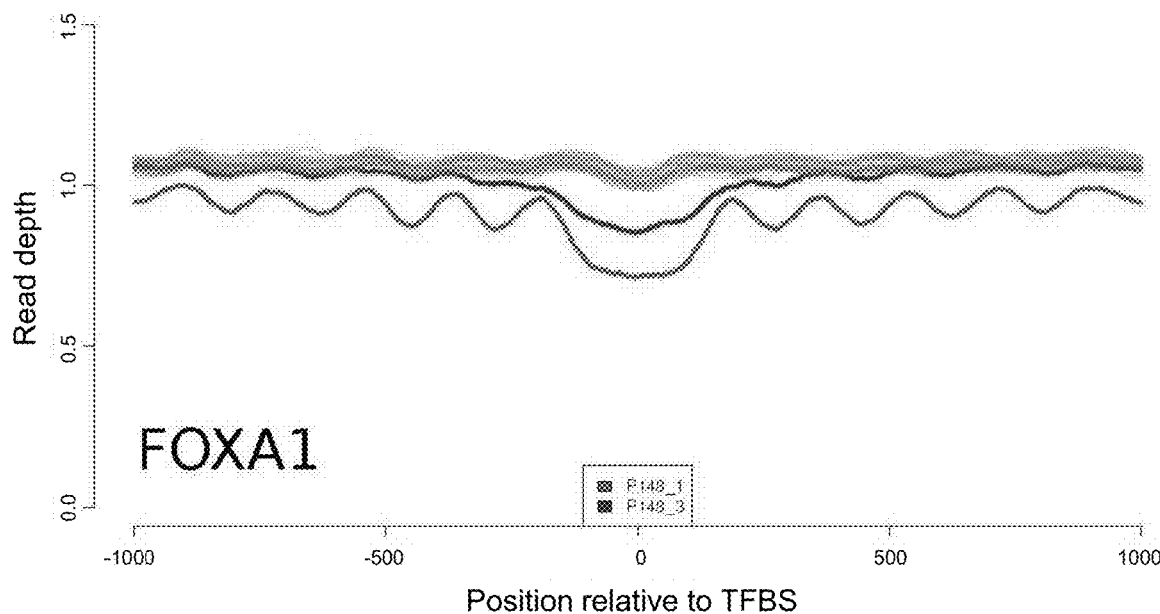
Figure 16E:
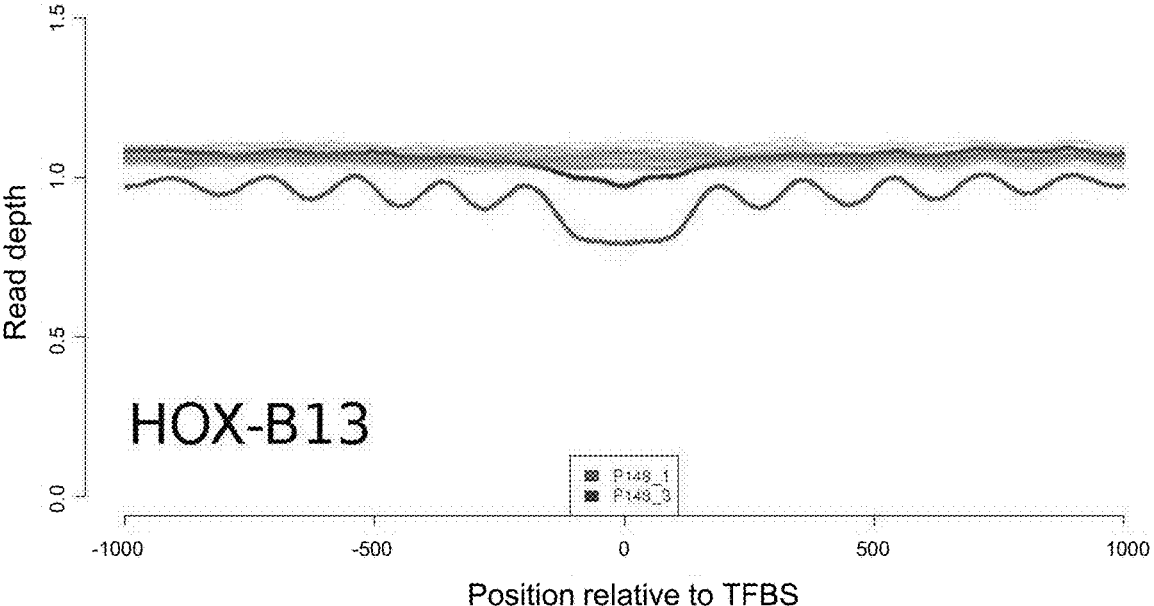
Figure 16F:
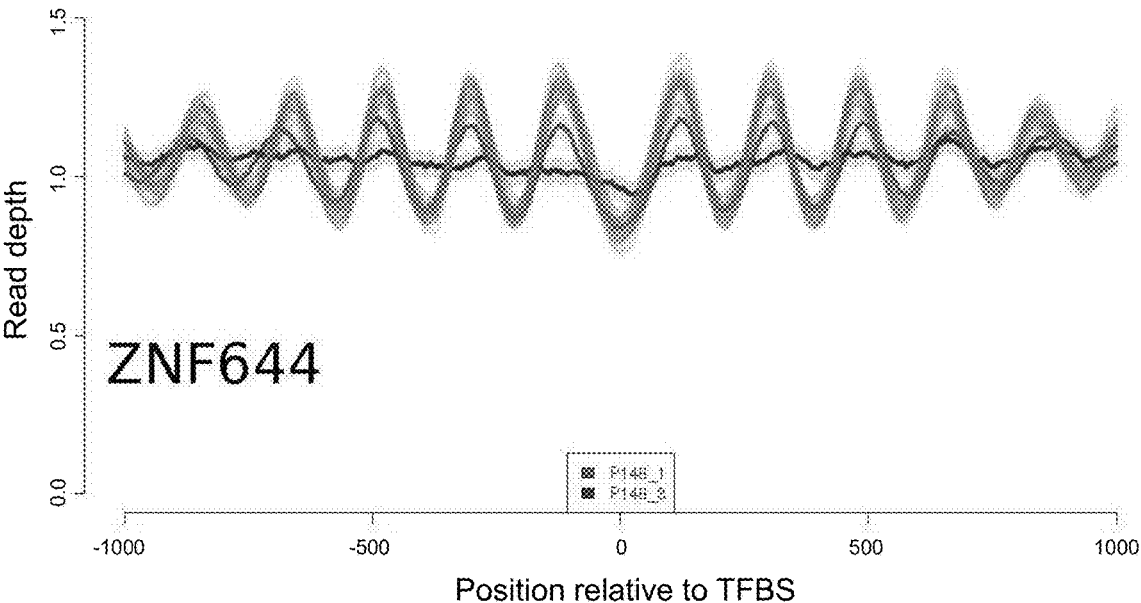
Figure 16G:
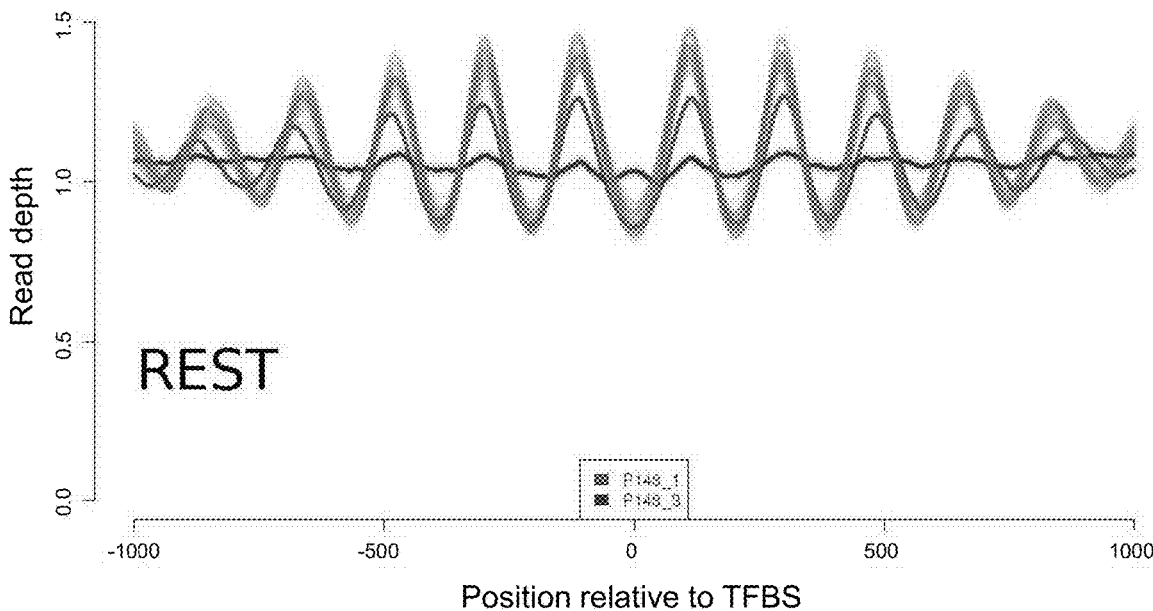
Figure 18A:
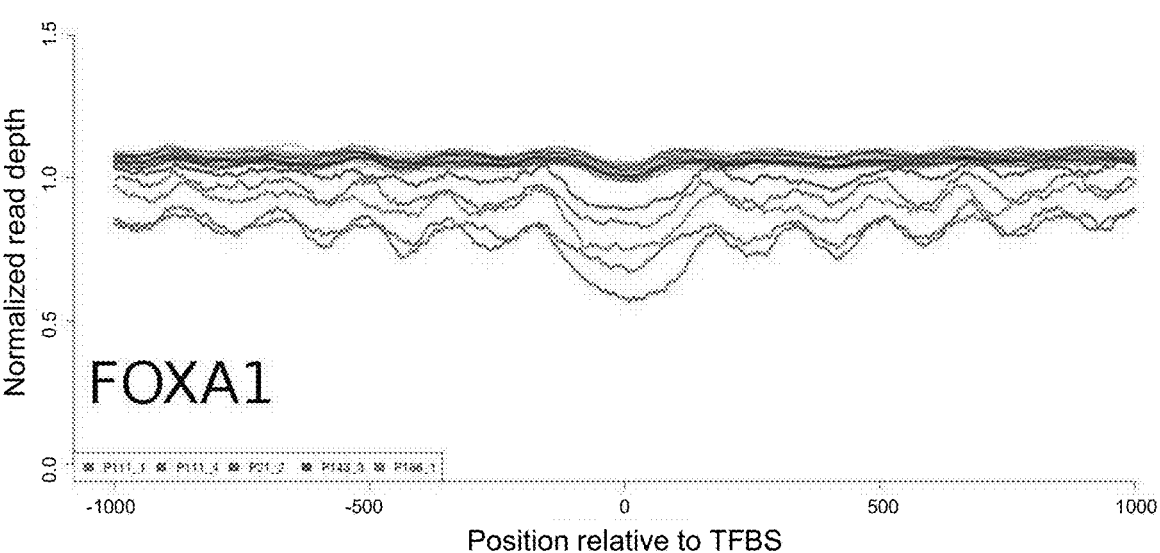
FIGS. 18A-18F show analyses of prostate cancer cases with tandem duplicator phenotype or chromothripsis, including four cfDNA samples (P21_2, P111_1, P111_4, and P166_1) with a tandem duplicator phenotype and one case (P143_3) with chromothripsis on chromosome 10. Accessibility of epithelial TFs FOXA1 in FIG. 18A. GRHL1 in FIG. 18B, and GRHL2 in FIG. 18C, and prostate lineage-specific TFs AR in FIG. 18D. HOXB13 in FIG. 18E, and NKX3-1 in FIG. 18F.
Figure 18B:
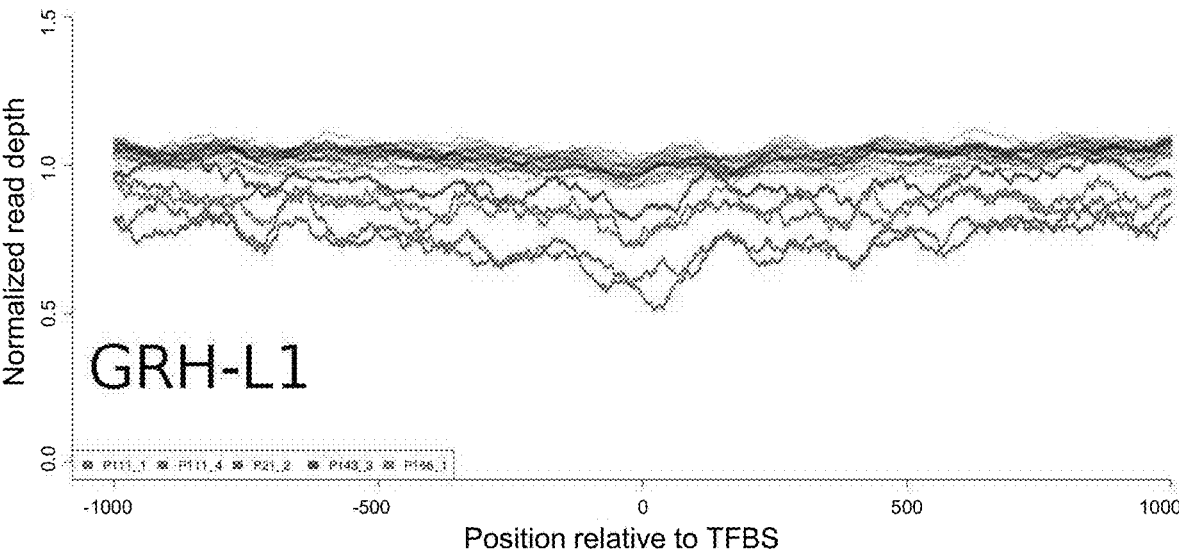
Figure 18C:
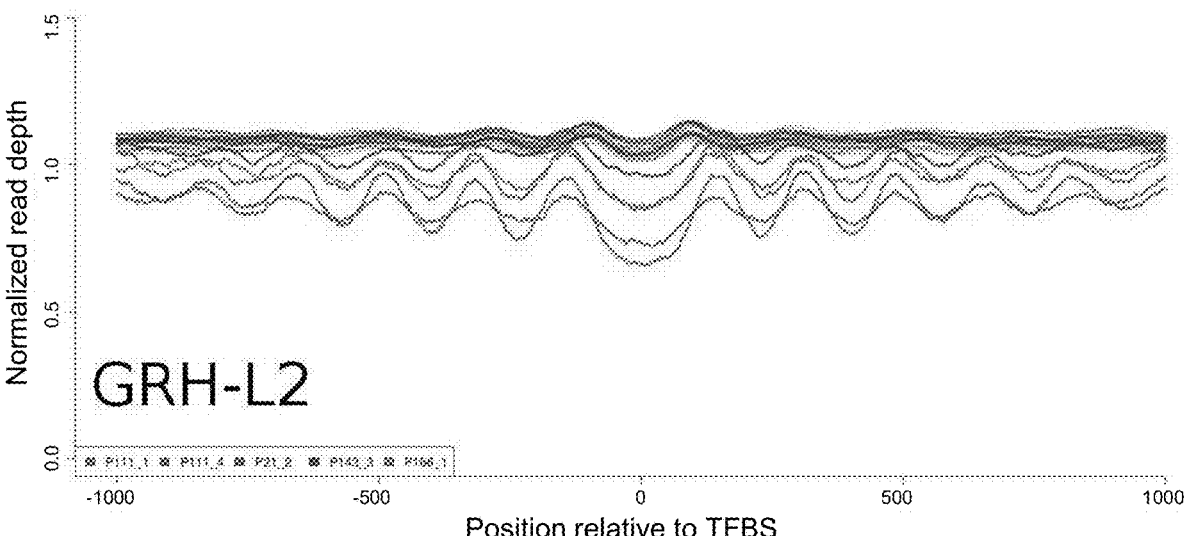
Figure 18D:
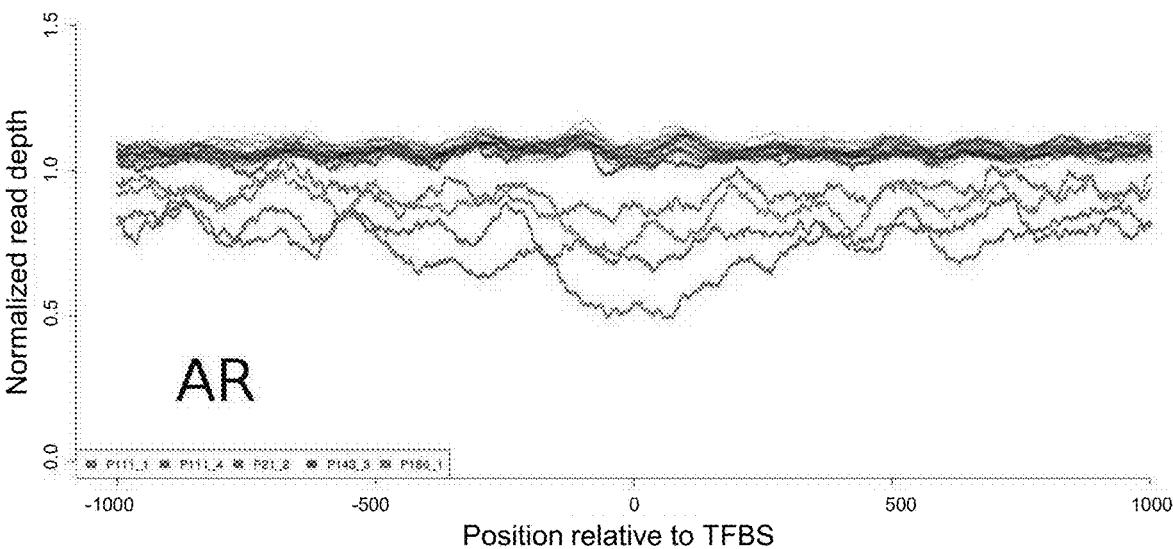
Figure 18E:
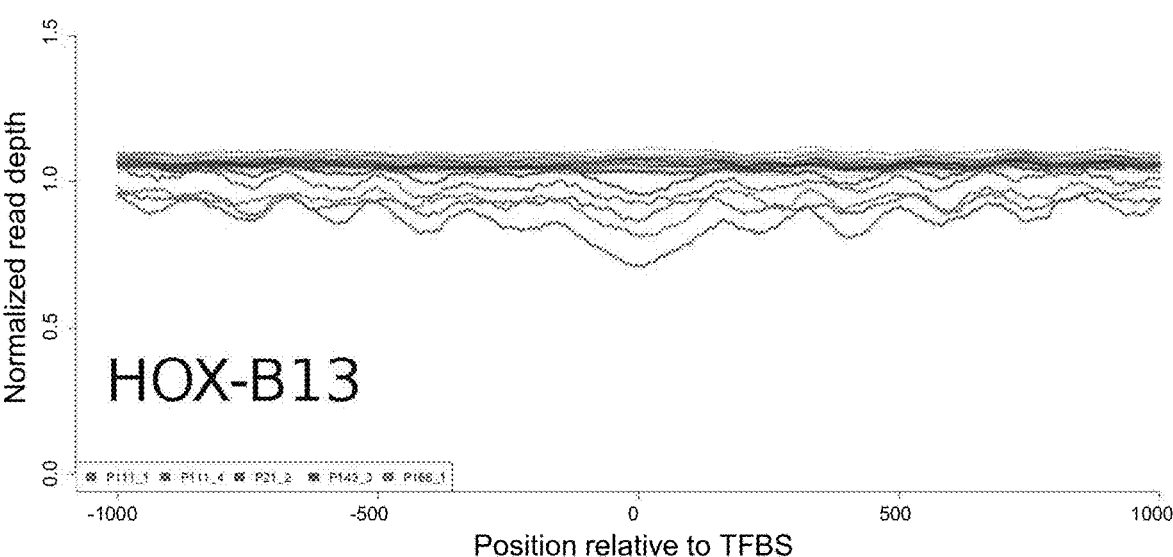
Figure 18F:
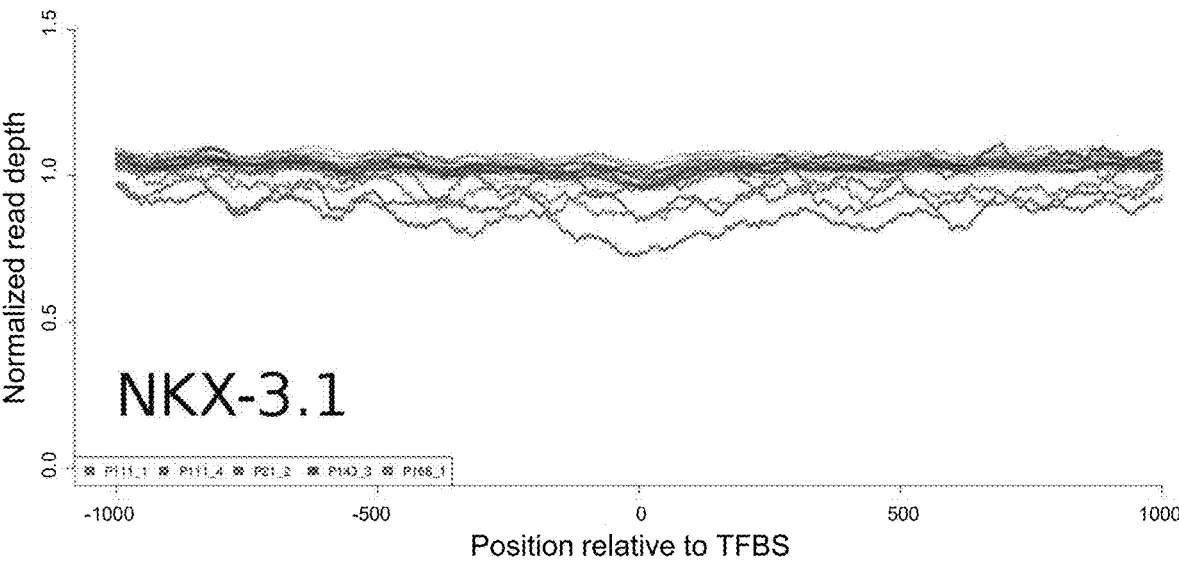
Figure 19:
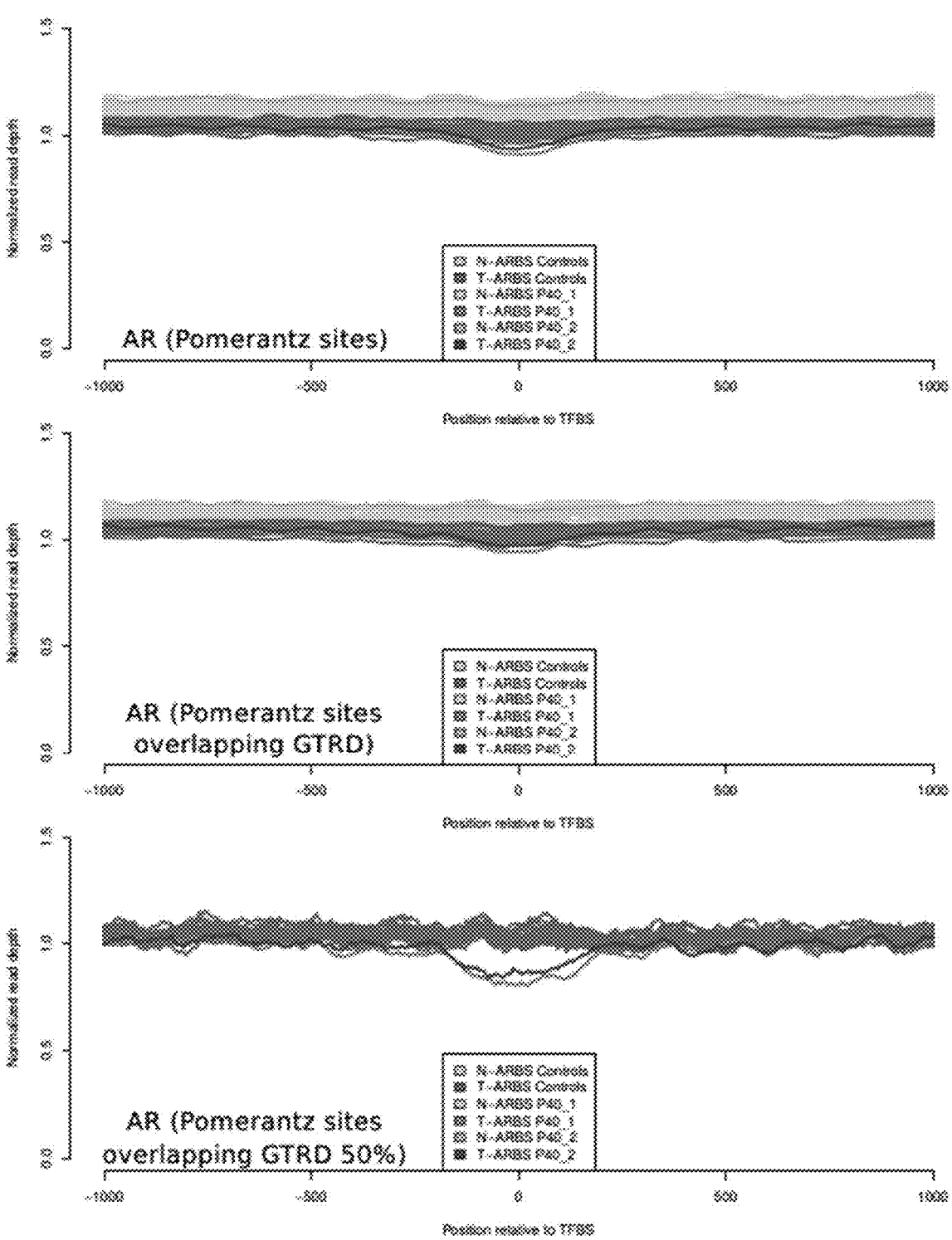
FIG. 19 shows analyses of AR binding sites for plasma samples from P40. This patient with prostate cancer received ADT treatment and developed a high-level AR amplification between samples P40_1 and P40_2.

For tumor subclassification, an index case was used, P148, where analysis was performed on two plasma samples (P148_1, P148_3) taken 12 months apart during which the prostate adenocarcinoma transdifferentiated to a t-SCNC. These two samples showed significant TFBS accessibility changes (Kendall's Tau: 0.7573), specifically reflected in several TFs. The t-SCNC is no longer an androgen-dependent stage of prostate cancer and, consequently, accessibility of AR binding sites was no longer observed in sample P148_3 (FIG. 4I). Due to its close cooperation with nuclear hormone receptors, accessibility to FOXA1 was correspondingly reduced (FIG. 4I). Furthermore, the change in the cell type identity became apparent as reduced accessibility to the binding sites of the prostate-specific lineage TFs HOXB13 and NKX3-1 (FIG. 4J) and the epithelial TF GRHL2 (FIG. 10A). TF changes associated with neuronal development included augmented accessibility of GLI-similar 1 (GLIS1) (FIG. 10B), a TF whose expression is dramatically increased under hypoxic conditions. Hypoxia has been discussed to facilitate the development of prostate adenocarcinoma to an androgen-independent state and furthermore to downregulate repressor element-1 (RE-1) silencing transcription factor (REST), which induces neuroendocrine reprogramming and indeed a significantly decreased accessibility of REST (FIG. 4K) was observed. Furthermore. N-MYC is involved in AR signaling suppression and neuroendocrine program regulation, which was mirrored in an increased accessibility (FIG. 4K). These observations indicated that in certain cancer disease stages. TFBSs may have a high plasticity affecting pathways.

In order to demonstrate that prostate cancer subtype classification based on TFBSs from cfDNA is possible, plasma samples from 4 further t-SCNCs cases (P170_2, P179_4, P198_5, and P240_1) were analyzed. For these cases, it was shown that this approach is also applicable to cfDNA sequenced with a lesser coverage by down-sampling plasma samples P148_1 (819,607,690 reads) and P148_3 (768,763,081 reads) to about 50 million reads. The reduction of reads resulted in an increase of noise levels, which was dependent on the number of TFBSs but negligible for TFs with more than 1,000 TFBSs (FIGS. 11A-11D) so that analyses for the aforementioned highly relevant TFs were not affected. The analyses were repeated for the aforementioned 4 samples, each sequenced with about 50 million reads, and the decreased accessibilities for TFs AR, FOXA1, HOX-B13, and NKX3-1, or the increased accessibility of N-MYC (FIGS. 4I-4K) were observed again. A decreased accessibility of REST was shown only in two of these four cases (P170_2 and P198_5; FIG. 4K), which is consistent with REST downregulation being usually observed in 50% of neuroendocrine prostate cancer cases. Only in these two cases did GLIS1 again have an increased accessibility (z-scores: P170_2: 4.3; P198_5: 4.4), demonstrating that this hypoxia-associated TF may be linked to REST downregulation.

Accessibility to TFBSs May Change During Disease Course

To address the question whether TF accessibility remains stable over time, serial samples were obtained and analyzed from 4 patients (P40, P147, P148, C2). The analyses were limited to 1,000 msTFBSs and did not show significant differences for three of the four plasma sample pairs (Controls: Median: 0.8404±0.0196 (IQR); P40: 0.8620; P147: 0.8370; C2: 0.8719; each Kendall's Tau) (FIGS. 12A-12D).

Between P147_1 and P147_3 a novel, high-amplitude amplification including the RET gene evolved whereas C2_7 had lost an amplification including KRAS, which was observed in C2_6. RET in prostate cancer and KRAS in CRC both may affect the PI3K/AKT/mTOR pathway and therefore downstream targets such as TF CREB were investigated; however, the accessibility was not different from the control plasma samples and furthermore remained unchanged. Between P40_1 and P40_2, resistance against androgen deprivation therapy (ADT) had evolved, which was reflected in a high level amplification of the AR gene. However, if AR expanded its repertoire of transcriptional targets, it did not become apparent at the aforementioned T-ARBSs and N-ARBSs (FIGS. 18A-18F). A conservative approach was used for this analysis, and a change was observed only if the accessibility score differed by ≥100 from one analysis to the next and may explain reduced or limited differences between these samples.

There were significant changes in TF accessibility for case P148 (Pearson Correlation: 0.777291), where the tumor transdifferentiated from a prostate adenocarcinoma (P148_1) to a neuroendocrine tumor (P148_3). The neuroendocrine tumor is no longer an androgen-dependent stage of prostate cancer and consequently accessibility of AR binding sites is no longer needed, which was accordingly reflected in these analyses (FIGS. 16B-16G). The change in the cell type identity of this prostate cancer case was apparent as accessibility to the binding sites of the epithelial cell fate determining TFs GRHL2 and GRHL3 was lost (FIGS. 16B-16G). In addition, a similar decrease in accessibility was observed for other prostate specific lineage TFs HOXB13, NKX3-1, FOXA1, GATA2, and GATA3.

Importantly, as noted above, changes in TFs associated with neuronal development were also observed. Hypoxia occurs frequently in advanced solid tumors and may facilitate the development of prostate adenocarcinoma to an androgen-independent state and may induce neuroendocrine programs. Indeed, an increased accessibility of GLI-similar 1 (GLIS1) was observed, a TF whose expression is dramatically increased under hypoxic conditions. Furthermore, hypoxia down-regulates repressor element-1 (RE-1) silencing transcription factor (REST) in prostate cancer epithelia and induces expression of neuronal genes implicated in neuroendocrine reprogramming. REST is a key mediator of neuroendocrine differentiation caused by androgen depletion and indeed the decreased accessibility of REST (FIG. 16G) was observed.

Differences were also observed associated with stem cell features. TFs SOX2 and SOX11 are upregulated during neuroendocrine transdifferentiation. An increased accessibility for these two TFs was observed; however, these were already present in plasma sample P148_1 and hence preceded the other changes (FIG. 6G-6L). This example demonstrated another feature of this real-time analysis, e.g., that the order of events can be established. A further stem cell-associated change was decreased accessibility of FOXA2 (FIGS. 16B-16G).

Changes were also observed in poorly characterized TFs, such as TFs ZNF644 (ZNF644 is one of the core subunits in the G9a/GLP complex, which mediates mono- and dimethylation of Lys9 of histone H3 at specific gene loci, which is associated with transcriptional repression) or ZNF701 (FIGS. 16A-16G), whose potential role in the transdifferentiation process remains unclear.

Classification of Prostate Cancer Based on TFs from cfDNA

To show that this approach is applicable to samples sequenced with a lesser coverage and down-sampled plasma samples P148_1 (819,607,690 reads) and P148_3 (768,763, 081 reads) to about 50 million reads. The reduction of reads resulted in an increase of noise levels, which was dependent on the number of TFBSs and neglectable for TFs with more than 1,000 TFBSs (FIGS. 18A-18F). Accordingly, accessibility analyses for the aforementioned highly relevant TFs involved in transdifferentiation to neuroendocrine carcinoma were not affected.

| | PSA | NSE | REST |
|---|---|---|---|
| P170_2 | 3.5 | 133 | down |
| P179_4 | 0.56 | 218 | nl |
| P198_5 | 29.4 | >370 | down |
| P240_1 | 3.2 | 542.4 | nl |

DISCUSSION

This study provides a method and bioinformatics software pipeline for inferring tumor cell-specific transcription factor binding from cell-free DNA in the blood, with relevance for clinical diagnostics and non-invasive tumor classification. While some studies have adopted a gene-centric focus when evaluating somatically acquired alterations, this analysis uses an important part of the noncoding genome, focusing on TFBSs. As many TFs bind preferentially within open chromatin and have to therefore interact with nucleosomes, the largely mono-nucleosomal cfDNA is used because it allows the mapping of nucleosome positions. A unique feature of this approach is to generate in vivo data on TFBSs from an endogenous physiological process in contrast to technical variations associated with in vitro assays. Nevertheless, these data correlated strongly with DNase I hypersensitivity data for cell lines GM12878, LNCaP, or HCT116, thereby demonstrating the reliability of this approach.

In contrast to other analyses, which may use general tissue-specific patterns using mixtures of cfDNA signals resulting from multiple cell types and analyses by Fourier transformation, methods and systems of the present disclosure may profile individual TFs and thereby establish lineage-specific TFs for clinical applications. Due to the improved resolution of TFBS analyses, monitoring the accessibility of TFBSs from cfDNA is enabled and may reveal their plasticity during a disease course, such as reprogramming to a different cell lineage. Furthermore, whereas other analyses may require more than 1.5 billion reads per sample, this study demonstrates that about 50 million reads are sufficient for an in-depth TF analysis, making this approach more efficient and cost-effective for clinical applications. Importantly, this cfDNA TFBS bioinformatics pipeline allows classification of tumors and hence fills an important diagnostic gap in the managing of patients with, for example, prostate cancer.

This work provides some substantial improvements to current technologies for TF profiling. First, using cfDNA, the curated list of TFBSs from GTRD, which are annotated with a list of high-confidence TFs, 676 TFs are amenable to analysis from cfDNA. Second, this bioinformatics pipeline was used to establish an improved metric, the accessibility score, to allow comparing the accessibility of TFBSs between different cfDNA samples. Third, use of a z-score statistic based on a comparison between control samples (e.g., reference samples) and case samples (e.g., a test sample obtained from a subject) permits identification of significant changes in TFBSs accessibility. Fourth, the use of lineage-specific TFs for the hematologic (PU.1, LYL1, and SPIB), the epithelial (GRHL2), and the prostate lineage (AR, HOXB13, NKX3-1) is shown for cfDNA-based clinical applications. This is in contrast to other methods that involve mixtures of signals resulting from multiple cell types contributing to cfDNA and analyses by Fourier transformation. The present assessment of the clinical utility indicates that these TFs are broadly applicable to identify individuals with epithelial or prostate cancer. The ability to monitor the accessibility of TFBSs over time is demonstrated and that in particular during the transdifferentiation of a prostate adenocarcinoma to a neuroendocrine tumor drastic changes, involving AR, epithelial, prostate, and neuronal lineages can be assessed non-invasively from peripheral blood.

TF nucleosome interaction maps may be heterogeneous, comprising signals of all cell types that give rise to cfDNA. Plasma samples from individuals who appeared to have large burdens of ctDNA may be used, which may affect the sensitivity of measurements. Furthermore, this approach uses whole-genome sequencing with relatively high coverage (about 50 million reads), which is more than shallow sequencing plasma approaches for the establishment of SCNAs.

Nevertheless, advanced prostate cancer, a tumor entity analyzed here, is a classic example of the intractability and consequent lethality that characterizes metastatic carcinomas. Clinical biopsies of metastatic lesions are not routinely performed, so that detailed knowledge of the molecular mechanisms that control prostate cancer cell survival and progression is missing. Indeed, tumor studies lack dynamic models, and in particular dynamic profiling of clinical samples, to explore transitions and interplays between pathways. Because of the potential of TFs to regulate gene transcription throughout the genome and their often exquisitely lineage-specific manner, their detailed analyses offer a unique opportunity to improve clinical diagnostics. This data may also provide the foundation for further dissection of the non-coding genome through improved approaches for transcription regulation profiling.

Methods

Subjects

The study was approved by the Ethics Committee of the Medical University of Graz (approval numbers 21-227 ex 09/10 [breast cancer], 21-228 ex 09/10 [prostate cancer], 21-229 ex 09/10 [colorectal cancer], and 29-272 ex 16/17 [High resolution analysis of plasma DNA]), conducted according to the Declaration of Helsinki and written informed consent was obtained from all patients and healthy probands, respectively. Some plasma samples, e.g., of patients B7 and B13 and P40, P147, and P148, have been analyzed within other studies.

B7 and B13: These studies analyzed matching and synchronously obtained primary tumors from two metastatic breast cancer cases (B7, B13) in addition to the plasma DNA by whole-genome sequencing and RNA-Seq. Plasma DNA was sequenced with high coverage (B7: about 411 million reads; about 8.2×; B13: about 455 million reads; about 9.1×) and calculated copy number alterations. Focal amplifications were identified which are frequent in breast cancer, such as amplifications of 11q13.3 (15 genes including CCND1) in B7 or of 8p11 (31 genes including FGFR1) and 17q12 (46 genes including ERBB2) in B13.

P40: An initial plasma DNA analysis for patient P40 revealed multiple copy number changes on the majority of autosomes, whereas no copy number change was observed on the X chromosome (FIG. 3C). Prior to this therapy, the patient was treated with local radiation. Due to disease progression, treatment was switched to the third generation LHRH antagonist degarelix. However, despite this therapy switch, progression was noted 10 months later, and a repeated plasma analysis revealed that while the changes on the autosomes were the same, there was a focal amplification on chromosome Xq12, which harbors the AR gene.

B7 and B13: These studies analyzed matching and synchronously obtained primary tumors from two metastatic breast cancer cases (B7, B13) in addition to the plasma DNA by whole-genome sequencing and RNA-Seq. Plasma DNA was sequenced with high coverage (B7: about 411 million reads; about 8.2×; B13: about 455 million reads; about 9.1×) and calculated copy number alterations. Focal amplifications were identified as defined previously (Ulz et al., 2016b) which are frequent in breast cancer, such as amplifications of 11q13.3 (15 genes including CCND1) in B7 or of 8p11 (31 genes including FGFR1) and 17q12 (46 genes including ERBB2) in B13.

P21: Patient P21 was diagnosed with metastatic castration-resistance prostate cancer (CRPC). After 4 months of treatment with LHRH antagonist degarelix, the patient showed signs of clinical progression followed by increase of PSA values. At the progression (P21_2), the cfDNA profile was observed with a tandem duplicator phenotype.

P40: At the diagnosis, patient P40 was classified to have castration-sensitive prostate cancer (CSPC). Since the patient did not show clinical response on previous radiation therapy, treatment was switch to LHRH antagonist degarelix. Initially, the patient showed a good response on androgen blockade (PSA values dropped from 425.3 ng/ml to 115.3 ng/ml), but after 10 months, he progressed to CRPC (PSA: 656.0 ng/ml). The patient's cfDNA profile at progression (P40)_2) revealed high-level AR amplification on chromosome X.

P40: An initial plasma DNA analysis of patient P40 revealed multiple copy number changes on the majority of autosomes, whereas no copy number change was observed on the X chromosome (FIGS. 4B and 4C). Prior to this therapy, the patient was treated with local radiation. Due to disease progression, the patient's treatment was switched to the third generation LHRH antagonist degarelix (Rick et al., 2013). However, despite this therapy switch, progression was noted 10 months later, and a repeated plasma analysis revealed that while the changes on the autosomes were the same, there was a focal amplification on chromosome Xq12, which harbors the AR gene.

P111: The first sample P111_I was obtained at diagnosis of prostate cancer. The patient had already multiple malignant lesions in the bones, lymph nodes, and kidney. The first line treatment was GnRH-analog goserelin, followed by radiation therapy. Between two samples P111_1 and P111_4, the patient responded well on the treatment (CSPC, PSA dropped to 15.5 ng/mL)). Two months prior to P111_4 sampling, clinical progression was noted, and the patient developed CRPC. Analyzing cfDNA sample at the progression (P111_4), partial AR amplification was observed. Furthermore, the patient received chemotherapy (docetaxel), but no further response was noticed.

P143: Patient P143 was diagnosed with metastatic prostate cancer 6 years before collection of sample P143_3. Previously, the patient was treated with different antiandrogens including second generation antiandrogens (abiraterone). Hence, he was heavily pretreated when the sample P143_3 was obtained. Because of progressive disease and after multiple treatment failures with different ADTs, chemotherapy was introduced (microtubule inhibitor-cabazitaxel).

P147: The first blood sample (P147_1) was obtained 5 years after the diagnosis. The patient had multiple bone metastases and was characterized as CRPC. During these 5 years, he was treated with radiation therapy and received multiple anti-androgens. At the time of P147_1 sample collection, a new PSA increase was noticed. Analysis of cfDNA discovered high-level amplifications on Xq12 (AR) and on chromosome 5q14.3. After 6 months under chemotherapy (docetaxel) and antiandrogens (abiraterone and enzalutamide), a new cfDNA sample (P147_3) was analyzed. This analysis revealed a novel RET amplification on chromosome 10. Development of novel focal events and increase in ctDNA content (P147_1 ichorCNA: 52%; 147_3 ichorCNA: 73%) correlated with clinical progression.

In patient P147, the time period between prostatectomy and the first plasma sample was 56 months. Twenty months after surgery, an increase in PSA levels was noted, and treatment with radiation was initiated. Twenty-eight months after diagnosis, the PSA levels increased again. This patient was treated for 13 months with the non-steroidal antiandrogen bicalutamide and for the subsequent 4 months, the GnRH-analog leuprorelin was additionally administered and eventually later, the monoclonal antibody denosumab was added due to detection of bone metastases. When the PSA levels increased, a plasma sample was obtained, and novel high-level amplifications were detected on Xq12 (AR) and on chromosome 5q14.3. A further high-level focal amplification evolved on chromosome 10q11.21, which occurred between collection of the first and second plasma samples (e.g., P147_1 and P147_2); the time period between these two samples was 6 months. During this time, the patient was treated with chemotherapy, e.g., docetaxel.

P148: P148 was diagnosed with an adenocarcinoma of the prostate. The patient received ADT in the period prior to first blood collection (P148_1). Clinicians reported progressive disease (PSA: 694.4) with novel bone and lymph nodes lesions. At the time of the P148_1 sample collection, chemotherapy (docetaxel) was introduced. Multiple focal events were identified (MYC amplification; PTEN loss; FOXP1, RYBP, SHQ1 loss; TMPRSS2-ERG fusion) including AR amplification (patient was previously characterized as CRPC).

Six months after the first sample collection, sample P147_3 was obtained. During this period, massive progression with multiple liver and bone metastases was noted, with a PSA level of 52.0 ng per mL and an NSE value of greater than 370 ng/ml. Interestingly, AR amplification was not detected in the sample P147_3, which is characteristic for the transdifferentiation from adenocarcinoma to neuroendocrine prostate cancer (as described by Ulz et al. 2016. Belic et al. 2018). After a short response on palliative treatment with carboplatin and etoposide, disease progression was noted, and the patient deceased 2 months later.

Patient P148 was diagnosed with an adenocarcinoma of the prostate. A first plasma sample was obtained at 16 months after the initial diagnosis, and at this time the patient had clearly progressive disease with increasing metastases to the bone and newly diagnosed lymphadenopathy. Because of the progressive disease (PSA: 694.41 ng/ml), the patient was treated with docetaxel for 7 months. A second plasma DNA analysis during this time confirmed the presence of the high-level AR amplification. Five months after the last docetaxel treatment, massive progression with multiple liver and bone metastases was noted, with a PSA level of 52.0 ng/ml and an NSE value of greater than 370) ng/ml. The patient received palliative treatment with carboplatin and etoposide with an initial partial response lasting 3 months. Thereafter, his disease progressed, and he deceased 2 months later.

P166: A blood sample of patient P166 was obtained 2 years after initial diagnosis of metastatic prostate cancer. He was treated with antiandrogen bicalutamide, but developed progressive disease (CRPC). AR amplification at chromosome X as a sign of progression was identified in sample P166_1. Since patient developed CRPC, chemotherapy (docetaxel) was further introduced. After 3 months under chemotherapy the patient he showed a partial response.

P190: Five years before blood collection, the patient was diagnosed with localized prostate cancer. Two years afterwards, he had local progression and during next 2 years he developed metastatic disease, with, predominantly with bone metastasis. During these years he was treated with the antiandrogen bicalutamide. The patient developed a bone metastasis and disease progression, and some bone metastases were characterized with neuroendocrine phenotype. Hence, the clinicians treated him with carboplatin-based chemotherapy (carboplatin/etoposide). A cfDNA analysis was performed 3 months after the beginning of the carboplatin/etoposide treatment. At the time of this analysis, the patient showed a good response with ≥50% PSA-response and normalization of NSE values.

Tandem Duplicator Phenotype:
    P21_2: 59,849,368 reads
    P111_1: 58,258,680 reads
    P111_4: 61,085,342 reads
    P166_1: 52,829,575 reads
Chromothripsis (Chromosome 10):
    P143_3: 111,958,416 reads (least PC-specific changes)
Pairwise Comparison of Plasma Samples To address whether TF accessibility remains stable over time, two samples were analyzed each from patients P40, P147, and C2. However, with very stringent criteria, e.g., by confining the analyses to 1,000-msTFBSs, no significant differences were observed in these plasma sample pairs (Controls: Median: 0.8404±0.0196 (IQR); P40: 0.8620; P147: 0.8370; C2: 0.8719; each Kendall's Tau) (FIGS. 12A-12D).

Between samples P147_1 and P147_3 collected from patient P147, a novel, high-amplitude amplification including the RET gene evolved, whereas C2_7 had lost an amplification including KRAS, which had been observed in the previous sample C2_6. RET in prostate cancer and KRAS in CRC both may affect the PI3K/AKT/mTOR pathway and therefore downstream targets such as the TF CREB were investigated; however, the accessibility was not different from the control plasma samples and furthermore remained unchanged. Between samples P40_1 and P40_2 of patient P40, resistance against androgen deprivation therapy (ADT) had evolved, which was reflected in a high level amplification of the AR gene. However, if AR expanded its repertoire of transcriptional targets, it did not become apparent at the aforementioned T-ARBSs and N-ARBSs (FIG.

19). A very conservative approach limiting the analyses to 1,000-msTFBSs may explain why differences between these samples was not observed.

The Shape of TFBSs

TF-specific nucleosome coverage profiles were investigated because some TFs showed evenly spaced nucleosome peaks, including their binding sites (e.g. PU.1 and GRHL2 in FIGS. 2E and 2K), whereas other TFs had wider troughs at their binding sites (e.g. CREM in FIG. 6A), resembling those observed for TSSs. Altogether, 55 TFBSs were identified where the TFBS exceeded 300 bp, and from these, 26 had binding sites close to di-nucleosomal sizes (312-352 bps; FIGS. 8M-8P). For these patterns, highly significant increases of overlap were identified for both CpG islands ($p=4.2\times10^{-11}$; Mann-Whitney U test) and TSSs ($p=8.5\times10^{-12}$; Mann-Whitney U test) for TFBSs with sizes greater than 300 bp (FIGS. 8Q and 8R).

CTCF as Extraordinary Example for a TF with Multiple Different Binding Sites

To explore different TFBSs of the same TF, CCTC-binding factor (CTCF) was used. CTCF is present at 55,000-65,000 binding sites in mammalian genomes. Of these sites, about 5,000 are ultraconserved, about 50% are in intergenic regions, about 15% are located near promoters, and about 40% are intragenic. Furthermore, chromosomes are partitioned into evolutionary conserved higher-order chromosome structures, named topologically associating domains (TADs), and their boundaries are enriched for binding sites of CTCF and cohesin. In mammals, 15% of genomic CTCF-binding sites are present at TAD borders, whereas the other 85% of genomic CTCF-binding sites are inside TADs.

Blood Sampling and Library Preparation

Peripheral blood was collected from patients with metastatic prostate, breast, and colon cancer at the Department of Oncology and from anonymous healthy donors without known chronic or malignant disease at the Department of Hematology at the Medical University of Graz. CfDNA was isolated from plasma using the QIAamp Circulating Nucleic Acids kit (QIAGEN, Hilden, Germany) in accordance with the manufacturer's protocol. Library preparation for WGS was performed as described previously (Heitzer et al., 2013).

Sequencing

Control and high-coverage tumor samples were sequenced on the Illumina NovaSeq S4 flowcell at 2×150 bp by the Biomedical Sequencing Facility at CeMM, Vienna, Austria. For the control samples, an average of 435,135,450 (range: 352,904,231-556,303,420) paired-end reads were obtained. For the tumor samples (P40_1, P40_2, P147_1, P147_3, P148_1, P148_3, C2_6, and C27), an average of 688,482,253 reads (range: 541,216,395-870,285,698) were sequenced. Additional samples were sequenced using the Illumina NextSeq platform (B7_1, B13_1, and P190_3; average sequencing yield: 296,733,931 reads; range: 181, 953,656-379,733,061) and the HiSeq platform (P21_2, P111_1, P111_4, P143_3, and P166_1; average sequencing yield: 52,869,911 reads; range: 41,780819-84,049,593), respectively.

Low-coverage tumor samples which were used to create single-entity pools, were sequenced on either the Illumina Next-Seq or MiSeq platform. This resulted in 382,306,130 reads from 69 prostate cancer samples, 254,490,128 reads from 60 breast cancer samples, and 604,080,473 reads from 100 colon cancer samples.

Characterization of Plasma Samples

Some plasma samples, e.g., of patients B7 and B13 and P40, P147, and P148 were analyzed and included information regarding mutations, specific SCNAs, and tumor content of the plasma samples based on the algorithm ichorDNA.

The ETS family of oncogenic transcription factors (inspired by (Sizemore et al., 2017)) Approximately 50% of localized and approximately 40% of metastatic prostate carcinomas contain TMPRSS2-ETS fusion. The recurrent gene fusion of the 5' untranslated region of TMPRSS2, which is androgen-regulated, to ERG (the TMPRSS2-ERG gene fusion), which is observed in about 50% of primary prostate cancers, results in the hijacking of ETS expression and transcriptional program by the AR.

ERG has also been found to block prostatic neuroendocrine cell differentiation. One possible mechanism for TMPRSS2-ERG-mediated maintenance of prostatic stem and progenitor cells is through SOX9.

Given their roles as transcription factors, it is not surprising that ETS factors mediate tumorigenesis through multiple mechanisms that range from basic survival cues to complete epigenetic reprogramming. ETS factors also affect nucleotide, energy and steroid metabolism.

P40: Mutations in BRCA1: NM_007294: Q975R; specific SCNAs: TMPRSS2-ERG fusion; AR amplification in sample 2; chr12 amplification (containing ARID2, HDAC7); tumor content: P40_1: 30%, P40_2: 24%. Additional focal amplifications on chromosomes 15 (contains SNORD (small nucleolar RNAs, C/D box) genes, 16 (2×), and 19 (BRD4); P40_1 ichorCNA: 30%; P40_2 ichorCNA: 24%.

P147: Mutations: BRCA2: T298fs; TP53: F338I; specific SCNAs: RET amplification in sample 3; AR amplification; BRAF amplification (7q34); PTEN loss; tumor content: P147_1: 52%; P147_3: 73%. Additional focal amplifications on chromosomes 5 (XRCC4) and 21 (RBM11); P147_1 ichorCNA: 52%; 147_3 ichorCNA: 73%.

P148: Mutations: TP53: R213X; specific SCNAs: MYC amplification; PTEN loss; FOXP1, RYBP, SHQ1 loss; TMPRSS2-ERG fusion; AR amplification (gone in P148_3); tumor content: P148_1: 38%; 148_3: 49%.

C2: specific SCNAs: high level amplification on chromosome 12 (KRAS) in C2_6, not visible in C2_7; tumor content: C2_6: 18%; C2_7: 28%.

Transcription Factor Binding Site Definitions

Data from the GTRD database were downloaded, and individual BED files per TF were extracted. The position was recalculated by focusing on the reported point where the meta-cluster has the highest ChIP-seq signal. An additional BED file was created which only includes peaks that are supported by more than 50% of the maximum number of samples analyzed for this specific transcription factor. All BED files were then converted to hg19 (from original hg38) using the liftOver tool provided by UCSC.

Transcription Factor Binding Site Overlaps

In order to check whether binding sites of transcription factors overlap, regions of the binding sites from GTRD (of the sites supported by more than 50% of the samples) were increased by 25 bp, 50 bp, and 100 bp, respectively, on either side using bedtools slop. Subsequently, the number of overlap was calculated by using bedtools intersect via pybedtools for every transcription factor with every other transcription factor.

Single-End Sequencing Data Preparation

In order to enhance the nucleosome signal, sequencing reads were trimmed to remove parts of the sequencing read that are associated with the linker region. Hence, forward sequencing reads were trimmed to only contain base 53-113 (this may correspond to the central 60 bp of a 166-bp fragment). Reads were then aligned to the human hg19 genome using a Burrows-Wheeler aligner (bwa), and PCR-duplicates were removed using samtools rmdup. Average coverage is calculated by bedtools genomecov.

Paired-End Sequencing Data Preparation

Paired-end sequencing reads were aligned to the human hg19 genome using bwa mem, and PCR duplicates were marked with picard MarkDuplicates.

MNase-Seq Data Preparation

BAM files of MNase-seq experiments of GM12878 were downloaded from the ENCODE portal. Sequencing reads in BAM files were trimmed directly from the BAM file using pysam. In brief, left-most alignment positions in the BAM file were shifted 53 bp in the respective direction and the sequence length was adjusted to 60 bp. The coverage patterns were then calculated in the same way as the trimmed cell-free DNA sequencing data.

Coverage Patterns at Transcription Factor Binding Sites

For every transcription factor in the GTRD, coverage patterns were calculated. To this end, coverage data was extracted for every region using pysam count_coverage in a region ±1000 bp around the defined binding sites. Coverage data at every site were normalized by regional copy-number variation and by mean coverage. For every position around the TFBS, coverage was averaged, and 95% confidence intervals were calculated. If more than 100,000 positions were defined for a transcription factor, then 100,000 sites were randomly chosen to be analyzed.

Insert Sizes Around Transcription Factor Binding Sites

To assess whether fragment sizes around transcription factor binding sites were biased, insert size data from paired-end analyses were used. Every position from −1000 bp to 1000 bp from the binding site was traversed and (single-end) sequencing reads where the central 3 bp around the midpoint are located at this position were fetched using pysam. Also, paired-end alignments from the same sample were fetched, and the insert size information was designated to the respective reads. All insert sizes at specific positions relative to the TFBS were then summarized, and 1000 data points were sampled and plotted for each position in the range of −1000 bp to 1000 bp from the TFBS.

Measuring Transcription Factor Binding Site Size

In order to measure the size of the transcription factor binding site, the respective coverage pattern was smoothed using a third-order Savitzky-Golay filter (window-size: 31). Peaks were identified by searching for data points that were larger than the neighboring 20 data points on either side. Peaks were removed if they resided within 50 bp of the center of the supposed binding site. The distance between the closest peaks next to the binding site peak was specified as the transcription factor binding site size.

Since binding site estimates are only reasonable if nucleosome synchronization is detectable, the signals were filtered by various criteria:

High-frequency signal amplitude is more than 0.1

Mean normalized coverage of the central 100 bp is less than 1

Number of peaks is less than 15

Median distance between peaks is more than 150 bp

The binding site sets comprises over 500 sites

A total of 228 binding site sets passed these filters and were used for binding site estimation.

Measures of Transcription Factor Accessibility Using Savitzky-Golay Filters

Two distinct signals make up the coverage pattern, and two signals of different frequencies were extracted into lower and higher range frequency. The lower range frequency data was extracted by a Savitzky-Golay filter (third-order polynomial and window size of 1001). A high-frequency signal was extracted by a different Savitzky-Golay filter (third-order polynomial and window size of 51). The high-frequency signal then was normalized by division by the results of the low-frequency signal. The data range of the high-frequency signal then was recorded. Since coverage profiles from transcription factors with few described binding sites are inherently noisier, a LOESS (locally weighted smoothing) was performed over the signal range and the amount of described binding sites. The range values were corrected by the smoothed LOESS, and ranks of the adjusted range were calculated.

Measures of Transcription Factor Accessibility Using Wavelet Transformation

As an additional method to measure accessibility of transcription factors, wavelet transformation was applied by using the R-package "WaveletComp." For every signal, peaks were recorded in the power spectrum along the periods between 2 bp and 512 bp. The highest peak in the range between 135 bp and 235 bp (185 bp±50 bp) was used to reconstruct a de-noised higher-frequency nucleosome signal at that specific period. Moreover, any residual baseline was removed using de-trending of the original data series. Three parameters of the reconstructed signal were analyzed: The maximum amplitude of the signal, the sum of the signal powers (amplitudes squared) and the sum of the absolute amplitudes along the 2000 bp surrounding the transcription factor binding site.

For comparing tumor to normal samples, the mean value and standard deviation for the respective parameters were recorded in normal samples for every transcription factor, and Z-scores were calculated by taking the respective parameter in the cancer sample, subtracting the mean value of the normal, and dividing by the standard deviation.

Comparing Tumor and Control Samples

In order to compare tumor and control samples, the ranks of the respective transcription factors in the adjusted range values were compared. Rank differences were calculated between a tumor sample, and every control sample and mean rank differences were recorded. Moreover, z-scores were calculated for every transcription factor from the accessibility ranks, by taking the respective rank, subtracting the mean rank of the control samples, and dividing by the standard deviation of this transcription factor ranks of the control samples.

DNase Hypersensitivity Data Analysis

BAM-files from DNase hypersensitivity experiments were downloaded from the ENCODE database for GM12878, LNCaP, and HCT116 cell lines. Binding site regions of a transcription factor were increased by 25 bp on either side using bedtools slop. Coverage at the respective binding sites was extracted using mosdepth and normalized by million mapped reads per sample.

Analysis of Somatic Copy-Number Alterations (SCNAs)

For control data, paired-end alignments were subsampled using samtools view to only include 2% of the initial alignments and converted to FastQ using samtools fastq. For the cancer samples, separate low-coverage whole-genome sequencing was performed. Plasma-Seq was applied to the subsampled FastQ files and the low-coverage data of the cancer samples, respectively. In brief, sequencing reads were aligned to the human hg19 genome, and sequencing reads were counted within pre-specified bins. The bin size was determined by the amount of theoretically mappable positions to account for differences in mappability throughout the genome. Read counts were normalized for total amount of reads and GC content of bins were corrected for by LOESS smoothing over the GC spectrum. Moreover, corrected read counts were normalized by the mean read counts of non-cancer controls per bin to control for additional positional variation.

The Accessibility Score Enables Accurate Inference of TF Binding from cfDNA

Figures 29A, 29B, 29C, 29D, 29E:
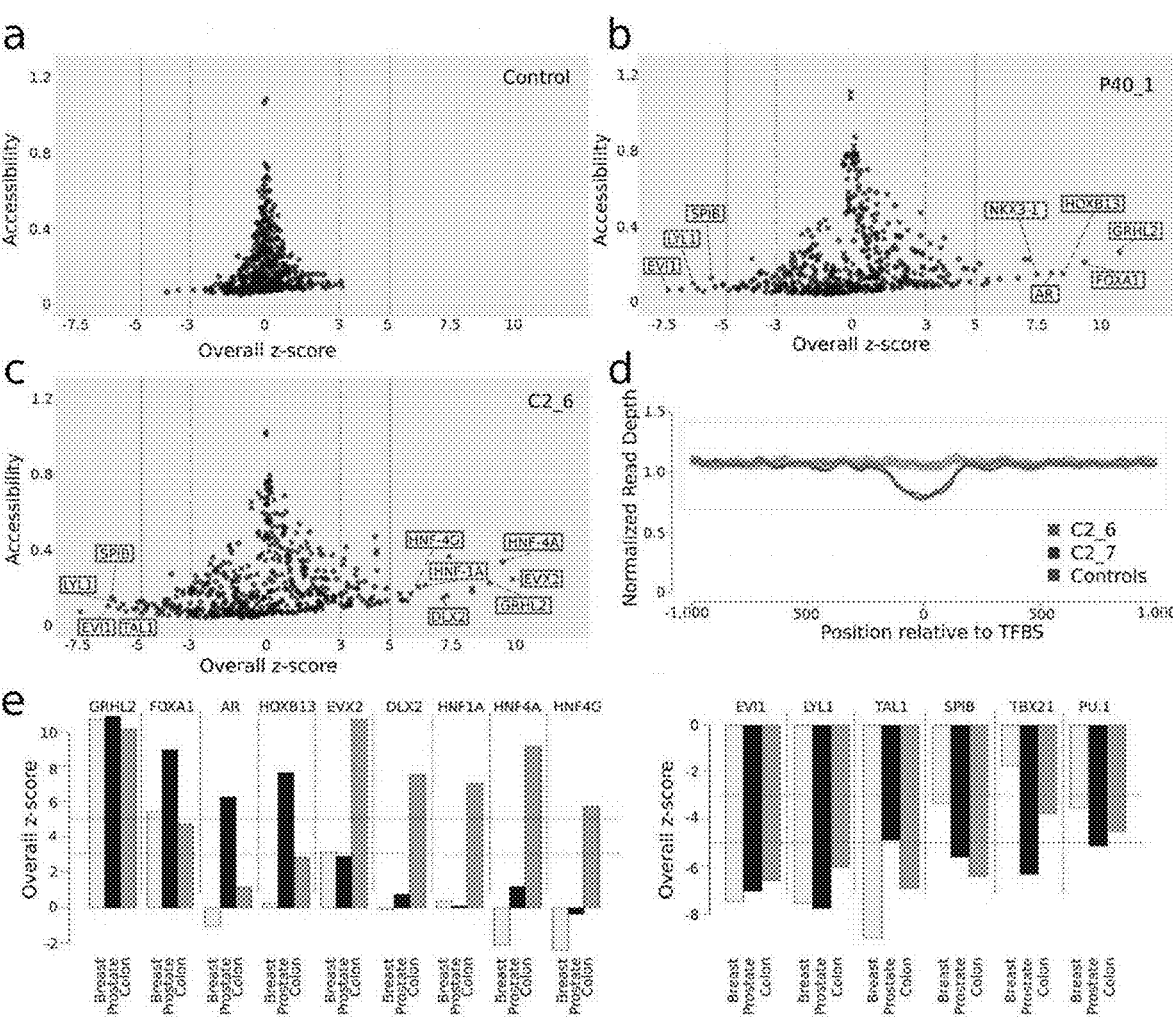
FIGS. 29A-29E provide identification of transcription factors with altered accessibility in plasma samples from patients with cancer.

Samples from healthy donors showed no TFs exceeding the ±5 z-score threshold (FIG. 29A); however, very different patterns were observed in samples derived from patients with cancer. For example, in prostate sample P40_1 from patient P40, TFs with accessibilities above the +5 z-score threshold included, in addition to GRHL2, FOXA1, which cooperates with nuclear hormone receptors in endocrine-driven tumors of the prostate and breast, as well as the prostate lineage-specific TFs HOXB13, AR, and NKX3-1 (FIG. 29B). In contrast, hematopoietic TFs, such as LYL1, SPIB, and EVIL (transcriptional regulator ecotropic viral integration site 1 (FIG. 29B) had low accessibilities. These results were in excellent agreement to the TF ranking based on the ATAC-seq data. In breast cancer samples B7 and B13, an increased accessibility was detected in concordance with the ATAC-seq data for GRHL2, FOXA1, and ZNF121, a zinc finger protein, which has been implicated in regulation of cell proliferation and breast cancer development.

In the samples from colon cancer patient C2, it was unexpectedly observed that the ATAC-seq data had ranked EVX2, a TF that has not been strongly linked to cancer, as most accessible in COAD. Indeed, EVX2 was ranked with the highest accessibility in this analysis (FIG. 29C) and the nucleosome position map showed an enormously increased accessibility of EVX2 (FIG. 29D). In agreement with the ATAC-seq data, an increased accessibility was also observed for the TFs HNF4A, GRHL2, DLX2, HNF4G, and HNF1A (FIG. 29D).

Furthermore, and as predicted by evaluation of the ATAC-seq data, the accessibilities for hematopoietic-related TFs, such as LYL1, TAL1 (SCL/TAL1 (stem cell leukemia/T-cell acute lymphoblastic leukemia [T-ALL] 1, EVI1, TBX21 (T-bet), and PU.1 were reduced in all tumor samples (FIGS. 29B-29C). As a further confirmation for the robustness and reproducibility of lineage-specific TFs in cfDNA, in pools of multiple cfDNA samples generated by shallow-coverage (<0.2×), it was shown that those TFs with increased accessibility in the majority of samples have an increased accessibility score, whereas others may be averaged out. To this end, cfDNA samples were pooled separately for prostate (n=69), for colon (n=100), and for breast (n=60) cancer cases. When the analyses were repeated, the epithelial TF GRHL2 and hematopoietic TFs reiterated their increased and decreased accessibility patterns, respectively, in the three epithelial lineages. In the colon cfDNA pool, TFs EVX2, DLX2, HNF1A, HNF4A, and HNF4G, as well as TFs AR and HOXB13 in the prostate cancer cfDNA pool, had increased accessibilities, whereas FOXA1 exceeded the >5 z-score threshold in both the prostate and breast pool. This confirmed that TF accessibility estimation derived from ATAC-seq data can be reliably inferred from plasma DNA nucleosome mapping.

FIG. 29E provides bar charts of overall z-score plots for merged breast, prostate, and colon cancer pools. The left panel displays TFs with increased accessibility in at least one tumor entity; the right panel summarized the accessibilities of hematopoietic related TFs.

Figures 30A, 30B:
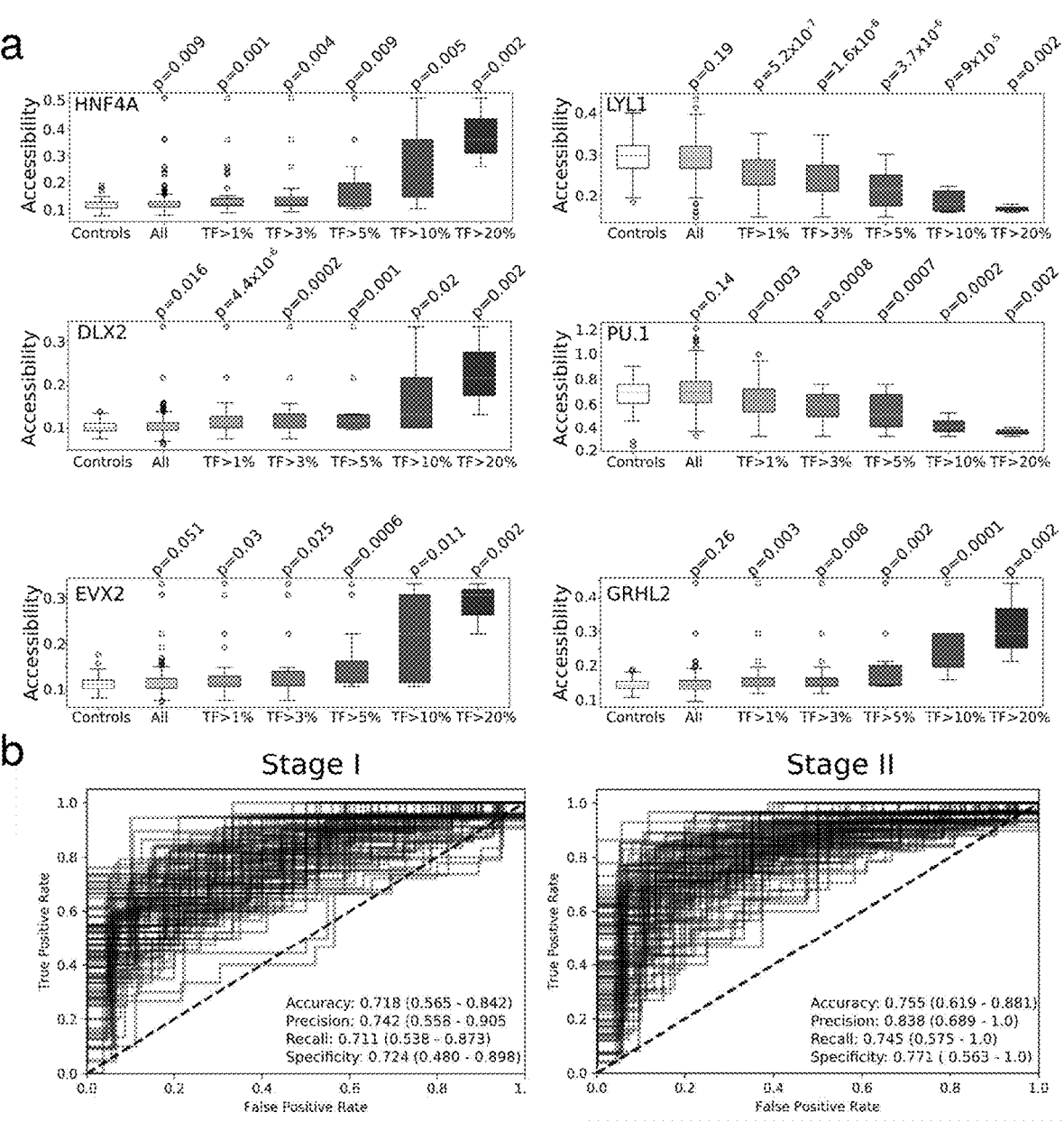
FIGS. 30A-30B provide graphs showing TF-based plasma resolution limits and early cancer detection.

FIGS. 30A-30B provide graphs showing TF-based plasma resolution limits and early cancer detection. FIG. 30A provides graphs showing comparisons of accessibilities for selected TFs in subsamples of the COAD cohort based on their tumor fraction. FIG. 30B provides graphs showing logistic regression with all 504 TFs for samples from the colon cancer cohort with stage I (left panel) and stage II (right panel), respectively. All presented results are cross-validated test-set values.

While certain examples of methods and systems have been shown and described herein, one of skill in the art will realize that these are provided by way of example only and not intended to be limiting within the specification. Numerous variations, changes, and substitutions will now occur to those skilled in the art without departing from the scope described herein. Furthermore, it shall be understood that all aspects of the described methods and systems are not limited to the specific depictions, configurations or relative proportions set forth herein which depend upon a variety of conditions and variables and the description is intended to include such alternatives, modifications, variations or equivalents.

What is claimed is:

1. A method for treating a cancer in a human subject, said method comprising:

(a) providing a set of sequence reads obtained by whole genome sequencing of cell-free deoxyribonucleic acid (cfDNA) obtained or derived from said human subject;

(b) aligning each sequence read of said set of sequence reads to a human reference genome to provide a set of aligned sequence reads;

(c) for each binding site of a set of binding sites of a transcription factor, selecting a genomic region of said set of aligned sequence reads that flanks each binding site of said set of binding sites to provide a set of flanking genomic regions, wherein each binding site of said set of binding sites exhibits differential accessibility to a target enhancer of said transcription factor in a first population of human subjects having said cancer as compared to a second population of human subjects not having said cancer, wherein said cancer comprises breast cancer, colon cancer, prostate adenocarcinoma, or small-cell neuroendocrine prostate cancer, wherein said transcription factor is selected from the group consisting of GRHL1, GRHL2, GRHL3, AR, ASH-2, HOXB13, EVX2, PU.1, LYL1, SPIB, FOXA1, FOXA2, GATA2, GATA3, ZNF121, HNF1A, HNF4A, HNF4G, DLX2, REST, GLIS1, SOX2, SOX11, and NKX3-1, and wherein each binding site of said set of binding sites is different;

(d) for each flanking genomic region of said set of flanking genomic regions, using at least a portion of said set of aligned sequence reads to generate a read depth coverage pattern, thereby providing a set of read depth coverage patterns for said set of binding sites of said transcription factor, respectively, wherein said set of read depth coverage patterns comprise nucleosome data;

(e) processing said set of read depth coverage patterns to provide a signal, wherein said signal characterizes binding site accessibility of said set of binding sites of said transcription factor;

(f) splitting said set of read depth coverage patterns into a low-frequency signal and a high-frequency signal using a low-pass filter, wherein said high-frequency signal is a measure of binding site accessibility for a given binding site, and wherein said splitting comprises applying a detrending filter to suppress effects on said read depth coverage pattern not contributed by preferential nucleosome positioning and to remove local biases from said nucleosome data;

(g) determining an accessibility score for each binding site of said set of binding sites of said transcription factor, wherein said determining comprises using said low-frequency signal to normalize said high-frequency signal;

(h) detecting a presence of said cancer in said human subject, based at least in part on a deviation of said accessibility score from a reference accessibility score; and (i) upon detecting said presence of said cancer in said human subject, administering a therapeutic intervention to said human subject, thereby treating said cancer.

2. The method of claim 1, wherein said accessibility score that deviates from said reference accessibility score by greater than ±3 mean of a standard deviation of a set of accessibility scores for each binding site of said set of binding sites of said transcription factor, when said accessibility score is calculated using a Savitzky-Golay filter, is indicative of said presence of said cancer in said human subject.

3. The method of claim 2, wherein said accessibility score comprises a z-score determined based on said standard deviation of said set of accessibility scores for each binding site of said set of binding sites of said transcription factor.

4. The method of claim 1, wherein said transcription factor is selected from the group consisting of FOXA1, GRHL1, GRHL2, and GRHL3.

5. The method of claim 1, wherein said transcription factor is selected from the group consisting of GRHL2, PU.1, LYL1, SPIB, AR, HOXB13, and NKX3-1.

6. The method of claim 1, wherein (h) further comprises identifying an increased accessibility score of a binding site of said transcription factor as compared to said reference accessibility score.

7. The method of claim 1, wherein (h) further comprises applying a trained machine learning algorithm to said accessibility score for each of said binding sites of said set of binding sites of said transcription factor to detect said presence of said cancer in said human subject.

8. The method of claim 7, wherein said trained machine learning algorithm is selected from the group consisting of a regression, a support vector machine, a tree-based method, a neural network, and a random forest.

9. The method of claim 1, wherein (g) further comprises performing a locally weighted smoothing using said high-frequency signal.

10. The method of claim 9, wherein said locally weighted smoothing comprises a locally estimated scatterplot smoothing (LOESS).

11. The method of claim 1, wherein said set of binding sites of said transcription factor comprises at least 25 different binding sites of said transcription factor.

12. The method of claim 1, wherein said set of sequence reads comprises at least 50 million sequence reads.

13. The method of claim 1, wherein said transcription factor is selected from the group consisting of GRHL2, FOXA1, and ZNF121; and wherein said cancer comprises said breast cancer.

14. The method of claim 1, wherein said transcription factor is selected from the group consisting of EVX2, DLX2, HNF1A, HNF4A, GRHL2, and HNF4G; and wherein said cancer comprises said colon cancer.

15. The method of claim 1, wherein said transcription factor is selected from the group consisting of LYL1 and PU.1; and wherein said cancer comprises said colon cancer.

16. The method of claim 1, wherein said transcription factor is selected from the group consisting of GRHL2, FOXA1, HOXB13, AR, and NKX3-1; and wherein said cancer comprises said prostate adenocarcinoma.

17. The method of claim 1, wherein said transcription factor is selected from the group consisting of REST, GRHL2, GRHL3, FOXA1, FOXA2, GATA2, GATA3, HOXB13, AR, and NKX3-1; and wherein said cancer comprises said prostate small-cell neuroendocrine prostate cancer.

18. The method of claim 1, wherein said transcription factor is selected from the group consisting of GLIS1, SOX2, and SOX11; and wherein said cancer comprises said small-cell neuroendocrine prostate cancer.

19. The method of claim 1, wherein said low-pass filter comprises a Savitzky-Golay filter.

20. The method of claim 19, wherein said Savitzky-Golay filter comprises a third-order Savitzky-Golay filter.

21. The method of claim 19, further comprising obtaining said low-frequency signal using a first Savitzky-Golay filter with a first window size, and obtaining said high-frequency signal using a second Savitzky-Golay filter with a second window size, wherein said first window size is larger than said second window size.

22. The method of claim 1, further comprising performing whole genome sequencing of said cfDNA obtained or derived from said human subject, thereby generating said set of sequence reads.

23. The method of claim 22, further comprising obtaining or deriving said cfDNA from a biological sample of said human subject.

24. The method of claim 23, wherein said biological sample is a blood sample, a plasma sample, a serum sample, a sweat sample, a urine sample, a saliva sample, a cell sample, a tissue sample, or a derivative thereof.

25. The method of claim 24, wherein said biological sample is said plasma sample.

26. The method of claim 1, further comprising, responsive at least in part to said detecting in (h), performing on said human subject a secondary clinical test, wherein said secondary clinical test comprises an imaging test, a blood test, a computed tomography (CT) scan, a magnetic resonance imaging (MRI) scan, an ultrasound scan, a chest X-ray, a positron emission tomography (PET) scan, a PET-CT scan, a cytology assay, or a combination thereof.

27. The method of claim 1, wherein said human reference genome is GrCH38, GrCH37, hg19, or hg38.

28. The method of claim 1, wherein said transcription factor is selected from the group consisting of ASH-2, HOX-B13, EVX2, PU.1, Lyl-1, Spi-B, FOXA1, HNF-1A, HNF-4A, HNF-4G, and DLX-2.

29. The method of claim 28, wherein said transcription factor comprises GRHL2.

30. The method of claim 1, wherein said detrending filter comprises a Savitzky-Golay filter.

31. The method of claim 1, wherein said therapeutic intervention comprises a chemotherapy, a surgery, or an androgen deprivation therapy.

32. The method of claim 31, wherein said therapeutic intervention comprises said chemotherapy.

33. The method of claim 31, wherein said therapeutic intervention comprises said surgery.

34. The method of claim 31, wherein said therapeutic intervention comprises said androgen deprivation therapy.

* * * * *